United States Patent
Schupp et al.

(12)
(10) Patent No.: US 6,346,404 B1
(45) Date of Patent: Feb. 12, 2002

(54) GENES FOR THE BIOSYNTHESIS OF EPOTHILONES

(75) Inventors: Thomas Schupp, Moh

GENES FOR THE BIOSYNTHESIS OF EPOTHILONES

CROSS REFERENCE TO RELATED APPLICATIONS

This application is a division of U.S. application Ser. No. 09/335,409, filed Jun. 17, 1999, now U.S. Pat. No. 6,121,029 which claims the benefit of U.S. Provisional Application No. 60/155,183, filed Jun. 18, 1998; U.S. Provisional Application No. 60/101,631, filed Sep. 24, 1998; and U.S. Provisional Application No. 60/118,906, filed Feb. 5, 1999. The full disclosure of each of these provisional applications is incorporated herein by reference.

FIELD OF THE INVENTION

The present invention relates generally to polyketides and genes for their synthesis. In particular, the present invention relates to the isolation and characterization of novel polyketide synthase and nonribosomal peptide synthetase genes from *Sorangium cellulosum* that are necessary for the biosynthesis of epothilones A and B.

BACKGROUND OF THE INVENTION

Polyketides are compounds synthesized from two-carbon building blocks, the β-carbon of which always carries a keto group, thus the name polyketide. These compounds include many important antibiotics, immunosuppressants, cancer chemotherapeutic agents, and other compounds possessing a broad range of biological properties. The tremendous structural diversity derives from the different lengths of the polyketide chain, the different side-chains introduced (either as part of the two-carbon building blocks or after the polyketide backbone is formed), and the stereochemistry of such groups. The keto groups may also be reduced to hydroxyls, enoyls, or removed altogether. Each round of two-carbon addition is carried out by a complex of enzymes called the polyketide synthase (PKS) in a manner similar to fatty acid biosynthesis.

The biosynthetic genes for an increasing number of polyketides have been isolated and sequenced. For example, see U.S. Pat. Nos. 5,639,949, 5,693,774, and 5,716,849, all of which are incorporated herein by reference, which describe genes for the biosynthesis of soraphen. See also, Schupp et al, *FEMS Microbiology Letters* 159: 201–207 (1998) and WO 98/07868, which describe genes for the biosynthesis of rifamycin, and U.S. Pat. No. 5,876,991, which describes genes for the biosynthesis of tylactone, all of which are incorporated rated herein by reference. The encoded proteins generally fall into two types: type I and type II. Type I proteins are polyfunctional, with several catalytic domains carrying out different enzymatic steps covalently linked together (e.g. PKS for erythromycin, soraphen, rifamycin, and avermectin (MacNeil et al, in *Industrial Microorganisms: Basic and Applied Molecular Genetics*, (ed.: Baltz et al), American Society for Microbiology, Washington D. C. pp. 245–256 (1993)); whereas type II proteins are monofunctional (Hutchinson et al, in *Industrial Microorganisms: Basic and Applied Molecular Genetics,* (ed.: Baltz et al.), American Society for Microbiology, Washington D. C. pp. 203–216 (1993)).

For the simpler polyketides such as actinorhodin (produced by *Streptomyces coelicolor*), the several rounds of two-carbon additions are carried out iteratively on PKS enzymes encoded by one set of PKS genes. In contrast, synthesis of the more complicated compounds such as erythromycin and soraphen involves PKS enzymes that are organized into modules, whereby each module carries out one round of two-carbon addition (for review, see Hopwood et al, in *Industrial Microorganisms: Basic and Applied Molecular Genetics*, (ed.: Baltz et al), American Society for Microbiology, Washington D. C., pp. 267–275 (1993)).

Complex polyketides and secondary metabolites in general may contain substructures that are derived from amino acids instead of simple carboxylic acids. Incorporations of these building blocks are accomplished by non-ribosomal polypeptide synthetases (NRPSs). NRPSs are multienzymes that are organized in modules. Each module is responsible for the addition (and the additional processing, if required) of one amino acid building block. NRPSs activate amino acids by forming aminoacyl-adenylates, and capture the activated amino acids on thiol groups of phophopantheteinyl prosthetic groups on peptidyl carrier protein domains. Further, NRPSs modify the amino acids by epimerization, N-methylation, or cyclization if necessary, and catalyse the formation of peptide bonds between the enzyme-bound amino acids. NRPSs are responsible for the biosynthesis of peptide secondary metabolites like cyclosporin, could provide polyketide chain terminator units as in rapamycin, or form mixed systems with PKSs as in yersiniabactin biosynthesis.

Epothilones A and B are 16-membered macrocyclic polyketides with an acylcysteine-derived starter unit that are produced by the bacterium *Sorangium cellulosum* strain So ce90 (Gerth et al., J. Antibiotics 49: 560–563 (1996), incorporated herein by reference). The structure of epothilone A and B wherein R signifies hydrogen (epothilone A) or methyl (epothilone B) is:

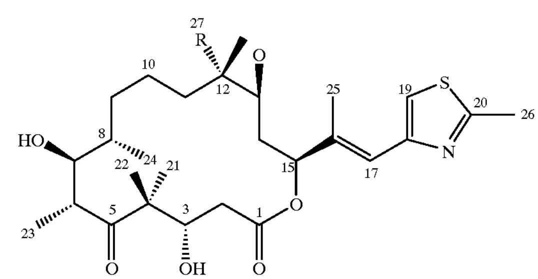

The epothilones have a narrow antifungal spectrum and especially show a high cytotoxicity in animal cell cultures (see, Höfle et al, U.S. Pat. No. Des. 4,138,042 (1993), incorporated herein by reference). Of significant importance, epothilones mimic the biological effects of taxol, both in vivo and in cultured cells (Bollag et al., *Cancer Research* 55: 2325–2333 (1995), incorporated herein by reference). Taxol and taxotere, which stabilize cellular microtubules, are cancer chemotherapeutic agents with significant activity against various human solid tumors (Rowinsky et al., *J. Natl. Cancer Inst.* 83: 1778–1781 (1991)). Competition studies have revealed that epothilones act as competitive inhibitors of taxol binding to microtubules, consistent with the interpretation that they share the same microtubule-binding site and possess a similar microtubule affinity as taxol. However, epothilones enjoy a significant advantage over taxol in that epothilones exhibit a much lower drop in potency compared to taxol against a multiple drug-resistant cell line (Bollag et al (1995)). Furthermore, epothilones are considerably less efficiently exported from the cells by P-glycoprotein than is taxol (Gerth et al. (1996)). In addition, several epothilone analogs have been synthesized that have a superior cytotoxic activity as compared to epothilone A or epothilone B as demonstrated by their enhanced ability to induce the polymerization and stabilization of microtubules (WO 98/25929, incorporated herein by reference).

Despite the promise shown by the epothilones as anticancer agents, problems pertaining to the production of these compounds presently limit their commercial potential. The compounds are too complex for industrial-scale chemical synthesis and so must be produced by fermentation. Techniques for the genetic manipulation of myxobacteria such as *Sorangium cellulosum* are described in U.S. Pat. No. 5,686, 295, incorporated herein by reference. However, *Sorangium cellulosum* is notoriously difficult to ferment and production levels of epothilones are therefore low. Recombinant production of epothilones in heterologous hosts that are more amenable to fermentation could solve current production problems. However, the genes that encode the polypeptides responsible for epothilone biosynthesis have heretofore not been isolated. Furthermore, the strain that produces epothilones, i.e. So ce90, also produces at least one additional polyketide, spirangien, which would be expected to greatly complicate the isolation of the genes particularly responsible for epothilone biosynthesis.

Therefore, in view of the foregoing, one object of the present invention is to isolate the genes that are involved in the synthesis of epothilones, particularly the genes that are involved in the synthesis of epothilones A and B in myxobacteria of the Sorangium/Polyangium group, i.e., Sorangium cellulosum strain So ce90. A further object of the invention is to provide a method for the recombinant production of epothilones for application in anticancer formulations.

SUMMARY OF THE INVENTION

In furtherance of the aforementioned and other objects, the present invention unexpectedly overcomes the difficulties set forth above to provide for the first time a nucleic acid molecule comprising a nucleotide sequence that encodes at least one polypeptide involved in the biosynthesis of epothilone. In a preferred embodiment, the nucleotide sequence is isolated from a species belonging to Myxobacteria, most preferably *Sorangium cellulosum*.

In another preferred embodiment, the present invention provides an isolated nucleic acid molecule comprising a nucleotide sequence that encodes at least one polypeptide involved in the biosynthesis of an epothilone, wherein said polypeptide comprises an amino acid sequence substantially similar to an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, amino acids 1314–1385 of SEQ ID NO:2, SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, amino acids 1344–1351 of SEQ ID NO:3, SEQ ID NO:4, amino acids 7–432 of SEQ ID NO:4, amino acids 539–859 of SEQ ID NO:4, amino acids 869–1037 of SEQ ID NO:4, amino acids 1439–1684 of SEQ ID NO:4, amino acids 1722–1792 of SEQ ID NO:4, SEQ ID NO:5, amino acids 39–457 of SEQ ID NO:5, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, amino acids 7140–7211 of SEQ ID NO:5, SEQ ID NO:6, amino acids 35–454 of SEQ ID NO:6, amino acids 561–881 of SEQ ID NO:6, amino acids 1143–1393 of SEQ ID NO:6, amino acids 1430–1503 of SEQ ID NO:6, amino acids 1522–1946 of SEQ ID NO: 6, amino acids 2053–2373 of SEQ ID NO:6, amino acids 2383–2551 of SEQ ID NO:6, amino acids 2671–3045 of SEQ ID NO:6, amino acids 3392–3636 of SEQ ID NO:6, amino acids 3673–3745 of SEQ ID NO:6, SEQ ID NO:7, amino acids 32–450 of SEQ ID NO:7, amino acids 556–877 of SEQ ID NO:7, amino acids 887–1051 of SEQ ID NO:7, amino acids 1478–1790 of SEQ ID NO:7, amino acids 1810–2055 of SEQ ID NO:7, amino acids 2093–2164 of SEQ ID NO:7, amino acids 2165–2439 of SEQ ID NO:7, SEQ ID NO:8, SEQ ID NO:10, SEQ ID NO:11, and SEQ ID NO:22.

In a more preferred embodiment, the present invention provides an isolated nucleic acid molecule comprising a nucleotide sequence that encodes at least one polypeptide involved in the biosynthesis of an epothilone, wherein said polypeptide comprises an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, amino acids 1314–1385 of SEQ ID NO:2, SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, amino acids 1344–1351 of SEQ ID NO:3, SEQ ID NO:4, amino acids 7–432 of SEQ ID NO:4, amino acids 539–859 of SEQ ID NO:4, amino acids 869–1037 of SEQ ID NO:4, amino acids 1439–1684 of SEQ ID NO:4, amino acids 1722–1792 of SEQ ID NO:4, SEQ ID NO:5, amino acids 39–457 of SEQ ID NO:5, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, amino acids 7140–7211 of SEQ ID NO:5, SEQ ID NO:6, amino acids 35–454 of SEQ ID NO:6, amino acids 561–881 of SEQ ID NO:6, amino acids 1143–1393 of SEQ ID NO:6, amino acids 1430–1503 of SEQ ID NO:6, amino acids 1522–1946 of SEQ ID NO: 6, amino acids 2053–2373 of SEQ ID NO:6, amino acids 2383–2551 of SEQ ID NO:6, amino acids 2671–3045 of SEQ ID NO:6, amino acids 3392–3636 of SEQ ID NO:6, amino acids 3673–3745 of SEQ ID NO:6, SEQ ID NO:7, amino acids 32–450 of SEQ ID NO:7, amino acids 556–877 of SEQ ID NO:7, amino acids 887–1051 of SEQ ID NO:7, amino acids 1478–1790 of SEQ ID NO:7, amino acids 1810–2055 of SEQ ID NO:7, amino acids 2093–2164 of SEQ ID NO:7, amino acids 2165–2439 of SEQ ID NO:7, SEQ ID NO:8, SEQ ID NO:10, SEQ ID NO:11, and SEQ ID NO:22.

In yet another preferred embodiment, the present invention provides an isolated nucleic acid molecule comprising a nucleotide sequence that encodes at least one polypeptide involved in the biosynthesis of an epothilone, wherein said nucleotide sequence is substantially similar to a nucleotide sequence selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

In an especially preferred embodiment, the present invention provides a nucleic acid molecule comprising a nucleotide sequence that encodes at least one polypeptide involved in the biosynthesis of an epothilone, wherein said nucleotide sequence is selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

In yet another preferred embodiment, the present invention provides an isolated nucleic acid molecule comprising a nucleotide sequence that encodes at least one polypeptide involved in the biosynthesis of an epothilone, wherein said nucleotide sequence comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

The present invention also provides a chimeric gene comprising a heterologous promoter sequence operatively linked to a nucleic acid molecule of the invention. Further, the present invention provides a recombinant vector comprising such a chimeric gene, wherein the vector is capable of being stably transformed into a host cell. Still further, the present invention provides a recombinant host cell comprising such a chimeric gene, wherein the host cell is capable of expressing the nucleotide sequence that encodes at least one polypeptide necessary for the biosynthesis of an epothilone. In a preferred embodiment, the recombinant host cell is a bacterium belonging to the order Actinomycetales, and in a more preferred embodiment the recombinant host cell is a strain of Streptomyces. In other embodiments, the recombinant host cell is any other bacterium amenable to fermentation, such as a pseudomonad or *E. coli*. Even further, the present invention provides a Bac clone comprising a nucleic acid molecule of the invention, preferably Bac clone pEPO15.

In another aspect, the present invention provides an isolated nucleic acid molecule comprising a nucleotide sequence that encodes an epothilone synthase domain.

According to one embodiment, the epothilone synthase domain is a β-ketoacyl-synthase (KS) domain comprising an amino acid sequence substantially similar to an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7. According to this embodiment, said KS domain preferably comprises an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7. Also, according to this embodiment, said nucleotide sequence preferably is substantially similar to a nucleotide sequence selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1. In addition, according to this embodiment, said nucleotide sequence most preferably is selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1.

According to another embodiment, the epothilone synthase domain is an acyltransferase (AT) domain comprising an amino acid sequence substantially similar to an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. According to this embodiment, said AT domain preferably comprises an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. Also, according to this embodiment, said nucleotide sequence preferably is substantially similar to a nucleotide sequence selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1. In addition, according to this embodiment, said nucleotide sequence most preferably is selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1.

According to still another embodiment, the epothilone synthase domain is an enoyl reductase (ER) domain comprising an amino acid sequence substantially similar to an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. According to this embodiment, said ER domain preferably comprises an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. Also, according to this embodiment, said nucleotide sequence preferably is substantially similar to a nucleotide sequence selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1. In addition, according to this embodiment, said nucleotide sequence most preferably is selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1.

According to another embodiment, the epothilone synthase domain is an acyl carrier protein (ACP) domain, wherein said polypeptide comprises an amino acid sequence substantially similar to an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. According to this embodiment, said ACP domain preferably comprises an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. Also, according to this embodiment, said nucleotide sequence preferably is substantially similar to a nucleotide sequence selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1. In addition, according to this embodiment, said nucleotide sequence most preferably is selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1.

According to another embodiment, the epothilone synthase domain is a dehydratase (DH) domain comprising an amino acid sequence substantially similar to an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. According to this embodiment, said DH domain preferably comprises an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. Also, according to this embodiment, said nucleotide sequence preferably is substantially similar to a nucleotide sequence selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1. In addition, according to this embodiment, said nucleotide sequence most preferably is selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1.

According to yet another embodiment, the epothilone synthase domain is a β-keto-reductase (KR) domain comprising an amino acid sequence substantially similar to an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. According to this embodiment, said KR domain preferably comprises an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. Also, according to this embodiment, said nucleotide sequence preferably is substantially similar to a nucleotide sequence selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1. In addition, according to this embodiment, said nucleotide sequence most preferably is selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1.

According to an additional embodiment, the epothilone synthase domain is a methyltransferase (MT) domain comprising an amino acid sequence substantially similar to amino acids 2671–3045 of SEQ ID NO:6. According to this embodiment, said MT domain preferably comprises amino acids 2671–3045 of SEQ ID NO:6. Also, according to this embodiment, said nucleotide sequence preferably is substantially similar to nucleotides 51534–52657 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of nucleotides 51534–52657 of SEQ ID NO:1. In addition, according to this embodiment, said nucleotide sequence most preferably is nucleotides 51534–52657 of SEQ ID NO:1.

According to another embodiment, the epothilone synthase domain is a thioesterase (TE) domain comprising an amino acid sequence substantially similar to amino acids 2165–2439 of SEQ ID NO:7. According to this embodiment, said TE domain preferably comprises amino acids 2165–2439 of SEQ ID NO:7. Also, according to this embodiment, said nucleotide sequence preferably is substantially similar to nucleotides 61427–62254 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of nucleotides 61427–62254 of SEQ ID NO:1. In addition, according to this embodiment, said nucleotide sequence most preferably is nucleotides 61427–62254 of SEQ ID NO:1.

In still another aspect, the present invention provides an isolated nucleic acid molecule comprising a nucleotide sequence that encodes a non-ribosomal peptide synthetase, wherein said non-ribosomal peptide synthetase comprises an amino acid sequence substantially similar to an amino acid sequence selected from the group consisting of: SEQ; ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, and amino acids 1344–1351 of SEQ ID NO:3. According to this embodiment, said non-ribosomal peptide synthetase preferably comprises an amino acid sequence selected from the group consisting of: SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, and amino acids 1344–1351 of SEQ ID NO:3. Also, according to this embodiment, said nucleotide sequence preferably is substantially similar to a nucleotide sequence selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1. In addition, according to this embodiment, said nucleotide sequence most preferably is selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1.

The present invention further provides an isolated nucleic acid molecule comprising a nucleotide sequence that encodes a polypeptide comprising an amino acid sequence selected from the group consisting of SEQ ID NOs:2–23.

In accordance with another aspect, the present invention also provides methods for the recombinant production of polyketides such as epothilones in quantities large enough to enable their purification and use in pharmaceutical formulations such as those for the treatment of cancer. A specific advantage of these production methods is the chirality of the molecules produced; production in transgenic organisms avoids the generation of populations of racemic mixtures, within which some enantiomers may have reduced activity. In particular, the present invention provides a method for heterologous expression of epothilone in a recombinant host, comprising: (a) introducing into a host a chimeric gene comprising a heterologous promoter sequence operatively linked to a nucleic acid molecule of the invention that comprises a nucleotide sequence that encodes at least one polypeptide involved in the biosynthesis of epothilone; and (b) growing the host in conditions that allow biosynthesis of epothilone in the host. The present invention also provides a method for producing epothilone, comprising: (a) expressing epothilone in a recombinant host by the aforementioned method; and (b) extracting epothilone from the recombinant host.

According to still another aspect, the present invention provides an isolated polypeptide comprising an amino acid sequence that consists of an epothilone synthase domain.

According to one embodiment, the epothilone synthase domain is a $\mu$-ketoacylsynthase (KS) domain comprising an amino acid sequence substantially similar to an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO:6, and amino acids 32–450 of SEQ ID NO:7. According to this embodiment, said KS domain preferably comprises an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7.

According to another embodiment, the epothilone synthase domain is an acyltransferase (AT) domain comprising an amino acid sequence substantially similar to an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. According to this embodiment, said AT domain preferably comprises an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7.

According to still another embodiment, the epothilone synthase domain is an enoyl reductase (ER) domain comprising an amino acid sequence substantially similar to an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. According to this embodiment, said ER domain preferably comprises an amino acid sequence selected from the group consisting of: amino acids 974–1273 of SEQ ID NO:2, amino acids 4433–4719 of SEQ ID NO:5, amino acids 6542–6837of SEQ ID NO:5, and amino acids 1478–1790 of SEQ ID NO:7.

According to another embodiment, the epothilone synthase domain is an acyl carrier protein (ACP) domain, wherein said polypeptide comprises an amino acid sequence substantially similar to an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. According to this embodiment, said ACP domain preferably comprises an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7.

According to another embodiment, the epothilone synthase domain is a dehydratase (DH) domain comprising an amino acid sequence substantially similar to an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. According to this embodiment, said DH domain preferably comprises an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7.

According to yet another embodiment, the epothilone synthase domain is a β-ketoreductase (KR) domain comprising an amino acid sequence substantially similar to an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. According to this embodiment, said KR domain preferably comprises an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7.

According to an additional embodiment, the epothilone synthase domain is a methyltransferase (MT) domain comprising an amino acid sequence substantially similar to amino acids 2671–3045 of SEQ ID NO:6. According to this embodiment, said MT domain preferably comprises amino acids 2671–3045 of SEQ ID NO:6.

According to another embodiment, the epothilone synthase domain is a thioesterase (TE) domain comprising an amino acid sequence substantially similar to amino acids 2165–2439 of SEQ ID NO:7. According to this embodiment, said TE domain preferably comprises amino acids 2165–2439 of SEQ ID NO:7.

Other aspects and advantages of the present invention will become apparent to those skilled in the art from a study of the following description of the invention and non-limiting examples.

DEFINITIONS

In describing the present invention, the following terms will be employed, and are intended to be defined as indicated below.

Associated With/Operatively Linked: Refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene: A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene is not normally operatively linked to the associated DNA sequence as found in nature.

Coding DNA Sequence: A DNA sequence that is translated in an organism to produce a protein.

Domain: That part of a polyketide synthase necessary for a given distinct activity. Examples include acyl carrier protein (ACP), β-ketosynthase (KS), acyltransferase (AT), β-ketoreductase (KR), dehydratase (DH), enoylreductase (ER), and thioesterase (TE) domains.

Epothilones: 16-membered macrocyclic polyketides naturally produced by the bacterium *Sorangium cellulosum* strain So ce90, which mimic the biological effects of taxol. In this application, "epothilone" refers to the class of polyketides that includes epothilone A and epothilone B, as well as analogs thereof such as those described in WO 98/25929.

Epothilone Synthase: A polyketide synthase responsible for the biosynthesis of epothilone.

Gene: A defined region that is located within a genome and that, besides the aforementioned coding DNA sequence, comprises other, primarily regulatory, DNA sequences responsible for the control of the expression, that is to say the transcription and translation, of the coding portion.

Heterologous DNA Sequence: A DNA sequence not naturally associated with a host cell into which it is introduced, including non-naturally occurring multiple copies of a naturally occurring DNA sequence.

Homologous DNA Sequence: A DNA sequence naturally associated with a host cell into which it is introduced.

Homologous Recombination: Reciprocal exchange of DNA fragments between homologous DNA molecules.

Isolated: In the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

Module: A genetic element encoding all of the distinct activities required in a single round of polyketide biosynthesis, i.e., one condensation step and all the β-carbonyl processing steps associated therewith. Each module encodes an ACP, a KS, and an AT activity to accomplish the condensation portion of the biosynthesis, and selected post-condensation activities to effect the β-carbonyl processing.

NRPS: A non-ribosomal polypeptide synthetase, which is a complex of enzymatic activities responsible for the incorporation of amino acids into secondary metabolites including, for example, amino acid adenylation, epimerization, N-methylation, cyclization, peptidyl carrier protein, and condensation domains. A functional NRPS is one that catalyzes the incorporation of an amino acid into a secondary metabolite.

NRPS gene: One or more genes encoding NRPSs for producing functional secondary metabolites, e.g., epothilones A and B, when under the direction of one or more compatible control elements.

Nucleic Acid Molecule: A linear segment of single- or double-stranded DNA or RNA that can be isolated from any source. In the context of the present invention, the nucleic acid molecule is preferably a segment of DNA.

ORF: Open Reading Frame.

PKS: A polyketide synthase, which is a complex of enzymatic activities (domains) responsible for the biosynthesis of polyketides including, for example, ketoreductase, dehydratase, acyl carrier protein, enoylreductase, ketoacyl ACP synthase, and acyltransferase. A functional PKS is one that catalyzes the synthesis of a polyketide.

PKS Genes: One or more genes encoding various polypeptides required for producing functional polyketides, e.g., epothilones A and B, when under the direction of one or more compatible control elements.

Substantially Similar: With respect to nucleic acids, a nucleic acid molecule that has at least 60 percent sequence identity with a reference nucleic acid molecule. In a preferred embodiment, a substantially similar DNA sequence is at least 80% identical to a reference DNA sequence; in a more preferred embodiment, a substantially similar DNA sequence is at least 90% identical to a reference DNA sequence; and in a most preferred embodiment, a substantially similar DNA sequence is at least 95% identical to a reference DNA sequence. A substantially similar DNA sequence preferably encodes a protein or peptide having substantially the same activity as the protein or peptide encoded by the reference DNA sequence. A substantially similar nucleotide sequence typically hybridizes to a reference nucleic acid molecule, or fragments thereof, under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C. With respect to proteins or peptides, a substantially similar amino acid sequence is an amino acid sequence that is at least 90% identical to the amino acid sequence of a reference protein or peptide and has substantially the same activity as the reference protein or peptide.

Transformation: A process for introducing heterologous nucleic acid into a host cell or organism.

Transformed/Transgenic/Recombinant: Refers to a host organism such as a bacterium into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, i.e., a bacterium, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DESCRIPTION OF THE SEQUENCES IN THE SEQUENCE LISTING

SEQ ID NO:1 is the nucleotide sequence of a 68750 bp contig containing 22 open reading frames (ORFs), which comprises the epothilone biosynthesis genes.

SEQ ID NO:2 is the protein sequence of a type I polyketide synthase (EPOS A) encoded by epoA (nucleotides 7610–11875 of SEQ ID NO:1).

SEQ ID NO:3 is the protein sequence of a non-ribosomal peptide synthetase (EPOS P) encoded by epoP (nucleotides 11872–16104 of SEQ ID NO:1).

SEQ ID NO:4 is the protein sequence of a type I polyketide synthase (EPOS B) encoded by epoB (nucleotides 16251–21749 of SEQ ID NO:1).

SEQ ID NO:5 is the protein sequence of a type I polyketide synthase (EPOS C) encoded by epoC (nucleotides 21746–43519 of SEQ ID NO:1).

SEQ ID NO:6 is the protein sequence of a type I polyketide synthase (EPOS D) encoded by epoD (nucleotides 43524–54920 of SEQ ID NO:1).

SEQ ID NO:7 is the protein sequence of a type I polyketide synthase (EPOS E) encoded by epoE (nucleotides 54935–62254 of SEQ ID NO:1).

SEQ ID NO:8 is the protein sequence of a cytochrome P450 oxygenase homologue (EPOS F) encoded by epoF (nucleotides 62369–63628 of SEQ ID NO:1).

SEQ ID NO:9 is a partial protein sequence (partial Orf 1) encoded by orf1 (nucleotides 1–1826 of SEQ ID NO:1).

SEQ ID NO:10 is a protein sequence (Orf 2) encoded by orf2 (nucleotides 3171–1900 on the reverse complement strand of SEQ ID NO:1).

SEQ ID NO:11 is a protein sequence (Orf 3) encoded by orf3 (nucleotides 3415–5556; of SEQ ID NO:1).

SEQ ID NO:12 is a protein sequence (Orf 4) encoded by orf4 (nucleotides 5992–5612 on the reverse complement strand of SEQ ID NO:1).

SEQ ID NO:13 is a protein sequence (Orf 5) encoded by orf5 (nucleotides 6226–6675 of SEQ ID NO:1).

SEQ ID NO:14 is a protein sequence (Orf 6) encoded by orf6 (nucleotides 63779–64333 of SEQ ID NO:1).

SEQ ID NO:15 is a protein sequence (Orf 7) encoded by orf7 (nucleotides 64290–63853 on the reverse complement strand of SEQ ID NO:1).

SEQ ID NO:16 is a protein sequence (Orf 8) encoded by orf8 (nucleotides 64363–64920 of SEQ ID NO:1).

SEQ ID NO:17 is a protein sequence (Orf 9) encoded by orf9 (nucleotides 64727–64287 on the reverse complement strand of SEQ ID NO:1).

SEQ ID NO:18 is a protein sequence (Orf 10) encoded by orf10 (nucleotides 65063–65767 of SEQ ID NO:1).

SEQ ID NO:19 is a protein sequence (Orf 11) encoded by orf11 (nucleotides 65874–65008 on the reverse complement strand of SEQ ID NO:1).

SEQ ID NO:20 is a protein sequence (Orf 12) encoded by orf12 (nucleotides 66338–65871 on the reverse complement strand of SEQ ID NO:1).

SEQ ID NO:21 is a protein sequence (Orf 13) encoded by orf13 (nucleotides 66667–67137 of SEQ ID NO:1).

SEQ ID NO:22 is a protein sequence (Orf 14) encoded by orf14 (nucleotides 67334–68251 of SEQ ID NO:1).

SEQ ID NO:23 is a partial protein sequence (partial Orf 15) encoded by orf15 (nucleotides 68346–68750 of SEQ ID NO:1).

SEQ ID NO:24 is the universal reverse PCR primer sequence.

SEQ ID NO:25 is the universal forward PCR primer sequence.

SEQ ID NO:26 is the NH24 end "B" PCR primer sequence.

SEQ ID NO:27 is the NH2 end "A" PCR primer sequence.

SEQ ID NO:28 is the NH2 end "B" PCR primer sequence.

SEQ ID NO:29 is the pEPO15-NH6 end "B" PCR primer sequence.

SEQ ID NO:30 is the pEPO15-H2.7 end "A" PCR primer sequence.

DEPOSIT INFORMATION

The following material has been deposited with the Agricultural Research Service, Patent Culture Collection (NRRL), 1815 North University Street, Peoria, Ill. 61604, under the Budapest Treaty on the International Recognition of the Deposit of Microorganisms for the Purposes of Patent Procedure. All restrictions on the availability of the deposited material will be irrevocably removed upon the granting of a patent.

| Deposited Material | Accession Number | Deposit Date |
| --- | --- | --- |
| pEPO15 | NRRLB-30033 | June 11, 1998 |
| pEPO32 | NRRL B-30119 | April 16, 1999 |

DETAILED DESCRIPTION OF THE INVENTION

The genes involved in the biosynthesis of epothilones can be isolated using the techniques according to the present invention. The preferable procedure for the isolation of epothilone biosynthesis genes requires the isolation of genomic DNA from an organism identified as producing epothilones A and B, and the transfer of the isolated DNA on a suitable plasmid or vector to a host organism that does not normally produce the polyketide, followed by the identification of transformed host colonies to which the epothilone-producing ability has been conferred. Using a technique such as λ::n5 transposon mutagenesis (de Bruijn & Lupski, *Gene* 27: 131–149 (1984)), the exact region of the transforming epothilone-conferring DNA can be more precisely defined. Alternatively or additionally, the transforming epothilone-conferring DNA can be cleaved into smaller fragments and the smallest that maintains the epothilone-conferring ability further characterized. Whereas the host organism lacking the ability to produce epothilone may be a different species from the organism from which the polyketide derives, a variation of this technique involves the transformation of host DNA into the same host that has had its epothilone-producing ability disrupted by mutagenesis. In this method, an epothilone-producing organism is mutated and non-epothilone-producing mutants are isolated. These are then complemented by genomic DNA isolated from the epothilone-producing parent strain.

A further example of a technique that can be used to isolate genes required for epothilone biosynthesis is the use of transposon mutagenesis to generate mutants of an epothilone-producing organism that, after mutagenesis, fails to produce the polyketide. Thus, the region of the host genome responsible for epothilone production is tagged by the transposon and can be recovered and used as a probe to isolate the native genes from the parent strain. PKS genes that are required for the synthesis of polyketides and that are similar to known PKS genes may be isolated by virtue of their sequence homology to the biosynthetic genes for which the sequence is known, such as those for the biosynthesis of rifamycin or soraphen. Techniques suitable for isolation by homology include standard library screening by DNA hybridization.

Preferred for use as a probe molecule is a DNA fragment that is obtainable from a gene or another DNA sequence that plays a part in the synthesis of a known polyketide. A preferred probe molecule comprises a 1.2 kb SmaI DNA fragment encoding the ketosynthase domain of the fourth module of the soraphen PKS (U.S. Pat. No. 5,716,849), and a more preferred probe molecule comprises the β-ketoacyl synthase domains from the first and second modules of the rifamycin PKS (Schupp et al., *FEMS Microbiology Letters* 159: 201–207 (1998)). These can be used to probe a gene library of an epothilone-producing microorganism to isolate the PKS genes responsible for epothilone biosynthesis.

Despite the well-known difficulties with PKS gene isolation in general and despite the difficulties expected to be encountered with the isolation of epothilone biosynthesis genes in particular, by using the methods described in the instant specification, biosynthetic genes for epothilones A and B can surprisingly be cloned from a microorganism that produces that polyketide. Using the methods of gene manipulation and recombinant production described in this specification, the cloned PKS genes can be modified and expressed in transgenic host organisms.

The isolated epothilone biosynthetic genes can be expressed in heterologous hosts to enable the production of the polyketide with greater efficiency than might be possible from native hosts. Techniques for these genetic manipulations are specific for the different available hosts and are known in the art. For example, heterologous genes can be expressed in Streptomyces and other actinomycetes using techniques such as those described in McDaniel et al., *Science* 262: 1546–1550 (1993) and Kao et al., *Science* 265: 509–512 (1994), both of which are incorporated herein by reference. See also, Rowe et al., *Gene* 216: 215–223 (1998); Holmes et al., *EMBO Journal* 12(8): 3183–3191 (1993) and Bibb et al., *Gene* 38: 215–226 (1985), all of which are incorporated herein by reference.

Alternately, genes responsible for polyketide biosynthesis, i.e., epothilone biosynthetic genes, can also be expressed in other host organisms such as pseudomonads and *E. coli*. Techniques for these genetic manipulations are specific for the different available hosts and are known in the art. For example, PKS genes have been successfully expressed in *E. coli* using the pT7–7 vector, which uses the T7 promoter. See, Tabor et al., *Proc. Natl. Acad. Sci. USA* 82:1074–1078 (1985), incorporated herein by reference. In addition, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al., in: *Industrial Microorganisms: Basic and Applied Molecular Genetics*, Eds. Baltz et al., American Society for Microbiology, Washington (1993)).

Other expression systems that may be used with the epothilone biosynthetic genes of the invention include yeast and baculovirus expression systems. See, for example, "The Expression of Recombinant Proteins in Yeasts," Sudbery, P. E., *Curr. Opin. Biotechnol.* 7(5): 517–524 (1996); "Methods for Expressing Recombinant Proteins in Yeast," Mackay, et al., Editor(s): Carey, Paul R., *Protein Eng. Des.* 105–153, Publisher: Academic, San Diego, Calif. (1996); "Expression of heterologous gene products in yeast," Pichuantes, et al., Editor(s): Cleland, J. L., Craik, C. S., *Protein Eng.* 129–161, Publisher: Wiley-Liss, New York, N.Y. (1996); WO 98/27203; Kealey et al., *Proc. Natl. Acad. Sci. USA* 95: 505–509 (1988); "Insect Cell Culture: Recent Advances, Bioengineering Challenges And Implications In Protein Production," Palomares, et al., Editor(s): Galindo, Enrique; Ramirez, Octavio T., *Adv. Bioprocess Eng.* Vol. 11, Invited Pap. Int. Symp., 2nd (1998) 25–52, Publisher: Kluwer, Dordrecht, Neth; "Baculovirus Expression Vectors," Jarvis, Donald L., Editor(s): Miller, Lois K., *Baculoviruses* 389–431, Publisher: Plenum, New York, N.Y. (1997); "Production Of Heterologous Proteins Using The Baculovirus/ Insect Expression System," Grittiths, et al., Methods Mol. Biol. (Totowa, N.J.) 75 (Basic Cell Culture Protocols (2nd Edition)) 427–440 (1997); and "Insect Cell Expression Technology," Luckow, Verne A., *Protein Eng.* 183–218, Publisher: Wiley-Liss, New York, N.Y. (1996); all of which are incorporated herein by reference.

Another consideration for expression of PKS genes in heterologous hosts is the requirement of enzymes for post-translational modification of PKS enzymes by phosphopantetheinylation before they can synthesize polyketides. However, the enzymes responsible for this modification of type I PKS enzymes, phosphopantetheinyl (P-pant) transferases are not normally present in many hosts such as *E. coli*. This problem can be solved by coexpression of a P-pant transferase with the PKS genes in the heterologous host, as described by Kealey et al., *Proc. Natl. Acad. Sci. USA* 95: 505–509 (1998), incorporated herein by reference.

Therefore, for the purposes of polyketide production, the significant criteria in the choice of host organism are its ease of manipulation, rapidity of growth (i.e. fermentation), possession or the proper molecular machinery for processes such as posttranslational modification, and its lack of susceptibility to the polyketide being overproduced. Most preferred host organisms are actinomycetes such as strains of Streptomyces. Other preferred host organisms are pseudomonads and *E. coli*. The above-described methods of polyketide production have significant advantages over the technology currently used in the preparation of the compounds. These advantages include the cheaper cost of production, the ability to produce greater quantities of the compounds, and the ability to produce compounds of a preferred biological enantiomer, as opposed to racemic mixtures inevitably generated by organic synthesis. Compounds produced by heterologous hosts can be used in medical (e.g. cancer treatment in the case of epothilones) as well as agricultural applications.

EXPERIMENTAL

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), *Current Protocols in Molecular Biology*, John Wiley and Sons, Inc. (1994); T. Maniatis, E. F. Fritsch and J. Sambrook, *Molecular Cloning: A Laboratory Manual*, Cold Spring Harbor laboratory, Cold Spring Harbor, N.Y. (1989); and by T. J. Silhavy, M. L. Berman, and L. W. Enquist, *Experiments with Gene Fusions*, Cold Spring Harbor Laboratory, Cold Spring Harbor, N.Y. (1984).

EXAMPLE 1

Cultivation of an Epothilone-Producing Strain of *Sorangium cellulosum*

*Sorangium cellulosum* strain 90 (DSM 6773, Deutsche Sammiung von Mikroorganismen und Zelikulturen, Braunschweig) is streaked out and grown (30° C.) on an agar plate of SolE medium (0.35% glucose, 0.05% tryptone, 0.15% $MgSO_4 \times 7H_2O$, 0.05% ammonium sulfate, 0.1% $CaCl_2$, 0.006% $K_2HPO_4$, 0.01% sodium dithionite, 0.0008% Fe-EDTA, 1.2% HEPES, 3.5% [vol/vol] supernatant of sterilized stationary *S. cellulosum* culture) pH ad. 7.4. Cells from about 1 square cm are picked and inoculated into 5 mls of G51t liquid medium (0.2% glucose, 0.5% starch, 0.2% tryptone, 0.1% probion S, 0.05% $CaCl_2 \times 2H_2O$, 0.05% $MgSO_4 \times 7H_2O$, 1.2% HEPES, pH ad. 7.4) and incubated at 30° C. with shaking at 225 rpm. After 4 days, the culture is transferred into 50 mls of G51 t and incubated as above for 5 days. This culture is used to inoculate 500 mls of G51t and incubated as above for 6 days. The culture is centrifuged for 10 minutes at 4000 rpm and the cell pellet is resuspended in 50 mls of G51t.

EXAMPLE 2
Generation of a Bacterial Artificial Chromosome (Bac) Library

To generate a Bac library, S. cellulosum cells cultivated as described in Example 1 above are embedded into agarose blocks, lysed, and the liberated genomic DNA is partially digested by the restriction enzyme HindIII. The digested DNA is separated on an agarose gel by pulsed-field electrophoresis. Large (approximately 90–150 kb) DNA fragments are isolated from the agarose gel and ligated into the vector pBelobacII. pBelobacII contains a gene encoding chloramphenicol resistance, a multiple cloning site in the lacZ gene providing for blue/white selection on appropriate medium, as well as the genes required for the replication and maintenance of the plasmid at one or two copies per cell. The ligation mixture is used to transform *Escherichia coli* DH10B electrocompetent cells using standard electroporation techniques. Chloramphenicol-resistant recombinant (white, lacZ mutant) colonies are transferred to a positively charged nylon membrane filter in 384 3×3 grid format. The clones are lysed and the DNA is cross-linked to the filters. The same clones are also preserved as liquid cultures at −800° C.

EXAMPLE 3
Screening the Bac Library of *Sorangium cellulosum* 90 for the Presence of Type I Polyketide Synthase-Related Sequences The Bac library filters are probed by standard Southern hybridization procedures. The DNA probes used encode β-ketoacyl synthase domains from the first and second modules of the rifamycin polyketide synthase (Schupp et al., FEMS Microbiology Letters 159: 201–207 (1998)). The probe DNAs are generated by PCR with primers flanking each ketosynthase domain using the plasmid pNE95 as the template (pNE95 equals cosmid 2 described in Schupp et al. (1998)). 25 ng of PCR-amplified DNA is isolated from a 0.5% agarose gel and labeled with $^{32}$P-dCTP using a random primer labeling kit (Gibco-BRL, Bethesda Md., USA) according to the manufacturer's instructions. Hybridization is at 65° C. for 36 hours and membranes are washed at high stringency (3 times with 0.1×SSC and 0.5% SDS for 20 min at 650° C.). The labeled blot is exposed on a phosphorescent screen and the signals are detected on a Phospholmager 445SI (screen and 445SI from Molecular Dynamics). This results in strong hybridization of certain Bac clones to the probes. These clones are selected and cultured overnight in 5 mls of Luria broth (LB) at 37° C. Bac DNA from the Bac clones of interest is isolated by a typical miniprep procedure. The cells are resuspended in 200 μl lysozyme solution (50 mM glucose, 10 mM EDTA, 25 mM Tris-HCl, 5mg/ml lysozyme), lysed in 400 μl lysis solution (0.2 N NaOH and 2% SDS), the proteins are precipitated (3.0 M potassium acetate, adjusted to pH5.2 with acetic acid), and the Bac DNA is precipitated with isopropanol. The DNA is resuspended in 20 μl of nuclease-free distilled water, restricted with BamHI (New England Biolabs, Inc.) and separated on a 0.7% agarose gel. The gel is blotted by Southern hybridization as described above and probed under conditions described above, with a 1.2 kb SmaI DNA fragment encoding the ketosynthase domain of the fourth module of the soraphen polyketide synthase as the probe (see, U.S. Pat. No. 5,716,849). Five different hybridization patterns are observed. One clone representing each of the five patterns is selected and named pEPO15, pEPO20, pEPO30, pEPO31, and pEPO33, respectively.

EXAMPLE 4
Subcloning of BamHI Fragments from pEPO15, pEPO20, pEPO30, pEPO31, and pEPO33

The DNA of the five selected Bac clones is digested with BamHI and random fragments are subcloned into pBluescript II SK+ (Stratagene) at the BamHI site. Subclones carrying inserts between 2 and 10 kb in size are selected for sequencing of the flanking ends of the inserts and also probed with the 1.2 SmaI probe as described above. Subclones that show a high degree of sequence homology to known polyketide synthases and/or strong hybridization to the soraphen ketosynthase domain are used for gene disruption experiments.

EXAMPLE 5
Preparation of Streptomycin-Resistant Spontaneous Mutants of *Sorangium cellulosum* strain So ce90

0.1 ml of a three day old culture of *Sorangium cellulosum* strain So ce90, which is raised in liquid medium G52-H (0.2% yeast extract, 0.2% soyameal defatted, 0.8% potato starch, 0.2% glucose, 0.1% MgSO4×7H2O, 0.1% CaCl2× 2H$_2$O, 0.008% Fe-EDTA, pH ad 7.4 with KOH), is plated out on agar plates with SoIE medium supplemented with 100 μg/ml streptomycin. The plates are incubated at 30° C. for 2 weeks. The colonies growing on this medium are streptomycin-resistant mutants, which are streaked out and cultivated once more on the same agar medium with streptomycin for purification. One of these streptomycin-resistant mutants is selected and is called BCE28/2.

EXAMPLE 6
Gene Disruptions in *Sorangium cellulosum* BCE28/2 Using the Subcloned BamHI Fragments The BamHI inserts of the subclones generated from the five selected Bac clones as described above are isolated and ligated into the unique BamHI site of plasmid pCIB132 (see, U.S. Pat. No. 5,716,849). The pCIB132 derivatives carrying the inserts are transformed into *Escherichia coli* ED8767 containing the helper plasmid pUZ8 (Hedges and Matthew, Plasmid2: 269–278 (1979). The transformants are used as donors in conjugation experiments with *Sorangium cellulosum* BCE28/2 as recipient. For the conjugation, 5–10×10$^9$ cells of *Sorangium cellulosum* BCE28/2 from an early stationary phase culture (reaching about 5×10$^8$ cells/ml) grown at 30° C. in liquid medium G51b (G51 b equals medium G51 t with tryptone replaced by peptone) are mixed in a 1:1 cellular ratio with a late-log phase culture (in LB liquid medium) of *E coli* ED8767 containing pCIB132 derivatives carrying the subcloned BamHI fragments and the helper plasmid pUZ8. The mixed cells are then centrifuged at 4000 rpm for 10 minutes and resuspended in 0.5 ml G51b medium. This cell suspension is then plated as a drop in the center of a plate with So1E agar containing 50 mg/l kanamycin. The cells obtained after incubation for 24 hours at 30° C. are harvested and resuspended in 0.8 ml of G51b medium, and 0.1 to 0.3 ml of this suspension is plated out on a selective So1E solid medium containing phleomycin (30 mg/l), streptomycin (300 mg/l), and kanamycin (50 mg/l). The counterselection of the donor *Escherichia coli* strain takes place with the aid of streptomycin. The colonies that grow on this selective medium after an incubation time of 8–12 days at a temperature of 30° C. are isolated with a plastic loop and streaked out and cultivated on the same agar medium for a second round of selection and purification. The colony-derived cultures that grow on this selective agar medium after 7 days at a temperature of 30° C. are transconjugants of *Sorangium cellulosum* BCE28/2 that have acquired phleomycin resistance by conjugative transfer of the pCIB132 derivatives carrying the subcloned BamHI fragments.

Integration of the pCIB132-derived plasmids into the chromosome of *Sorangium cellulosum* BCE28/2 by homologous recombination is verified by Southern hybridization. For this experiment, complete DNA from 5–10 tranconjugants per transferred BamHI fragment is isolated (from 10 ml cultures grown in medium G52-H for three days) applying the method described by Pospiech and Neumann, *Trends Genet.* 11: 217 (1995). For the Southern blot, the DNA isolated as described above is cleaved either with the restriction enzymes BglII, ClaI, or NotI, and the respective BamHI inserts or pCIB132 are used as 32P labelled probes.

EXAMPLE 7

Analysis of the Effect of the Integrated BamHI Fragments on Epothilone Production by *Sorangium cellulosum* After Gene Disruption Transconjugant cells grown on about 1 square cm surface of the selective So1E plates of the second round of selection (see Example 6) are transferred by a sterile plastic loop into 10 ml of medium G52-H in an 50 ml Erlenmeyer flask. After incubation at 30° C. and 180 rpm for 3 days, the culture is transferred into 50 ml of medium G52-H in an 200 ml Erlenmeyer flask. After incubation at 30° C. and 180 rpm for 4–5 days, 10 ml of this culture is transferred into 50 ml of medium 23B3 (0.2% glucose, 2% potato starch, 1.6% soyameal defatted, 0.0008% Fe-EDTA Sodium salt, 0.5% HEPES (4-(2-hydroxyethyl)-piperazine-1-ethane-sulfonic-acid), 2% vol/vol polysterole resin XAD16 (Rohm & Haas), pH adjusted to 7.8 with NaOH) in an 200 ml Erlenmeyer flask.

Quantitative determination of the epothilone produced takes place after incubation of the cultures at 30° C. and 180 rpm for 7 days. The complete culture broth is filtered by suction through a 150 µm nylon filter. The resin remaining on the filter is then resuspended in 10 ml isopropanol and extracted by shaking the suspension at 180 rpm for 1 hour. 1 ml is removed from this suspension and centrifuged at 12,000 rpm in an Eppendorff Microfuge. The amount of epothilones A and B therein is determined by means of an HPLC and detection at 250 nm with a UV_DAD detector (HPLC with Waters—Symetry C18 column and a gradient of 0.02% phosphoric acid 60%–0% and acetonitrile 40%–100%).

Transconjugants with three different integrated BamHI fragments subcloned from pEPO15, namely transconjugants with the BamHI fragment of plasmid pEPO15-21, transconjugants with the BamHI fragment of plasmid pEPO15-4-5, and transconjugants with the BamHI fragment of plasmid pEPO15-4-1, are tested in the manner described above. HPLC analysis reveals that all transconjugants no longer produce epothilone A or B. By contrast, epothilone A and B are detectable in a concentration of 2–4 mg/l in transconjugants with BamHI fragments integrated that are derived from pEPO20, pEPO30, pEPO31, pEPO33, and in the parental strain BCE28/2.

EXAMPLE 8

Nucleotide Sequence Determination of the Cloned Fragments and Construction of Contigs A. BamHI Insert of Plasmid pEPO15-21

Plasmid DNA is isolated from the strain *Escherichia coli* DH10B [pEPO15-21], and the nucleotide sequence of the 2.3-kb BamHI insert in pEPO15-21 is determined.. Automated DNA sequencing is done on the double-stranded DNA template by the dideoxynucleotide chain termination method, using Applied Biosystems model 377 sequencers. The primers used are the universal reverse primer (5' GGA AAC AGC TAT GAC CAT G 3' (SEQ ID NO:24)) and the universal forward primer (5' GTA AAA CGA CGG CCA GT 3' (SEQ ID NO:25)). In subsequent rounds of sequencing reactions, custom-synthesized oligonucleotides, designed for the 3' ends of the previously determined sequences, are used to extend and join contigs. Both strands are entirely sequenced, and every nucleotide is sequenced at least two times. The nucleotide sequence is compiled using the program Sequencher vers. 3.0 (Gene Codes Corporation), and analyzed using the University of Wisconsin Genetics Computer Group programs. The nucleotide sequence of the 2213-bp insert corresponds to nucleotides 20779–22991 of SEQ ID NO:1.

B. BamHI Insert of Plasmid pEPO15-4-1

Plasmid DNA is isolated from the strain *Escherichia coli* DH10B [pEPO15-4-1], and the nucleotide sequence of the 3.9-kb BamHI insert in pEPO15-4-1 is determined as described in (A) above. The nucleotide sequence of the 3909-bp insert corresponds to nucleotides 16876–20784 of SEQ ID NO:1.

C. BamHI Insert of Plasmid pEPO15-4-5

Plasmid DNA is isolated from the strain *Escherichia coli* DH10B [pEPO15-4-5], and the nucleotide sequence of the 2.3-kb BamHI insert in pEPO15-4-5 is determined as described in (A) above. The nucleotide sequence of the 2233-bp insert corresponds to nucleotides 42528–44760 of SEQ ID NO:1.

EXAMPLE 9

Subcloning and Ordering of DNA Fragments from pEPO15 Containing Epothilone Biosynthesis Genes pEPO15 is digested to completion with the restriction enzyme HindIII and the resulting fragments are subcloned into pBluescript II SK– or pNEB193 (New England Biolabs) that has been cut with HindIII and dephosphorylated with calf intestinal alkaline phosphatase. Six different clones are generated and named pEPO15-NH1, pEPO15-NH2, pEPO15-NH6, pEPO15-NH24 (all based on. pNEB193), and pEPO15-H2.7 and pEPO15-H3.0 (both based on pBluescript II SK–).

The BamHI insert of pEPO15-21 is isolated and DIG-labeled (Non-radioactive DNA labeling and detection system, Boehringer Mannheim), and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signal is detected for pEPO15-NH24, indicating that pEPO15-21 is contained within pEPO15-NH24.

The BamHI insert of pEPO15-4-1 is isolated and DIG-labeled as above, and used as, a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signals are detected for pEPO15-NH24 and pEPO15-H2.7. Nucleotide sequence data generated from one end each of pEPO15-NH24 and pEPO15-H2.7 are also in complete agreement with the previously determined sequence of the BamHI insert of pEPO15-4-1. These experiments demonstrate that pEPO15-4-1 (which contains one internal HindIII site) overlaps pEPO15-H2.7 and pEPO15-NH24, and that pEPO15-H2.7 and pEPO15-NH24, in this order, are contiguous.

The BamHI insert of pEPO15-4-5 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signal is detected for pEPO15-NH2, indicating that pEPO15-21 is contained within pEPO15-NH2.

Nucleotide sequence data is generated from both ends of pEPO15-NH2 and from the end of pEPO15-NH24 that does not overlap with pEPO15-4-1. PCR primers NH24 end "B": GTGACTGGCGCCTGGAATCTGCATGAGC (SEQ ID NO:26), NH2 end "A": AGCGGGAGCTTGCTAGACAT-TCTGTTTC (SEQ ID NO:27), and NH2 end "B": GACGCGCCTCGGGCAGCGCCCCAA (SEQ ID NO:28), pointing towards the HindIII sites, are designed based on these sequences and used in amplification reactions with pEPO15 and, in separate experiments, with *Sorangium cellulosum* So ce90 genomic DNA as the templates. Specific amplification is found with primer pair NH24 end "B" and NH2 end "A" with both templates. The amplimers are cloned into pBluescript II SK– and completely sequenced. The sequences of the amplimers are identical, and also agree completely with the end sequences of pEPO15-NH24 and pEPO15-NH2, fused at the HindIII site, establishing that the HindIII fragments of pEPO15-NH2 and pEPO15-NH24 are, in this order, contiguous.

The HindIII insert of pEPO15-H2.7 is isolated and DIG-labeled as above, and used as a probe in a DNA hybridization experiment at high stringency against pEPO15 digested by Notl. A Notl fragment of about 9 kb in size shows a strong a hybridization, and is further subcloned into pBluescript II SK– that has been digested with Notl and dephosphorylated with calf intestinal alkaline phosphatase, to yield pEPO15-N9-16. The Notl insert of pEPO15-N9-16 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signals are detected for pEPO15-NH6, and also for the expected clones pEPO15-H2.7 and pEPO15-NH24. Nucleotide sequence data is generated from both ends of pEPO15-NH6 and from the end of pEPO15-H2.7 that does not overlap with pEPO15-4-1. PCR primers are designed pointing towards the HindIII sites and used in amplification reactions with pEPO15 and, in separate experiments, with *Sorangium cellulosum* So ce90 genomic DNA as the templates. Specific amplification is found with primer pair pEPO15-NH6 end "B": CACCGAAGCGTCGATCTG-GTCCATC (SEQ ID NO:29) and pEPO15-H2.7 end "A": CGGTCAGATCGACGACGGGCTTTCC (SEQ ID NO:30) with both templates. The amplimers are cloned into pBluescript II SK– and completely sequenced. The sequences of the amplimers are identical, and also agree completely with the end sequences of pEPO15-NH6 and pEPO15-H2.7, fused at the HindIII site, establishing that the HindIII fragments of pEPO15-NH6 and pEPO15-H2.7 are, in this order, contiguous.

All of these experiments, taken together, establish a contig of HindIII fragments covering a region of about 55 kb and consisting of the HindIII inserts of pEPO15-NH6, pEPO15-H2.7; pEPO15-NH24, and pEPO15-NH2, in this order. The inserts of the remaining two HindIII subclones, namely pEPO15-NH1 and pEPO15-H3.0, are not found to be parts of this contig.

EXAMPLE 10
Further Extension of the Subclone Contig Covering the Epothilone Biosynthesis Genes An approximately 2.2 kb BamHI-HindIII fragment derived from the downstream end of the insert of pEPO15-NH2 and thus representing the downstream end of the subclone contig described in Example 9 is isolated, DIG-labeled, and used in Southern hybridization experiments against pEPO15 and pEPO15-NH2 DNAs digested with several enzymes. The strongly hybridizing bands are always found to be the same in size between the two target DNAs indicating that the *Sorangium cellulosum* So ce90 genomic DNA fragment cloned into pEPO15 ends with the HindIII site at the downstream end of pEPO15-NH2.

A cosmid DNA library of *Sorangium cellulosum* So ce90 is generated, using established procedures, in pScosTriplex-II (Ji, et al., Genomics 31: 185–192 (1996)). Briefly, high-molecular weight genomic DNA of *Sorangium cellulosum* So ce90 is partially digested with the restriction enzyme Sau3AI to provide fragments with average sizes of about 40 kb, and ligated to BamHI and XbaI digested pScosTriplex-II. The ligation mix is packaged with Gigapack III XL (Stratagene) and used to transfect *E. coli* XL1 Blue MR cells.

The cosmid library is screened with the approximately 2.2 kb BamHI-HindIII fragment, derived from the downstream end of the insert of pEPO15-NH2, used as a probe in colony hybridization. A strongly hybridizing clone, named pEPO4E7 is selected.

pEPO4E7 DNA is isolated, digested with several restriction endonucleases, and probed in Southern hybridization experiments with the 2.2 kb BamHI-HindIII fragment. A strongly hybridizing Notl fragment of approximately 9 kb in size is selected and subcloned into pBluescript II SK– to yield pEPO4E7-N9-8. Further Southern hybridization experiments reveal that the approximately 9 kb Notl insert of pEPO4E7-N9-8 overlaps pEPO15-NH2 over 6 kb in a Notl-HindIII fragment, while the remaining approximately 3 kb HindIII-Notl fragment would extend the subclone contig described in Example 9. End sequencing reveals, however, that the downstream end of the insert of pEPO4E7-N9-8 contains the BamHI-Notl polylinker of pScosTriplex-II, thereby indicating that the genomic DNA insert of pEPO4E7 ends at a Sau3AI site within the extending HindIII-Notl fragment and that the Notl site is derived from pScosTriplex-II.

An approximately 1.6 kb PstI-SalI fragment derived from the approximately 3 kb extending HindIII-Notl subfragment of pEPO4E7-N9-8, containing only *Sorangium cellulosum* So ce90-derived sequences free of vector, is used as a probe against the bacterial artificial chromosome library described in Example 2. Besides the previously-isolated EPO15, a Bac clone, named EPO32, is found to strongly hybridize to the probe. pEPO32 is isolated, digested with several restriction endonucleases, and hybridized with the approximately 1.6 kb PstI-SalI probe. A HindIII-EcoRV fragment of about 13 kb in size is found to strongly hybridize to the probe, and is subcloned into pBluescript II SK– digested with HindIII and HindIII to yield pEPO32-HEV15.

Oligonucleotide primers are designed based on the downstream end sequence of pEPO15-NH2 and on the upstream (HindIII) end sequence derived from pEPO32-HEV15, and used in sequencing reactions with pEPO4E7-N9-8 as the template. The sequences reveal the existence of a small HindIII fragment (EPO4E7-H0.02) of 24 bp, undetectable in standard restriction analysis, separating the HindIII site at the downstream end of pEPO15-NH2 from the HindIII site at the upstream end of pEPO32-HEV15.

Thus, the subclone contig described in Example 9 is extended to include the HindIII fragment EPO4E7-H0.02 and the insert of pEPO32-HEV15, and constitutes the inserts of: pEPO15-NH6, pEPO15-H2.7, pEPO15-NH24, pEPO15-NH2, EPO4E7-H0.02 and pEPO32HEV15, in this order.

EXAMPLE 11

Nucleotide Sequence Determination of the Subclone Contig Covering the Epothilone Biosynthesis Genes The nucleotide sequence of the subclone contig described in Example 10 is determined as follows.

pEPO15-H2.7. Plasmid DNA is isolated from the strain *Escherichia coli* DH10B [pEPO15-H2.7], and the nucleotide sequence of the 2.7-kb BamHI insert in pEPO15-H2.7 is determined. Automated DNA sequencing is done on the double-stranded DNA template by the dideoxynucleotide chain termination method, using Applied Biosystems model 377 sequencers. The primers used are the universal reverse primer (5' GGA AAC AGC TAT GAC CAT G 3' (SEQ ID NO:24)) and the universal forward primer (5' GTA AAA CGA CGG CCA GT 3' (SEQ ID NO:25)). In subsequent rounds of sequencing reactions, custom-synthesized oligonucleotides, designed for the 3' ends of the previously determined sequences, are used to extend and join contigs.

pEPO15-NH6, pEPO15-NH24 and pEPO15-NH2. The HindIII inserts of these plasmids are isolated, and subjected to random fragmentation using a Hydroshear apparatus (Genomic Instrumentation Services, Inc.) to yield an average fragment size of 1–2 kb. The fragments are end-repaired using T4 DNA Polymerase and Klenow DNA Polymerase enzymes in the presence of desoxynucleotide triphosphates, and phosphorylated with T4 DNA Kinase in the presence of ribo-ATP. Fragments in the size range of 1.5–2.2 kb are isolated from agarose gels, and ligated into pBluescript II SK– that has been cut with EcoRV and dephosphorylated. Random subclones are sequenced using the universal reverse and the universal forward primers.

pEPO32-HEV15. pEPO32-HEV15 is digested with HindIII and SspI, the approximately 13.3 kb fragment containing the ~13 kb HindIII-EcoRV insert from *So. cellulosum* So ce90 and a 0.3 kb HincII-SspI fragment from pBluescript II SK– is isolated, and partially digested with HaeIII to yield fragments with an average size of 1–2 kb. Fragments in the size range of 1.5–2.2 kb are isolated from agarose gels, and ligated into pBluescript II SK– that has been cut with EcoRV and dephosphorylated. Random subclones are sequenced using the universal reverse and the universal forward primers.

The chromatograms are analyzed and assembled into contigs with the Phred, Phrap and Consed programs (Ewing, et al., *Genome Res.* 8(3): 175–185 (1998); Ewing, et al., *Genome Res.* 8(3): 186–194(1998); Gordon, et al., *Genome Res.* 8(3): 195–202 (1998)). Contig gaps are filled, sequence discrepancies are resolved, and low-quality regions are resequenced using custom-designed oligonucleotide primers for sequencing on either the original subclones or selected clones from the random subclone libraries. Both strands are completely sequenced, and every basepair is covered with at least a minimum aggregated Phred score of 40 (confidence level of 99.99%).

The nucleotide sequence of the 68750 bp contig is shown as SEQ ID NO:1.

EXAMPLE 12

Nucleotide Sequence Analysis of the Epothilone Biosynthesis Genes

SEQ ID NO:1 is found to contain 22 ORFs as detailed below in Table 1:

TABLE 1

| ORF | Start codon | Stop codon | Homology of deduced protein | Proposed function of deduced protein |
| --- | --- | --- | --- | --- |
| orf1 | outside of sequenced range | 1826 | | |
| orf2* | 3171 | 1900 | Hypothetical protein SP: Q11037; DD-peptidase SP:P15555 | |
| orf3 | 3415 | 5556 | Na/H antiporter PID: D1017724 | Transport |
| orf4* | 5992 | 5612 | | |
| orf5 | 6226 | 6675 | | |
| epoA | 7610 | 11875 | Type I polyketide synthase | Epothilone synthase: Thiazole ring formation |
| epoP | 11872 | 16104 | Non-ribosomal peptide synthetase | Epothilone synthase: Thiazole ring formation |
| epoB | 16251 | 21749 | Type I polyketide synthase | Epothilone synthase: Polyketide backbone formation |
| epoC | 21746 | 43519 | Type I polyketide synthase | Epothilone synthase: Polyketide backbone formation |
| epoD | 43524 | 54920 | Type I polyketide synthase | Epothilone synthase: Polyketide backbone formation |
| epoE | 54935 | 62254 | Type I polyketide synthase | Epothilone synthase: Polyketide backbone formation |
| epoF | 62369 | 63628 | Cytochrome P450 | Epothilone macrolactone oxidase |
| orf6 | 63779 | 64333 | | |
| orf7* | 64290 | 63853 | | |
| orf8 | 64363 | 64920 | | |
| orf9* | 64727 | 64287 | | |
| orf10 | 65063 | 65767 | | |
| orf11* | 65874 | 65008 | | |
| orf12* | 66338 | 65871 | | |
| orf13 | 66667 | 67137 | | |
| orf14 | 67334 | 68251 | Hypothetical protein GI:3293544; Cation efflux system protein GI:2623026 | Transport |

TABLE 1-continued

| ORF | Start codon | Stop codon | Homology of deduced protein | Proposed function of deduced protein |
| --- | --- | --- | --- | --- |
| orf15 | 68346 | outside of sequenced range | | |

*On the reverse complementer strand. Numbering according to SEQ ID NO:1.

epoA (nucleotides 7610–11875 of SEQ ID NO:1) codes for EPOS A (SEQ ID NO:2), a type I polyketide synthase consisting of a single module, and harboring the following domains mains: β-ketoacyl-synthase (KS) (nucleotides 7643–8920 of SEQ ID NO:1, amino acids 11–437 of SEQ ID NO:2); acyltransferase (AT) (nucleotides 9236–10201 of SEQ ID NO:1, amino acids 543–864 of SEQ ID NO:2); enoyl reductase (ER) (nucleotides 10529–11428 of SEQ ID NO:1, amino acids 974–1273 of SEQ ID NO:2); and acyl carrier protein homologous domain (ACP) (nucleotides 11549–11764 of SEQ ID NO:1, amino acids 1314–1385 of SEQ ID NO:2). Sequence comparisons and motif analysis (Haydock, et al. FEBS Lett. 374: 246–248 (1995); Tang, et al., Gene 216: 255–265 (1998)) reveal that the AT encoded by EPOS A is specific for malonyl-CoA. EPOS A should be involved in the initiation of epothilone biosynthesis by loading the acetate unit to the multienzyme complex that will eventually form part of the 2-methylthiazole ring (C26 and C20).

epoP (nucleotides 11872–16104 of SEQ ID NO:1) codes for EPOS P (SEQ ID NO:3), a non-ribosomal peptide synthetase containing one module. EPOS P harbors the following domains:

peptide bond formation domain, as delineated by motif K (amino acids 72–81 [FPLTDIQESY] of SEQ ID NO:3, corresponding to nucleotide positions 12085–12114 of SEQ ID NO:1); motif L (amino acids 118–125 [VVARHDML] of SEQ ID NO:3, corresponding to nucleotide positions 12223–12246 of SEQ ID NO:1); motif M (amino acids 199–212 [SIDLINVDLGSLSI] of SEQ ID NO:3, corresponding to nucleotide positions 12466–12507 of SEQ ID NO:1); and motif O (amino acids 353–363 [GDFTSMVLLDI] of SEQ ID NO:3, corresponding to nucleotide positions 12928–12960 of SEQ ID NO:1);

aminoacyl adenylate formation domain, as delineated by motif A (amino acids 549–565 [LTYEELSRRSRRLGARL] of SEQ ID NO:3, corresponding to nucleotide positions 13516–13566 of SEQ ID NO:1); motif B (amino acids 588–603 [VAVLAVLESGAAYVPI] of SEQ ID NO:3, corresponding to nucleotide positions 13633–13680 of SEQ ID NO:1); motif C (amino acids 669–684 [AYVIYTSGSTGLPKGV] of SEQ ID NO:3, corresponding to nucleotide positions 13876–13923 of SEQ ID NO:1); motif D (amino acids 815–821 [SLGGATE] of SEQ ID NO:3, corresponding to nucleotide positions 14313–14334 of SEQ ID NO:1); motif E (amino acids 868–892 [GQLYIGGVGLALGYWRDEEKTRKSF] of SEQ ID NO:3, corresponding to nucleotide positions 14473–14547 of SEQ ID NO:1); motif F (amino acids 903–912 [YKTGDLGRYL] of SEQ ID NO:3, corresponding to nucleotide positions 14578–14607 of SEQ ID NO:1); motif G (amino acids 918–940 [EFMGREDNQIKLRGYRVELGEIE] of SEQ ID NO:3, corresponding to nucleotide positions 14623–14692 of SEQ ID NO:1); motif H (amino acids 1268–1274 [LPEYMVP] of SEQ ID NO:3, corresponding to nucleotide positions 15673–15693 of SEQ ID NO:1); and motif I (amino acids 1285–1297 [LTSNGKVDRKALR] of SEQ ID NO:3, corresponding to nucleotide positions 15724–15762 of SEQ ID NO:1);

an unknown domain, inserted between motifs G and H of the aminoacyl adenylate formation domain (amino acids 973–1256 of SEQ ID NO:3, corresponding to nucleotide positions 14788–15639 of SEQ ID NO:1); and a peptidyl carrier protein homologous domain (PCP), delineated by motif J (amino acids 1344–1351 [GATSIHIV] of SEQ ID NO:3, corresponding to nucleotide positions 15901–15924 of SEQ ID NO:1).

It is proposed that EPOS P is involved in the activation of a cysteine by adenylation, binding the activated cysteine as an aminoacyl-S-PCP, forming a peptide bond between the enzyme-bound cysteine and the acetyl-S-ACP supplied by EPOS A, and the formation of the initial thiazoline ring by intramolecular heterocyclization. The unknown domain of EPOS P displays very weak homologies to NAD(P)H oxidases and reductases from Bacillus species. Thus, this unknown domain and/or the ER domain of EPOS A may be involved in the oxidation of the initial 2-methylthiazoline ring to a 2-methylthiazole.

epoB (nucleotides 16251–21749 of SEQ ID NO:1) codes for EPOS B (SEQ ID NO:4), a type I polyketide synthase consisting of a single module, and harboring the following domains: KS (nucleotides 16269–17546 of SEQ ID NO:1, amino acids 7–432 of SEQ ID NO:4); AT (nucleotides 17865–18827 of SEQ ID NO:1, amino acids 539–859 of SEQ ID NO:4); dehydratase (DH) (nucleotides 18855–19361 of SEQ ID NO:1, amino acids 869–1037 of SEQ ID NO:4); β-ketoreductase (KR) (nucleotides 20565–21302 of SEQ ID NO:1, amino acids 1439–1684 of SEQ ID NO:4); and ACP (nucleotides 21414–21626 of SEQ ID NO:1, amino acids 1722–1792 of SEQ ID NO:4). Sequence comparisons and motif analysis reveal that the AT encoded by EPOS B is specific for methylmalonyl-CoA. EPOS A should be involved in the first polyketide chain extension by catalysing the Claisen-like condensation of the 2-methyl-4-thiazolecarboxyl-S-PCP starter group with the methylmalonyl-S-ACP, and the concomitant reduction of the b-keto group of C17 to an enoyl.

epoC (nucleotides 21746–43519 of SEQ ID NO:1) codes for EPOS C (SEQ ID NO:5), a type I polyketide synthase consisting of 4 modules. The first module harbors a KS (nucleotides 21860–23116 of SEQ ID NO:1, amino acids 39–457 of SEQ ID NO:5); a malonyl CoA-specific AT (nucleotides 23431–24397 of SEQ ID NO:1, amino acids 563–884 of SEQ ID NO:5); a KR (nucleotides 25184–25942 of SEQ ID NO:1, amino acids 1147–1399 of SEQ ID NO:5); and an ACP (nucleotides 26045–26263 of SEQ ID NO:1, amino acids 1434–1506 of SEQ ID NO:5). This module incorporates an acetate extender unit (C14-C13) and reduces the β-keto group at C15 to the hydroxyl group that takes part in the final lactonization of the epothilone macrolactone ring. The second module of EPOS C harbors a KS (nucleotides 26318–27595 of SEQ ID NO:1, amino acids 1524–1950 of SEQ ID NO:5); a malonyl CoA-specific AT (nucleotides 27911–28876 of SEQ ID NO:1, amino acids 2056–2377 of SEQ ID NO:5); a KR (nucleotides 29678–30429 of SEQ ID NO:1, amino acids 2645–2895 of SEQ ID NO:5); and an ACP (nucleotides 30539–30759 of SEQ ID NO:1, amino acids 2932–3005 of SEQ ID NO:5). This module incorporates an acetate extender unit (C12-C11) and reduces the β-keto group at C13 to a hydroxyl group. Thus, the nascent polyketide chain of epothilone corresponds to epothilone A, and the incorporation of the methyl side chain at C12 in epothilone B would require a post-PKS C-methyltransferase activity. The formation of the epoxi ring at C13-C12 would also require a post-PKS oxidation step. The third module of EPOS C harbors a KS (nucleotides 30815–32092 of SEQ ID NO:1, amino acids 3024–3449 of SEQ ID NO:5); a malonyl CoA-specific AT (nucleotides 32408–33373 of SEQ ID NO:1, amino acids 3555–3876 of SEQ ID NO:5); a DH (nucleotides 33401–33889 of SEQ ID NO:1, amino acids 3886–4048 of SEQ ID NO:5); an ER (nucleotides 35042–35902 of SEQ ID NO:1, amino acids 4433–4719 of SEQ ID NO:5); a KR (nucleotides 35930–36667 of SEQ ID NO:1, amino acids 4729–4974 of SEQ ID NO:5); and an ACP (nucleotides 36773–36991 of SEQ ID NO:1, amino acids 5010–5082 of SEQ ID NO:5). This module incorporates an acetate extender unit (C10-C9) and fully reduces the β-keto group at C11. The fourth module of EPOS C harbors a KS (nucleotides 37052–38320 of SEQ ID NO:1, amino acids 5103–5525 of SEQ ID NO:5); a methylmalonyl CoA-specific AT (nucleotides 38636–39598 of SEQ ID NO:1, amino acids 5631–5951 of SEQ ID NO:5); a DH (nucleotides 39635–40141 of SEQ ID NO:1, amino acids 5964–6132 of SEQ ID NO:5); an ER (nucleotides 41369–42256 of SEQ ID NO:1, amino acids 6542–6837 of SEQ ID NO:5); a KR (nucleotides 42314–43048 of SEQ ID NO:1, amino acids 6857–7101 of SEQ ID NO:5); and an ACP (nucleotides 43163–43378 of SEQ ID NO:1, amino acids 7140–7211 of SEQ ID NO:5). This module incorporates a propionate extender unit (C24 and C8-C7) and fully reduces the β-keto group at C9.

epoD (nucleotides 43524–54920 of SEQ ID NO:1) codes for EPOS D (SEQ ID NO:6), a type I polyketide synthase consisting of 2 modules. The first module harbors a KS (nucleotides 43626–44885 of SEQ ID NO:1, amino acids 35–454 of SEQ ID NO:6); a methylmalonylCoA-specific AT (nucleotides 45204–46166 of SEQ ID NO:1, amino acids 561–881 of SEQ ID NO:6); a KR (nucleotides 46950–47702 of SEQ ID NO:1, amino acids 1143–1393 of SEQ ID NO:6); and an ACP (nucleotides 47811–48032 of SEQ ID NO:1, amino acids 1430–1503 of SEQ ID NO:6). This module incorporates a propionate extender unit (C23 and C6-C5) and reduces the β-keto group at C7 to a hydroxyl group. The second module harbors a KS (nucleotides 48087–49361 of SEQ ID NO:1, amino acids 1522–1946 of SEQ ID NO: 6); a methylmalonyl CoA-specific AT (nucleotides 49680–50642 of SEQ ID NO:1, amino acids 2053–2373 of SEQ ID NO:6); a DH (nucleotides 50670–51176 of SEQ ID NO:1, amino acids 2383–2551 of SEQ ID NO:6); a methyltransferase (MT, nucleotides 51534–52657 of SEQ ID NO:1, amino acids 2671–3045 of SEQ ID NO:6); a KR (nucleotides 53697–54431 of SEQ ID NO:1, amino acids 3392–3636 of SEQ ID NO:6); and an ACP (nucleotides 54540–54758 of SEQ ID NO:1, amino acids 3673–3745 of SEQ ID NO:6). This module incorporates a propionate extender unit (C21 or C22 and C4-C3) and reduces the β-keto group at C5 to a hydroxyl group. This reduction is somewhat unexpected, since epothilones contain a keto group at C5. Discrepancies of this kind between the deduced reductive capabilities of PKS modules and the redox state of the corresponding positions in the final polyketide products have been, however, reported in the literature (see, for example, Schwecke, et al., *Proc. Natl. Acad. Sci. USA* 92: 7839–7843 (1995) and Schupp, et al., *FEMS Microbiology Letters* 159: 201–207 (1998)). An important feature of epothilones is the presence of gem-methyl side groups at C4 (C21 and C22). The second module of EPOS D is predicted to incorporate a propionate unit into the growing polyketide chain, providing one methyl side chain at C4. This module also contains a methyltransferase domain integrated into the PKS between the DH and the KR domains, in an arrangement similar to the one seen in the HMWP1 yersiniabactin synthase (Gehring, A. M., DeMoll, E., Fetherston, J. D., Mori, I., Mayhew, G. F., Blattner, F. R., Walsh, C. T., and Perry, R. D.: Iron acquisition in plague: modular logic in enzymatic biogenesis of yersiniabactin by Yersinia pestis. *Chem. Biol.* 5, 573–586,1998). This MT domain in EPOS D is proposed to be responsible for the incorporation of the second methyl side group (C21 or C22) at C4.

epoE (nucleotides 54935–62254 of SEQ ID NO:1) codes for EPOS E (SEQ ID NO:7), a type I polyketide synthase consisting of one module, harboring a KS (nucleotides 55028–56284 of SEQ ID NO:1, amino acids 32–450 of SEQ ID NO:7); a malonyl CoA-specific AT (nucleotides 56600–57565 of SEQ ID NO:1, amino acids 556–877 of SEQ ID NO:7); a DH (nucleotides 57593–58087 of SEQ ID NO:1, amino acids 887–1051 of SEQ ID NO:7); a probably nonfunctional ER (nucleotides 59366–60304 of SEQ ID NO:1, amino acids 1478–1790 of SEQ ID NO.7); a KR (nucleotides 60362–61099 of SEQ ID NO:1, amino acids 1810–2055 of SEQ ID NO:7); an ACP (nucleotides 61211–61426 of SEQ ID NO:1, amino acids 2093–2164 of SEQ ID NO:7); and a thioesterase (TE) (nucleotides 61427–62254 of SEQ ID NO:1, amino acids 2165–2439 of SEQ ID NO:7). The ER domain in this module harbors an active site motif with some highly unusual amino acid substitutions that probably render this domain inactive. The module incorporates an acetate extender unit (C2-Cl), and reduces the β-keto at C3 to an enoyl group. Epothilones contain a hydroxyl group at C3, so this reduction also appears to be excessive as discussed for the second module of EPOS D. The TE domain of, EPOS E takes part in the release and cyclization of the grown polyketide chain via lactonization between the carboxyl group of C1 and the hydroxyl group of C15.

Five ORFs are detected upstream of epoA in the sequenced region. The partially sequenced orf1 has no homologues in the sequence databanks. The deduced protein product (Orf 2, SEQ ID NO:10) of orf2 (nucleotides 3171–1900 on the reverse complement strand of SEQ ID NO:1) shows strong similarities to hypothetical ORFs from Mycobacterium and *Streptomyces coelicolor*, and more distant similarities to carboxypeptidases and DD-peptidases of different bacteria. The deduced protein product of orf3 (nucleotides 3415–5556 of SEQ ID NO:1), Orf 3 (SEQ ID NO:11), shows homologies to Na/H antiporters of different bacteria. Orf 3 might take part in the export of epothilones from the producer strain. orf4 and orf5 have no homologues in the sequence databanks.

Eleven ORFs are found downstream of epoE in the sequenced region. epoF (nucleotides 62369–63628 of SEQ ID NO:1) codes for EPOS F (SEQ ID NO:8), a deduced protein, with strong sequence similarities to cytochrome P450 oxygenases. EPOS F may take part in the adjustment of the redox state of the carbons C12, C5, and/or C3. The deduced protein product of orf14 (nucleotides 67334–68251 of SEQ ID NO:1), Orf 14 (SEQ ID NO:22) shows strong similarities to GI:3293544, a hypothetic protein with no proposed function from *Streptomyces coelicolor*, and also to GI:2654559, the human embrionic lung protein. It is also more distantly related to cation efflux system proteins like GI:2623026 from *Methanobacterium thermoautotrophicum*, so it might also take part in the export of epothilones from the producing cells. The remaining ORFs (orf6–orf13 and orf15) show no homologies to entries in the sequence databanks.

EXAMPLE 13

Recombinant Expression of Epthilone Biosynthesis Genes

Epothilone synthase genes according to the present invention are expressed in heterologous organisms for the purposes of epothilone production at greater quantities than can be accomplished by fermentation of *Sorangium cellulosum*. A preferable host for heterologous expression is Streptomyces, e.g. *Streptomyces coelicolor*, which natively produces the polyketide actinorhodin. Techniques for recombinant PKS gene expression in this host are described in McDaniel et al., *Science* 262: 1546–1550 (1993) and Kao et al, *Science* 265: 509–512 (1994). See also, Holmes et al., *EMBO Journal* 12(8): 3183–3191 (1993) and Bibb et al., *Gene* 38: 215–226 (1985), as well as U.S. Pat. Nos. 5,521, 077, 5,672,491, and 5,712,146, which are incorporated herein by reference.

According to one method, the heterologous host strain is engineered to contain a chromosomal deletion of the actinorhodin (act) gene cluster. Expression plasmids containing the epothilone synthase genes of the invention are constructed by transferring DNA from a temperature-sensitive donor plasmid to a recipient shuttle vector in *E. coli* (McDaniel et al. (1993) and Kao et al. (1994)), such that the synthase genes are built-up by homologous recombination within the vector. Alternatively, the epothilone synthase gene cluster is introduced into the vector by restriction fragment ligation. Following selection, e.g. as described in Kao et al. (1994), DNA from the vector is introduced into the act-minus *Streptomyces coelicolor* strain according to protocols set forth in Hopwood et al., *Genetic Manipulation of Streptomyces. A Laboratory Manual* (John Innes Foundation, Norwich, United Kingdom, 1985), incorporated herein by reference. The recombinant Streptomyces strain is grown on R2YE medium (Hopwood et al. (1985)) and produces epothilones. Alternatively, the epothilone synthase genes according to the present invention are expressed in other host organisms such as pseudomonads, Bacillus, yeast, insect cells and/or *E. coli*. PKS and NRPS genes are preferably expressed in *E. coli* using the pT7-7 vector, which uses the T7 promoter. See, Tabor et al., *Proc. Natl. Acad. Sci. USA* 82:1074–1078 (1985). In another embodiment, the expression vectors pKK223-3 and pKK223-2 are used to express PKS and NRPS genes in *E. coli* either in transcriptional or translational fusion, behind the tac or trc promoter. Expression of PKS and NRPS genes in heterologous hosts, which do not naturally have the phosphopantetheinyl (P-pant) transferases needed for post-translational modification of PKS enzymes, requires the coexpression in the host of a P-pant transferase, as described by Kealey et al., *Proc. Natl. Acad. Sci. USA* 95: 505–509 (1998).

EXAMPLE 14

Isolation of Epothilones from Producing Strains

Examples of cultivation, fermentation, and extraction procedures for polyketide isolation, which are useful for extracting epothilones from both native and recombinant hosts according to the present invention, are given in WO 93/10121, incorporated herein by reference, in Example 57 of U.S. Pat. No. 5,639,949, in Gerth et al, *J. Antibiotics* 49: 560–563 (1996), and in Swiss patent application no. 396/98, filed Feb. 19, 1998, and U.S. patent application Ser. No. 09/248,910 (that discloses also preferred mutant strains of *Sorangium cellulosum*), both of which are incorporated herein by reference. The following are procedures that are useful for isolating epothilones from cultured *Sorangium cellulosum* strains, e.g., So ce90, and may also be used for the isolation of epothilone from recombinant hosts.

A: Cultivation of Epothilone-producing Strains
Strain: *Sorangium cellulosum* Soce-90 or a recombinant host strain according to the present invention.
Preservation of the strain: In liquid $N_2$.

Media:

Precultures and intermediate cuitures: G52
Mainculture: 1B12
G52 Medium:

| | |
|---|---|
| yeast extract, low in salt (Biospringer, Maison Alfort, France) | 2 g/l |
| $MgSO_4$ (7 $H_2O$) | 1 g/l |
| $CaCl_2$ (2 $H_2O$) | 1 g/l |
| soya meal defatted Soyamine 50T (Lucas Meyer, Hamburg, Germany) | 2 g/l |
| potato starch Noredux A-150 (Biattmann, Waedenswil, Switzerland) | 8 g/l |
| glucose anhydrous | 2 g/l |
| EDTA-Fe(III)-Na salt (8 g/l) | 1 ml/l |
| pH 7.4, corrected with KOH | |
| Sterilisation: 20 mins. 120° C. | |

1B12 Medium:

| | |
|---|---|
| potato starch Noredux A-150 (Biattmann, Waedenswil, Switzerland) | 20 g/l |
| soya meal defatted Soyamine 50T (Lucas Meyer, Hamburg, Germany) | 11 g/l |
| EDTA-Fe(III)-Na salt | 8 mg/l |
| pH 7.8, corrected with KOH | |
| Sterilisation: 20 mins. 120° C. | |

Addition of Cyclodextrins and Cyclodextrin Derivatives
  Cyclodextrins (Fluka, Buchs, Switzerland, or Wacker Chemie, Munich, Germany) in different concentrations are sterilised separately and added to the 1B12 medium prior to seeding.
Cultivation: 1 ml of the suspension of *Sorangium cellulosum* Soce-90 from a liquid $N_2$ ampoule is transferred to 10 ml of G52 medium (in a 50 ml Erlenmeyer flask) and incubated for 3 days at 180 rpm in an agitator at 30° C., 25 mm displacement. 5 ml of this culture is added to 45 ml of G52 medium (in a 200 ml Erlenmeyer flask) and incubated for 3 days at 180 rpm in an agitator at 30° C., 25 mm displacement. 50 ml of this culture is then added to 450 ml of G52 medium (in a 2 liter Erlenmeyer flask) and incubated for 3 days at 180 rpm in an agitator at 30° C., 50 mm displacement.
Maintenance culture: The culture is overseeded every 3–4 days, by adding 50 ml of culture to 450 ml of G52 medium (in a 2 liter Erlenmeyer flask). All experiments and fermentations are carried out by starting with this maintenance culture.
Tests in a Flask (I) Preculture in an Agitating Flask Starting with the 500 ml of maintenance culture, 1×450 ml of G52 medium are seeded with 50 ml of the maintenance culture and incubated for 4 days at 180 rpm in an agitator at 30° C., 50 mm displacement.

(ii) Main Culture in the Agitating Flask 40 ml of 1B12 medium plus 5 g/l 4-morpholine-propane-sulfonic acid (=MOPS) powder (in a 200 ml Erlenmeyer flask) are mixed with 5 ml of a 10×concentrated cyclodextrin solution, seeded with 10 ml of preculture and incubated for 5 days at 180 rpm in an agitator at 30° C., 50 mm displacement.

Fermentation: Fermentations are carried out on a scale of 10 liters, 100 liters and 500 liters. 20 liter and 100 liter fermentations serve as an intermediate culture step. Whereas the precultures and intermediate cultures are seeded as the maintenance culture 10% (v/v), the main cultures are seeded with 20% (v/v) of the intermediate culture. In contrast to the agitating cultures, ingredients of the fermentation media are calculated on the final culture volume including the inoculum. If, for example, 18 liters of medium 30 2 liters of inoculum are combined, then substances for 20 liters are weighed in, but are only mixed with 18 liters.

Preculture in an Agitating Flask

Starting with the 500 ml maintenance culture, 4×450 ml of G52 medium (in a 2 liter Erlenmeyer flask) are each seeded with 50 ml thereof, and incubated for 4 days at 180 rpm in an agitator at 30° C., 50 mm displacement.

Intermediate Culture, 20 Liters or 100 Liters 20 liters: 18 liters of G52 medium in a fermenter having a total volume of 30 liters are seeded with 2 liters of preculture. Cultivation lasts for 3–4 days, and the conditions are: 30° C., 250 rpm, 0.5 liters of air per liter liquid per min, 0.5 bars excess pressure, no pH control.

100 liters: 90 liters of G52 medium in a fermenter having a total volume of 150 liters are seeded with 10 liters of the 20 liter intermediate culture. Cultivation lasts for 3–4 days, and the conditions are: 30° C., 150 rpm, 0.5 liters of air per liter liquid per min, 0.5 bars excess pressure, no pH control.

Main Culture, 10 Liters, 100 Liters or 500 Liters 10 liters: The media substances for 10 liters of 1B12 medium are sterilised in 7 liters of water, then 1 liter of a sterile 10% 2-(hydroxypropyl)-β-cyclodextrin solution are added, and seeded with 2 liters of a 20 liter intermediate culture. The duration of the main culture is 6–7 days, and the conditions are: 30° C., 250 rpm, 0.5 liters of air per liter of liquid per min, 0.5 bars excess pressure, pH control with $H_2SO_4$/KOH to pH 7.6+/−0.5 (i.e. no control between pH 7.1 and 8.1).

100 liters: The media substances for 100 liters of 1B12 medium are sterilised in 70 liters of water, then 10 liters of a sterile 10% 2-(hydroxypropyl)-β-cyclodextrin solution are added, and seeded with 20 liters of a 20 liter intermediate culture. The duration of the main culture is 6–7 days, and the conditions are: 30° C., 200 rpm, 0.5 liters air per liter liquid per min., 0.5 bars excess pressure, pH control with $H_2SO_4$/KOH to pH 7.6+/−0.5. The chain of seeding for a 100 liter fermentation is shown schematically as follows:

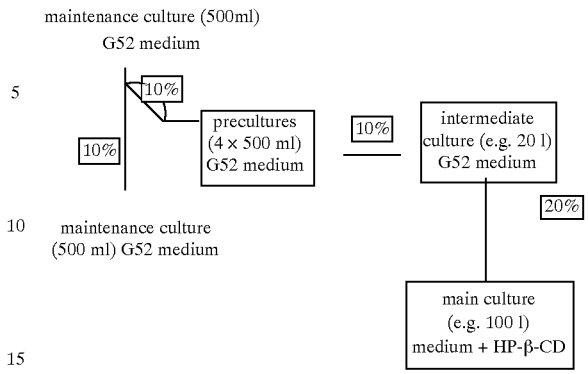

500 liters: The media substances for 500 liters of 1B12 medium are sterilised in 350 liters of water, then 50 liters of a sterile 10% 2-(hydroxypropyl)-β-cyclodextrin solution are added, and seeded with 100 liters of a 100 liter intermediate culture. The duration of the main culture is 6–7 days, and the conditions are: 300° C., 120 rpm, 0.5 liters air per liter liquid per min., 0.5 bars excess pressure, pH control with $H_2SO_4$/KOH to pH 7.6+/−0.5.

Product Analysis

Preparation of the Sample 50 ml samples are mixed with 2 ml of polystyrene resin Amberlite XAD16 (Rohm+Haas, Frankfurt, Germany) and shaken at 180 rpm for one hour at 30° C. The resin is subsequently filtered using a 150 μm nylon sieve, washed with a little water and then added together with the filter to a 15 ml Nunc tube.

Elution of the Product from the Resin 10 ml of isopropanol (>99%) are added to the tube with the filter and the resin. Afterwards, the sealed tube is shaken for 30 minutes at room temperature on a Rota-Mixer (Labinco BV, Netherlands). Then, 2 ml of the liquid are centrifuged off and the supernatant is added using a pipette to HPLC tubes.

| HPLC analysis: | |
|---|---|
| Column: | Waters-Symetry C18, 100 × 4 mm, 3.5 μm |
| | WAT066220 + preliminary column 3.9 × 20 mm |
| | WAT054225 |
| Solvents: | A: 0.02% phosphoric acid |
| | B: Acetonitrile (HPLC-Quality) |
| Gradient: | 41% B from 0 to 7 min. |
| | 100% B from 72 to 7.8 min. |
| | 41% B from 8 to 12 min. |
| Oven temp.: | 30° C. |
| Detection: | 250 nm, UV-DAD detection |
| Injection vol.: | 10 μl |
| Retention time: | Epo A: 4.30 min   Epo B: 5.38 min |

B: Effect of the Addition of Cyclodextrin and Cyclodextrin Derivatives to the Epothilone Concentrations Attained Cyclodextrins are cyclic (α-1,4)-linked oligosaccharides of α-D-glucopyranose with a relatively hydrophobic central cavity and a hydrophilic external surface area.

The following are distinguished in particular (the figures in parenthesis give the number of glucose units per molecule): α-cyclodextrin (6), β-cyclodextrin (7), γ-cyclodextrin (8), δ-cyclodextrin (9), ε-cyclodextrin (10), ζ-cyclodextrin (11), η-cyclodextrin (12), and θ-cyclodextrin (13). Especially preferred are δ-cyclodextrin and in particular α-cyclodextrin, β-cyclodextrin or γ-cyclodextrin, or mixtures thereof.

Cyclodextrin derivatives are primarily derivatives of the above-mentioned cyclodextrins, especially of α-cyclodextrin, β-cyclodextrin or γ-cyclodextrin, primarily those in which one or more up to all of the hydroxy groups (3 per glucose radical) are etherified or esterified. Ethers are primarily alkyl ethers, especially lower alkyl, such as methyl or ethyl ether, also propyl or butyl ether; the arylhydroxyalkyl ethers, such as phenyl-hydroxy-lower-alkyl, especially phenyl-hydroxyethyl ether; the hydroxyalkyl ethers, in particular hydroxy-lower-alkyl ethers, especially 2-hydroxyethyl, hydroxypropyl such as 2-hydroxypropyl or hydroxybutyl such as 2-hydroxybutyl ether; the carboxyalkyl ethers, in particular carboxy-lower-alkyl ethers, especially carboxymethyl or carboxyethyl ether; derivatised carboxyalkyl ethers, in particular derivatised carboxy-lower-alkyl ether in which the derivatised carboxy is etherified or amidated carboxy (primarily aminocarbonyl, mono- or di-lower-alkyl-aminocarbonyl, morpholino-, piperidino-, pyrrolidino- or piperazino-carbonyl, or alkyloxycarbonyl), in particular lower alkoxycarbonyl-lower-alkyl ether, for example methyloxycarbonylpropyl ether or ethyloxycarbonylpropyl ether; the sulfoalkyl ethers, in particular sulfolower-alkyl ethers, especially sulfobutyl ether; cyclodextrins in which one or more OH groups are etherified with a radical of formula

wherein alk is alkyl, especially lower alkyl, and n is a whole number from 2 to 12, especially 2 to 5, in particular 2 or 3; cyclodextrins in which one or more OH groups are etherified with a radical of formula

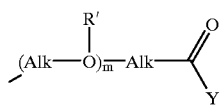

wherein R' is hydrogen, hydroxy, —O-(alk-O)$_z$—H, —O-(alk(-R)—O—)$_p$—H or —O-(alk(-R)—O—)$_q$-alk-CO—Y; alk in all cases is alkyl, especially lower alkyl; m, n, p, q and z are a whole number from 1 to 12, preferably 1 to 5, in particular 1 to 3; and Y is OR$_1$ or NR$_2$R$_3$, wherein R$_1$, R$_2$ and R$_3$ independently of one another, are hydrogen or lower alkyl, or R$_2$ and R$_3$ combined together with the linking nitrogen signify morpholino, piperidino, pyrrolidino or piperazino; or branched cyclodextrins, in which etherifications or acetals with other sugar molecules are present, especially glucosyl-, diglucosyl- (G$_2$-β-cyclodextrin), maltosyl- or dimaltosyl-cyclodextrin, or N-acetylglucosaminyl-, glucosaminyl-, N-acetylgalactosaminyl- or galactosaminyl-cyclodextrin.

Esters are primarily alkanoyl esters, in particular lower alkanoyl esters, such as acetyl esters of cyclodextrins.

It is also possible to have cyclodextrins in which two or more different said ether and ester groups are present at the same time.

Mixtures of two or more of the said cyclodextrins and/or cyclodextrin derivatives may also exist.

Preference is given in particular to α-, β- or γ-cyclodextrins or the lower alkyl ethers thereof, such as methyl-β-cyclodextrin or in particular 2,6-di-O-methyl-β-cyclodextrin, or in particular the hydroxy lower alkyl ethers thereof, such as 2-hydroxypropyl-=-, 2-hydroxypropyl-β- or 2-hydroxypropyl-γ-cyclodextrin.

The cyclodextrins or cyclodextrin derivatives are added to the culture medium preferably in a concentration of 0.02 to 10, preferably 0.05 to 5, especially 0.1 to 4, for example 0.1 to 2 percent by weight (w/v).

Cyclodextrins or cyclodextrin derivatives are known or may be produced by known processes (see for example U.S. Pat. Nos. 3,459,731; 4,383,992; 4,535,152; 4,659,696; EP 0 094 157; EP 0 149 197; EP 0 197 571; EP 0 300 526; EP 0 320 032; EP 0 499 322; EP 0 503 710; EP 0 818 469; WO 90/12035; WO 91/11200; WO 93/19061; WO 95/08993; WO 96/14090; GB 2,189,245; DE 3,118,218; DE 3,317,064 and the references mentioned therein, which also refer to the synthesis of cyclodextrins or cyclodextrin derivatives, or also: T. Loftsson and M. E. Brewster (1996): Pharmaceutical Applications of Cyclodextrins: Drug Solubilization and Stabilisation: Journal of Pharmaceutical Science 85 (10) :1017–1025; R. A. Rajewski and V. J. Stella (1996): Pharmaceutical Applications of Cyclodextrins: In Vivo Drug Delivery: Journal of Pharmaceutical Science 85 (11): 1142–1169).

All the cyclodextrin derivatives tested here are obtainable from the company Fluka, Buchs, CH. The tests are carried out in 200 ml agitating flasks with 50 ml culture volume. As controls, flasks with adsorber resin Amberlite XAD-16 (Rohm & Haas, Frankfurt, Germany) and without any adsorber addition are used. After incubation for 5 days, the following epothilone titres can be determined by HPLC:

TABLE 2

| Addition | order No. | Conc [% w/v][1] | Epo A [mg/l] | Epo B [mg/l] |
| --- | --- | --- | --- | --- |
| Amberlite XAD-16 (v/v) | | 2.0 (% v/v) | 9.2 | 3.8 |
| 2-hydroxypropyl-β-cyclodextrin | 56332 | 0.1 | 2.7 | 1.7 |
| 2-hydroxypropyl-β-cyclodextrin | " | 0.5 | 4.7 | 3.3 |
| 2-hydroxypropyl-β-cyclodextrin | " | 1.0 | 4.7 | 3.4 |
| 2-hydroxypropyl-β-cyclodextrin | " | 2.0 | 4.7 | 4.1 |
| 2-hydroxypropyl-β-cyclodextrin | " | 5.0 | 1.7 | 0.5 |
| 2-hydroxypropyl-α-cyclodextrin | 56330 | 0.5 | 1.2 | 1.2 |
| 2-hydroxypropyl-α-cyclodextrin | " | 1.0 | 4.2 | 1.2 |
| 2-hydroxypropyl-α-cyclodextrin | " | 5.0 | 2.5 | 2.3 |
| β-cyclodextrin | 28707 | 0.1 | 1.6 | 1.3 |
| β-cyclodextrin | " | 0.5 | 3.6 | 2.5 |
| β-cyclodextrin | " | 1.0 | 4.8 | 3.7 |
| β-cyclodextrin | " | 2.0 | 4.8 | 2.9 |
| β-cyclodextrin | " | 5.0 | 1.1 | 0.4 |
| methyl-β-cyclodextrin | 66292 | 9.5 | 0.8 | <0.3 |
| methyl-β-cyclodextrin | " | 1.0 | <0.3 | <0.3 |
| methyl-β-cyclodextrin | " | 2.0 | <0.3 | <0.3 |
| 2,6 di-o-methyl-β-cyclodextrin | 39915 | 1.0 | <0.3 | <0.3 |
| 2-hydroxypropyl-γ-cyclodextrin | 56334 | 0.1 | 0.3 | <0.3 |
| 2-hydroxypropyl-γ-cyclodextrin | " | 0.5 | 0.9 | 0.8 |
| 2-hydroxypropyl-γ-cyclodextrin | " | 1.0 | 1.1 | 0.7 |
| 2-hydroxypropyl-γ-cyclodextrin | " | 2.0 | 2.6 | 0.7 |
| 2-hydroxypropyl-γ-cyclodextrin | " | 5.0 | 5.0 | 1.1 |
| no addition | | | 0.5 | 0.5 |

[1]Apart from Amberlite (% v/v), all percentages are by weight (% w/v).

Few of cyclodextrins tested (2,6-di-o-methyl-β-cyclodextrin, methyl-β-cyclodextrin) display no effect or a negative effect on epothilone production at the concentrations used. 1–2% 2-hydroxy-propyl-βcyclodextrin and β-cyclodextrin increase epothilone production in the examples by 6 to 8 times compared with production using no cyclodextrins.

C: 10 Liter Fermentation with 1% 2-(hydroxypropyl)-β-cyclodextrin

Fermentation is carried out in a 15 liter glass fermenter. The medium contains 10 g/l of 2-(hydroxypropyl)-β-cyclodextrin from Wacker Chemie, Munich, DE. Fermentation progress is illustrated in Table 3. Fermentation is ended after 6 days and working up takes place.

TABLE 3

Progress of a 10 litre fermentation

| duration of culture [d] | Epothilone A [mg/l] | Epothilone B [mg/l] |
| --- | --- | --- |
| 0 | 0 | 0 |
| 1 | 0 | 0 |
| 2 | 0.5 | 0.3 |
| 3 | 1.8 | 2.5 |
| 4 | 3.0 | 5.1 |
| 5 | 3.7 | 5.9 |
| 6 | 3.6 | 5.7 |

D: 100 Liter Fermentation with 1% 2-(hydroxypropyl)-β-cyclodextrin)

Fermentation is carried out in a 150 liter fermenter. The medium contains 10 g/l of 2-(Hydroxypropyl)-β-cyclohexdrin. The progress of fermentation is illustrated in Table 4. The fermentation is harvested after 7 days and worked up.

TABLE 4

Progress of a 100 litre fermentation

| duration of culture [d] | Epothilone A [mg/l] | Epothilone B [mg/] |
| --- | --- | --- |
| 0 | 0 | 0 |
| 1 | 0 | 0 |
| 2 | 0.3 | 0 |
| 3 | 0.9 | 1.1 |
| 4 | 1.5 | 2.3 |
| 5 | 1.6 | 3.3 |
| 6 | 1.8 | 3.7 |
| 7 | 1.8 | 3.5 |

E: 500 Liter Fermentation 1% 2-(hydroxypropyl)-β-cyclodextrin)

Fermentation is carried out in a 750 liter fermenter. The medium contains 10 g/l of 2-(Hydroxypropyl)-β-cyclodextrin. The progress of fermentation is illustrated in Table 5. The fermentation is harvested after 7 days and worked up.

TABLE 5

Progress of a 500 litre fermentation

| duration of culture [d] | Epothilone A [mg/l] | Epothilone B [mg/l] |
| --- | --- | --- |
| 0 | 0 | 0 |
| 1 | 0 | 0 |
| 2 | 0 | 0 |
| 3 | 0.6 | 0.6 |
| 4 | 1.7 | 2.2 |
| 5 | 3.1 | 4.5 |
| 6 | 3.1 | 5.1 |

F: Comparison Example 10 Liter Fermentation without Adding an Adsorber

Fermentation is carried in a 15 liter glass fermenter. The medium does not contain any cyclodextrin or other absorber. The progress of fermentation is illustrated in Table 6. The fermentation is not harvested and worked up.

TABLE 6

Progress of a 10 litre fermentation without adsorber.

| duration of culture [d] | Epothilone A [mg/l] | Epothilone B [mg/l] |
| --- | --- | --- |
| 0 | 0 | 0 |
| 1 | 0 | 0 |
| 2 | 0 | 0 |
| 3 | 0 | 0 |
| 4 | 0.7 | 0.7 |
| 5 | 0.7 | 1.0 |
| 6 | 0.8 | 1.3 |

G: Working Up of the Epothilones: Isolation from a 500 Liter Main Culture

The volume of harvest from the 500 liter main culture of example 2D is 450 liters and is separated using a Wesufalia clarifying separator Type SA-20-06 (rpm=6500) into the liquid phase (centrifuge+rinsing water=650 liters) and solid phase (cells=ca. 15 kg). The main part of the epothilones found in the centrifugate, The centrifuged cell pulp contains <15% of the determined epothilone portion and is not further processed. The 650 liter centrifuge is then placed in a 4000 liter stirring vessel, mixed with 10 liters of Amberlite XAD-16 (centrifuge:resin volume=65:1) and stirred. After a period of contact of ca. 2 hours, the resin is centrifuged away in a Heine overflow centrifuge (basket content 40 liters; rpm=2800). The resin is discharged from the centrifuge and washed with 10–15 liters of deionised water. Desorption is effected by stirring the resin twice, each time in portions with 30 liters of isopropanol in 30 liter glass stirring vessels for 30 minutes. Separation of the isopropanol phase from the resin takes place using a suction filter. The isopropanol is then removed from the combined isopropanol phases by adding 15–20 liters of writer in a vacuum-operated circulating evaporator (Schmid-Verdampfer) and the resulting water phase of ca. 10 liters is extracted 3× each time with 10 liters of ethyl acetate. Extraction is effected in 30 liter glass stirring vessels. The ethyl acetate extract is concentrated to 3–5 liters in a vacuum-operated circulating vaporator (Schmid-Verdampfer) and afterwards concentrated to dryness in a rotary (Büchi type) under vacuum. The result is an ethyl acetate extract of 50.2 g. The ethyl acetate extract is dissolved in 500 ml of methanol, the insoluble portions filtered off using a folded filter, and the solution added to a 10 kg Sephadex LH 20 column (Pharmacia, Uppsala, Sweden) (column diameter 20 cm, filling level ca. 1.2 m). Elution is effected with methanol as eluant. Epothilone A and B is present predominantly in fractions 21–23 (at a fraction size of 1 liter). These fractions are concentrated to dryness in a vacuum on a rotary evaporator (total weight 9.0 g). These Sephadex peak fractions (9.0 g) are thereafter dissolved in 92 ml of acetonitrile:-water:-methylene chloride=50:40:2, the solution filtered through a folded filter and added to a RP column (equipment Prepbar 200, Merck; 2. 0 kg LiChrospher RP-18 Merck, grain size 12 μm, column diameter 10 cm, filling level 42 cm; Merck, Darmstadt, Germany). Elution is effected with acetonitrile:water=3:7 (flow rate=500 ml/min.; retention time of epothilone A=ca. 51–59 mins.; retention time of epothilone B=ca. 60–69 mins.). Fractionation is monitored with a UV detector at 250 nm. The fractions are concentrated to dryness under vacuum on a Büchi-Rotavapor rotary evaporator. The weight of the epothilone A peak fraction is 700 mg, and according to HPLC (external standard) it has a content of 75.1%. That of the epothilone B peak fraction is 1980 mg, and the content according to HPLC (external standard) is 86.6%. Finally, the epothilone A fraction (700 mg) is crystallised from 5 ml of ethyl acetate:toluene=2:3, and yields 170 mg of epothilone A pure crystallisate [content according to HLPC (% of area)=94.3%]. Crystallisation of the epothilone B fraction (1980 mg) is effected from 18 ml of methanol and yields 1440 mg of epothilone B pure crystallisate [content according to HPLC (% of area)=99.2%]. m.p. (Epothilone B): e.g. 124–125° C.; $^1$H-NMR data for Epothilone B: 500 MHz-NMR, solvent: DMSO-d6. Chemical displacement δ in ppm relative to TMS. s=singlet; d=doublet; m=multiplet

| δ (Multiplicity) | Integral (number of H) |
|---|---|
| 7.34 (s) | 1 |
| 6.50 (s) | 1 |
| 5.28 (d) | 1 |
| 5.08 (d) | 1 |
| 4.46 (d) | 1 |
| 4.08 (m) | 1 |
| 3.47 (m) | 1 |
| 3.11 (m) | 1 |
| 2.83 (dd) | 1 |
| 2.64 (s) | 3 |
| 2.36 (m) | 2 |
| 2.09 (s) | 3 |
| 2.04 (m) | 1 |
| 1.83 (m) | 1 |
| 1.61 (m) | 1 |
| 1.47–1.24 (m) | 4 |
| 1.18 (s) | 6 |
| 1.13 (m) | 2 |
| 1.06 (d) | 3 |
| 0.89 (d + s, overlapping) | 6 |
| | Σ = 41 |

EXAMPLE 15

Medical Uses of Recombinantly Produced Epothilones

Pharmaceutical preparations or compositions comprising epothilones are used for example in the treatment of cancerous diseases, such as various human solid tumors. Such anticancer formulations comprise, for example, an active amount of an epothilone together with one or more organic or inorganic, liquid or solid, pharmaceutically suitable carrier materials. Such formulations are delivered, for example, enterally, nasally, rectally, orally, or parenterally, particularly intramuscularly or intravenously. The dosage of the active ingredient is dependent upon the weight, age, and physical and pharmacokinetical condition of the patient and is further dependent upon the method of delivery. Because epothilones mimic the biological effects of taxol, epothilones may be substituted for taxol in compositions and methods utilizing taxol in the treatment of cancer. See, for example, U.S. Pat. Nos. 5,496,804, 5,565,478, and 5,641,803, all of which are incorporated herein by reference.

For example, for treatments, epothilone B is supplied in individual 2 ml glass vials formulated as 1 mg/1 ml of clear, colorless intravenous concentrate. The substance is formulated in polyethylene glycol 300 (PEG 300) and diluted with 50 or 100 ml 0.9% Sodium Chloride Injection, USP, to achieve the desired final concentration of the drug for infusion. It is administered as a single 30-minute intravenous infusion every 21 days (treatment three-weekly) for six cycles, or as a single 30-minute intravenous infusion every 7 days (weekly treatment).

Preferably, for weekly treatment, the dose is between about 0.1 and about 6, preferably about 0.1 and about 5 mg/m$^2$, more preferably about 0.1 and about 3 mg/m$^2$, even more preferably 0.1 and 1.7 mg/m$^2$, most preferably about 0.3 and about 1 mg/m$^2$; for three-weekly treatment (treatment every three weeks or every third week) the dose is between about 0.3 and about 18 mg/m$^2$, preferably about 0.3 and about 15 mg/m$^2$, more preferably about 0.3 and about 12 mg/m$^2$, even more preferably about 0.3 and about 7.5 mg/m$^2$, still more preferably about 0.3 and about 5 mg/m$^2$, most preferably about 1.0 and about 3.0 mg/m$^2$. This dose is preferably administered to the human by intravenous (i.v.) administration during 2 to 180 min, preferably 2 to 120 min, more preferably during about 5 to about 30 min, most preferably during about 10 to about 30 min, e.g. during about 30 min.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. An isolated nucleic acid fragment comprising a nucleotide sequence that encodes at least one polypeptide required for the biosynthesis of epothilone, wherein the complement of said nucleotide sequence hybridizes to a sequence selected from the group consisting of: nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, and nucleotides 11549–11764 of SEQ ID NO:1, under conditions of hybridization at 65° C. for 36 hours and washing 3 times at high stringency with 0.1×SSC and 0.5% SDS for 20 minutes at 65° C.

2. A chimeric gene comprising a heterologous promoter sequence operatively linked to a nucleic acid fragment according to claim 1.

3. A recombinant vector comprising a chimeric gene according to claim 2.

4. A recombinant host cell comprising a chimeric gene according to claim 2.

5. The recombinant host cell of claim 4, which is a bacteria.

6. The recombinant host cell of claim 5, which is an Actinomycete.

7. The recombinant host cell of claim 6, which is Streptomyces.

8. An isolated nucleic acid fragment according to claim 1, wherein said polypeptide comprises a β-ketoacyl-synthase domain and wherein the complement of said nucleotide sequence hybridizes to nucleotides 7643–8920 of SEQ ID NO:1 under conditions of hybridization at 65° C. for 36 hours and washing 3 times at high stringency with 0.1×SSC and 0.5% SDS for 20 minutes at 65° C.

9. A chimeric gene comprising a heterologous promoter sequence operatively linked to a nucleic acid fragment according to claim 8.

10. A recombinant vector comprising a chimeric gene according to claim 9.

11. A recombinant host cell comprising a chimeric gene according to claim 9.

12. The recombinant host cell of claim 11, which is a bacteria.

13. The recombinant host cell of claim 12, which is an Actinomycete.

14. The recombinant host cell of claim 13, which is Streptomyces.

15. An isolated nucleic acid fragment according to claim 1, wherein said polypeptide comprises an acyltransferase domain and wherein the complement of said nucleotide sequence hybridizes to nucleotides 9236–10201 of SEQ ID NO:1 under conditions of hybridization at 65° C. for 36 hours and washing 3 times at high stringency with 0.1×SSC and 0.5% SDS for 20 minutes at 65° C.

16. A chimeric gene comprising a heterologous promoter sequence operatively linked to a nucleic acid fragment according to claim 15.

17. A recombinant vector comprising a chimeric gene according to claim 16.

18. A recombinant host cell comprising a chimeric gene according to claim 16.

19. The recombinant host cell of claim 18, which is a bacteria.

20. The recombinant host cell of claim 19, which is an Actinomycete.

21. The recombinant host cell of claim 20, which is Streptomyces.

22. An isolated nucleic acid fragment according to claim 1, wherein said polypeptide comprises an enoyl reductase domain and wherein the complement of said nucleotide sequence hybridizes to nucleotides 10529–11428 of SEQ ID NO:1 under conditions of hybridization at 65° C. for 36 hours and washing 3 times at high stringency with 0.1×SSC and 0.5% SDS for 20 minutes at 65° C.

23. A chimeric gene comprising a heterologous promoter sequence operatively linked to a nucleic acid fragment according to claim 22.

24. A recombinant vector comprising a chimeric gene according to claim 23.

25. A recombinant host cell comprising a chimeric gene according to claim 23.

26. The recombinant host cell of claim 25, which is a bacteria.

27. The recombinant host cell of claim 26, which is an Actinomycete.

28. The recombinant host cell of claim 27, which is Streptomyces.

29. An isolated nucleic acid fragment according to claim 1, wherein said polypeptide comprises an acyl carrier protein domain and wherein the complement of said nucleotide sequence hybridizes to nucleotides 11549–11764 of SEQ ID NO:1 under conditions of hybridization at 65° C. for 36 hours and washing 3 times at high stringency with 0.1×SSC and 0.5% SDS for 20 minutes at 65° C.

30. A chimeric gene comprising a heterologous promoter sequence operatively linked to a nucleic acid fragment according to claim 29.

31. A recombinant vector comprising a chimeric gene according to claim 30.

32. A recombinant host cell comprising a chimeric gene according to claim 30.

33. The recombinant host cell of claim 32, which is a bacteria.

34. The recombinant host cell of claim 33, which is an Actinomycete.

35. The recombinant host cell of claim 34, which is Streptomyces.

36. An isolated nucleic acid fragment comprising a nucleotide sequence that encodes a polypeptide comprising an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, and amino acids 1314–1385 of SEQ ID NO:2.

37. An isolated nucleic acid fragment according to claim 36, wherein said nucleotide sequence is selected from the group consisting of: nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, and nucleotides 11549–11764 of SEQ ID NO:1.

38. An isolated nucleic acid fragment according to claim 36, wherein said polypeptide comprises a β-ketoacyl-synthase domain comprising amino acids 11–437 of SEQ ID NO:2.

39. An isolated nucleic acid fragment according to claim 38, wherein said nucleotide sequence is nucleotides 7643–8920 of SEQ ID NO:1.

40. An isolated nucleic acid fragment according to claim 36, wherein said polypeptide comprises an acyltransferase domain comprising amino acids 543–864 of SEQ ID NO:2.

41. An isolated nucleic acid fragment according to claim 40, wherein said nucleotide sequence is nucleotides 9236–10201 of SEQ ID NO:1.

42. An isolated nucleic acid fragment according to claim 36, wherein said polypeptide comprises an enoyl reductase domain comprising amino acids 974–1273 of SEQ ID NO:2.

43. An isolated nucleic acid fragment according to claim 42, wherein said nucleotide sequence is nucleotides 10529–11428 of SEQ ID NO:1.

44. An isolated nucleic acid fragment according to claim 36, wherein said polypeptide comprises an acyl carrier protein domain comprising amino acids 1314–1385 of SEQ ID NO:2.

45. An isolated nucleic acid fragment according to claim 44, wherein said nucleotide sequence is nucleotides 11549–11764 of SEQ ID NO:1.

46. A chimeric gene comprising a heterologous promoter sequence operatively linked to a nucleic acid fragment according to claim 36.

47. A recombinant vector comprising a chimeric gene according to claim 46.

48. A recombinant host cell comprising a chimeric gene according to claim 46.

49. The recombinant host cell of claim 48, which is a bacteria.

50. The recombinant host cell of claim 49, which is an Actinomycete.

51. The recombinant host cell of claim 50, which is Streptomyces.

52. An isolated polypeptide required for the biosynthesis of epothilone, wherein said polypeptide comprises an amino acid sequence encoded by a nucleotide sequence whose complement hybridizes to a sequence selected from the group consisting of: nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, and nucleotides 11549–11764 of SEQ ID NO:1, under conditions of hybridization at 65° C. for 36 hours and washing 3 times at high stringency with 0.1×SSC and 0.5% SDS for 20 minutes at 65° C.

53. A recombinant host cell comprising a recombinantly expressed polypeptide according to claim 52.

54. The recombinant host cell of claim 53, which is a bacteria.

55. The recombinant host cell of claim 53, which is an Actinomycete.

56. The recombinant host cell of claim 53, which is Streptomyces.

57. An isolated polypeptide according to claim 52, wherein said polypeptide comprises a β-ketoacyl-synthase domain and wherein the complement of said nucleotide sequence hybridizes to nucleotides 7643–8920 of SEQ ID NO:1 under conditions of hybridization at 65° C. for 36 hours and washing 3 times at high stringency with 0.1×SSC and 0.5% SDS for 20 minutes at 65° C.

58. A recombinant host cell comprising a recombinantly expressed polypeptide according to claim 57.

59. The recombinant host cell of claim 58, which is a bacteria.

60. The recombinant host cell of claim 59, which is an Actinomycete.

61. The recombinant host cell of claim 60, which is Streptomyces.

62. An isolated polypeptide according to claim 52, wherein said polypeptide comprises an acyltransferase domain and wherein the complement of said nucleotide sequence hybridizes to nucleotides 9236–10201 of SEQ ID NO:1 under conditions of hybridization at 65° C. for 36 hours and washing 3 times at high stringency with 0.1×SSC and 0.5% SDS for 20 minutes at 65° C.

63. A recombinant host cell comprising a recombinantly expressed polypeptide according to claim 62.

64. The recombinant host cell of claim 63, which is a bacteria.

65. The recombinant host cell of claim 64, which is an Actinomycete.

66. The recombinant host cell of claim 65, which is Streptomyces.

67. An isolated polypeptide according to claim 52, wherein said polypeptide comprises an enoyl reductase domain and wherein the complement of said nucleotide sequence hybridizes to nucleotides 10529–11428 of SEQ ID NO:1 under conditions of hybridization at 65° C. for 36 hours and washing 3 times at high stringency with 0.1×SSC and 0.5% SDS for 20 minutes at 65° C.

68. A recombinant host cell comprising a recombinantly expressed polypeptide according to claim 67.

69. The recombinant host cell of claim 68, which is a bacteria.

70. The recombinant host cell of claim 69, which is an Actinomycete.

71. The recombinant host cell of claim 70, which is Streptomyces.

72. An isolated polypeptide according to claim 52, wherein said polypeptide comprises an acyl carrier protein domain and wherein the complement of said nucleotide sequence hybridizes to nucleotides 11549–11764 of SEQ ID NO:1 under conditions of hybridization at 65° C. for 36 hours and washing 3 times at high stringency with 0.1×SSC and 0.5% SDS for 20 minutes at 65° C.

73. A recombinant host cell comprising a recombinantly expressed polypeptide according to claim 72.

74. The recombinant host cell of claim 73, which is a bacteria.

75. The recombinant host cell of claim 74, which is an Actinomycete.

76. The recombinant host cell of claim 75, which is Streptomyces.

77. An isolated polypeptide comprising an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, and amino acids 1314–1385 of SEQ ID NO:2.

78. An isolated polypeptide according to claim 77, wherein said polypeptide comprises a β-ketoacyl-synthase domain comprising amino acids 11–437 of SEQ ID NO:2.

79. An isolated polypeptide according to claim 77, wherein said polypeptide comprises an acyltransferase domain comprising amino acids 543–864 of SEQ ID NO:2.

80. An isolated polypeptide according to claim 77, wherein said polypeptide comprises an enoyl reductase domain comprising amino acids 974–1273 of SEQ ID NO:2.

81. An isolated polypeptide according to claim 77, wherein said polypeptide comprises an acyl carrier protein domain comprising amino acids 1314–1385 of SEQ ID NO:2.

82. A recombinant host cell comprising a recombinantly expressed polypeptide according to claim 77.

83. The recombinant host cell of claim 82, which is a bacteria.

84. The recombinant host cell of claim 83, which is an Actinomycete.

85. The recombinant host cell of claim 84, which is Streptomyces.

\* \* \* \* \*

UNITED STATES PATENT AND TRADEMARK OFFICE
CERTIFICATE OF CORRECTION

PATENT NO. : 6,346,404 B1
DATED : February 12, 2002
INVENTOR(S) : Schupp et al.

It is certified that error appears in the above-identified patent and that said Letters Patent is hereby corrected as shown below:

<u>Column 220,</u>
Line 8, should read:
-- 55. The recombinant host cell of claim 54, which is an Actinomycete. --.
Line 10, should read:
-- 56. The recombinant host cell of claim 55 which is Streptomyces. --.

Signed and Sealed this

Sixteenth Day of July, 2002

*Attest:*

*Attesting Officer*

JAMES E. ROGAN
*Director of the United States Patent and Trademark Office*

SEQUENCE LISTING

```
<160> NUMBER OF SEQ ID NOS: 30

<210> SEQ ID NO 1
<211> LENGTH: 68750
<212> TYPE: DNA
<213> ORGANISM: Sorangium cellulosum

<400> SEQUENCE: 1
aagcttcgct cgacgccctc ttcgcccgcg ccacctctgc ccgtgtgctc gatgatggcc      60
acggccgggc cacggagcgg catgtgctcg ccgaggcgcg cgggatcgag gacctccgcg     120
ccctccgaga gcacctccgc atccaggaag gggggccgtc ctttcactgc atgtgcctcg     180
gcgacctgac ggtggagctc ctcgcgcacg accagcccct cgcgtccatc agcttccacc     240
atgcccgcag cctgaggcac cccgactgga cctcggacgc gatgctcgtc gacggcccg     300 cgctcgtccg gtggctcgcc gcgcgcggcg cgccgggtcc cctccgcgag tacgaagagg     360
agcgcgagcg agcccgaacc gcgcaggagg cgaggcgcct gtggctcgcg gccgcgccgc     420
```

-continued

| | | |
|---|---|---|
| cctgcttcgc gcccgatctg ccccgcttcg aggacgacgc caacgggctg ccgctcggcc | 480 | |
| cgatgtcgcc tgaagtcgcc gaggccgagc ggcgcctccg cgcctcgtac gcgactcctg | 540 | |
| agctcgcctg tgccgcgctg ctcgcctggc tcgggacggg cgcgggtccc tggtccggat | 600 | |
| atcccgccta cgagatgctg ccagagaatc tgctcctcgg gtttggcctc ccgaccgcga | 660 | |
| tcgccgcggc ctccgcgccc ggcacatcgg aggccgctct ccgcggcgca gcgcggctgt | 720 | |
| tcgcctcctg ggaggtcgta tcgagcaaga agagccagct cggcaacatc cccgaagccc | 780 | |
| tgtgggagcg gctccggacg atcgtccgcg cgatgggcaa tgccgacaac ctctctcgct | 840 | |
| tcgagcgcgc cgaggcgatc gcggcggagg tgcgccgcct gcgcgcacag ccggcgccct | 900 | |
| tcgcggcggg cgccggcctg gcggtcgctg ggtctcctc gagcggccgg ctctcgggcc | 960 | |
| tcgtgaccga cggagacgca ttgtactccg gcgacggcaa cgacatcgtc atgttccaac | 1020 | |
| ccggccggat ctcgccggtc gtgctgctcg ccggaaccga tcccttcttc gagctcgcac | 1080 | |
| cgcccctcag ccagatgctc ttcgtcgcgc acgccaacgc gggcaccatc tccaaggtcc | 1140 | |
| tgacggaagg cagcccccctc atcgtgatgg caagaaacca ggcgcgaccg atgagcctcg | 1200 | |
| tccacgctcg cgggttcatg gcgtgggtca accaggccat ggtgcccgac ccgagcgggg | 1260 | |
| gcgcgccctt cgtcgtccag cgctcgacca tcatggaatt cgagcacccc acgcctcgtt | 1320 | |
| gtctccacga gcccgccggc agcgctttct ccctcgcctg cgacgaggag cacctctact | 1380 | |
| ggtgcgagct ttcggctggc cggctcgagc tatggcgcca cccgcaccac cgccccggcg | 1440 | |
| ccccgagccg cttcgcgtac ctcggcgagc acccccattgc ggcgacctgg taccccctcgc | 1500 | |
| tcaccctcaa tgcgacccac gtgctgtggg ccgaccctga tcgcagggcc atcctcgggg | 1560 | |
| tcgacaagcg caccggcgta gagcccatcg tcctcgcgga gacgcgccat cccccggcgc | 1620 | |
| acgtcgtgtc cgaggaccgg gacatcttcg cgcttaccgg acagcccgac tcccgcgact | 1680 | |
| ggcacgtcga gcacatccgc tccggcgcct ccacgtcgt ggccgactac cagcgccagc | 1740 | |
| tatgggaccg ccctgacatg gtgctcaatc ggcgcggcct cttcttcacg acgaacgacc | 1800 | |
| gcatcctgac gctcgcccgc agctgacatc gctcgacgcc gggccgctca tcgagggcgc | 1860 | |
| ccggaccgag ctggcgaccc gccgctggcg ggccgcagct catgccgatt cggtggcgac | 1920 | |
| gtagacgctg cgccagaaac gctcgagagc ccccgagaac aggaagccgg cggattgtgt | 1980 | |
| catcacgatc ccgatcagct cgcggcccgg atcattgatc caggacgtcc cgaacccgcc | 2040 | |
| gtcccaccca tagcgcccgg gcacctccga gaccgcgtcc ggcgccgtga ccacggccat | 2100 | |
| cccataaccc cagccgtgcg tctcgaagaa gcccgggaaa acgaggacg ccgccttctg | 2160 | |
| ggccggcgta aggtgatcgg ccgtcatctc gcgcaccgag gcggcgctca agagccgccg | 2220 | |
| gccctcgtgc acaccgccgt tcatgagcat gcgcgcgaac aggaggtagt cgtccaccgt | 2280 | |
| cgacacgagc ccggcggcgc ccgaagggaa cgccggcggg ctggcatagg cgctctcggc | 2340 | |
| cccgtcgcga tccatgcgcg tcttctcccc cgtctgctcg tcggtgaagt aaccgcagcc | 2400 | |
| cgcgaaccga gcgagcttgt ccgccgggac gtgaaagtcg gtgtcccgca tcccgagcgg | 2460 | |
| cgcgaggatg cgctcgcgca cgaacgcatc gaagccctgt cggccgcgc gccccacgag | 2520 | |
| caccccctgc accaggctcc ccgtgttgta catccactgc gcccccggct gatgcatgag | 2580 | |
| cggcagcgtc ccgagccgcc ggatccactc gtctggcccg tgcggcgtca tcggcaccgg | 2640 | |
| ctgcgcgttg acgagcccga gctcgtcgat ggccgctgg atcggcgacg atgcgtcgaa | 2700 | |
| cgagattccg aagcccatcg tgaacgtcat caggtcgcgc accgtgatcg gccgctccgc | 2760 | |
| gggcaccgtc tcgtcgatcg gaccatcgat gcgcgccagc accttccggt tcgcgagctc | 2820 | |

-continued

```
cggcaaccat cggtcgacgg gggagtcgag gtcgagcttg ccttcctcga cgagcatcat    2880
caccgccgtc gcggtgaccg ccttcgtcat cgaggcgatc cggaagatcg tgtcccgccg    2940
catgggcgcg ctgccgccga gctcggtcac gcccaccgcg tccacgtgca cgtcgtcgcc    3000
gcgcgcgacc agccagaccg ctcccggcat ctgccccgcc gccacctccg ccgccatcac    3060
ctcgcgcgcg ggcgccagcg cgccggcccc cgcgtcctgc cctggctgcc cctcctcctc    3120
ggccccaccc aacgcgcacc ccggcgccgc cacgctgatc aaagctccca taaactcccg    3180
ccttctcatg accgtcgatg cctctccgag cgggggcgcg tgcccctgcc gagagcactg    3240
actgcccgcg cccgaaaaaa tcatcggtgc cccgtcacga tcgccgccgg gcgtggctcc    3300
gcccggccgc ccgctcgggc gcccgcccct ggacgagcaa agctcgcccg cccgcgctca    3360
gcacgccgct tgccatgtcc ggcctgcacc cacaccgagg agccacccac cctgatgcac    3420
ggcctcaccg agcggcaggt cctgctctcg ctcgtcaccc tcgcgctcat cctcgtgacc    3480
gcgcgcgcct ccggcgagct cgcgcggcgg ctgcgccagc ccgaggtgct cggggagctc    3540
ttcggcggcg tcgtgctggg ccctccgtc gtcggcgcgc tcgcgcccgg gttccatcga    3600
gccctcttcc aggagccggc ggtcggggtc gtgctctcgg gcatctcctg gataggcgcg    3660
ctcctcctgc tgctgatggc gggcatcgag gtcgacgtgg gcatcctgcg caaggaggcg    3720
cgccccgggg cgctctcggc gctcggcgcg atcgcgcccc cgctcgcggc gggcgccgcc    3780
ttctcggcgc tcgtgctcga tcggcccctt ccgagcggcc tcttcctcgg gatcgtgctc    3840
tcggtgacgg cggtcagcgt gatcgcgaag gtgctgatcg agcgcgagtc gatgcgccgc    3900
agctatcgcc aggtgacgct cgcggcgggg gtggtcagcg aggtcgctgc ctgggtgctc    3960
gtcgcgatga cgtcgtcgag ctacggcgcg tcgcccgcgc tggcggtcgc ccggagcgcg    4020
ctcctggcga gcggattctt gctgttcatg gtgctcgtcg ggcggcggct cacccacctc    4080
gcgatgcgct gggtggccga cgcgacgcgc gtctccaagg acaggtgtc gctcgtcctc    4140 gtcctcacgt tcctggccgc ggcgctgacg cagcggctcg gcctgcaccc gctgctcggc    4200
gcgttcgcgc tcggcgtgct gctcaacagc gctcctcgca ccaaccgccc tctcctcgac    4260
ggcgtgcaga cgctcgtggc gggcctcttc gcgcctgtgt tcttcgtcct cgcgggcatg    4320
cgcgtcgacg tgtcgcagct gcgcacgccg gcggcgtggg ggacggtcgc gttgctgctg    4380
gcgaccgcga cggcggcgaa ggtcgtcccc gccgcgctcg gcgcgcggct cggcgggctc    4440
aggggcagcg aggcggcgct cgtggcggtg ggcctgaaca tgaagggcgg cacggacctc    4500
atcgtcgcga tcgtcggcgt cgagctcggg ctcctctcca acgaggctta tacgatgtac    4560
gccgtcgtcg cgctggtcac ggtgaccgcc tcacccgcgc tcctcatctg gctcgagaaa    4620
agggcgcctc cgacgcagga ggagtcggct cgcctcgagc gcgaggaggc cgcgaggcgc    4680
gcgtacatcc ccggggtcga gcggatcctc gtcccgatcg tggcgcacgc cctgcccggg    4740
ttcgccacgg acatcgtgga gagcatcgtc gcctccaagc gaaagctcgg cgagacggtc    4800
gacatcacgg agctctccgt ggagcagcag gcgcccggcc atcgcgcgcg cgcggggggag    4860 gcgagccggg ggctcgcgag gctcggcgcg cgcctccgcg tcggcatctg gcggcaaagg    4920
cgcgagctgc gcggctcgat ccaggcgatc ctgcgcgcct cgcgggatca cgatctgctc    4980
gtgatcggcg cgcgatcgcc ggcgcgcgcg cgcggaatgt cgttcggtcg cctgcaggac    5040
gcgatcgtcc agcgggccga gtccaacgtg ctcgtcgtgg tgggcgaccc tccggcggcg    5100
gagcgcgcct ccgcgcggcg gatcctcgtc ccgatcatcg gcctcgagta ctccttcgcc    5160
```

-continued

```
gccgccgatc tcgcggccca cgtggcgctg gcgtgggacg ccgagctcgt gctgctcagc      5220
agcgcgcaga ccgatccggg cgcggtcgtc tggcgcgatc gcgagccatc ccgggtgcgc      5280
gcggtggcgc ggagcgtcgt cgacgaggcg gtcttccggg ggcgccggct cggcgtgcgc      5340
gtctcgtcgc gcgtgcacgt gggcgcgcac ccgagcgacg agataacgcg ggagctcgcg      5400
cgcgccccgt acgatctgct cgtgctcgga tgctacgacc atgggccgct cggccggctc      5460
tacctcggca gcacggtcga gtcggtggtg gtccggagcc gggtgccggt cgcgttgctc      5520
gtcgcgcatg gagggactcg agagcaggtg aggtgaggct tccaccgcgc tcgcccgtga      5580
ggaagcgagc gcccggctct gccgacgatc gtcactcccg gtccgtgtag gcgatcgtgc      5640
tgagcagcgc gttctccgcc tgacgcgagt cgagccgggt atgctgcacg acgatggggg      5700
cgtccgattc gatcacgctg gcatagtccg tatcgcgcgg gatcggctcg ggttcggtca      5760
gatcgttgaa ccgacgtgc cgggtgcgcc tcgctggaac ggtcacccgg taaggcccgg       5820
cggggtcgcg gtcgctgaag taaacggtga tggcgacctg cgcgtcccgg tccgacgcat      5880
tcaacaggca ggccgtctca tggctcgtca tctgcggctc aggtccgttg ctcccgcctg      5940
ggatgtagcc ctctgcgatt gcacagcgcg tccgcccgat cggcttgtcc atgtgtcctc      6000
cctcctggct cctctttggc agcctccctc tgctgtccag gagcgatggc ctcttcgctc      6060
gacgcgctcg gggatccatg gctgaggatc ctcgccgagc gctccctgcc gaccggcgcg      6120
ccgagcgccg acgggctttg aaagcgcgcg accggccagc ccggacgcgg gcccgagagg      6180
gacagtgggt ccgccgtgaa gcagagaggc gatcgaggtg gtgagatgaa acacgtcgac      6240
acgggccgac gattcggccg ccggataggg cacacgctcg gtcttctcgc gagcatggcg      6300
ctcgccggct gcggcggtcc gagcgagaaa accgtgcagg gcacgcggct cgcgcccggc      6360
gccgatgcgc gcgtcaccgc cgacgtcgac cccgacgccg cgaccacgcg gctggcggtg      6420
gacgtcgttc acctctcgcc gcccgagcgg ctcgaggccg cagcgagcg gttcgtcgtc       6480 tggcagcgtc cgagccccga gtccccgtgg cgacgggtcg gagtgctcga ctacaatgct      6540
gacagccgaa gaggcaagct ggccgagacg accgtgccgt atgccaactt cgagctgctc      6600
atcaccgccg agaagcagag cagccctcag tcgccatcgt ctgccgccgt catcgggccg      6660
acgtctgtcg ggtgacatcg cgctatcagc agcgctgagc ccgccagcag gccccagggc      6720
cctgcctcga tggccttccc catcaccccct gcgcactcct ccagcgacgg ccgcgcagcg      6780
acggccgcgt ccaagcaacc gccgtgccgg cgcggctcca cgcgcgcgac aggcgagcgt      6840
cctggcgcgg cctgcgcatc gctggaagga tcggcggagc atggatagag aatcgaggat      6900
cgcgatcttt gttgccatcg cagccaacgt ggcgatcgcg gcggtcaagt tcatcgccgc      6960
cgccgtgacc ggcagctcgg cgaggcgttt gccgacttcg gcggcgtccc gcgcgtgctg      7020
ctctacgaca acctcaagag cgccgtcgtc gagcgccacg gcgacgcgat ccggttccac      7080
cccacgctgc tggctctgtc ggcgcattac cgcttcgagc gcgcccccgt cgccgtcgcc      7140
cgcggcaacg agaagggccg cgtccagcgc gccatcacgg cgtggacgac atggcgcgga      7200
aacgtcgtcg taaccgccca gcaatgtcat gggaatggcc ccttgaaatg gccccttgag      7260
ggggctggcc ggggtcgacg atatcgcgcg atctccccgt caattcccga tggtaaaaga      7320
aaaatttgtc atagatcgta agctgtgata gtggtctgtc ttacgttgcg tcttccgcac      7380
ctcgagcgag ttctctcgga taactttcaa ttttccgag gggggcttgg tctctggttc       7440
ctcaggaagc ctgatcggga cgagctaatt cccatccatt tttttgaggc tctgctcaaa      7500
gggattagat cgagtgagac agttcttttg cagtgcgcga agaacctggg cctcgaccgg      7560
```

```
aggacgatcg acgtccgcga gcgggtcagc cgctgaggat gtgcccgtcg tggcggatcg    7620
tcccatcgag cgcgcagccg aagatccgat tgcgatcgtc ggagcgagtt gccgtctgcc    7680
cggtggcgtg atcgatctga gcgggttctg gacgctcctc gagggctcgc gcgacaccgt    7740
cgggcgagtc cccgccgaac gctgggatgc agcagcgtgg tttgatcccg accccgatgc    7800
cccggggaag acgcccgtta cgcgcgcatc tttcctgagc gacgtagcct gcttcgacgc    7860
ctccttcttc ggcatctcgc ctcgcgaagc gctgcggatg gaccctgcac atcgactctt    7920
gctggaggtg tgctgggagg cgctggagaa cgccgcgatc gctccatcgg cgctcgtcgg    7980
tacggaaacg ggagtgttca tcgggatcgg cccgtccgaa tatgaggccg cgctgccgca    8040
agcgacggcg tccgcagaga tcgacgctca tggcgggctg gggacgatgc ccagcgtcgg    8100
agcgggccga atctcgtatg ccctcgggct gcgagggccg tgtgtcgcgg tggatacggc    8160
ctattcgtcc tcgctggtgg ccgttcatct ggcctgtcag agcttgcgct ccggggaatg    8220
ctccacggcc ctggctggtg gggtatcgct gatgttgtcg ccgagcaccc tcgtgtggct    8280
ctcgaagacc cgggcgctgg ccagggacgg tcgctgcaag gcattttcgg cggaggccga    8340
tgggttcgga cgaggcgaag ggtgcgccgt cgtggtcctc aagcggctca gtggagcccg    8400
cgcggacggc gatcggatat tggcggtgat tcgaggatcc gcgatcaatc acgacggtgc    8460
gagcagcggt ctgaccgtgc cgaacgggag ctcccaagaa atcgtgctga acgggccct    8520
ggcggacgca ggctgcgccg cgtcttcggt gggttatgtc gaggcacacg gcacgggcac    8580
gacgcttggt gaccccatcg aaatccaagc tctgaatgcg gtatacggcc tcgggcgaga    8640
tgtcgccacg ccgctgctga tcgggtcggt gaagaccaac cttggccatc ctgagtatgc    8700
gtcggggatc actgggctgc tgaaggtcgt cttgtcccct cagcacgggc agattcctgc    8760
gcacctccac gcgcaggcgc tgaaccccccg gatctcatgg ggtgatcttc ggctgaccgt    8820
cacgcgcgcc cggacaccgt ggccggactg gaatacgccg cgacgggcgg gggtgagctc    8880
gttcggcatg agcgggacca acgcgcacgt ggtgctggaa gaggcgccgg cggcgacgtg    8940
cacaccgccg gcgccggagc gaccggcaga gctgctggtg ctgtcggcaa ggaccgcgtc    9000
agccctggat gcacaggcgg cgcggctgcg cgaccatctg gagacctacc cttcgcagtg    9060
tctgggcgat gtggcgttca gtctggcgac gacgcgcagc gcgatggagc accggctcgc    9120
ggtggcggcg acgtcgaggg aggggctgcg ggcagccctg gacgctgcgg cgcagggaca    9180
gacgtcgccc ggtgcggtgc gcagtatcgc cgattcctca cgcggcaagc tcgcctttct    9240
cttcaccgga caggggcgc agacgctggg catgggccgt gggctgtacg atgtatggtc    9300
cgcgttccgc gaggcgttcg acctgtgcgt gaggctgttc aaccaggagc tcgaccggcc    9360
gctccgcgag gtgatgtggg ccgaaccggc cagcgtcgac gccgcgctgc tcgaccagac    9420
agccttcacc cagccggcgc tgttcacctt cgaatatgcg ctcgccgcgc tgtggcggtc    9480
gtggggtgta gagccggagt tggtcgccgg ccatagcatc ggtgagctgg tggctgcctg    9540
cgtggcgggc gtgttctcgc ttgaggacgc ggtgttcctg gtggctgcgc gcgggcgcct    9600
gatgcaggcg ctgccggccg gcggggcgat ggtgtcgatc gaggcgccgg aggccgatgt    9660
ggctgctgcg gtgcgccgc acgcagcgtc ggtgtcgatc gccgcggtca acgtccgga    9720
ccaggtggtc atcgcgggcg ccgggcaacc cgtgcatgcg atcgcggcgg cgatggccgc    9780
gcgcggggcg cgaaccaagg cgctccacgt ctcgcatgcg ttccactcac cgctcatggc    9840
cccgatgctg gaggcgttcg ggcgtgtggc cgagtcggtg agctaccggc ggccgtcgat    9900
```

-continued

| | |
|---|---|
| cgtcctggtc agcaatctga gcgggaaggc ttgcacagac gaggtgagct cgccgggcta | 9960 |
| ttgggtgcgc cacgcgcgag aggtggtgcg cttcgcggat ggagtgaagg cgctgcacgc | 10020 |
| ggccggtgcg ggcaccttcg tcgaggtcgg tccgaaatcg acgctgctcg gcctggtgcc | 10080 |
| tgcctgcatg ccggacgccc ggccggcgct gctcgcatcg tcgcgcgctg ggcgtgacga | 10140 |
| gccggcgacc gtgctcgagg cgctcggcgg gctctgggcc gtcggtggcc tggtctcctg | 10200 |
| ggccggcctc ttcccctcag gggggcggcg ggtgccgctg cccacgtacc cttggcagcg | 10260 |
| cgagcgctac tggatcgaca cgaaagccga cgacgcggcg cgtggcgacc gccgtgctcc | 10320 |
| gggagcgggt cacgacgagg tcgaggaggg gggcgcggtg cgcggcggcg accggcgcag | 10380 |
| cgctcggctc gaccatccgc cgcccgagag cggacgccgg gagaaggtcg aggccgccgg | 10440 |
| cgaccgtccg ttccggctcg agatcgatga gccaggcgtg cttgatcacc tcgtgcttcg | 10500 |
| ggtcacggag cggcgcgccc ctggtctggg cgaggtcgag atcgccgtcg acgcggcggg | 10560 |
| gctcagcttc aatgatgtcc agctcgcgct gggcatggtg cccgacgacc tgccgggaaa | 10620 |
| gcccaaccct ccgctgctgc tcggaggcga gtgcgccggg cgcatcgtcg ccgtgggcga | 10680 |
| gggcgtgaac ggcctcgtgg tgggccaacc ggtcatcgcc ctttcggcgg gagcgtttgc | 10740 |
| tacccacgtc accacgtcgg ctgcgctggt gctgcctcgg cctcaggcgc tctcggcgat | 10800 |
| cgaggcggcc gccatgcccg tcgcgtacct gacggcatgg tacgcgctcg acagaatagc | 10860 |
| ccgccttcag ccgggggagc gggtgctgat ccatgcggcg accggcgggg tcggtctcgc | 10920 |
| cgcggtgcag tgggcgcagc acgtgggagc cgaggtccat cgacggccg gcacgcccga | 10980 |
| gaaacgcgcc tacctggagt cgctgggcgt gcggtatgtg agcgattccc gctcggaccg | 11040 |
| gttcgtcgcc gacgtgcgcg cgtggacggg cggcgaggga gtagacgtcg tgctcaactc | 11100 |
| gctctcgggc gagctgatcg acaagagttt caatctcctg cgatcgcacg gccggtttgt | 11160 |
| ggagctcggc aagcgcgact gttacgcgga taaccagctc gggctgcggc cgttcctgcg | 11220 |
| caatctctcc ttctcgctgg tggatctccg ggggatgatg ctcgagcggc cggcgcgggt | 11280 |
| ccgtgcgctc ttggaggagc tcctcggcct gatcgcggca ggcgtgttca cccctccccc | 11340 |
| catcgcgacg ctcccgatcg cccgtgtcgc cgatgcgttc cggagcatgg cgcaggcgca | 11400 |
| gcatcttggg aagctcgtac tcacgctggg tgacccggag gtccagatcc gtattccaac | 11460 |
| ccacgcaggc gccggcccgt ccaccgggga tcgggacctg ctcgacaggc tcgcgtcagc | 11520 |
| tgcgccggcc gcgcgcgcgg cggcgctgga ggcgttcctc cgtacgcagg tctcgcaggt | 11580 |
| gctgcgcacg cccgaaatca aggtcggcgc ggaggcgctg ttcacccgcc tcggcatgga | 11640 |
| ctcgctcatg gccgtggagc tgcgcaatcg tatcgaggcg agcctcaagc tgaagctgtc | 11700 |
| gacgacgttc ctgtccacgt cccccaatat cgccttgttg gcccaaaacc tgttggatgc | 11760 |
| tctcgccaca gctctctcct tggagcgggt ggcggcggag aacctacggg caggcgtgca | 11820 |
| aaacgacttc gtctcatcgg cgcagatca agactgggaa atcattgccc tatgacgatc | 11880 |
| aatcagcttc tgaacgagct cgagcaccag ggtatcaagc tggcggccga tggggagcgc | 11940 |
| ctccagatac aggcccccaa gaacgccctg aacccgaacc tgctcgctcg aatctccgag | 12000 |
| cacaaaagca cgatcctgac gatgctccgt cagagactcc ccgcagaatc catcgtgccc | 12060 |
| gccccagccg agcggcacgc tccgtttcct ctcacagaca tccaagaatc ctactggctg | 12120 |
| ggccggacag gagcgtttac ggtccccagc gggatccacg cctatcgcga atacgactgt | 12180 |
| acggatctcg acgtgccgag gctgagccgc gcctttcgga aagtcgtcgc gcggcacgac | 12240 |
| atgcttcggg cccacacgct gcccgacatg atgcaggtga tcgagcctaa agtcgacgcc | 12300 |

```
gacatcgaga tcatcgatct gcgcgggctc gaccggagca cacgggaagc gaggctcgtg   12360
tcgttgcgag atgcgatgtc gcaccgcatc tatgacaccg agcgccctcc gctctatcac   12420
gtcgtcgccg ttcggctgga cgagcggcaa acccgtctcg tgctcagtat cgatctcatt   12480
aacgttgacc taggcagcct gtccatcatc ttcaaggact ggctcagctt ctacgaagat   12540
cccgagacct ctctccctgt cctggagctc tcgtaccgcg attatgtact cgcgctggag   12600
tctcgcaaga agtctgaggc gcatcaacga tcgatggatt actggaagcg gcgcatcgcc   12660
gagctcccac ctccgccgac gcttccgatg aaggccgatc catctaccct gaaggagatc   12720
cgcttccggc acacggagca atggctgccg tcggactcct ggggtcgatt gaagcggcgt   12780
gtcggggagc gcgggctgac cccgacgggc gtcatcctgg ctgcattttc cgaggtgatc   12840
gggcgctgga gcgcgagccc ccggtttacg ctcaacataa cgctcttcaa ccggctcccc   12900
gtccatccgc gcgtgaacga tatcaccggg gacttcacgt cgatggtcct cctggacatc   12960
gacaccactc gcgacaagag cttcgaacag cgcgctaagc gtattcaaga gcagctgtgg   13020
gaagcgatgg atcactgcga cgtaagcggt atcgaggtcc agcgagaggc cgcccgggtc   13080
ctggggatcc aacgaggcgc attgttcccc gtggtgctca cgagcgcgct taaccagcaa   13140
gtcgttggtg tcacctcgtt gcagaggctc ggaactccgg tgtacaccag cacgcagact   13200
cctcagctgc tgctggatca tcagctctac gagcacgatg gggacctcgt cctcgcgtgg   13260
gacatcgtcg acggagtgtt cccgcccgac cttctggacg acatgctcga agcgtacgtc   13320 gttttttctcc ggcggctcac tgaggaacca tggggtgaac aggtgcgctg ttcgcttccg   13380
cctgcccagc tagaagcgcg ggcgagcgca aacgcgacca acgcgctgct gagcgagcat   13440
acgctgcacg gcctgttcgc ggcgcgggtc gagcagctgc ccatgcagct cgccgtggtg   13500
tcggcgcgca agacgctcac gtacgaagag ctttcgcgcc gttcgcggcg acttggcgcg   13560
cggctgcgcg agcaggggc acgcccgaac acattggtcg cggtggtgat ggagaaaggc   13620
tgggagcagg ttgtcgcggt tctcgcggtg ctcgagtcag gcgcggccta cgtgccgatc   13680
gatgccgacc taccggcgga gcgtatccac tacctcctcg atcatggtga ggtaaagctc   13740
gtgctgacgc agccatggct ggatggcaaa ctgtcatggc cgccggggat ccagcggctg   13800
ctcgtgagcg aggccggcgt cgaaggcgac ggcgaccagc ctccgatgat gcccattcag   13860
acaccttcgg atctcgcgta tgtcatctac acctcgggat ccacagggtt gcccaagggg   13920
gtgatgatcg atcatcgggg tgccgtcaac accatcctgg acatcaacga gcgcttcgaa   13980
atagggcccg gagacagggt gctggcgctc tcctcgctga gcttcgatct ctcggtctat   14040
gatgtgttcg ggatcctggc ggcgggcggt acgatcgtgg tgccggacgc gtccaagctg   14100
cgcgatccgg cgcattgggc agagttgatc gaacgagaga aggtgacggt gtggaactcg   14160
gtgccggcgc tgatgcggat gctcgtcgag cattttgagg gtcgccccga ttcgctcgct   14220
aggtctctgc ggctttcgct gctgagcggc gactggatcc cggtgggcct gcctggcgag   14280
ctccaggcca tcaggcccgg cgtgtcggtg atcagcctgg gcggggccac cgaagcgtcg   14340
atctggtcca tcgggtaccc cgtgaggaac gtcgacctat cgtgggcgag catcccctac   14400
ggccgtccgc tgcgcaacca gacgttccac gtgctcgatg aggcgctcga accgcgcccg   14460 gtctggggttc cggggcaact ctacattggc ggggtcgggc tggcactggg ctactggcgc   14520
gatgaagaga agacgcgcaa gagcttcctc gtgcaccccg agaccgggga gcgcctctac   14580
aagaccggcg atctgggccg ctacctgccc gatggaaaca tcgagttcat ggggcgtgag   14640
```

-continued

```
gacaaccaaa tcaagcttcg cggataccgc gttgagctcg gggaaatcga ggaaacgctc    14700
aagtcgcatc cgaacgtacg cgacgcggtg attgtgcccg tcgggaacga cgcggcgaac    14760
aagctccttc tagcctatgt ggtcccggag ggcacacgga gacgcgctgc cgagcaggac    14820
gcgagcctca agaccgagcg gatcgacgcg agagcacacg ccgccgaagc ggacggcttg    14880
agcgacggcg agagggtgca gttcaagctc gctcgacacg gactccggag ggacctggac    14940
ggaaagcccg tcgtcgatct gaccgggcag gatccgcggg aggcggggct ggacgtctac    15000
gcgcgtcgcc gtagcgtccg aacgttcctt gaggccccga ttccgtttgt tgagtttggt    15060
cgattcctga gctgcttgag cagcgtggag cccgacggcg cgacccttcc caaattccgt    15120
tatccatcgg cgggcagcac gtacccggtg caaacctacg cgtatgtcaa atccggccgc    15180
atcgagggcg tggacgaggg cttctattat taccacccgt tcgagcaccg tttgctgaag    15240
ctctccgatc acgggatcga gcgcggagcg cacgttcggc aaaacttcga cgtgttcgat    15300
gaagcggcgt tcaacctcct gttcgtgggc aggatcgacg ccatcgagtc gctgtatgga    15360
tcgtcgtcgc gagaattttg cctgctggag gccggatata tggcgcagct cctgatggag    15420
caggcgcctt cctgcaacat cggcgtctgt ccggtggggc aattcaattt tgaacaggtt    15480
cggccggttc tcgacctgcg acattcggac gtttacgtgc acggcatgct gggcgggcgg    15540
gtagacccgc ggcagttcca ggtctgtacg ctcggtcagg attcctcacc gaggcgcgcc    15600
acgacgcgcg gcgcccctcc cggccgcgag cagcacttcg ccgatatgct tcgcgacttc    15660
ttgaggacca aactacccga gtacatggtg cctacagtct tcgtggagct cgatgcgttg    15720
ccgctgacgt ccaacggcaa ggtcgatcgt aaggccctgc gcgagcggaa ggatacctcg    15780
tcgccgcggc attcggggca cacggcgcca cgggacgcct tggaggagat cctcgtcgcg    15840
gtcgtacggg aggtgctcgg gctggaggtg gtcgggctcc agcagagctt cgtcgatctt    15900
ggtgcgacat cgattcacat cgttcgcatg aggagcctgt tgcagaagag gctggatagg    15960
gagatcgcca tcaccgagtt gttccagtac ccgaacctcg gctcgctggc gtccggtttg    16020
cgccgagact cgagagatct agatcagcgg ccgaacatgc aggaccgagt ggaggttcgg    16080
cgcaagggca ggagacgtag ctaagagcgc cgaacaaaac caggccgagc gggccgatga    16140
gccgcaagcc cgcctgcgtc accctgggac tcatctgatc tgatcgcggg tacgcgtcgc    16200
gggtgtgcgc gttgagccgt gttgttcgaa cgctgaggaa cggtgagctc atggaagaac    16260
aagagtcctc cgctatcgca gtcatcggca tgtcgggccg ttttccgggg gcgcgggatc    16320
tggacgaatt ctggaggaac cttcgagacg gcacggaggc cgtgcagcgc ttctccgagc    16380
aggagctcgc ggcgtccgga gtcgaccccg cgctggtgct ggaccgagc tacgtccggg    16440 cgggcagcgt gctggaagac gtcgaccggt tcgacgctgc tttcttcggc atcagcccgc    16500
gcgaggcaga gctcatggat ccgcagcacc ggatcttcat ggaatgcgcc tgggaggcgc    16560
tggagaacgc cggatacgac ccgacggctt acgagggctc tatcggcgtg tacgccggcg    16620
ccaacatgag ctcgtacttg acgtcgaacc tccacgagca cccagcgatg atgcggtggc    16680
ccggctggtt tcagacgttg atcggcaacg acaaggatta cctcgcgacc cacgtctcct    16740
acaggctgaa tctgagaggg ccgagcatct ccgttcaaac tgcctgctcc acctcgctcg    16800
tggcggttca cttggcgtgc atgagcctcc tggaccgcga gtgcgacatg gcgctggccg    16860
gcgggattac cgtccggatc ccccatcgag ccggctatgt atatgctgag gggggcatct    16920
tctctcccga cggccattgc cgggccttcg acgccaaggc gaacggcacg atcatgggca    16980
acggctgcgg cgttgtcctc ctgaagccgc tggaccgggc gctctccgat ggtgatcccg    17040
```

```
tccgcgcggt tatccttggg tctgccacaa acaacgacgg agcgaggaag atcgggttca   17100
ctgcgcccag tgaggtgggc caggcgcaag cgatcatgga ggcgctggcg ctggcagggg   17160
tcgaggcccg gtccatccaa tacatcgaga cccacgggac cggcacgctg ctcggagacg   17220
ccatcgagac ggcggcgctg cggcgggtgt tcggtcgcga cgcttcggcc cggaggtctt   17280
gcgcgatcgg ctccgtgaag accggcatcg acacctcga atcggcggct ggcatcgccg   17340
gtttgatcaa gacggtcttg gcgctggagc accggcagct gccgcccagc ctgaacttcg   17400
agtctcctaa cccatcgatc gatttcgcga gcagcccgtt ctacgtcaat acctctctta   17460
aggattggaa taccggctcg actccgcggc gggccggcgt cagctcgttc gggatcggcg   17520
gcaccaacgc ccatgtcgtg ctggaggaag cgcccgcggc gaagcttcca gccgcggcgc   17580
cggcgcgctc tgccgagctc ttcgtcgtct cggccaagag cgcagcggcg ctggatgccg   17640
cggcggcacg gctacgagat catctgcagg cgcaccaggg gatttcgttg ggcgacgtcg   17700
ccttcagcct ggcgacgacg cgcagcccca tggagcaccg gctcgcgatg gcggcgccgt   17760
cgcgcgaggc gttgcgagag gggctcgacg cagcggcgcg aggccagacc ccgccggggc   17820
ccgtgcgtgg ccgctgctcc ccaggcaacg tgccgaaggt ggtcttcgtc tttcccggcc   17880
agggctctca gtgggtcggc atgggccggc agctcctggc tgaggaaccc gtcttccacg   17940
cggcgctttc ggcgtgcgac cgggccatcc aggccgaagc tggttggtcg ctgctcgcgg   18000
agctcgccgc cgacgaaggg tcctcccagc tcgagcgcat cgacgtggtg cagccggtgc   18060
tgttcgccct cgcggtggca tttgcggcgc tgtggcggtc gtggggtgtc gcgcccgacg   18120
tcgtgatcgg ccacagcatg ggcgaggtag ccgccgcgca tgtggccggg gcgctgtcgc   18180
tcgaggatgc ggtggcgatc atctgccggc gcagccggct gctccggcgc atcagcggtc   18240
agggcgagat ggcggtgacc gagctgtcgc tggccgaggc cgaggcggcg ctccgaggct   18300
acgaggatcg ggtgagcgtg gccgtgagca acagcccgcg ctcgacggtg ctctcgggcg   18360
agccggcagc gatcggcgag gtgctgtcgt ccctgaacgc gaaggggtg ttctgccgtc   18420 gggtgaaggt ggatgtcgcc agccacagcc cgcaggtcga cccgctgcgc gaggacctct   18480
tggcagccct gggcgggctc cggccggggtg cggctgcggt gccgatgcgc tcgacggtga   18540
cgggcgccat ggtagcgggc ccggagctcg gagcgaatta ctggatgaac aacctcaggc   18600
agccagtgcg cttcgccgag gtagtccagg cgcagctcca aggcggccac ggtctgttcg   18660
tggagatgag cccgcatccg atcctaacga cttcggtcga ggagatgcgg cgcgcggccc   18720
agcgggcggg cgcagcggtg ggctcgctgc ggcggggca ggacgagcgc ccggcgatgc   18780
tggaggcgct gggcacgctg tgggcgcagg gctaccctgt accctggggg cggctgtttc   18840 ccgcggggg gcggcgggta ccgctgccga cctatccctg gcagcgcgag cggtactgga   18900
tcgaagcgcc ggccaagagc gccgcgggcg atccgcgcg cgtgcgtgcg ggcggtcacc   18960
cgctcctcgg tgaaatgcag accctgtcaa cccagacgag cacgcggctg tgggagacga   19020
cgctggatct caagcggctg ccgtggctcg gcgaccaccg ggtgcaggga gcggtcgtgt   19080
ttccgggcgc ggcgtacctg gagatggcga tttcgtcggg ggccgaggct ttgggcgatg   19140
gccctttgca gataactgac gtggtgctcg ccgaggcgct ggccttcgcg ggcgacgcgg   19200
cggtgttggt ccaggtggtg acgacggagc agccgtcggg gcggctgcag ttccagatcg   19260
cgagccgggc gccgggcgct ggccacgcgt ccttccgggt ccacgctcgc ggcgcgttgc   19320
tccgagtgga gcgcaccgag gtcccggctg ggcttacgct ttccgctgtg cgcgcgcggc   19380
```

-continued

```
tccaggccag catacccgcc gcggccacct acgcggagct gaccgagatg gggctgcagt   19440
acggccctgc cttccagggg attgctgagc tatggcgggg tgaaggcgag gcgctgggac   19500
gggtacgcct gcccgacgcg gccggctcgg cagcggagta tcggttgcat cctgcgctgc   19560
tggacgcgtg cttccagatc gtcggcagcc tcttcgcccg cagtggcgag gcgacgccgt   19620
gggtgcccgt ggagttgggc tcgctgcggc tcttgcagcg gccttcgggg gagctgtggt   19680
gccatgcgcg cgtcgtgaac catgggcacc aaaccccga tcggcagggc gccgactttt   19740
gggtggtcga cagctcgggt gcagtggtcg ccgaagtttg cgggctcgtg gcgcagcggc   19800
ttccgggagg ggtgcgccgg cgcgaagaag acgattggtt cctggagctc gagtgggaac   19860
ccgcagcggt cggcacagcc aaggtcaacg cgggccggtg gctgctcctc ggcggcggcg   19920
gtgggctcgg cgccgcgttg cgcgcgatgc tggaggccgg cggccatgcc gtcgtgcatg   19980
cggcagagaa caacacgagc gctgccggcg tacgcgcgct cctggcaaag gcctttgacg   20040
gccaggctcc gacggcggtg gtgcacctcg gcagcctcga tggggtggc gagctcgacc   20100
cagggctcgg ggcgcaaggc gcattggacg cgccccggag cgccgacgtc agtcccgatg   20160
ccctcgatcc ggcgctggta cgtggctgcg acagcgtgct ctggaccgtg caggccctgg   20220
ccggcatggg ctttcgagac gccccgcgat tgtggctttt gacccgcggc gcacaggccg   20280
tcggcgccgg cgacgtctcc gtgacacagg caccgctgct ggggctgggc cgcgtcatcg   20340
ccatggagca cgcggatctg cgctgcgctc gggtcgacct cgatccagcc cggcccgagg   20400
gggagctcgc tgccctgctg gccgagctgc tggccgacga cgccgaagcg gaagtcgcgt   20460
tgcgcggtgg cgagcgatgc gtcgctcgga tcgtccgccg gcagcccgag acccggcccc   20520
gggggaggat cgagagctgc gttccgaccg acgtcaccat ccgcgcggac agcacctacc   20580
ttgtgaccgg cggtctgggt gggctcggtc tgagcgtggc cggatggctg ccgagcgcg   20640
gcgctggtca cctggtgctg gtgggccgct ccggcgcggc gagcgtggag caacgggcag   20700
ccgtcgcggc gctcgaggcc cgcggcgcgc gcgtcaccgt ggcgaaggcg gatgtcgccg   20760
atcgggcgca gctcgagcgg atcctccgcg aggttaccac gtcggggatg ccgctgcggg   20820
gcgtcgtcca tgcggccggc atcttggacg acgggctgct gatgcagcag actcccgcgc   20880
ggtttcgtaa ggtgatggcg cccaaggtcc aggggccctt gcacctgcac gcgttgacgg   20940
gcgaagcgcc gctttccttc ttcgtgctgt acgcttcggg agtagggctc ttgggctcgc   21000
cgggccaggg caactacgcc gcggccaaca cgttcctcga cgctctggcg caccaccgga   21060
ggcgcagggg gctgccagcg ttgagcgtcg actgggcct gttcgcggag gtgggcatgg   21120
cggccgcgca ggaagatcgc ggcgcgcggc tggtctcccg cggaatgcgg agcctcaccc   21180
ccgacgaggg gctgtccgct ctggcacggc tgctcgaaag cggccgcgct caggtggggg   21240
tgatgccggt gaaccgcgg ctgtgggtgg agctctaccc cgcggcgcg tcttcgcgaa   21300
tgttgtcgcg cctggtgacg gcgcatcgcg cgagcgccgg cgggccagcc ggggacgggg   21360
acctgctccg ccgcctcgcc gctgccgagc cgagcgcgcg gagcgcgctc ctggagccgc   21420
tcctccgcgc gcagatctcg caggtgctgc gcctccccga gggcaagatc gaggtggacg   21480
ccccgctcac gagcctgggc atgaactcgc tgatggggct cgagctgcgc aaccgcatcg   21540
aggccatgct gggcatcacc gtaccggcaa cgctgttgtg gacctatccc acggtggcgg   21600
cgctgagcgg gcatctggcg cgggaggcat gcgaagccgc tcctgtggag tcaccgcaca   21660
ccaccgccga ctctgccgtc gagatcgagg agatgtcgca ggacgatctg acgcagttga   21720
tcgcagcaaa attcaaggcg cttacatgac tactcgcggt cctacggcac agcagaatcc   21780
```

```
gctgaaacaa gcggccatca tcattcagcg gctggaggag cggctcgctg ggctcgcaca    21840
ggcggagctg gaacggaccg agccgatcgc catcgtcggt atcggctgcc gcttccctgg    21900
cggtgcggac gctccggaag cgttttggga gctgctcgac gcggagcgcg acgcggtcca    21960
gccgctcgac atgcgctggg cgctggtggg tgtcgctccc gtcgaggccg tgccgcactg    22020
ggcggggctg ctcaccgagc cgatagattg cttcgatgct gcgttcttcg gcatctcgcc    22080 tcggaggcg cgatcgctcg acccgcagca tcgtctgttg ctggaggtcg cttgggaggg    22140
gctcgaggac gccggtatcc cgccccggtc catcgacggg agccgcaccg gtgtgttcgt    22200
cggcgctttc acggcggact acgcgcgcac ggtcgctcgg ctgccgcgcg aggagcgaga    22260
cgcgtacagc gccaccggca acatgctcag catcgccgcc ggacggctgt cgtacacgct    22320
ggggttgcag ggaccttgcc tgaccgtcga cacggcgtgc tcgtcatcgc tggtggcgat    22380
tcacctcgcc tgccgcagcc tgcgcgcagg agagagcgat ctcgcgttgg cgggaggggt    22440
cagcgcgctc ctctcccccg acatgatgga agccgcggcg cgcacgcaag cgctgtcgcc    22500
cgatggtcgt tgccggacct tcgatgcttc ggccaacggg ttcgtccgtg gcagggctg    22560 tggcctggtc gtcctcaaac ggctctccga cgcgcaacgg gatggcgacc gcatctgggc    22620
gctgatccgg ggctcggcca tcaaccatga tggccggtcg accgggttga ccgcgcccaa    22680
cgtgctggct caggagacgg tcttgcgcga ggcgctgcgg agcgcccacg tcgaagctgg    22740
ggccgtcgat tacgtcgaga cccacggaac agggacctcg ctgggcgatc ccatcgaggt    22800
cgaggcgctg cgggcgacgg tggggccggc gcgctccgac ggcacacgct gcgtgctggg    22860
cgcggtgaag accaacatcg gccatctcga ggccgcggca ggcgtagcgg gcctgatcaa    22920
ggcagcgctt tcgctgacgc acgagcgcat cccgagaaac ctcaacttcc gcacgctcaa    22980
tccgcggatc cggctcgagg gcagcgcgct cgcgttggcg accgagccgg tgccgtggcc    23040
gcgcacggac cgcccgcgct tcgcgggggt gagctcgttc gggatgagcg gaacgaacgc    23100
gcatgtggtg ctggaagagg cgccggccgt ggagctgtgg cctgccgcgc cggagcgctc    23160
ggcggagctt ttggtgctgt cgggcaagag cgaggggcg ctcgatgcgc aggcggcgcg    23220
gctgcgcgag cacctggaca tgcacccgga gctcgggctc ggggacgtgg cgttcagcct    23280
ggcgacgacg cgcagcgcga tgagccaccg gctcgcggtg gcggtgacgt cgcgcgaggg    23340
gctgctggcg gcgctctcgg ccgtggcgca ggggcagacg ccggcggggg cggcgcgctg    23400
catcgcgagc tcctcgcgcg gcaagctggc gttcctgttc accggacagg gcgcgcagac    23460
gccgggcatg ggccgggggc tttcgcgcgg cgtggccagcg ttccggagg cgttcgaccg    23520 gtgcgtggcg ctgttcgacc gggagctgga ccgcccgctg cgcgaggtga tgtggcgga    23580 ggcggggagc gccgagtcgt tgttgctcga ccagacggcg ttcacccagc ccgcgctctt    23640
cgcggtggag tacgcgctga cggcgctgtg cggtcgtgg ggcgtagagc cggagctcct    23700
ggttgggcat agcatcgggg agctggtggc ggcgtgcgtg gcggggtgt tctcgctgga    23760 agatggggtg aggctcgtgg cggcgcgcgg gcggctgatg cagggctct cggcgggcgg    23820 cgcgatggtg tcgctcggag cgccggaggc ggaggtggcg gcgcggtgg cgccgcacgc    23880 ggcgtcggtg tcgatcgcgg cggtcaatgg gccggagcag gtggtgatcg cgggcgtgga    23940
gcaagcggtg caggcgatcg cggcggggtt cgcggcgcgc ggcgcgcgca ccaagcggct    24000
gcatgtctcg cacgcgttcc actcgccgct gatggaaccg atgctggagg agttcgggcg    24060
ggtggcggcg tcggtgacgt accggcggcc aagcgtttcg ctggtgagca acctgagcgg    24120
```

```
gaaggtggtc acggacgagc tgagcgcgcc ggggtactgg gtgcggcacg tgcgggaggc   24180
ggtgcgcttc gcggacgggg tgaaggcgct gcacgaagcc ggcgcgggga cgttcgtcga   24240
agtgggcccg aagccgacgc tgctcgggct gttgccagcc tgcctgccgg aggcggagcc   24300
gacgctgctg gcgtcgttgc gcgccgggcg cgaggaggct gcggggggtgc tcgaggcgct   24360 gggcaggctg tgggccgccg gcggctcggt cagctggccg ggcgtcttcc ccacggctgg   24420
gcggcgggtg ccgctgccga cctatccgtg gcagcggcag cggtactgga tcgaggcgcc   24480
ggccgaaggg ctcggagcca cggccgccga tgcgctggcg cagtggttct accgggtgga   24540
ctggcccgag atgcctcgct catccgtgga ttcgcggcga gcccggtccg gcgggtggct   24600
ggtgctggcc gaccggggtg gagtcgggga ggcggccgcg gcggcgcttt cgtcgcaggg   24660
atgttcgtgc gccgtgctcc atgcgcccgc cgaggcctcc gcggttgccg agcaggtgac   24720
ccaggccctc ggtggccgca acgactggca gggggtgctg tacctgtggg gtctggacgc   24780
cgtcgtggag gcgggggcat cggccgaaga ggtcgccaaa gtcacccatc ttgccgcggc   24840
gccggtgctc gcgctgattc aggcgctcgg cacggggccg cgctcacccc ggctctggat   24900
cgtgacccga ggggcctgca cggtgggcgg cgagcctgac gctgcccct gtcaggcggc   24960 gctgtggggt atgggccggg tcgcggcgct agagcatccc ggctcctggg gcgggctcgt   25020
ggacctggat ccggaggaga gcccgacgga ggtcgaggcc ctggtggccg agctgctttc   25080
gccggacgcc gaggatcagc tggcattccg ccagggggcgc cggcgcgcag cgcggcttgt   25140
ggccgcccca ccgagggaa acgcagcgcc ggtgtcgctg tctgcggagg ggagttactt   25200
ggtgacgggt gggctggggcg cccttggcct cctcgttgcg cggtggttgg tggagcgcgg   25260
ggcggggcac cttgtgctga tcagccggca cggattgccc gaccgcgagg aatggggccg   25320
agatcagccg ccagaggtgc gcgcgcgcat tgcggcgatc gaggcgctgg aggcgcaggg   25380
cgcgcgggtc accgtggcgg cggtcgacgt ggccgatgcc gaaggcatgg cggcgctctt   25440
ggcggccgtc gagccgccgc tgcgggggt agtgcacgcc gcgggtctgc tcgacgacgg   25500
gctgctggcc caccaggacg ctggtcggct cgcccggtg ttgcgcccca aggtggaggg   25560
ggcatgggtg ctgcacaccc ttacccgcga gcagccgctg gacctcttcg tactgttttc   25620
ctcggcgtcg ggcgtcttcg gctcgatcgg ccagggcagc tacgcggcag gcaatgcctt   25680
tttggacgcg ctggcggacc tccgccgaac gcagggggctc gccgccctga gcatcgcctg   25740
gggcctgtgg gcgagggggg ggatgggctc gcaggcgcag cgccgggaac acgaggcatc   25800
gggaatctgg gcgatgccga cgagtcgggc cctggcggcg atggaatggc tgctcggtac   25860
gcgcgcgacg cagcgcgtgg tcatccagat ggattgggcc catgcgggag cggcgccgcg   25920
cgacgcgagc cgaggccgct tctgggatcg gctggtaact gccacgaaag aggcctcctc   25980
ctcggccgtg ccagctgtgg agcgctggcg caacgcgtct gttgtggaga cccgctcggc   26040
gctctacgag cttgtgcgcg gcgtggtcgc cggggtgatg ggctttaccg accagggcac   26100
gctcgacgtg cgacgaggct tcgccgagca gggcctcgac tccctgatgg ccgtggagat   26160
ccgcaaacgg cttcagggtg agctgggtat gccgctgtcg gcgacgctag cgttcgacca   26220
tccgaccgtg gagcggctgg tggaatactt gctgagccag gcgctggagc tgcaggaccg   26280
caccgacgtg cggagcgttc ggttgccggc gacagaggac ccgatcgcca tcgtgggtgc   26340
cgcctgccgc ttcccgggcg gggtcgagga cctggagtcc tactggcagc tgttgaccga   26400
gggcgtggtg gtcagcaccg aggtgccggc cgaccggtgg aatggggcag acgggcgcgt   26460
ccccggctcg ggagaggcac agagacagac ctacgtgccc aggggtggct ttctgcgcga   26520
```

-continued

```
ggtggagacg ttcgatgcgg cgttcttcca catctcgcct cgggaggcga tgagcctgga   26580
cccgcaacag cggctgctgc tggaagtgag ctgggaggcg atcgagcgcg cgggccagga   26640
cccgtcggcg ctgcgcgaga gccccacggg cgtgttcgtg ggcgcgggcc ccaacgaata   26700
tgccgagcgg gtgcaggaac tcgccgatga ggcggcgggg ctctacagcg gcaccggcaa   26760
catgctcagc gttgcggcgg gacggctatc attttttcctg ggcctgcacg ggccgaccct   26820
ggctgtggat acggcgtgct cctcgtcgct ggtggcgctg cacctcggct gccagagctt   26880
gcgacggggc gagtgcgacc aagccctggt tggcggggtc aacatgctgc tctcgccgaa   26940
gaccttcgcg ctgctctcac ggatgcacgc actttcgccc ggcgggcggt gcaagacgtt   27000
ctcggccgac gcgacggct acgcgcgggc cgagggctgc gccgtggtgg tgctcaagcg   27060
gctctccgac gcgcagcgcg accgcgaccc catcctggcg gtgatccggg gtacggcgat   27120
caatcatgat ggcccgagca gcgggctgac agtgcccagc ggccctgccc aggaggcgct   27180
gttacgccag gcgctggcgc acgcaggggt ggttccggcc gacgtcgatt tcgtggaatg   27240
ccacgggacc gggacggcgc tgggcgaccc gatcgaggtg cgtgcgctga gcgacgtgta   27300
cgggcaagcc cgccctgcgg accgaccgct gatcctggga gccgccaagg ccaaccttgg   27360
gcacatggag cccgcggcgg gcctggccgg cttgctcaag gcggtgctcg cgctggggca   27420
agagcaaata ccagcccagc cggagctggg cgagctcaac ccgctcttgc cgtgggaggc   27480
gctgccggtg gcggtggccc gcgcagcggt gccgtggccg cgcacggacc gcccgcgctt   27540 cgcggggggtg agctcgttcg ggatgagcgg aacgaacgcg catgtggtgc tggaagaggc   27600
gccggcggtg gagctgtggc ctgccgcgcc ggagcgctcg gcggagctt tggtgctgtc   27660 gggcaagagc gagggggcgc tcgatgcgca ggcggcgcgg ctgcgcgagc acctggacat   27720
gcacccggag ctcgggctcg gggacgtggc gttcagcctg gcgacgacgc gcagcgcgat   27780
gaaccaccgg ctcgcggtgg cggtgacgtc gcgcgagggg ctgctggcgg cgctttcggc   27840
cgtggcgcag gggcagacgc cgccgggggc ggcgcgctgc atcgcgagct cgtcgcgcgg   27900
caagctggcg ttcctgttca ccggacaggg cgcgcagacg ccgggcatgg gccgggggct   27960
ttgcgcggcg tggccagcgt tccgggaggc gttcgaccgg tgcgtggcgc tgttcgaccg   28020
ggagctggac cgcccgctgc gcgaggtgat gtgggcggag ccggggagcg ccgagtcgtt   28080
gttgctcgac cagacggcgt tcacccagcc cgcgctcttc acggtggagt acgcgctgac   28140
ggcgctgtgg cggtcgtggg cgtagagcc ggagctggtg gctgggcata cgccggggga   28200
gctggtggcg gcgtgcgtgg cggggtgtt ctcgctggaa gatggggtga ggctcgtggc   28260
ggcgcgcggg cggctgatgc aggggctctc ggcggcggc gcgatggtgt cgctcggagc   28320
gccggaggcg gaggtggcgg cggcggtggc gccgcacgcg cgtcggtgt cgatcgcggc   28380 ggtcaatggg ccggagcagg tggtgatcgc gggcgtggga caagcggtgc aggcgatcgc   28440
ggcggggttc gcggcgcgcg cgcgcgcac caagcggctg catgtctcgc acgcgtccca   28500
ctcgccgctg atggaaccga tgctggagga gttcgggcg gtggcggcgt cggtgacgta   28560
ccggcggcca agcgtttcgc tggtgagcaa cctgagcggg aaggtggtcg cggacgagct   28620
gagcgcgccg gggtactggg tgcggcacgt gcgggaggcg gtgcgcttcg cggacggggt   28680
gaaggcgctg cacgaagccg gtgcgggcac gttcgtcgaa gtgggcccga gccgacgct   28740 gctcgggctg ttgccagcct gcctgccgga ggcggagcca acgctgctgg cgtcgttgcg   28800
cgccgggcgc gaggaggctg cgggggtgct cgaggcgctg ggcaggctgt gggccgccgg   28860
```

```
cggctcggtc agctggccgg gcgtcttccc cacggctggg cggcgggtgc cgctgccgac   28920
ctatccgtgg cagcggcagc ggtactggcc cgacatcgag cctgacagcc gtcgccacgc   28980
agccgcggat ccgacccaag gctggttcta tcgcgtggac tggccggaga tacctcgcag   29040
cctccagaaa tcagaggagg cgagccgcgg gagctggctg gtattggcgg ataagggtgg   29100
agtcggcgag gcggtcgctg cagcgctgtc gacacgtgga cttccatgcg tcgtgctcca   29160
tgcgccggca gagacatccg cgaccgccga gctggtgacc gaggctgccg gcggtcgaag   29220
cgattggcag gtagtgctct acctgtgggg tctggacgcc gtcgtcggtg cggaggcgtc   29280
gatcgatgag atcggcgacg cgacccgtcg tgctaccgcg ccggtgctcg gcttggctcg   29340
gtttctgagc accgtgtctt gttcgccccg actctgggtc gtgacccggg gggcatgcat   29400
cgttggcgac gagcctgcga tcgccccttg tcaggcggcg ttatgggggca tgggccgggt   29460
ggcggcgctc gagcatcccg gggcctgggg cgggctcgtg gacctggatc ccgagcgag    29520
cccgccccaa gccagcccga tcgacggcga gatgctcgtc accgagctat tgtcgcagga   29580
gaccgaggat cagctcgcct tccgccatgg gcgccggcac gcggcacggc tggtggccgc   29640
cccgccacag gggcaagcgg caccggtgtc gctgtctgcg gaggcgagct acctggtgac   29700
gggaggcctc ggtgggctgg gcctgatcgt ggcccagtgg ctggtggagc tgggagcgcg   29760
gcacttggtg ctgaccagcc ggcgcgggtt gcccgaccgg caggcgtggt gcgagcagca   29820
gccgcctgag atccgcgcgc ggatcgcagc ggtcgaggcg ctggaggcgc ggggtgcacg   29880
ggtgaccgtg gcagcggtgg acgtggccga cgtcgaaccg atgacagcgc tggtttcgtc   29940
ggtcgagccc ccgctgcgag gggtggtgca cgccgctggc gtcagcgtca tgcgtccact   30000
ggcggagacg gacgagaccc tgctcgagtc ggtgctccgt cccaaggtgg ccgggagctg   30060
gctgctgcac cggctgctgc acggccggcc tctcgacctg ttcgtgctgt tctcgtcggg   30120
cgcagcggtg tggggtagcc atagccaggg tgcgtacgcg gcggccaacg ctttcctcga   30180
cgggctcgcg catcttcggc gttcgcaatc gctgcctgcg ttgagcgtcg cgtgggtct    30240
gtgggccgag ggaggcatgg cggacgcgga ggctcatgca cgtctgagcg acatcggggt   30300
tctgcccatg tcgacgtcgg cagcgttgtc ggcgctccag cgcctggtgg agaccggcgc   30360
ggctcagcgc acggtgaccc ggatggactg ggcgcgcttc gcgccggtgt acaccgctcg   30420
agggcgtcgc aacctgcttt cggcgctggt cgcagggcgc gacatcatcg cgccttcccc   30480
tccggcggca gcaacccgga actggcgtgg cctgtccgtt gcggaagccc gcgtggctct   30540
gcacgagatc gtccatgggg ccgtcgctcg ggtgctgggc ttcctcgacc cgagcgcgct   30600
cgatcctggg atggggttca atgagcaggg cctcgactcg ttgatggcgg tggagatccg   30660
caacctcctt caggctgagc tggacgtgcg gctttcgacg acgctggcct ttgatcatcc   30720
gacggtacag cggctggtgg agcatctgct cgtcgatgta ctgaagctgg aggatcgcag   30780
cgacacccag catgttcggt cgttggcgtc agacgagccc atcgccatcg tgggagccgc   30840
ctgccgcttc ccgggcgggg tggaggacct ggagtcctac tggcagctat tggccgaggg   30900
cgtggtggtc agcgccgagg tgccggccga ccggtgggat gcggcggact ggtacgaccc   30960
tgatccggag atcccaggcc ggacttacgt gaccaaaggc gccttcctgc gcgatttgca   31020
gagattggat gcgaccttct tccgcatctc gcctcgcgag gcgatgagcc tcgacccgca   31080
gcagcggttg ctcctggagg taagctggga agcgctcgag agcgcgggta tcgctccgga   31140
tacgctgcga gatagcccca ccggggtgtt cgtgggtgcg gggcccaatg agtactacac   31200
gcagcggctg cgaggcttca ccgacggagc ggcagggttg tacggcggca ccgggaacat   31260
```

-continued

```
gctcagcgtt acggctggac ggctgtcgtt tttcctgggt ctgcacggcc cgacgctggc   31320
catggatacg gcgtgctcgt catccctggt cgcgctgcac ctcgcctgcc agagcctgcg   31380
actgggcgag tgcgatcaag cgctggttgg cggggtcaac gtgctgctcg cgccggagac   31440
cttcgtgctg ctctcacgga tgcgcgcgct ttcgcccgac gggcggtgca agacgttctc   31500
ggccgacgcg gacggctacg cgcggggcga ggggtgcgcc gtggtggtgc tcaagcggct   31560
gcgcgatgcg cagcgcgccg gcgactccat cctggcgctg atccggggaa gcgcggtgaa   31620
ccacgacggc ccgagcagcg ggctgaccgt acccaacgga cccgcccagc aagcattgct   31680
gcgccaggcg ctttcgcaag caggcgtgtc tccggtcgac gttgattttg tggagtgtca   31740
cgggacaggg acgcgctggg cgacccgat cgaggtgcag gcgctgagcg aggtgtatgg   31800
tccagggcgc tccggggacc gaccgctggt gctgggggcc gccaaggcca acgtcgcgca   31860
tctggaggcg gcatctggct tggccagcct gctcaaggcc gtgcttgcgc tgcggcacga   31920
gcagatcccg gcccagccgg agctggggga gctcaacccg cacttgccgt ggaacacgct   31980
gccggtggcg gtgccacgta aggcggtgcc gtggggggcgc ggcgcacgcc cgcgtcgggc   32040
cggcgtgagc gcgttcgggt tgagcggaac caacgtgcat gtcgtgctgg aggaggcacc   32100
ggaggtggag ccggcgcccg cggcgccggc gcgaccggtg gagctggtcg tgctatcggc   32160
caagagcgcg gcggcgctgg acgccgcggc ggcacggctc tcggcgcacc tgtccgcgca   32220
cccggagctg agcctcggcg acgtggcgtt cagcctggcg acgacgcgca gcccgatgga   32280
gcaccggctc gccatcgcga cgacctcgcg cgaggccctg cgaggcgcgc tggacgccgc   32340
ggcgcagcaa aagacgccgc agggcgcggt gcgcggcaag gccgtgtcct cacgcggtaa   32400
gctggctttc ctgttcaccg gacagggcgc gcaaatgccg ggcatgggcc gtgggctgta   32460
cgaaacgtgg cctgcgttcc gggaggcgtt cgaccggtgc gtggcgctct tcgatcggga   32520
gatcgaccag cctctgcgcg aggtgatgtg ggctgcgccg ggcctcgctc aggcggcgcg   32580
gctcgatcag accgcgtacg cgcagccggc tctctttgcg ctggagtacg cgctggctgc   32640
cctgtggcgt tcgtggggcg tggagccgca cgtactgctc ggtcatagca tcggcgagct   32700
ggtcgccgcc tgcgtggcgg gcgtgttctc gctcgaagat gcggtgaggt tggtggccgc   32760
gcgcgggcgg ctgatgcagg cgctacccgc cggcggtgcc atggtagcca tcgcagcgtc   32820
cgaggccgag gtggccgcct ccgtggcgcc ccacgccgcc acgtgtcga tcgccgcggt   32880 caacggtcct gacgccgtcg tgatcgccgg cgccgaggta caggtgctcg ccctcggcgc   32940
gacgttcgcg gcgcgtggga tacgcacgaa gaggctcgcc gtctcccatg cgttccactc   33000
gccgctcatg gatccgatgc tggaagactt ccagcgggtc gctgcgacga tcgcgtaccg   33060
cgcgccagac cgcccggtgg tgtcgaatgt caccggccac gtcgcaggcc ccgagatcgc   33120
cacgcccgag tattgggtcc ggcatgtgcg aagcgccgtg cgcttcggcg acggggcaaa   33180
ggcgttgcat gccgcgggtg ccgccacgtt cgtcgaggtt ggcccgaagc cggtcctgct   33240
cgggctgttg ccagcgtgcc tcggggaagc ggacgcggtc ctcgtgccgt cgctacgcgc   33300
ggaccgctcg gaatgcgagg tggtcctcgc ggcgctcggg gcttggtatg cctgggggg   33360 tgcgctcgac tggaagggcg tgttcccga tggcgcgcgc cgcgtggctc tgcccatgta   33420
tccatggcag cgtgagcgcc attggatgga cctcacccg cgaagcgccg cgcctgcagg   33480
gatcgcaggt cgctggccgc tggctggtgt cgggctctgc atgcccggcg ctgtgttgca   33540
ccacgtgctc tcgatcggac cacgccatca gcccttcctc ggtgatcacc tcgtgtttgg   33600
```

```
caaggtggtg gtgcccggcg cctttcatgt cgcggtgatc ctcagcatcg ccgccgagcg    33660
ctggcccgag cggcgatcg agctgacagg cgtggagttc ctgaaggcca tcgcgatgga    33720
gcccgaccag gaggtcgagc tccacgccgt gctcaccccc gaagccgccg gggatggcta    33780
cctgttcgag ctggcgaccc tggcggcgcc ggagaccgaa cgccgatgga cgacccacgc    33840
ccgcggtcgg gtgcagccga cagacggcgc gcccggcgcg ttgccgcgcc tcgaggtgct    33900
ggaggaccgc gcgatccagc ccctcgactt cgccggattc ctcgacaggt tatcggcggt    33960
gcggatcggc tggggtccgc tttggcgatg gctgcaggac gggcgcgtcg gcgacgaggc    34020
ctcgcttgcc accctcgtgc cgacctatcc gaacgcccac gacgtggcgc ccttgcaccc    34080
gatcctgctg gacaacggct tgcggtgag cctgctgtca acccgagcg agccggagga     34140 cgacgggacg ccccgctgc cgttcgccgt ggaacgggtg cggtggtggc gggcgccggt    34200
tggaagggtg cggtgtggcg gcgtgccgcg gtcgcaggca ttcggtgtct cgagcttcgt    34260
gctggtcgac gaaactggcg aggtggtcgc cgaggtggag ggatttgttt gccgccgggc    34320
gccgcgagag gtgttcctgc ggcaggagtc gggcgcgtcg actgcagcct tgtaccgcct    34380
cgactggccc gaagcgccct tgcccgatgc gcctgcggaa cggatcgagg agagctgggt    34440
cgtggtggca gcacctggct cggagatggc cgcggcgctc gcaacacggc tcaaccgctg    34500
cgtcctcgcc gaacccaaag gcctcgaggc ggccctcgcg ggggtgtctc ccgcaggtgt    34560
gatctgcctc tgggaggctg gagcccacga ggaagctccg gcggcggcgc agcgtgtggc    34620
gaccgagggc ctctcggtgg tgcaggcgct cagggaccgc gcggtgcgcc tgtggtgggt    34680
gaccatgggc gcagtggccg tcgaggccgg tgagcgggtg caggtcgcca cagcgccggt    34740
atggggcctc ggccggacag tgatgcagga gcgcccggga ctcagctgca ctctggtgga    34800
tttggagccg gaggccgatg cagcgcgctc agctgacgtt ctgttgcggg agctcggtcg    34860
cgctgacgac gagacacagg tggctttccg ttccggaaag cgccgcgtag cgcggctggt    34920
caaagcgacg accccgaag ggctcctggt ccctgacgca gagtcctatc gactggaggc     34980
tgggcagaag ggcacattgg accagctccg cctcgcgccg gcacagcgcc gggcacctgg    35040
cccgggcgag gtcgagatca aggtaaccgc ctcgggctc aacttccgga ccgtcctcgc     35100
tgtgctggga atgtatccgg gcgacgccgg gccgatgggc ggagattgtg ccggtgtcgc    35160
cacggcggtg ggccaggggg tgcgccacgt cgcggtcggc gatgctgtca tgacgctggg    35220
gacgttgcat cgattcgtca cggtcgacgc gcggctggtg gtccggcagc ctgcagggct    35280
gactcccgcg caggcagcta cggtgccggt cgcgttcctg acggcctggc tcgctctgca    35340
cgacctgggg aatctgcggc gcggcgagcg ggtgctgatc catgctgcgg ccggcggtgt    35400
gggcatggcc gcggtgcaaa tcgcccgatg gatagggcc gaggtgttcg ccacggcgag     35460
cccgtccaag tgggcagcgg ttcaggccat gggcgtgccg cgcacgcaca tcgccagctc    35520
gcggacgctg gagtttgctg agacgttccg gcaggtcacc ggcggccggg gcgtggacgt    35580
ggtgctcaac gcgctggccg gcgagttcgt ggacgcgagc ctgtccctgc tgtcgacggg    35640
cgggcggttc ctcgagatgg gcaagaccga catacgggat cgagccgcgg tcgcggcggc    35700
gcatcccggt gttcgctatc gggtattcga catcctggag ctcgctccgg atcgaactcg    35760
agagatcctc gagcgcgtgg tcgagggctt tgctgcggga catctgcgcg cattgccggt    35820
gcatgcgttc gcgatcacca aggccgaggc agcgtttcgg ttcatggcgc aagcgcggca    35880
tcagggcaag gtcgtgctgc tgccggcgcc ctccgcagcc cccttggcgc cgacgggcac    35940
cgtactgctg accggtgggc tgggagcgtt ggggctccac gtggcccgct ggctcgccca    36000
```

-continued

```
gcagggcgtg ccgcacatgg tgctcacagg tcggcggggc ctggatacgc cgggcgctgc   36060
caaagccgtc gcggagatcg aagcgctccg cgctcgggtg acgatcgcgg cgtcggatgt   36120
cgccgatcgg aatgcgctgg aggctgtgct ccaggccatt ccggcggagt ggccgttaca   36180
gggcgtgatc catgcagccg gagcgctcga tgatggtgtg cttgatgagc agaccaccga   36240
ccgcttctcg cgggtgctgg caccgaaggt gactggcgcc tggaatctgc atgagctcac   36300
ggcgggcaac gatctcgctt tcttcgtgct gttctcctcc atgtcggggc tcttgggctc   36360 ggcccgggcag tccaactatg cggcggccaa caccttcctc gacgcgctgg ccgcgcatcg   36420
gcgggccgaa ggcctggcgg cgcagagcct cgcgtggggc ccatggtcgg acggaggcat   36480
ggcagcgggg ctcagcgcgg cgctgcaggc gcggctcgct cggcatggga tgggagctct   36540
gtcgccggct caggcaccg cgctgctcgg gcaggcgctg gctcggccgg aaacgcagct   36600
cggggcgatg tcgctcgacg tgcgtgcggc aagccaagct tcgggagcgg cagtgccgcc   36660
tgtgtggcgc gcgttggtgc gcgcggaggc gcgccatacg gcggctgggg cgcaggggc    36720 attggccgcg cgtcttgggg cgctgcccga ggcgcgtcgc gccgacgagg tgcgcaaggt   36780
cgtgcaggcc gagatcgcgc gcgtgctttc atggagcgcc gcgagcgccg tgcccgtcga   36840
tcggccgctg tcggacttgg gcctcgactc gctcacggcg gtggagctgc gcaacgtgct   36900
cggccagcgg gtgggtgcga cgctgccggc gacgctggca ttcgatcacc cgacggtcga   36960
cgcgctcacg cgctggctgc tcgataaggt cctggccgtg gccgagccga gcgtatcgtc   37020
cgcaaagtcg tcgccgcagg tcgccctcga cgagcccatt gccatcatcg gcatcggctg   37080
ccgtttccca ggcggcgtgg ccgatccgga gtcgttttgg cggctgctcg aagagggcag   37140
cgatgccgtc gtcgaggtgc cgcatgagcg atgggacatc gacgcgttct atgatccgga   37200
tccggatgtg cgcggcaaga tgacgacacg ctttggcggc ttcctgtccg atatcgaccg   37260
gttcgatccg gccttcttcg gcatctcgcc gcgcgaagcg acgaccatgg atccgcagca   37320
gcggctgctc ctggagacga gctgggaggc gttcgagcgc gccgggatttt tgcccgagcg   37380 gctgatgggc agcgataccg cgcgtgttcgt ggggctcttc taccaggagt acgctgcgct   37440
cgccggcggc atcgaggcgt tcgatggcta tctaggcacc ggcaccacgg ccagcgtcgc   37500
ctcgggcagg atctcttatg tgctcgggct aaaggggccg agcctgacgg tggacaccgc   37560
gtgctcctcg tcgctggtcg cggtgcacct ggcctgccag gcgctgcggc ggggcgagtg   37620
ttcggtggcg ctggccggcg gcgtggcgct gatgctcacg ccggcgacgt tcgtggagtt   37680
cagccggctg cgaggcctgg ctcccgacgg acggtgcaag agcttctcgg ccgcagccga   37740
cggcgtgggg tggagcgaag gctgcgccat gctcctgctc aaaccgcttc gcgatgcgca   37800
gcgcgatggg gatccgatcc tggcggtgat ccgcggcacc gcggtgaacc aggatgggcg   37860
cagcaacggg ctgacggcgc ccaacgggtc gtcgcagcaa gaggtgatcc gtcgggccct   37920
ggagcaggcg ggctggctc cggcggacgt cagctacgtc gagtgccacg gcaccggcac   37980
gacgttgggc gaccccatcg aagtgcaggc cctgggcgcc gtgctggcac aggggcgacc   38040
ctcggaccgg ccgctcgtga tcgggtcggt gaagtccaat atcggacata cgcaggctgc   38100
ggcgggcgtg ccggtgtca tcaaggtggc gctggcgctc gagcgcgggc ttatcccgag   38160
gagcctgcat ttcgacgcgc ccaatccgca cattccgtgg tcggagctcg ccgtgcaggt   38220
ggccgccaaa cccgtcgaat ggacgagaaa cggcgtgccg cgacgagccg gggtgagctc   38280
gtttggcgtc agcgggacca acgcgcacgt ggtgctggag gaggcgccag cggcggcgtt   38340
```

```
cgcgcccgcg gcggcgcgtt cagcggagct tttcgtgctg tcggcgaaga gcgccgcggc    38400
gctggacgcg caggcggcgc ggctttcggc gcacgtcgtt gcgcacccgg agctcggcct    38460
cggcgacctg gcgttcagcc tggcgacgac ccgcagcccg atgacgtacc ggctcgcggt    38520
ggcggcgacc tcgcgcgagg cgctgtctgc cgcgctcgac acagcggcgc aggggcaggc    38580
gccgcccgca gcggctcgcg gccacgcttc cacaggcagc gccccaaagg tggttttcgt    38640
ctttcctggc cagggctccc agtggctggg catgggccaa aagctcctct cggaggagcc    38700
cgtcttccgc gacgcgctct cggcgtgtga ccgagcgatt caggccgaag ccggctggtc    38760
gctgctcgcc gagctcgcgg ccgatgagac cacctcgcag ctcggccgca tcgacgtggt    38820
gcagccggcg ctgttcgcga tcgaggtcgc gctgtcggcg ctgtggcggt cgtggggcgt    38880
cgagccggat gcagtggtag gccacagcat gggcgaagtg gcggccgcgc acgtcgccgg    38940
cgccctgtcg ctcgaggatg ctgtagcgat catctgccgg cgcagcctgc tgctgcggcg    39000
gatcagcggc caaggcgaga tggcggtcgt cgagctttcc ctggccgagg ccgaggcagc    39060
gctcctgggc tacagaagacc ggctcagcgt ggcggtgagc aacagcccgc gctcgacggt    39120
gctggcgggc gagccggcag cgctcgcaga ggtgctggcg atccttgcgg caaaggggggt    39180 gttctgccgt cgagtcaagg tggacgtcgc cagccacagc ccacagatcg acccgctgcg    39240
cgacgagcta ttggcagcat tgggcgagct cgagccgcga caagcgaccg tgtcgatgcg    39300
ctcgacggtg acgagcacga tcatggcggg cccggagctc gtggcgagct actgggcgga    39360
caacgttcga cagccggtgc gcttcgccga agcggtgcaa tcgttgatgg aagacggtca    39420
tgggctgttc gtggagatga gcccgcatcc gatcctgacg acatcggtcg aggagatccg    39480
acgggcgacg aagcgggagg gagtcgcggt gggctcgttg cggcgtggac aggacagagcg    39540 cctgtccatg ttggaggcgc tgggagcgct ctgggtacac ggccaggcgg tgggctggga    39600
gcggctgttc tccgcgggcg gcgcgggcct ccgtcgcgtg ccgctgccga cctatccctg    39660
gcagcgcgag cggtactggg tcgatgcgcc gaccggcggc gcggcgggcg gcagccgctt    39720
tgctcatgcg ggcagtcacc cgctcctggg tgaaatgcag accctgtcga cccagaggag    39780
cacgcgcgtg tgggagacga cgctggatct caaacggctg ccgtggctcg gcgatcaccg    39840
ggtgcagggg gcggtcgtgt tcccgggcgc ggcgtacctg gagatggcgc tttcgtccgg    39900
ggccgaggcc ttgggtgacg gtccgctcca ggtcagcgat gtggtgctcg ccgaggcgct    39960
ggccttcgcg gatgatacgc cggcggcggt gcaggtcatg gcgaccgagg agcgaccagg    40020
ccgcctgcaa ttccacgttg cgagccgggt gccgggccac ggcggtgctg cctttcgaag    40080
ccatgcccgc ggggtgctgc gccagatcga gcgcgccgag gtcccggcga ggctggatct    40140
ggccgcgctt cgtgcccggc ttcaggccag cgcacccgct gcggctacct atgcggcgct    40200
ggccgagatg gggctcgagt acggcccagc gttccagggg cttgtcgagc tgtggcgggg    40260
ggagggcgag gcgctgggac gtgtgcggct ccccgaggcc gccggctccc cagccgcgtg    40320
ccggctccac cccgcgctct tggatgcgtg cttccacgtg agcagcgcct tcgctgaccg    40380
cggcgaggcg acgccatggg tacccgtgga aatcggctcg ctgcggtggt tccagcggcc    40440
gtcgggggag ctgtggtgtc atgcgcgag tgtgagccac ggaaagccaa cacccgaccg    40500
gcggagtacc gacttctggg tggtcgacag cacgggcgcg atcgtcgccg agatctccgg    40560
gctcgtggcg cagcggctcg cgggaggtgt acgccggcgc gaagaagacg actggttcat    40620
ggagccggct tggaaccga ccgcggtccc cggatccgag gtcatggcgg gccggtggct    40680
gctcatcggc tcgggcggcg ggctcggcgc tgcgctccac tcggcgctga cggaagctgg    40740
```

```
ccattccgtc gtccacgcga cagggcgcgg cacgagcgcc gccggttgc aggcactctt   40800 gacggcgtcc ttcgacggcc aggccccgac gtcggtggtg cacctcggca gcctcgatga   40860
gcgtggcgtg ctcgacgcgg atgccccctt cgacgccgat gcgcttgagg agtcgctggt   40920
gcgcggctgc gacagcgtgc tctggaccgt gcaggccgtg gccggggcgg gcttccgaga   40980
tcctccgcgg ttgtggctcg tgacacgcgg cgctcaggcc atcggcgccg gcgacgtctc   41040
tgtggcgcaa gcgccgctcc tggggctggg ccgcgttatc gccttggagc acgccgagct   41100
gcgctgcgct cggatcgacc tcgatccagc gcggcgcgac ggagaagtcg atgagctgct   41160
tgccgagctg ttggccgacg acgccgagga ggaagtcgcg tttcgcggcg gtgagcggcg   41220
cgtggcccgg ctcgtccgaa ggctgcccga gaccgactgc cgagagaaaa tcgagcccgc   41280
ggaaggccgg ccgttccggc tggagatcga tgggtccggc gtgctcgacg acctggtgct   41340
ccgagccacg gagcggcgcc ctcctggccc ggcgaggtc gagatcgccg tcgaggcggc   41400
ggggctcaac tttctcgacg tgatgagggc catgggatc taccctgggc ccggggacgg   41460
tccggttgcg ctgggcgccg agtgctccgg ccgaattgtc gcgatgggcg aaggtgtcga   41520
gagccttcgt atcggccagg acgtcgtggc cgtcgcgccc ttcagtttcg gcacccacgt   41580
caccatcgac gcccggatgc tcgcacctcg ccccgcggcg ctgacggccg cgcaggcagc   41640
cgcgctgccc gtcgcattca tgacggcctg gtacggtctc gtccatctgg ggaggctccg   41700
ggccggcgag cgcgtgctca tccactcggc gacgggggc accgggctcg ctgctgtgca   41760
gatcgcccgc cacctcggcg cggagatatt tgcgaccgct ggtacaccgg agaagcgggc   41820
gtggctgcgc gagcagggga tcgcgcacgt gatggactcg cggtcgctgg acttcgccga   41880
gcaagtgctg gccgcgacga agggcgaggg ggtcgacgtc gtgttgaact cgctgtctgg   41940
cgccgcgatc gacgcgagcc tttcgaccct cgtgccggac ggccgcttca tcgagctcgg   42000
caagacggac atctatgcag atcgctcgct ggggctcgct cacttcagga agagcctgtc   42060
ctacagcgcc gtcgatcttg cgggcttggc cgtgcgtcgg cccgagcgcg tcgcagcgct   42120
gctggcggag gtggtggacc tgctcgcacg gggagcgctg cagccgcttc cggtagagat   42180
cttccccctc tcgcgggccg cggacgcgtt ccggaaaatg gcgcaagcgc agcatctcgg   42240
gaagctcgtg ctcgcgctgg aggacccgga cgtgcggatc cgcgttccgg gcgaatccgg   42300
cgtcgccatc cgcgcggacg gcgcctacct cgtgaccggc ggtctggggg gctcggtct   42360 gagcgtggct ggatggctgg ccgagcaggg ggctgggcat ctggtgctgg tgggccgctc   42420
cggcgcggtg agcgcggagc agcagacggc tgtcgccgcg ctcgaggcgc acggcgcgcg   42480
tgtcacggta gcgagggcag acgtcgccga tcgggcgcag atggagcgga tcctccgcga   42540
ggttaccgcg tcggggatgc cgctccgcgg cgtcgttcat gcggccggaa tcctggacga   42600
cgggctgctg atgcagcaaa ccccgcgcg gttccgcgcg tcatggcgc caaggtccg   42660 aggggccttg cacctgcatg cgttgacacg cgaagcgccg ctctccttct tcgtgctgta   42720
cgcttcggga gcagggctct tggctcgcc gggccaggg aactacgccg cggccaacac   42780
gttcctcgac gcactggcac accaccggag ggcgcagggg ctgccagcat tgagcatcga   42840
ctggggcctg ttcgcggacg tgggtttggc cgccgggcag caaaatcgcg gcgcacggct   42900
ggtcacccgc gggacgcgga gcctcacccc cgacgaaggg ctgtgggcgc tcgagcgcct   42960
gctcgacgga gatcgcaccc aggccggggt catgccgttc gacgtgcggc agtgggtgga   43020
gttctacccg gcggcggcat cttcgcggag gttgtcgcgg ctcatgacgg cacggcgcgt   43080
```

```
ggcttccggt cggctcgccg gggatcggga cctgctcgaa cggctcgcca ccgccgaggc   43140
gggcgcgcgg gcagggatgc tgcaggaggt cgtgcgcgcg caggtctcgc aggtgctgcg   43200
cctctccgaa ggcaagctcg acgtggatgc gccgctcacg agcctgggaa tggactcgct   43260 gatgggcta gagctgcgca accgcatcga ggccgtgctc ggcatcacca tgccggcgac   43320
cctgctgtgg acctacccca cggtggcagc gctgagtgcg catctggctt ctcatgtcgt   43380
ctctacgggg gatggggaat ccgcgcgccc gccggataca gggagcgtgg ctccaacgac   43440
ccacgaagtc gcttcgctcg acgaagacgg gttgttcgcg ttgattgatg agtcactcgc   43500
gcgcgcggga aagaggtgat tgcgtgacag accgagaagg ccagctcctg gagcgcttgc   43560
gtgaggttac tctggccctt cgcaagacgc tgaacgagcg cgatacccctg gagctcgaga   43620 agaccgagcc gatcgccatc gtggggatcg gctgccgctt ccccggcgga gcgggcactc   43680
cggaggcgtt ctgggagctg ctcgacgacg ggcgcgacgc gatccggccg ctcgaggagc   43740
gctgggcgct cgtaggtgtc gacccaggcg acgacgtacc gcgctgggcg gggctgctca   43800
ccgaggccat cgacggcttc gacgccgcgt tcttcggtat cgccccccgg gaggcacggt   43860
cgctcgaccc gcagcatcgc ctgctgctgg aggtcgcctg ggaggggttc gaagacgccg   43920
gcatcccgcc caggtccctc gtcgggagcc gcaccggcgt gttcgtcggc gtctgcgcca   43980
cggagtacct ccacgccgcc gtcgcgcacc agccgcgcga agagcgggac gcgtacagca   44040
ccaccggcaa catgctcagc atcgccgccg gacggctatc gtacacgctg gggctgcagg   44100
gaccttgcct gaccgtcgat acggcgtgct cgtcatcgct ggtggccatt cacctcgcct   44160
gccgcagcct gcgcgctcga gagagcgatc tcgcgctggc gggaggggtc aacatgcttc   44220
tctcccccga cacgatgcga gctctggcgc gcacccaggc gctgtcgccc aatggccgtt   44280
gccagacctt cgacgcgtcg gccaacgggt tcgtccgtgg ggagggctgc ggtctgatcg   44340
tgctcaagcg attgagcgac gcgcggcggg atggggaccg gatctgggcg ctgatccgag   44400
gatcggccat caatcaggac ggccggtcga cggggttgac ggcgcccaac gtgctcgccc   44460 aggggcgct cttgcgcgag gcgctgcgga acgccgcgt cgaggccgag gccatcggtt   44520
acatcgagac ccacgggcg gcaacctcgc tgggcgaccc catcgagatc gaagcgctgc   44580
gcgctgtggt ggggccggcg cgagccgacg gagcgcgctg cgtgctgggc gcggtgaaga   44640
ccaacctcgg ccacctggag ggcgctgccg gcgtggcggg cctgatcaag gcgacgcttt   44700
cgctacatca cgagcgcatc ccgaggaacc tcaactttcg tacgctcaat ccgcggatcc   44760
ggatcgaggg gaccgcgctc gcgttggcga ccgaaccggt gccctggccg cggacgggcc   44820
ggacgcgctt cgcgggagtg agctcgttcg ggatgagcgg gaccaacgcg catgtggtgt   44880
tggaggaggc gccggcggtg gagcctgagg ccgcggcccc cgagcgcgca gcggagctgt   44940
tcgtcctgtc ggcgaagagc gcggcggcgc tggatgcgca ggcagcccgg ctgcgggacc   45000
acctggagaa gcacgtcgag cttggcctcg gcgatgtggc gttcagcctg gcgacgacgc   45060
gcagcgcgat ggagcaccgg ctgcggtgg ccgcgagctc gcgcgaggcg ctgcgagggg   45120
cgctttcggc cgcagcgcag gggcacacgc cgccgggagc cgtgcgtggg cgggcctcgg   45180
gcggcagcgc gccgaaggtg gtcttcgtgt ttcccggtca gggctcgcag tgggtgggca   45240
tgggccgaaa gctcatggcc gaagagccgg tcttccgggc ggcgctggag ggttgcgacc   45300
gggccatcga gcggaagcg ggctggtcgc tgctcgggga gctctccgcc gacgaggccg   45360
cctcgcagct cgggcgcatc gacgtggttc agccggtgct cttcgccatg gaagtagcgc   45420
tttctgcgct gtggcggtcg tggggagtgg agccggaagc ggtggtgggc cacagcatgg   45480
```

-continued

```
gcgaggttgc ggcggcgcac gtggccggcg cgctgtcgct cgaggacgcg gtggcgatca    45540
tctgccggcg cagccggctg ctgcggcgga tcagcggtca gggggagatg gcgctggtcg    45600
agctgtcgct ggaggaggcc gaggcggcgc tgcgtggcca tgagggtcgg ctgagcgtgg    45660
cggtgagcaa cagcccgcgc tcgaccgtgc tcgccggcga gccggcgcg ctctcggagg     45720 tgctggcggc gctgacggcc aagggggtgt tctggcggca ggtgaaggtg gacgtcgcca    45780
gccatagccc gcaggtcgac ccgctgcgcg aagagctgat cgcggcgctg ggagcgatcc    45840
ggccgcgagc ggctgcggtg ccgatgcgct cgacggtgac gggcggggtg atcgcgggtc    45900
cggagctcgg tgcgagctac tgggcggaca accttcggca gccggtgcgc ttcgctgcgg    45960
cggcgcaagc gctgctggag ggtggccccg cgctgttcat cgagatgagc ccgcacccga    46020
tcctggtgcc gccctggac gagatccaga cggcggccga gcaaggggc gctgcggtgg      46080 gctcgctgcg gcgagggcag gacgagcgcg cgacgctgct ggaggcgctg gggacgctgt    46140
gggcgtccgg ctatccggtg agctgggctc ggctgttccc cgcgggcggc aggcgggttc    46200
cgctgccgac ctatccctgg cagcacgagc ggtgctggat cgaggtcgag cctgacgccc    46260
gccgcctcgc cgcagccgac cccaccaagg actggttcta ccgaacggac tggcccgagg    46320
tgccccgcgc cgccccgaaa tcggagacag ctcatgggag ctggctgctg ttggccgaca    46380
ggggtggggt cggtgaggcg gtcgctgcag cgctgtcgac gcgcggactt tcctgcaccg    46440
tgcttcatgc gtcggctgac gcctccaccg tcgccgagca ggtatccgaa gctgccagtc    46500
gccgaaacga ctgcaggga gtcctctacc tgtggggcct cgacgccgtc gtcgatgctg      46560
gggcatcggc cgacgaagtc agcgaggcta ccgccgtgc caccgcaccc gtccttgggc      46620
tggttcgatt cctgagcgct cgcccccatc ctcctcgctt ctgggtggtg acccgcgggg    46680
catgcacggt gggcggcgag ccagaggcct ctctttgcca agcggcgttg tggggcctcg    46740
cgcgcgtcgc ggcgctggag cacccgctg cctggggtgg cctcgtggac ctggatcctc      46800
agaagagccc gacggagatc gagccctgg tggccgagct gctttcgccg gacgccgagg      46860
atcaactggc gttccgcagc ggtcgcaggc acgcagcacg ccttgtagcc gccccgccgg    46920
agggcgacgt cgcaccgata tcgctgtccg cggaggggag ctacctggtg acgggcgggc    46980
tgggtggcct tggtctgctc gtggctcggt ggctggtgga gcggggagct cgacatctgg    47040
tgctcaccag ccggcacggg ctgccagagc gacaggcgtc gggcggagag cagccgccgg    47100
aggcccgcgc gcgcatcgca gcggtcgagg ggctggaagc gcaggcgcg cgggtgaccg      47160 tggcagcggt ggatgtcgcc gaggccgatc ccatgacggc gctgctggcc gccatcgagc    47220
ccccgttgcg cggggtggtg cacgccgccg gcgtcttccc cgtgcgtcac ctggcggaga    47280
cggacgaggc cctgctggag tcggtgctcc gtcccaaggt ggccgggagc tggctgctgc    47340
accggctgct gcgcgaccgg cctctcgacc tgttcgtgct gttctcgtcg ggcgcggcg     47400 tgtggggtgg caaaggccaa ggcgcatacg ccgcggccaa tgcgttcctc gacgggctcg    47460
cgcaccatcg ccgcgcgcac tcgctgccgg cgttgagcct cgcctgggc ttatgggccg     47520 agggaggcat ggttgatgca aaggctcatg cacgtctgag cgacatcggg gtcctgccca    47580
tggccacggg gccggccttg tcggcgctgg agcgcctggt gaacaccagc gctgtccagc    47640
gttcggtcac acggatggac tgggcgcgct tcgcgccggt ctatgccgcg cgaggcggc     47700 gcaacttgct ttcggctctg gtcgcggagg acgagcgcg tgcgtctccc ccggtgccga     47760
cggcaaaccg gatctggcgc ggcctgtccg ttgcggagag ccgctcagcc ctctacgagc    47820
```

-continued

| | |
|---|---|
| tcgttcgcgg catcgtcgcc cgggtgctgg gcttctccga cccggcgcg ctcgacgtcg | 47880 |
| gccgaggctt cgccgagcag gggctcgact ccctgatggc tctggagatc cgtaaccgcc | 47940 |
| ttcagcgcga gctgggcgaa cggctgtcgg cgactctggc cttcgaccac ccgacggtgg | 48000 |
| agcggctggt ggcgcatctc ctcaccgacg tgctgaagct ggaggaccgg agcgacaccc | 48060 |
| ggcacatccg gtcggtggcg gcggatgacg acatcgccat cgtcggtgcc gcctgccggt | 48120 |
| tcccaggtgg ggatgagggc ctggagacat actggcggca tctggccgag ggcatggtgg | 48180 |
| tcagcaccga ggtgccagcc gaccggtggc gcgcggcgga ctggtacgac cccgatccgg | 48240 |
| aggttccggg ccggacctat gtggccaagg gtgccttcct ccgcgatgtg cgcagcttgg | 48300 |
| atgcggcgtt cttcgccatt tcccctcgtg aggcgatgag cctggacccg caacagcggc | 48360 |
| tgttgctgga ggtgagctgg gaggcgatcg agcgcgctgg ccaggacccg atggcgctgc | 48420 |
| gcgagagcgc cacgggcgtg ttcgtgggca tgatcgggag cgagcacgcc gagcgggtgc | 48480 |
| agggcctcga cgacgacgcg gcgttgctgt acggcaccac cggcaacctg ctcagcgtcg | 48540 |
| ccgctggacg gctgtcgttc ttcctgggtc tgcacggccc gacgatgacg gtggacaccg | 48600 |
| cctgctcgtc gtcgctggtg gcgttgcacc tcgcctgcca gagcctgcga ttgggcgagt | 48660 |
| gcgaccaggc cctggccggc gggtccagcg tgcttttgtc gccgcggtca ttcgtcgcgg | 48720 |
| cgtcgcgcat gcgtttgctt tcgccagatg ggcggtgcaa gacgttctcg gccgctgcag | 48780 |
| acggctttgc gcgggccgag ggctgcgccg tggtggtgct caagcggctc cgtgacgcgc | 48840 |
| agcgcgaccg cgaccccatc ctggcggtgg tcaggagcac ggcgatcaac cacgatggcc | 48900 |
| cgagcagcgg gctcacggtg cccagcggtc ctgcccagca ggcgttgcta cgccaggcgc | 48960 |
| tggcgcaagc gggcgtggcg ccggccgagg tcgatttcgt ggagtgccac gggacgggga | 49020 |
| cagcgctggg tgacccgatc gaggtgcagg cgctgggcgc ggtgtacggg cggggccgcc | 49080 |
| ccgcggagcg gccgctctgg ctgggcgctg tcaaggccaa cctcggccac ctggaggccg | 49140 |
| cggcgggctt ggccggcgtg ctcaaggtgc tcttggcgct ggagcacgag cagattccgg | 49200 |
| ctcaaccgga gctcgacgag ctcaacccgc acatcccgtg gcagagctg ccagtggccg | 49260 |
| ttgtccgcag ggcggtcccc tggccgcgcg gcgcgcgccc gcgtcgtgca ggcgtgagcg | 49320 |
| ctttcggcct gagcgggacc aacgcgcatg tggtgttgga ggaggcgccg gcggtggagc | 49380 |
| ctgtggccgc ggcccccgag cgcgcagcgg agctgttcgt cctgtcggcg aagagcgcgg | 49440 |
| cggcgctgga tgcgcaggca gcccggctgc gggaccacct ggagaagcat gtcgagcttg | 49500 |
| gcctcggcga tgtggcgttc agcctggcga cgacgcgcag cgcgatggag caccggctgg | 49560 |
| cggtggccgc gagctcgcgc gaggcgctgc gaggggcgct ttcggccgca gcgcagggc | 49620 |
| acacgccgcc gggagccgtg cgtgggcggg cctcggcgg cagcgcgccg aaggtggtct | 49680 |
| tcgtgtttcc cggccagggc tcgcagtggg tgggcatggg ccgaaagctc atggccgaag | 49740 |
| agccggtctt ccggcggcg ctggagggtt gcgaccgggc catcgaggcg gaagcgggct | 49800 |
| ggtcgctgct cggggagctc tccgccgacg aggccgcctc gcagctcggg cgcatcgacg | 49860 |
| tggttcagcc ggtgctgttc gccatggaag tagcgctttc tgcgctgtgg cggtcgtggg | 49920 |
| gagtggagcc ggaagcggtg gtgggccaca gcatgggcga ggttgcggcg gcgcacgtgg | 49980 |
| ccggcgcgct gtcgctcgag gacgcggtgg cgatcatctg ccggcgcagc cggctgctgc | 50040 |
| ggcggatcag cggtcagggg gagatggcgc tggtcgagct gtcgctggag gaggccgagg | 50100 |
| cggcgctgcg tggccatgag ggtcggctga gcgtggcgg gagcaacagc ccgcgctcga | 50160 |
| ccgtgctcgc cggcgagccg gcggcgctct cggaggtgct ggcggcgctg acggccaagg | 50220 |

```
gggtgttctg gcggcaggtg aaggtggacg tcgccagcca tagcccgcag gtcgacccgc    50280
tgcgcgaaga gctgatcgcg gcgctgggag cgatccggcc gcgagcggct gcggtgccga    50340
tgcgctcgac ggtgacgggc ggggtgatcg cgggtccgga gctcggtgcg agctactggg    50400
cggacaacct tcggcagccg gtgcgcttcg ctgcggcggc gcaagcgctg ctggagggtg    50460
gccccgcgct gttcatcgag atgagcccgc acccgatcct ggtgccgccc ctggacgaga    50520
tccagacggc ggccgagcaa gggggcgctg cggtgggctc gctgcggcga gggcaggacg    50580
agcgcgcgac gctgctggag gcgctgggga cgctgtgggc gtccggctat ccggtgagct    50640
gggctcggct gttccccgcg gcggcaggc  gggttccgct gccgacctat ccctggcagc    50700
acgagcggta ctggatcgag gacagcgtgc atgggtcgaa gccctcgctg cggcttcggc    50760
agcttcgcaa cggcgccacg gaccatccgc tgctcggggc tccattgctc gtctcggcgc    50820
gacccggagc tcacttgtgg gagcaagcgc tgagcgacga gaggctatcc tacctttcgg    50880
aacatagggt ccatggcgaa gccgtgttgc ccagcgcggc gtatgtagag atggcgctcg    50940
ccgccggcgt agatctctat ggcacggcga cgctggtgct ggagcagctg gcgctcgagc    51000
gagccctcgc cgtgccctcc gaaggcggac gcatcgtgca agtggccctc agcgaagaag    51060
gtcccggtcg ggcctcattc caggtatcga gtcgtgagga ggcaggtagg agctgggtgc    51120
ggcacgccac ggggcacgtg tgtagcggcc agagctcagc ggtgggagcg ttgaaggaag    51180
ctccgtggga gattcaacgg cgatgtccga gcgtcctgtc gtcggaggcg ctctatccgc    51240
tgctcaacga gcacgccctc gactatggtc cctgcttcca gggcgtggag caggtgtggc    51300
tcggcacggg ggaggtgctc ggccgggtac gcttgccagg agacatggca tcctcaagtg    51360
gcgcctaccg gattcatccc gccttgttgg atgcatgttt tcaggtgctg acagcgctgc    51420
tcaccacgcc ggaatccatc gagattcgga ggcggctgac ggatctccac gaaccggatc    51480
tcccgcggtc cagggctccg gtgaatcaag cggtgagtga cacctggctg tgggacgccg    51540
cgctggacgg tggacggcgc cagagcgcga gcgtgcccgt cgacctggtg ctcggcagct    51600
tccatgcgaa gtgggaggtc atggagcgcc tcgcgcaggc gtacatcatc ggcactctcc    51660
gcatatggaa cgtcttctgc gctgctggag agcgtcacac gatagacgag ttgctcgtca    51720
ggcttcaaat ctctgtcgtc tacaggaagg tcatcaagcg atggatggaa caccttgtcg    51780
cgatcggcat cctcgtaggg gacgagagc  attttgtgag ctctcagccg ctgccggagc    51840
ctgatttggc ggcggtgctc gaggaggccg ggagggtgtt cgccgacctc ccagtcctat    51900
ttgagtggtg caagttttgcc ggggaacggc tcgcggacgt attgaccggt aagacgctcg    51960
cgctcgagat cctcttccct ggtggctcgt tcgatatggc ggagcgaatc tatcgagatt    52020
cgcccatcgc ccgttactcg aacggcatcg tgcgcggtgt cgtcgagtcg gcggcgcggg    52080
tggtagcacc gtcgggaatg ttcagcatct tggagatcgg agcagggacg ggcgcgacca    52140
ccgccgccgt cctcccggtg ttgctgcctg accggacgga gtaccatttc accgatgttt    52200
ctccgctctt ccttgctcgc gcggagcaaa gatttcgaga ttatccattc ctgaagtatg    52260
gcattctgga tgtcgaccag gagccagctg gccagggata cgcacatcag aggtttgacg    52320
tcatcgtcgc ggccaatgtc atccatgcga cccgcgatat aagagccacg gcgaagcgtc    52380
tcctgtcgtt gctcgcgccc ggaggccttc tggtgctggt cgagggcaca gggcatccga    52440
tctggttcga tatcaccacg ggattgattg aggggtggca gaagtacgaa gatgatcttc    52500
gtatcgacca tccgctcctg cctgctcgga cctggtgtga cgtcctgcgc cgggtaggct    52560
```

-continued

| | | | | |
|---|---|---|---|---|
| ttgcggacgc | cgtgagtctg | ccaggcgacg | gatctccggc | ggggatcctc ggacagcacg | 52620 |
| tgatcctctc | gcgcgcgccg | ggcatagcag | gagccgcttg | tgacagctcc ggtgagtcgg | 52680 |
| cgaccgaatc | gccggccgcg | cgtgcagtac | ggcaggaatg | ggccgatggc tccgctgacg | 52740 |
| tcgtccatcg | gatggcgttg | gagaggatgt | acttccaccg | ccggccgggc cggcaggttt | 52800 |
| gggtccacgg | tcgattgcgt | accggtggag | gcgcgttcac | gaaggcgctc gctggagatc | 52860 |
| tgctcctgtt | cgaagacacc | gggcaggtcg | tggcagaggt | tcagggctc cgcctgccgc | 52920 |
| agctcgaggc | ttctgctttc | gcgccgcggg | acccgcggga | agagtggttg tacgctttgg | 52980 |
| aatggcagcg | caaagaccct | ataccagagg | ctccggcagc | cgcgtcttct tcctccgcgg | 53040 |
| gggcttggct | cgtgctgatg | gaccaggcg | ggacaggcgc | tgcgctcgta tcgctgctgg | 53100 |
| aagggcgagg | cgaggcgtgc | gtgcgcgtca | tcgcgggtac | ggcatacgcc tgcctcgcgc | 53160 |
| cggggctgta | tcaagtcgat | ccggcgcagc | cagatggctt | tcataccctg ctccgcgatg | 53220 |
| cattcggcga | ggaccggatt | tgtcgcgcgg | tagtgcatat | gtggagcctt gatgcgacgg | 53280 |
| cagcagggga | gagggcgaca | gcggagtcgc | ttcaggccga | tcaactcctg gggagcctga | 53340 |
| gcgcgctttc | tctggtgcag | gcgctggtgc | gccggaggtg | gcgcaacatg ccgcggcttt | 53400 |
| ggctcttgac | ccgcgccgtg | catgcggtgg | gcgcggagga | cgcagcggcc tcggtggcgc | 53460 |
| aggcgccggt | gtggggcctc | ggtcggacgc | tcgcgctcga | gcatccagag ctgcggtgca | 53520 |
| cgctcgtgga | cgtgaacccg | cgccgtctc | cagaggacgc | agccgcactg gcggtggagc | 53580 |
| tcggggcgag | cgacagagag | gaccaggtcg | cattgcgctc | ggatgccgc tacgtggcgc | 53640 |
| gcctcgtgcg | gagctccttt | tccggcaagc | ctgctacgga | ttgcggcatc cgggcggacg | 53700 |
| gcagctatgt | gatcaccgat | ggcatgggga | gagtggggct | ctcggtcgcg caatggatgg | 53760 |
| tgatgcaggg | ggcccgccat | gtggtgctcg | tggatcgcgg | cggcgcttcc gaggcatccc | 53820 |
| gggatgccct | ccgtccatg | gccgaggctg | gcgcggaggt | gcagatcgtg gaggccgacg | 53880 |
| tggctcggcg | cgacgatgtc | gctcggctcc | tctcgaagat | cgaaccgtcg atgccgccgc | 53940 |
| ttcgggggat | cgtgtacgtg | gacgggacct | tccaggcgca | ctcctcgatg ctggagctgg | 54000 |
| atgcccgtcg | cttcaaggag | tggatgtatc | ccaaggtgct | cggagcgtgg aacctgcacg | 54060 |
| cgctgaccag | ggatagatcg | ctggacttct | tcgtcctgta | ttcctcgggc acctcgcttc | 54120 |
| tgggcttgcc | aggacagggg | agccgcgccg | ccggtgacgc | cttcttggac gccatcgcgc | 54180 |
| atcaccggtg | caagtgggc | cttacagcga | tgagcatcaa | ctggggattg ctctccgaag | 54240 |
| catcatcgcc | ggcgaccccg | aacgacggcg | gagcacggct | cgaataccgg gggatggaag | 54300 |
| gcctcacgct | ggagcaggga | gcggcggcgc | tcgggcgctt | gctcgcacga cccagggcgc | 54360 |
| aggtagggt | gatgcggctg | aatctgcgcc | agtggttgga | gttctatccc aacgcggccc | 54420 |
| gattggcgct | gtgggcggag | ctgctgaagg | agcgtgaccg | cgccgaccga ggcgcgtcga | 54480 |
| acgcgtcgaa | cctgcgcgag | gcgctgcaga | gcgccaggcc | cgaagatcgt cagttgattc | 54540 |
| tggagaagca | cttgagcgag | ctgttgggc | ggggctgcg | ccttccgccg gagaggatcg | 54600 |
| agcggcacgt | gccgttcagc | aatctcggca | tggactcgct | gataggcctg gagctccgca | 54660 |
| accgcatcga | ggccgcgctc | ggcatcaccg | tgccggcgac | cctgctatgg acctacccta | 54720 |
| acgtagcagc | tctgagcggg | agcttgctag | acattctgtt | tccgaatgcc ggcgcgaccc | 54780 |
| acgctccggc | caccgagcgg | gagaagagct | tcgagaacga | tgccgcagat ctcgaggctc | 54840 |
| tgcggggcat | gacggacgag | cagaaggacg | cgttgctcgc | cgaaaagctg gcgcagctcg | 54900 |
| cgcagatcgt | tggtgagtaa | gggaccgagg | gagtatggcg | accacgaatg ccgggaagct | 54960 |

```
tgagcatgcc cttctgctca tggacaagct tgcgaaaaag aacgcgtctt tggagcaaga  55020
gcggaccgag ccgatcgcca tcgtaggcat tggctgccgc ttccccggcg gagcggacac  55080
tccggaggca ttctgggagc tgctcgactc aggccgagac gcggtccagc cgctcgaccg  55140
gcgctgggcg ctggtcggcg tccatcccag cgaggaggtg ccgcgctggg ccggactgct  55200
caccgaggcg gtggacggct tcgacgccgc gttctttggc acctcgcctc gggaggcgcg  55260
gtcgctcgat cctcagcaac gcctgctgct ggaggtcacc tgggaagggc tcgaggacgc  55320
cggcatcgca ccccagtccc tcgacggcag ccgcaccggg tgttcctgg gcgcatgcag  55380
cagcgactac tcgcataccg ttgcgcaaca gcggcgcgag gagcaggacg catacgacat  55440
caccggcaat acgctcagcg tcgccgccgg acggttgtct tatacgctag gctgcaggg  55500
accctgcctg accgtcgaca cggcctgctc gtcgtcgctc gtggccatcc accttgcctg  55560
ccgcagcctg cgcgctcgcg agagcgatct cgcgctggcg ggaggcgtca acatgctcct  55620
ttcgtccaag acgatgataa tgctggggcg catccaggcg ctgtcgcccg atggccactg  55680
ccggacattc gacgcctcgg ccaacgggtt cgtccgtggg gagggctgcg gtatggtcgt  55740
gctcaaacgg ctctccgacg cccagcgaca cggcgatcgg atctgggctc tgatccgggg  55800
ttcggccatg aatcaggatg gccggtcgac agggttgatg gcacccaatg tgctcgctca  55860
ggaggcgctc ttgcgcgagg cgctgcagag cgctcgcgtc gacgccgggg ccatcggtta  55920
tgtcgagacc cacggaacgg ggacctcgct cggcgacccg atcgaggtcg aggcgctgcg  55980
tgccgtgttg gggccggcgc gggccgatgg gagccgctgc gtgctgggcg cagtgaagac  56040
aaacctcggc cacctggagg gcgctgcagg cgtggcgggt ttgatcaagg cggcgctggc  56100
tctgcaccac gaactgatcc cgcgaaacct ccatttccac acgctcaatc cgcggatccg  56160
gatcgagggg accgcgctcg cgctggcgac ggagccggtg ccgtggccgc gggcggggcc  56220
accgcgcttc gcggggtga gcgcgttcgg cctcagcggc accaacgtcc atgtcgtgct  56280
ggaggaggcg ccggccacgg tgctcgcacc ggcgacgccg gggcgctcag cggagctttt  56340
ggtgctgtcg gcgaagagcg ccgccgcgct ggacgcacag gcggcgcggc tctcagcgca  56400
catcgccgcg tacccggagc agggtctcgg agacgtcgcg ttcagcctgg tatcgacgcg  56460
tagcccgatg gagcaccggc tcgcggtggc ggcgacctcg cgcgaggcgc tgcgaagcgc  56520
gctggaggtt gcggcgcagg ggcagacccc ggcaggcgcg gcgcgcggca gggccgcttc  56580
ctcgcccggc aagctcgcct tcctgttcgc cgggcagggc gcgcaggtgc cgggcatggg  56640
ccgtgggttg tgggaggcgt ggccggcgtt ccgcgagacc ttcgaccggt gcgtcacgct  56700
cttcgaccgg gagctccatc agccgctctg cgaggtgatg tgggccgagc cgggcagcag  56760
caggtcgtcg ttgctggacc agacggcgtt cacccagccg gcgctctttg cgctggagta  56820
cgcgctggcc gcgctcttcc ggtcgtgggg cgtggagccg gagctcgtcg ctggccatag  56880
cctcggcgag ctggtggccg cctgcgtggc gggtgtgttc tccctcgagg acgccgtgcg  56940
cttggtggtc gcgcgcggcc ggttgatgca ggcgctgccg gccggcggcg cgatggtatc  57000
gatcgccgcg ccggaggccg acgtggctgc cgcggtggcg ccgcacgcag cgttggtgtc  57060
gatcgcggca gtcaatgggc cggagcaggt ggtgatcgcg gcgccgagaa attcgtgca  57120
gcagatcgcg gcggcgttcg cggcgcgggg ggcgcgaacc aaaccgctgc atgtctcgca  57180
cgcgttccac tcgccgctca tggatccgat gctggaggcg ttccggcggg tgactgagtc  57240
ggtgacgtac cggcggcctt cgatcgcgct ggtgagcaac ctgagcggga agccctgcac  57300
```

-continued

```
cgatgaggtg agcgcgccgg gttactgggt gcgtcacgcg cgagaggcgg tgcgcttcgc    57360
ggacggagtg aaggcgctgc acgcggccgg tgcgggcctc ttcgtcgagg tggggccgaa    57420
gccgacgctg ctcggccttg tgccggcctg cctgccggat gccaggccgg tgctgctccc    57480
agcgtcgcgc gccgggcgtg acgaggctgc gagcgcgcta aggcgctgg gtgggttctg     57540 ggtcgtcggt ggatcggtca cctggtcggg tgtcttccct tcgggcggac ggcgggtacc    57600
gctgccaacc tatccctggc agcgcgagcg ttactggatc gaagcgccgg tcgatcgtga    57660
ggcggacggc accggccgtg ctcggcgggg ggccacccc cttctgggtg aagtctttc      57720 cgtgtcgacc catgccggtc tgcgcctgtg ggagacgacg ctggaccgaa agcggctgcc    57780
gtggctcggc gagcaccggg cgcagggga gtcgtgttt cctggcgccg ggtacctgga      57840
gatggcgctg tcgtcggggg ccgagatctt gggcgatgga ccgatccagg tcacggatgt    57900
ggtgctcatc gagacgctga ccttcgcggg cgatacggcg gtaccggtcc aggtggtgac    57960
gaccgaggag cgaccgggac ggctgcggtt ccaggtagcg agtcgggagc cggggaacg     58020 tcgcgcgccc ttccggatcc acgcccgcgc cgtgctgcgc cggatcgggc gcgtcgagac    58080
cccggcgagg tcgaacctcg ccgccctgcg cgcccggctt catgccgccg tgcccgctgc    58140
ggctatctat ggtgcgctcg ccgagatggg gcttcaatac ggcccggcgt tgcgggggct    58200
cgccgagctg tggcggggtg agggcgaggc gctgggcagg gtgagactgc ctgaggccgc    58260
cggctccgcg acagcctacc agctgcatcc ggtgctgctg gacgcgtgcg tccaaatgat    58320
tgttggcgcg ttcgccgatc gcgatgaggc gacgccgtgg gcgccggtgg aggtgggctc    58380
ggtgcggctg ttccagcggt ctcctgggga gctatggtgc catgcgcgcg tcgtgagcga    58440
tggtcaacag gcctccagcc ggtggagcgc cgactttgag ttgatggacg gtacgggcgc    58500
ggtggtcgcc gagatctccc ggctggtggt ggagcggctt gcgagcggtg tacgccggcg    58560
cgacgcagac gactggttcc tggagctgga ttgggagccc gcggcgctcg gtgggcccaa    58620
gatcacagcc ggccggtggc tgctgctcgg cgagggtggt gggctcgggc gctcgttgtg    58680
ctcggcgctg aaggccgccg gccatgtcgt cgtccacgcc gcggggacg acacgagcac      58740 tgcaggaatg cgcgcgctcc tggccaacgc gttcgacggc caggccccga cggccgtggt    58800
gcacctcagc agcctcgacg ggggcggcca gctcggcccg gggctcgggg gcagggcgc     58860 gctcgacgcg ccccggagcc cagatgtcga tgccgatgcc ctcgaatcgg cgctgatgcg    58920
tggttgcgac agcgtgctct ccctggtgca agcgctggtc ggcatggacc tccgaaacgc    58980
gccgcggctg tggctcttga cccgcggggc tcaggcggcc gccgccggcg atgtctccgt    59040
ggtgcaagcg ccgctgttgg ggctgggccg caccatcgcc ttggagcacg ccgagctgcg    59100
ctgtatcagc gtcgacctcg atccagccga gcctgaaggg gaagccgatg ctttgctggc    59160
cgagctactt gcagatgatg ccgaggagga ggtcgcgctg cgcggtggcg accggctcgt    59220
tgcgcggctc gtccaccggc tgcccgacgc tcagcgccgg gagaaggtcg agcccgccgg    59280
tgacaggccc ttccggctag agatcgatga acccggcgcg ctggaccaac tggtgctccg    59340
agccacgggg cggcgcgctc ctggtccggg cgaggtcgag atctccgtcg aagcggcggg    59400
gctcgactcc atcgacatcc agctggcgtt gggcgttgct cccaatgatc tgcctggaga    59460
agaaatcgag ccgttggtgc tcggaagcga gtgcgccggg cgcatcgtcg ctgtgggcga    59520
gggcgtgaac ggccttgtgg tgggccagcc ggtgatcgcc cttgcggcgg gagtatttgc    59580
tacccatgtc accacgtcgg ccacgctggt gttgcctcg cctctgggc tctcggcgac       59640 cgaggcggcc gcgatgcccc tcgcgtattt gacggcctgg tacgccctcg acaaggtcgc    59700
```

```
ccacctgcag gcggggagc gggtgctgat ccatgcggag gccgtggtg tcggtctttg      59760 cgcggtgcga tgggcgcagc gcgtgggcgc cgaggtgtat gcgaccgccg acacgcccga    59820
gaaccgtgcc tacctggagt cgctgggcgt gcggtacgtg agcgattccc gctcgggccg    59880
gttcgtcaca gacgtgcatg catggacgga cggcgagggt gtggacgtcg tgctcgactc    59940
gctttcgggc gagcgcatcg acaagagcct catggtcctg cgcgcctgtg gtcgccttgt    60000
gaagctgggc aggcgcgacg actgcgccga cacgcagcct gggctgccgc cgctcctacg    60060 gaattttttcc ttctcgcagg tggacttgcg gggaatgatg ctcgatcaac cggcgaggat   60120
ccgtgcgctc ctcgacgagc tgttcgggtt ggtcgcagcc ggtgccatca gcccactggg    60180
gtcggggttg cgcgttggcg gatccctcac gccaccgccg gtcgagacct tcccgatctc    60240
tcgcgcagcc gaggcattcc ggaggatggc gcaaggacag catctcggga agctcgtgct    60300
cacgctggac gacccggagg tgcggatccg cgctccggcc gaatccagcg tcgccgtccg    60360
cgcggacggc acctaccttg tgaccggcgg tctgggtggc ctcggtctgc gcgtggccgg    60420
atggctggcc gagcggggcg cggggcaact ggtgctggtg ggccgctccg gtgcggcgag    60480
cgcagagcag cgagccgccg tggcggcgct ggaggcccac ggcgcgcgcg tcacggtggc    60540
gaaagcggac gtcgccgatc ggtcacagat cgagcgggtc ctccgcgagg ttaccgcgtc    60600
ggggatgccg ctgcggggtg tcgtgcatgc ggcaggtctc gtggatgacg ggctgctgat    60660
gcagcagact ccggcgcggt tccgcacggt gatgggacct aaggtccagg gggccttgca    60720
cttgcacacg ctgacacgcg aagcgcctct ttccttcttc gtgctgtacg cttctgcagc    60780
tgggcttttc ggctcgccag gccagggcaa ctatgccgca gccaacgcgt tcctcgacgc    60840
cctttcgcat caccgaaggg cgcagggcct gccggcgctg agcatcgact ggggcatgtt    60900
cacggaggtg gggatggccg ttgcgcaaga aaaccgtggc gcgcggcaga tctctcgcgg    60960 gatgcgggc atcacccccg atgagggtct gtcagctctg gcgcgcttgc tcgagggtga    61020
tcgcgtgcag acggggtga taccgatcac tccgcggcag tgggtggagt tctacccggc    61080
aacagcggcc tcacggaggt tgtcgcggct ggtgaccacg cagcgcgcgg tcgctgatcg    61140
gaccgccggg gatcgggacc tgctcgaaca gcttgcgtcg gctgagccga gcgcgcgggc    61200
ggggctgctg caggacgtcg tgcgcgtgca ggtctcgcat gtgctgcgtc tccctgaaga    61260
caagatcgag gtggatgccc cgctctcgag catgggcatg gactcgctga tgagcctgga    61320
gctgcgcaac cgcatcgagg ctgcgctggg cgtcgccgcg cctgcagcct tggggtggac    61380
gtacccaacg gtagcagcga taacgcgctg gctgctcgac gacgccctcg tcgtccggct    61440
tggcggcggg tcgacacgg acgaatcgac ggcgagcgcc ggttcgttcg tccacgtcct    61500
ccgctttcgt cctgtcgtca agccgcgggc tcgtctcttc tgttttcacg gttctggcgg    61560
ctcgcccgag ggcttccgtt cctggtcgga gaagtctgag tggagcgatc tggaaatcgt    61620
ggccatgtgg cacgatcgca gcctcgcctc cgaggacgcg cctggtaaga agtacgtcca    61680
agaggcggcc tcgctgattc agcactatgc agacgcaccg tttgcgttag tagggttcag    61740
cctgggtgtc cggttcgtca tggggacagc cgtggagctc gccagtcgtt ccggcgcacc    61800
ggctccgctg gccgtcttca cgttgggcgg cagcttgatc tcttcttcag agatcacccc    61860
ggagatggag accgatataa tagccaagct cttcttccga aatgccgcgg gtttcgtgcg    61920
atccacccaa caagtccagg ccgatgctcg cgcagacaag gtcatcacag acaccatggt    61980
ggctccggcc cccgggggact cgaaggagcc gcccgtgaag atcgcggtcc ctatcgtcgc    62040
```

| | | | | |
|---|---|---|---|---|
| catcgccggc | tcggacgatg | tgatcgtgcc | tccgagcgac | gttcaggatc tacaatctcg 62100 |
| caccacggag | cgcttctata | tgcatctcct | tcccggagat | cacgaatttc tcgtcgatcg 62160 |
| agggcgcgag | atcatgcaca | tcgtcgactc | gcatctcaat | ccgctgctcg ccgcgaggac 62220 |
| gacgtcgtca | ggcccgcgt | tcgaggcaaa | atgatggcag | cctccctcgg gcgcgcgaga 62280 |
| tggttgggag | cagcgtgggc | gctggcggcc | ggcggcaggc | cgcggaggcg catgagcctt 62340 |
| cctggacgtt | tgcagtatag | gagattttat | gacacaggag | caagcgaatc agagtgagac 62400 |
| gaagcctgct | ttcgacttca | agccgttcgc | gcctgggtac | gcggaggacc cgttccccgc 62460 |
| gatcgagcgc | ctgagagagg | caaccccat | cttctactgg | gatgaaggcc gctcctgggt 62520 |
| cctcacccga | taccgacg | tgtcggcggt | gttccgcgac | gaacgcttcg cggtcagtcg 62580 |
| agaagagtgg | gaatcgagcg | cggagtactc | gtcggccatt | cccgagctca gcgatatgaa 62640 |
| gaagtacgga | ttgttcgggc | tgccgccgga | ggatcacgct | cgggtccgca agctcgtcaa 62700 |
| cccgtcgttt | acgtcacgcg | ccatcgacct | gctgcgcgcc | gaaatacagc gcaccgtcga 62760 |
| ccagctgctc | gatgctcgct | ccggacaaga | ggagttcgac | gttgtgcggg attacgcgga 62820 |
| gggaatcccg | atgcgcgcga | tcagcgctct | gttgaaggtt | ccggccgagt gtgacgagaa 62880 |
| gttccgtcgc | ttcggctcgg | cgactgcgcg | cgcgctcggc | gtgggtttgg tgccccaggt 62940 |
| cgatgaggag | accaagaccc | tggtcgcgtc | cgtcaccgag | gggctcgcgc tgctccatga 63000 |
| cgtcctcgat | gagcggcgca | ggaacccgct | cgaaaatgac | gtcttgacga tgctgcttca 63060 |
| ggccgaggcc | gacggcagca | ggctgagcac | gaaggagctg | gtcgcgctcg tgggtgcgat 63120 |
| tatcgctgct | ggcaccgata | ccacgatcta | ccttatcgcg | ttcgctgtgc tcaacctgct 63180 |
| gcggtcgccc | gaggcgctcg | agctggtgaa | ggccgagccc | gggctcatga ggaacgcgct 63240 |
| cgatgaggtg | ctccgcttcg | acaatatcct | cagaatagga | actgtgcgtt tcgccaggca 63300 |
| ggacctggag | tactgcgggg | catcgatcaa | gaaagggag | atggtctttc tcctgatccc 63360 |
| gagcgccctg | agagatggga | ctgtattctc | caggccagac | gtgtttgatg tgcgacggga 63420 |
| cacgggcgcg | agcctcgcgt | acggtagagg | cccccatgtc | tgccccgggg tgtcccttgc 63480 |
| tcgcctcgag | gcggagatcg | ccgtgggcac | catcttccgt | aggttccccg agatgaagct 63540 |
| gaaagaaact | cccgtgtttg | ataccaccc | cgcgttccgg | aacatcgaat cactcaacgt 63600 |
| catcttgaag | ccctccaaag | ctggatagct | cgcggggta | tcgcttcccg aacctcattc 63660 |
| cctcatgata | cagctcgcgc | gcgggtgctg | tctgccgcgg | gtgcgattcg atccagcgga 63720 |
| caagcccatt | gtcagcgcgc | gaagatcgaa | tccacggccc | ggagaagagc ccgtccgggt 63780 |
| gacgtcggaa | gaagtgccgg | gcgccgccct | gggagcgcaa | agctcgctcg ttcgcgctca 63840 |
| gcacgccgct | cgtcatgtcc | ggccctgcac | ccgcgccgag | gagccgcccg ccctgatgca 63900 |
| cggcctcacc | gagcggcagg | ttctgctctc | gctcgtcgcc | ctcgcgctcg tcctcctgac 63960 |
| cgcgcgcgcc | ttcggcgagc | tcgcgcggcg | gctgcgccag | cccgaggtgc tcggcgagct 64020 |
| cttcggcggc | gtggtgctgg | gccgtccgt | cgtcggcgcg | ctcgctcctg ggttccatcg 64080 |
| agtcctcttc | caggatccgg | cggtcgggt | cgtgctctcc | ggcatctcct ggataggcgc 64140 |
| gctcgtcctg | ctgctcatgg | cgggtatcga | ggtcgatgtg | agcatcctgc gcaaggaggc 64200 |
| gcgcccggg | gcgctctcgg | cgctcggcgc | gatcgcgccc | ccgctgcgca cgccggggcc 64260 |
| gctggtgcag | cgcatgcagg | gcgcgttcac | gtgggatctc | gacgtctcgc cgcgacgctc 64320 |
| tgcgcaagcc | tgagcctcgg | cgcctgctcg | tacacctcgc | cggtgctcgc tccgcccgcg 64380 |
| gacatccggc | cgcccgccgc | ggcccagctc | gagccggact | cgccggatga cgaggccgac 64440 |

```
gaggccgacg aggcgctccg cccgttccgc gacgcgatcg ccgcgtactc ggaggccgtt    64500
cggtgggcgg aggcggcgca gcggccgcgg ctggagagcc tcgtgcggct cgcgatcgtg    64560
cggctgggca aggcgctcga caaggtccct ttcgcgcaca cgacggccgg cgtctcccag    64620
atcgccggca gactccagaa cgatgcggtc tggttcgatg tcgccgcccg gtacgcgagc    64680
ttccgcgcgg cgacggagca cgcgctccgc gacgcggcgt cggccatgga ggcgctcgcg    64740
gccggcccgt accgcggatc gagccgcgtg tccgctgccg tagggagtt tcgggggag    64800 gcggcgcgcc ttcaccccgc ggaccgtgta cccgcgtccg accagcagat cctgaccgcg    64860
ctgcgcgcag ccgagcgggc gctcatcgcg ctctacactg cgttcgcccg tgaggagtga    64920
gcctctctcg ggcgcagccg agcggcggcg tgccggtggt tccctcttcg caaccatgac    64980
cggagccgcg ctcggtccgc gcagcggcta gcgcgcgtcg cggcagagat cgctggagcg    65040
acaggcgacg acccgcccga gggtgtcgaa cggattgccg cagccctcat tgcggatccc    65100
ctccagacac tcgttcagct gcttggcgtc gatgccgcct gggcactcgc cgaaggtcag    65160
ctcgtcgcgc cactcggatc ggatcttgtt cgagcacgcg tccttgctcg aatactcccg    65220
gtcttgtccg atgttgttgc accgcgcctc gcggtcgcac cgcgccgcca cgatgctatc    65280
gacggcgctg ccgactggca ccggcgcctc gccctgcgcg ccacccgggg tttgcgcctc    65340
cccgcctgac cgcttttcgc cgccgcacgc cgcgagcagg ctcattcccg acaccgagat    65400
caggcccacg accagcttcc cagcaatctt ttgcatggct tcccctccct cacgacacgt    65460
cacatcagag actctccgct cggctcgtcg gttcgacagc cggcgacggc cacgagcaga    65520
accgtccccg accagaacag ccgcatgcgg gtttctcgca acatgccccg acatccttgc    65580
gactagcgtg cctccgctcg tgccgagatc ggctgtcctg tgcgacggca atatcctgcg    65640 atcgccggg caggaggtac cgacacgggc gccgggcggg aggtgccgcc acgggctcga    65700
aatgtgctgc ggcaggcgcc tccatgcccg cagccgggaa cgcggcgccc ggccagcctc    65760
ggggtgacgc cgcaaacggg agatgctccc ggagaggcgc cgggcacagc cgagcgccgt    65820
caccaccgtg cgcactcgtg agctccagct cctcggcata gaagagaccg tcactcccgg    65880
tccgtgtagg cgatcgtgct gatcagcgcg ttctccgcct gacgcgagtc gagccgggta    65940
tgctgcacga caatgggaac gtccgattcg atcacgctgg catagtccgt atcgcgcggg    66000
atcggctcgg gttcggtcag atcgttgaac cggacgtgcc gggtgcgcct cgctgggacg    66060
gtcacccggt acggcccggc ggggtcgcgg tcgctgaagt agacggtgat ggcgacctgc    66120
gcgtcccggt ccgacgcatt caacaggcag gccgtctcat ggctcgtcat ctgcggctcg    66180
ggtccgttgc tccggcctgg gatgtagccc tctgcgattg cccagcgcgt ccgcccgatc    66240
ggcttctcca tatgtcctcc ctgctggctc ctctttggct gcctccctct gctgtccagg    66300
agcgacggcc tcttctcccg acgcgctcgg ggatccatgg ctgaggatcc tcgccgagcg    66360
ctccttgccg accggcgcgc cgagcgccga cgggctttga aagcacgcga ccggacacgt    66420
gatgccggcc cgacgaggcc gccccgcgtc tgatcccgat cgtgacatcg cgacgtccgc    66480
cggcgcctct gcaggccggc ctgagcgttg cgcggtcatg gtcgtcctcg cgtcaccgcc    66540
acccgccgat tcacatccca ccgcggcacg acgcttgctc aaaccgcggc gagacggccg    66600
ggcggctgtg gtaccggcca gcccggacgc gaggcccgag agggacagtg ggtccgccgt    66660
gaagcagtga ggcgatcgag gtggcagatg aaacacgttg acacgggccg acgagtcggc    66720
cgccggatag ggctcacgct cggtctcctc gcgagcatgg cgctcgccgg ctgtggcggc    66780
```

-continued

```
ccgagcgaga aaatcgtgca gggcacgcgg ctcgcgcccg cgccgatgc gcacgtcgcc    66840 gccgacgtcg accccgacgc cgcgaccacg cggctggcgg tggacgtcgt tcacctctcg    66900
ccgcccgagc gcatcgaggc cggcagcgag cggttcgtcg tctggcagcg tccgagctcc    66960
gagtccccgt ggcaacgggt cggagtgctc gactacaacg ctgccagccg aagaggcaag    67020
ctggccgaga cgaccgtgcc gcatgccaac ttcgagctgc tcatcaccgt cgagaagcag    67080
agcagccctc agtctccatc ttctgccgcc gtcatcgggc cgacgtccgt cgggtaacat    67140
cgcgctatca gcagcgctga gcccgccagc aggccccaga gccctgcctc gatcgccttc    67200
tccatcatat catccctgcg tactcctcca gcgacggccg cgtcgaagca accgccgtgc    67260
cggcgcggct ctacgtgcgc gacaggagag cgtcctggcg cggcctgcgc atcgctggaa    67320
ggatcggcgg agcatggaga agaatcgag gatcgcgatc tacggcgcca tcgcagccaa    67380
cgtggcgatc gcggcggtca agttcatcgc cgccgccgtg accggcagct cggcgatgct    67440
ctccgagggc gtgcactccc tcgtcgatac tgcagacggg ctcctcctcc tgctcggcaa    67500
gcaccggagc gcacgcccgc ccgacgccga gcatccgttc ggccacggca aggagctcta    67560
tttctggacg ctgatcgtcg ccatcatgat cttcgccgcg ggcggcggcg tctcgatcta    67620
cgaagggatc ttgcacctct tgcacccgcg ccagatcgag gatccgacgt ggaactacgt    67680
cgtcctcggc gcagcggccg tcttcgaggg gacgtcgctc atcatctcga tccacgagtt    67740
caagaagaag gacggacagg gctacctcgc ggcgatgcgg tccagcaagg acccgacgac    67800
gttcacgatc gtcctggagg actccgcggc gctcgccggg ctcaccatcg ccttcctcgg    67860
cgtctggctc gggcaccgcc tgggaaaccc ctacctcgac ggcgcggcgt cgatcggcat    67920
cggcctcgtg ctcgccgcgg tcgcggtctt cctcgccagc cagagccgtg ggctcctcgt    67980
gggggagagc gcggacaggg agctcctcgc cgcgatccgc gcgctcgcca gcgcagatcc    68040
tggcgtgtcg gcggtgggc ggcccctgac gatgcacttc ggtccgcacg aagtcctggt    68100
cgtgctgcgc atcgagttcg acgccgcgct cacggcgtcc ggggtcgcgg aggcgatcga    68160
gcgcatcgag accggatac ggagcgagcg acccgacgtg aagcacatct acgtcgaggc    68220
caggtcgctc caccagcgcg cgagggcgtg acgcgccgtg gagagaccgc gcgcggcctc    68280
cgccatcctc cgcggcgccc gggctcaggt ggccctcgca gcagggcgcg cctggcgggc    68340
aaaccgtgca gacgtcgtcc ttcgacgcga ggtacgctgg ttgcaagtcg tcacgccgta    68400
tcgcgaggtc cggcagcgcc ggagcccggg cgggccgggc gcacgaaggc gcggcgagcg    68460
caggcttcga gggggcgac gtcatgagga aggccagggc gcatggggcg atgctcggcg    68520
ggcgagatga cggctggcgt cgcggcctcc ccggcgccgg cgcgcttcgc gccgcgctcc    68580
agcgcggtcg ctcgcgcgat ctcgcccggc gccggctcat cgcctccgtg tccctcgccg    68640
gcggcgccag catggcggtc gtctcgctgt tccagctcgg gatcatcgag cgcctgcccg    68700
atcctccgct tccagggttc gattcggcca aggtgacgag ctccgatatc              68750
```

<210> SEQ ID NO 2
<211> LENGTH: 1421
<212> TYPE: PRT
<213> ORGANISM: Sorangium cellulosum

<400> SEQUENCE: 2

Val Ala Asp Arg Pro Ile Glu Arg Ala Ala Glu Asp Pro Ile Ala Ile
 1               5                   10                  15

Val Gly Ala Ser Cys Arg Leu Pro Gly Gly Val Ile Asp Leu Ser Gly
             20                  25                  30

```
Phe Trp Thr Leu Leu Glu Gly Ser Arg Asp Thr Val Gly Arg Val Pro
        35                  40                  45

Ala Glu Arg Trp Asp Ala Ala Trp Phe Asp Pro Asp Ala
    50              55              60

Pro Gly Lys Thr Pro Val Thr Arg Ala Ser Phe Leu Ser Asp Val Ala
65              70                  75                  80

Cys Phe Asp Ala Ser Phe Phe Gly Ile Ser Pro Arg Glu Ala Leu Arg
                85              90                  95

Met Asp Pro Ala His Arg Leu Leu Glu Val Cys Trp Glu Ala Leu
            100             105             110

Glu Asn Ala Ala Ile Ala Pro Ser Ala Leu Val Gly Thr Glu Thr Gly
        115             120             125

Val Phe Ile Gly Ile Gly Pro Ser Glu Tyr Glu Ala Ala Leu Pro Gln
    130             135             140

Ala Thr Ala Ser Ala Glu Ile Asp Ala His Gly Gly Leu Gly Thr Met
145             150             155             160

Pro Ser Val Gly Ala Gly Arg Ile Ser Tyr Ala Leu Gly Leu Arg Gly
                165             170             175

Pro Cys Val Ala Val Asp Thr Ala Tyr Ser Ser Ser Leu Val Ala Val
            180             185             190

His Leu Ala Cys Gln Ser Leu Arg Ser Gly Glu Cys Ser Thr Ala Leu
    195             200             205

Ala Gly Gly Val Ser Leu Met Leu Ser Pro Ser Thr Leu Val Trp Leu
    210             215             220

Ser Lys Thr Arg Ala Leu Ala Arg Asp Gly Arg Cys Lys Ala Phe Ser
225             230             235             240

Ala Glu Ala Asp Gly Phe Gly Arg Gly Glu Gly Cys Ala Val Val Val
                245             250             255

Leu Lys Arg Leu Ser Gly Ala Arg Ala Asp Gly Asp Arg Ile Leu Ala
            260             265             270

Val Ile Arg Gly Ser Ala Ile Asn His Asp Gly Ala Ser Ser Gly Leu
    275             280             285

Thr Val Pro Asn Gly Ser Ser Gln Glu Ile Val Leu Lys Arg Ala Leu
    290             295             300

Ala Asp Ala Gly Cys Ala Ala Ser Val Gly Tyr Val Glu Ala His
305             310             315             320

Gly Thr Gly Thr Thr Leu Gly Asp Pro Ile Glu Ile Gln Ala Leu Asn
                325             330             335

Ala Val Tyr Gly Leu Gly Arg Asp Val Ala Thr Pro Leu Leu Ile Gly
            340             345             350

Ser Val Lys Thr Asn Leu Gly His Pro Glu Tyr Ala Ser Gly Ile Thr
    355             360             365

Gly Leu Leu Lys Val Val Leu Ser Leu Gln His Gly Gln Ile Pro Ala
    370             375             380

His Leu His Ala Gln Ala Leu Asn Pro Arg Ile Ser Trp Gly Asp Leu
385             390             395             400

Arg Leu Thr Val Thr Arg Ala Arg Thr Pro Trp Pro Asp Trp Asn Thr
            405             410             415

Pro Arg Arg Ala Gly Val Ser Ser Phe Gly Met Ser Gly Thr Asn Ala
            420             425             430

His Val Val Leu Glu Glu Ala Pro Ala Ala Thr Cys Thr Pro Pro Ala
        435             440             445
```

```
Pro Glu Arg Pro Ala Glu Leu Leu Val Leu Ser Ala Arg Thr Ala Ser
    450                 455                 460

Ala Leu Asp Ala Gln Ala Ala Arg Leu Arg Asp His Leu Glu Thr Tyr
465                 470                 475                 480

Pro Ser Gln Cys Leu Gly Asp Val Ala Phe Ser Leu Ala Thr Thr Arg
            485                 490                 495

Ser Ala Met Glu His Arg Leu Ala Val Ala Ala Thr Ser Arg Glu Gly
            500                 505                 510

Leu Arg Ala Ala Leu Asp Ala Ala Gln Gly Gln Thr Ser Pro Gly
        515                 520                 525

Ala Val Arg Ser Ile Ala Asp Ser Ser Arg Gly Lys Leu Ala Phe Leu
530                 535                 540

Phe Thr Gly Gln Gly Ala Gln Thr Leu Gly Met Gly Arg Gly Leu Tyr
545                 550                 555                 560

Asp Val Trp Ser Ala Phe Arg Glu Ala Phe Asp Leu Cys Val Arg Leu
            565                 570                 575

Phe Asn Gln Glu Leu Asp Arg Pro Leu Arg Glu Val Met Trp Ala Glu
            580                 585                 590

Pro Ala Ser Val Asp Ala Ala Leu Leu Asp Gln Thr Ala Phe Thr Gln
        595                 600                 605

Pro Ala Leu Phe Thr Phe Glu Tyr Ala Leu Ala Ala Leu Trp Arg Ser
    610                 615                 620

Trp Gly Val Glu Pro Glu Leu Val Ala Gly His Ser Ile Gly Glu Leu
625                 630                 635                 640

Val Ala Ala Cys Val Ala Gly Val Phe Ser Leu Glu Asp Ala Val Phe
                645                 650                 655

Leu Val Ala Ala Arg Gly Arg Leu Met Gln Ala Leu Pro Ala Gly Gly
                660                 665                 670

Ala Met Val Ser Ile Glu Ala Pro Glu Ala Asp Val Ala Ala Ala Val
            675                 680                 685

Ala Pro His Ala Ala Ser Val Ser Ile Ala Ala Val Asn Ala Pro Asp
    690                 695                 700

Gln Val Val Ile Ala Gly Ala Gly Gln Pro Val His Ala Ile Ala Ala
705                 710                 715                 720

Ala Met Ala Ala Arg Gly Ala Arg Thr Lys Ala Leu His Val Ser His
                725                 730                 735

Ala Phe His Ser Pro Leu Met Ala Pro Met Leu Glu Ala Phe Gly Arg
            740                 745                 750

Val Ala Glu Ser Val Ser Tyr Arg Arg Pro Ser Ile Val Leu Val Ser
            755                 760                 765

Asn Leu Ser Gly Lys Ala Cys Thr Asp Glu Val Ser Ser Pro Gly Tyr
    770                 775                 780

Trp Val Arg His Ala Arg Glu Val Val Arg Phe Ala Asp Gly Val Lys
785                 790                 795                 800

Ala Leu His Ala Ala Gly Ala Gly Thr Phe Val Glu Val Gly Pro Lys
                805                 810                 815

Ser Thr Leu Leu Gly Leu Val Pro Ala Cys Met Pro Asp Ala Arg Pro
            820                 825                 830

Ala Leu Leu Ala Ser Ser Arg Ala Gly Arg Asp Glu Pro Ala Thr Val
            835                 840                 845

Leu Glu Ala Leu Gly Gly Leu Trp Ala Val Gly Leu Val Ser Trp
    850                 855                 860

Ala Gly Leu Phe Pro Ser Gly Gly Arg Arg Val Pro Leu Pro Thr Tyr
```

-continued

```
865                 870                 875                 880

Pro Trp Gln Arg Glu Arg Tyr Trp Ile Asp Thr Lys Ala Asp Ala
                885                 890                 895

Ala Arg Gly Asp Arg Arg Ala Pro Gly Ala Gly His Asp Glu Val Glu
        900                 905                 910

Glu Gly Gly Ala Val Arg Gly Gly Asp Arg Arg Ser Ala Arg Leu Asp
        915                 920                 925

His Pro Pro Glu Ser Gly Arg Arg Glu Lys Val Glu Ala Ala Gly
        930                 935                 940

Asp Arg Pro Phe Arg Leu Glu Ile Asp Glu Pro Gly Val Leu Asp His
945                 950                 955                 960

Leu Val Leu Arg Val Thr Glu Arg Arg Ala Pro Gly Leu Gly Glu Val
                965                 970                 975

Glu Ile Ala Val Asp Ala Ala Gly Leu Ser Phe Asn Asp Val Gln Leu
        980                 985                 990

Ala Leu Gly Met Val Pro Asp Asp Leu Pro Gly Lys Pro Asn Pro Pro
        995                 1000                1005

Leu Leu Leu Gly Gly Glu Cys Ala Gly Arg Ile Val Ala Val Gly Glu
    1010                1015                1020

Gly Val Asn Gly Leu Val Val Gly Gln Pro Val Ile Ala Leu Ser Ala
1025                1030                1035                1040

Gly Ala Phe Ala Thr His Val Thr Thr Ser Ala Ala Leu Val Leu Pro
                1045                1050                1055

Arg Pro Gln Ala Leu Ser Ala Ile Glu Ala Ala Ala Met Pro Val Ala
            1060                1065                1070

Tyr Leu Thr Ala Trp Tyr Ala Leu Asp Arg Ile Ala Arg Leu Gln Pro
        1075                1080                1085

Gly Glu Arg Val Leu Ile His Ala Ala Thr Gly Gly Val Gly Leu Ala
    1090                1095                1100

Ala Val Gln Trp Ala Gln His Val Gly Ala Glu Val His Ala Thr Ala
1105                1110                1115                1120

Gly Thr Pro Glu Lys Arg Ala Tyr Leu Glu Ser Leu Gly Val Arg Tyr
                1125                1130                1135

Val Ser Asp Ser Arg Ser Asp Arg Phe Val Ala Asp Val Arg Ala Trp
            1140                1145                1150

Thr Gly Gly Glu Gly Val Asp Val Val Leu Asn Ser Leu Ser Gly Glu
        1155                1160                1165

Leu Ile Asp Lys Ser Phe Asn Leu Leu Arg Ser His Gly Arg Phe Val
    1170                1175                1180

Glu Leu Gly Lys Arg Asp Cys Tyr Ala Asp Asn Gln Leu Gly Leu Arg
1185                1190                1195                1200

Pro Phe Leu Arg Asn Leu Ser Phe Ser Leu Val Asp Leu Arg Gly Met
                1205                1210                1215

Met Leu Glu Arg Pro Ala Arg Val Arg Ala Leu Leu Glu Glu Leu Leu
            1220                1225                1230

Gly Leu Ile Ala Ala Gly Val Phe Thr Pro Pro Ile Ala Thr Leu
        1235                1240                1245

Pro Ile Ala Arg Val Ala Asp Ala Phe Arg Ser Met Ala Gln Ala Gln
    1250                1255                1260

His Leu Gly Lys Leu Val Leu Thr Leu Gly Asp Pro Glu Val Gln Ile
1265                1270                1275                1280

Arg Ile Pro Thr His Ala Gly Ala Gly Pro Ser Thr Gly Asp Arg Asp
                1285                1290                1295
```

-continued

```
Leu Leu Asp Arg Leu Ala Ser Ala Ala Pro Ala Ala Arg Ala Ala Ala
            1300                1305                1310

Leu Glu Ala Phe Leu Arg Thr Gln Val Ser Gln Val Leu Arg Thr Pro
        1315                1320                1325

Glu Ile Lys Val Gly Ala Glu Ala Leu Phe Thr Arg Leu Gly Met Asp
    1330                1335                1340

Ser Leu Met Ala Val Glu Leu Arg Asn Arg Ile Glu Ala Ser Leu Lys
1345                1350                1355                1360

Leu Lys Leu Ser Thr Thr Phe Leu Ser Thr Ser Pro Asn Ile Ala Leu
                1365                1370                1375

Leu Ala Gln Asn Leu Leu Asp Ala Leu Ala Thr Ala Leu Ser Leu Glu
            1380                1385                1390

Arg Val Ala Ala Glu Asn Leu Arg Ala Gly Val Gln Asn Asp Phe Val
        1395                1400                1405

Ser Ser Gly Ala Asp Gln Asp Trp Glu Ile Ile Ala Leu
    1410                1415                1420

<210> SEQ ID NO 3
<211> LENGTH: 1410
<212> TYPE: PRT
<213> ORGANISM: Sorangium cellulosum

<400> SEQUENCE: 3

Met Thr Ile Asn Gln Leu Leu Asn Glu Leu Glu His Gln Gly Ile Lys
  1               5                  10                  15

Leu Ala Ala Asp Gly Glu Arg Leu Gln Ile Gln Ala Pro Lys Asn Ala
             20                  25                  30

Leu Asn Pro Asn Leu Leu Ala Arg Ile Ser Glu His Lys Ser Thr Ile
         35                  40                  45

Leu Thr Met Leu Arg Gln Arg Leu Pro Ala Glu Ser Ile Val Pro Ala
     50                  55                  60

Pro Ala Glu Arg His Ala Pro Phe Pro Leu Thr Asp Ile Gln Glu Ser
 65                  70                  75                  80

Tyr Trp Leu Gly Arg Thr Gly Ala Phe Thr Val Pro Ser Gly Ile His
                 85                  90                  95

Ala Tyr Arg Glu Tyr Asp Cys Thr Asp Leu Asp Val Pro Arg Leu Ser
            100                 105                 110

Arg Ala Phe Arg Lys Val Val Ala Arg His Asp Met Leu Arg Ala His
        115                 120                 125

Thr Leu Pro Asp Met Met Gln Val Ile Glu Pro Lys Val Asp Ala Asp
    130                 135                 140

Ile Glu Ile Ile Asp Leu Arg Gly Leu Asp Arg Ser Thr Arg Glu Ala
145                 150                 155                 160

Arg Leu Val Ser Leu Arg Asp Ala Met Ser His Arg Ile Tyr Asp Thr
                165                 170                 175

Glu Arg Pro Pro Leu Tyr His Val Val Ala Val Arg Leu Asp Glu Arg
            180                 185                 190

Gln Thr Arg Leu Val Leu Ser Ile Asp Leu Ile Asn Val Asp Leu Gly
        195                 200                 205

Ser Leu Ser Ile Ile Phe Lys Asp Trp Leu Ser Phe Tyr Glu Asp Pro
    210                 215                 220

Glu Thr Ser Leu Pro Val Leu Glu Leu Ser Tyr Arg Asp Tyr Val Leu
225                 230                 235                 240

Ala Leu Glu Ser Arg Lys Lys Ser Glu Ala His Gln Arg Ser Met Asp
```

-continued

```
                245                 250                 255
Tyr Trp Lys Arg Arg Ile Ala Glu Leu Pro Pro Pro Thr Leu Pro
            260                 265                 270
Met Lys Ala Asp Pro Ser Thr Leu Lys Glu Ile Arg Phe Arg His Thr
        275                 280                 285
Glu Gln Trp Leu Pro Ser Asp Ser Trp Gly Arg Leu Lys Arg Arg Val
        290                 295                 300
Gly Glu Arg Gly Leu Thr Pro Thr Gly Val Ile Leu Ala Ala Phe Ser
305                 310                 315                 320
Glu Val Ile Gly Arg Trp Ser Ala Ser Pro Arg Phe Thr Leu Asn Ile
                325                 330                 335
Thr Leu Phe Asn Arg Leu Pro Val His Pro Arg Val Asn Asp Ile Thr
            340                 345                 350
Gly Asp Phe Thr Ser Met Val Leu Leu Asp Ile Asp Thr Thr Arg Asp
        355                 360                 365
Lys Ser Phe Glu Gln Arg Ala Lys Arg Ile Gln Glu Gln Leu Trp Glu
370                 375                 380
Ala Met Asp His Cys Asp Val Ser Gly Ile Glu Val Gln Arg Glu Ala
385                 390                 395                 400
Ala Arg Val Leu Gly Ile Gln Arg Gly Ala Leu Phe Pro Val Val Leu
                405                 410                 415
Thr Ser Ala Leu Asn Gln Gln Val Val Gly Val Thr Ser Leu Gln Arg
            420                 425                 430
Leu Gly Thr Pro Val Tyr Thr Ser Thr Gln Thr Pro Gln Leu Leu Leu
        435                 440                 445
Asp His Gln Leu Tyr Glu His Asp Gly Asp Leu Val Leu Ala Trp Asp
        450                 455                 460
Ile Val Asp Gly Val Phe Pro Pro Asp Leu Leu Asp Asp Met Leu Glu
465                 470                 475                 480
Ala Tyr Val Val Phe Leu Arg Arg Leu Thr Glu Glu Pro Trp Gly Glu
                485                 490                 495
Gln Val Arg Cys Ser Leu Pro Pro Ala Gln Leu Glu Ala Arg Ala Ser
            500                 505                 510
Ala Asn Ala Thr Asn Ala Leu Leu Ser Glu His Thr Leu His Gly Leu
        515                 520                 525
Phe Ala Ala Arg Val Glu Gln Leu Pro Met Gln Leu Ala Val Val Ser
        530                 535                 540
Ala Arg Lys Thr Leu Thr Tyr Glu Glu Leu Ser Arg Arg Ser Arg Arg
545                 550                 555                 560
Leu Gly Ala Arg Leu Arg Glu Gln Gly Ala Arg Pro Asn Thr Leu Val
                565                 570                 575
Ala Val Val Met Glu Lys Gly Trp Glu Gln Val Val Ala Val Leu Ala
            580                 585                 590
Val Leu Glu Ser Gly Ala Ala Tyr Val Pro Ile Asp Ala Asp Leu Pro
        595                 600                 605
Ala Glu Arg Ile His Tyr Leu Leu Asp His Gly Glu Val Lys Leu Val
        610                 615                 620
Leu Thr Gln Pro Trp Leu Asp Gly Lys Leu Ser Trp Pro Pro Gly Ile
625                 630                 635                 640
Gln Arg Leu Leu Val Ser Glu Ala Gly Val Glu Gly Asp Gly Asp Gln
                645                 650                 655
Pro Pro Met Met Pro Ile Gln Thr Pro Ser Asp Leu Ala Tyr Val Ile
            660                 665                 670
```

-continued

```
Tyr Thr Ser Gly Ser Thr Gly Leu Pro Lys Gly Val Met Ile Asp His
        675                 680                 685
Arg Gly Ala Val Asn Thr Ile Leu Asp Ile Asn Glu Arg Phe Glu Ile
        690                 695                 700
Gly Pro Gly Asp Arg Val Leu Ala Leu Ser Ser Leu Ser Phe Asp Leu
705                 710                 715                 720
Ser Val Tyr Asp Val Phe Gly Ile Leu Ala Ala Gly Gly Thr Ile Val
                725                 730                 735
Val Pro Asp Ala Ser Lys Leu Arg Asp Pro Ala His Trp Ala Glu Leu
        740                 745                 750
Ile Glu Arg Glu Lys Val Thr Val Trp Asn Ser Val Pro Ala Leu Met
        755                 760                 765
Arg Met Leu Val Glu His Phe Glu Gly Arg Pro Asp Ser Leu Ala Arg
        770                 775                 780
Ser Leu Arg Leu Ser Leu Ser Gly Asp Trp Ile Pro Val Gly Leu
785                 790                 795                 800
Pro Gly Glu Leu Gln Ala Ile Arg Pro Gly Val Ser Val Ile Ser Leu
                805                 810                 815
Gly Gly Ala Thr Glu Ala Ser Ile Trp Ser Ile Gly Tyr Pro Val Arg
        820                 825                 830
Asn Val Asp Leu Ser Trp Ala Ser Ile Pro Tyr Gly Arg Pro Leu Arg
        835                 840                 845
Asn Gln Thr Phe His Val Leu Asp Glu Ala Leu Glu Pro Arg Pro Val
        850                 855                 860
Trp Val Pro Gly Gln Leu Tyr Ile Gly Gly Val Gly Leu Ala Leu Gly
865                 870                 875                 880
Tyr Trp Arg Asp Glu Glu Lys Thr Arg Lys Ser Phe Leu Val His Pro
                885                 890                 895
Glu Thr Gly Glu Arg Leu Tyr Lys Thr Gly Asp Leu Gly Arg Tyr Leu
                900                 905                 910
Pro Asp Gly Asn Ile Glu Phe Met Gly Arg Glu Asp Asn Gln Ile Lys
        915                 920                 925
Leu Arg Gly Tyr Arg Val Glu Leu Gly Glu Ile Glu Glu Thr Leu Lys
        930                 935                 940
Ser His Pro Asn Val Arg Asp Ala Val Ile Val Pro Val Gly Asn Asp
945                 950                 955                 960
Ala Ala Asn Lys Leu Leu Leu Ala Tyr Val Val Pro Glu Gly Thr Arg
                965                 970                 975
Arg Arg Ala Ala Glu Gln Asp Ala Ser Leu Lys Thr Glu Arg Ile Asp
        980                 985                 990
Ala Arg Ala His Ala Ala Glu Ala Asp Gly Leu Ser Asp Gly Glu Arg
        995                 1000                1005
Val Gln Phe Lys Leu Ala Arg His Gly Leu Arg Arg Asp Leu Asp Gly
        1010                1015                1020
Lys Pro Val Val Asp Leu Thr Gly Gln Asp Pro Arg Glu Ala Gly Leu
1025                1030                1035                1040
Asp Val Tyr Ala Arg Arg Arg Ser Val Arg Thr Phe Leu Glu Ala Pro
                1045                1050                1055
Ile Pro Phe Val Glu Phe Gly Arg Phe Leu Ser Cys Leu Ser Ser Val
                1060                1065                1070
Glu Pro Asp Gly Ala Thr Leu Pro Lys Phe Arg Tyr Pro Ser Ala Gly
        1075                1080                1085
```

```
Ser Thr Tyr Pro Val Gln Thr Tyr Ala Tyr Val Lys Ser Gly Arg Ile
    1090                1095                1100

Glu Gly Val Asp Glu Gly Phe Tyr Tyr His Pro Phe Glu His Arg
1105                1110                1115                1120

Leu Leu Lys Leu Ser Asp His Gly Ile Glu Arg Gly Ala His Val Arg
            1125                1130                1135

Gln Asn Phe Asp Val Phe Asp Glu Ala Ala Phe Asn Leu Leu Phe Val
        1140                1145                1150

Gly Arg Ile Asp Ala Ile Glu Ser Leu Tyr Gly Ser Ser Arg Glu
        1155                1160                1165

Phe Cys Leu Leu Glu Ala Gly Tyr Met Ala Gln Leu Leu Met Glu Gln
    1170                1175                1180

Ala Pro Ser Cys Asn Ile Gly Val Cys Pro Val Gly Gln Phe Asn Phe
1185                1190                1195                1200

Glu Gln Val Arg Pro Val Leu Asp Leu Arg His Ser Asp Val Tyr Val
                1205                1210                1215

His Gly Met Leu Gly Gly Arg Val Asp Pro Arg Gln Phe Gln Val Cys
            1220                1225                1230

Thr Leu Gly Gln Asp Ser Ser Pro Arg Arg Ala Thr Thr Arg Gly Ala
        1235                1240                1245

Pro Pro Gly Arg Glu Gln His Phe Ala Asp Met Leu Arg Asp Phe Leu
    1250                1255                1260

Arg Thr Lys Leu Pro Glu Tyr Met Val Pro Thr Val Phe Val Glu Leu
1265                1270                1275                1280

Asp Ala Leu Pro Leu Thr Ser Asn Gly Lys Val Asp Arg Lys Ala Leu
                1285                1290                1295

Arg Glu Arg Lys Asp Thr Ser Ser Pro Arg His Ser Gly His Thr Ala
            1300                1305                1310

Pro Arg Asp Ala Leu Glu Glu Ile Leu Val Ala Val Arg Glu Val
        1315                1320                1325

Leu Gly Leu Glu Val Val Gly Leu Gln Gln Ser Phe Val Asp Leu Gly
    1330                1335                1340

Ala Thr Ser Ile His Ile Val Arg Met Arg Ser Leu Leu Gln Lys Arg
1345                1350                1355                1360

Leu Asp Arg Glu Ile Ala Ile Thr Glu Leu Phe Gln Tyr Pro Asn Leu
            1365                1370                1375

Gly Ser Leu Ala Ser Gly Leu Arg Arg Asp Ser Arg Asp Leu Asp Gln
        1380                1385                1390

Arg Pro Asn Met Gln Asp Arg Val Glu Val Arg Lys Gly Arg Arg
        1395                1400                1405

Arg Ser
    1410

<210> SEQ ID NO 4
<211> LENGTH: 1832
<212> TYPE: PRT
<213> ORGANISM: Sorangium cellulosum

<400> SEQUENCE: 4

Met Glu Glu Gln Glu Ser Ser Ala Ile Ala Val Ile Gly Met Ser Gly
  1               5                  10                  15

Arg Phe Pro Gly Ala Arg Asp Leu Asp Glu Phe Trp Arg Asn Leu Arg
                20                  25                  30

Asp Gly Thr Glu Ala Val Gln Arg Phe Ser Glu Gln Glu Leu Ala Ala
            35                  40                  45
```

```
Ser Gly Val Asp Pro Ala Leu Val Leu Asp Pro Ser Tyr Val Arg Ala
     50                  55                  60

Gly Ser Val Leu Glu Asp Val Asp Arg Phe Asp Ala Ala Phe Phe Gly
 65                  70                  75                  80

Ile Ser Pro Arg Glu Ala Glu Leu Met Asp Pro Gln His Arg Ile Phe
                 85                  90                  95

Met Glu Cys Ala Trp Glu Ala Leu Glu Asn Ala Gly Tyr Asp Pro Thr
                100                 105                 110

Ala Tyr Glu Gly Ser Ile Gly Val Tyr Ala Gly Ala Asn Met Ser Ser
                115                 120                 125

Tyr Leu Thr Ser Asn Leu His Glu His Pro Ala Met Met Arg Trp Pro
    130                 135                 140

Gly Trp Phe Gln Thr Leu Ile Gly Asn Asp Lys Asp Tyr Leu Ala Thr
145                 150                 155                 160

His Val Ser Tyr Arg Leu Asn Leu Arg Gly Pro Ser Ile Ser Val Gln
                165                 170                 175

Thr Ala Cys Ser Thr Ser Leu Val Ala Val His Leu Ala Cys Met Ser
                180                 185                 190

Leu Leu Asp Arg Glu Cys Asp Met Ala Leu Ala Gly Gly Ile Thr Val
                195                 200                 205

Arg Ile Pro His Arg Ala Gly Tyr Val Tyr Ala Glu Gly Gly Ile Phe
    210                 215                 220

Ser Pro Asp Gly His Cys Arg Ala Phe Asp Ala Lys Ala Asn Gly Thr
225                 230                 235                 240

Ile Met Gly Asn Gly Cys Gly Val Val Leu Leu Lys Pro Leu Asp Arg
                245                 250                 255

Ala Leu Ser Asp Gly Asp Pro Val Arg Ala Val Ile Leu Gly Ser Ala
                260                 265                 270

Thr Asn Asn Asp Gly Ala Arg Lys Ile Gly Phe Thr Ala Pro Ser Glu
                275                 280                 285

Val Gly Gln Ala Gln Ala Ile Met Glu Ala Leu Ala Leu Ala Gly Val
    290                 295                 300

Glu Ala Arg Ser Ile Gln Tyr Ile Glu Thr His Gly Thr Gly Thr Leu
305                 310                 315                 320

Leu Gly Asp Ala Ile Glu Thr Ala Ala Leu Arg Arg Val Phe Gly Arg
                325                 330                 335

Asp Ala Ser Ala Arg Arg Ser Cys Ala Ile Gly Ser Val Lys Thr Gly
                340                 345                 350

Ile Gly His Leu Glu Ser Ala Ala Gly Ile Ala Gly Leu Ile Lys Thr
                355                 360                 365

Val Leu Ala Leu Glu His Arg Gln Leu Pro Pro Ser Leu Asn Phe Glu
    370                 375                 380

Ser Pro Asn Pro Ser Ile Asp Phe Ala Ser Ser Pro Phe Tyr Val Asn
385                 390                 395                 400

Thr Ser Leu Lys Asp Trp Asn Thr Gly Ser Thr Pro Arg Arg Ala Gly
                405                 410                 415

Val Ser Ser Phe Gly Ile Gly Gly Thr Asn Ala His Val Val Leu Glu
                420                 425                 430

Glu Ala Pro Ala Ala Lys Leu Pro Ala Ala Ala Pro Ala Arg Ser Ala
                435                 440                 445

Glu Leu Phe Val Val Ser Ala Lys Ser Ala Ala Ala Leu Asp Ala Ala
                450                 455                 460
```

-continued

```
Ala Ala Arg Leu Arg Asp His Leu Gln Ala His Gln Gly Ile Ser Leu
465                 470                 475                 480

Gly Asp Val Ala Phe Ser Leu Ala Thr Thr Arg Ser Pro Met Glu His
            485                 490                 495

Arg Leu Ala Met Ala Ala Pro Ser Arg Glu Ala Leu Arg Glu Gly Leu
                500                 505                 510

Asp Ala Ala Ala Arg Gly Gln Thr Pro Pro Gly Ala Val Arg Gly Arg
                515                 520                 525

Cys Ser Pro Gly Asn Val Pro Lys Val Val Phe Val Phe Pro Gly Gln
    530                 535                 540

Gly Ser Gln Trp Val Gly Met Gly Arg Gln Leu Leu Ala Glu Glu Pro
545                 550                 555                 560

Val Phe His Ala Ala Leu Ser Ala Cys Asp Arg Ala Ile Gln Ala Glu
                565                 570                 575

Ala Gly Trp Ser Leu Leu Ala Glu Leu Ala Ala Asp Glu Gly Ser Ser
            580                 585                 590

Gln Leu Glu Arg Ile Asp Val Val Gln Pro Val Leu Phe Ala Leu Ala
        595                 600                 605

Val Ala Phe Ala Ala Leu Trp Arg Ser Trp Gly Val Ala Pro Asp Val
    610                 615                 620

Val Ile Gly His Ser Met Gly Glu Val Ala Ala Ala His Val Ala Gly
625                 630                 635                 640

Ala Leu Ser Leu Glu Asp Ala Val Ala Ile Ile Cys Arg Arg Ser Arg
                645                 650                 655

Leu Leu Arg Arg Ile Ser Gly Gln Gly Glu Met Ala Val Thr Glu Leu
            660                 665                 670

Ser Leu Ala Glu Ala Glu Ala Ala Leu Arg Gly Tyr Glu Asp Arg Val
        675                 680                 685

Ser Val Ala Val Ser Asn Ser Pro Arg Ser Thr Val Leu Ser Gly Glu
    690                 695                 700

Pro Ala Ala Ile Gly Glu Val Leu Ser Ser Leu Asn Ala Lys Gly Val
705                 710                 715                 720

Phe Cys Arg Arg Val Lys Val Asp Val Ala Ser His Ser Pro Gln Val
                725                 730                 735

Asp Pro Leu Arg Glu Asp Leu Leu Ala Ala Leu Gly Gly Leu Arg Pro
            740                 745                 750

Gly Ala Ala Ala Val Pro Met Arg Ser Thr Val Thr Gly Ala Met Val
        755                 760                 765

Ala Gly Pro Glu Leu Gly Ala Asn Tyr Trp Met Asn Asn Leu Arg Gln
    770                 775                 780

Pro Val Arg Phe Ala Glu Val Val Gln Ala Gln Leu Gln Gly Gly His
785                 790                 795                 800

Gly Leu Phe Val Glu Met Ser Pro His Pro Ile Leu Thr Thr Ser Val
                805                 810                 815

Glu Glu Met Arg Arg Ala Ala Gln Arg Ala Gly Ala Ala Val Gly Ser
            820                 825                 830

Leu Arg Arg Gly Gln Asp Glu Arg Pro Ala Met Leu Glu Ala Leu Gly
        835                 840                 845

Thr Leu Trp Ala Gln Gly Tyr Pro Val Pro Trp Gly Arg Leu Phe Pro
    850                 855                 860

Ala Gly Gly Arg Arg Val Pro Leu Pro Thr Tyr Pro Trp Gln Arg Glu
865                 870                 875                 880

Arg Tyr Trp Ile Glu Ala Pro Ala Lys Ser Ala Ala Gly Asp Arg Arg
```

-continued

```
                885                 890                 895
Gly Val Arg Ala Gly Gly His Pro Leu Leu Gly Glu Met Gln Thr Leu
            900                 905                 910

Ser Thr Gln Thr Ser Thr Arg Leu Trp Glu Thr Thr Leu Asp Leu Lys
        915                 920                 925

Arg Leu Pro Trp Leu Gly Asp His Arg Val Gln Gly Ala Val Val Phe
    930                 935                 940

Pro Gly Ala Ala Tyr Leu Glu Met Ala Ile Ser Ser Gly Glu Ala
945                 950                 955                 960

Leu Gly Asp Gly Pro Leu Gln Ile Thr Asp Val Val Leu Ala Glu Ala
            965                 970                 975

Leu Ala Phe Ala Gly Asp Ala Ala Val Leu Val Gln Val Val Thr Thr
        980                 985                 990

Glu Gln Pro Ser Gly Arg Leu Gln Phe Gln Ile Ala Ser Arg Ala Pro
    995                 1000                1005

Gly Ala Gly His Ala Ser Phe Arg Val His Ala Arg Gly Ala Leu Leu
    1010                1015                1020

Arg Val Glu Arg Thr Glu Val Pro Ala Gly Leu Thr Leu Ser Ala Val
1025                1030                1035                1040

Arg Ala Arg Leu Gln Ala Ser Ile Pro Ala Ala Ala Thr Tyr Ala Glu
            1045                1050                1055

Leu Thr Glu Met Gly Leu Gln Tyr Gly Pro Ala Phe Gln Gly Ile Ala
        1060                1065                1070

Glu Leu Trp Arg Gly Glu Gly Glu Ala Leu Gly Arg Val Arg Leu Pro
    1075                1080                1085

Asp Ala Ala Gly Ser Ala Ala Glu Tyr Arg Leu His Pro Ala Leu Leu
    1090                1095                1100

Asp Ala Cys Phe Gln Ile Val Gly Ser Leu Phe Ala Arg Ser Gly Glu
1105                1110                1115                1120

Ala Thr Pro Trp Val Pro Val Glu Leu Gly Ser Leu Arg Leu Leu Gln
            1125                1130                1135

Arg Pro Ser Gly Glu Leu Trp Cys His Ala Arg Val Val Asn His Gly
        1140                1145                1150

His Gln Thr Pro Asp Arg Gln Gly Ala Asp Phe Trp Val Val Asp Ser
    1155                1160                1165

Ser Gly Ala Val Val Ala Glu Val Cys Gly Leu Val Ala Gln Arg Leu
    1170                1175                1180

Pro Gly Gly Val Arg Arg Arg Glu Glu Asp Asp Trp Phe Leu Glu Leu
1185                1190                1195                1200

Glu Trp Glu Pro Ala Ala Val Gly Thr Ala Lys Val Asn Ala Gly Arg
            1205                1210                1215

Trp Leu Leu Leu Gly Gly Gly Gly Leu Gly Ala Ala Leu Arg Ala
        1220                1225                1230

Met Leu Glu Ala Gly Gly His Ala Val Val His Ala Ala Glu Asn Asn
    1235                1240                1245

Thr Ser Ala Ala Gly Val Arg Ala Leu Leu Ala Lys Ala Phe Asp Gly
    1250                1255                1260

Gln Ala Pro Thr Ala Val Val His Leu Gly Ser Leu Asp Gly Gly Gly
1265                1270                1275                1280

Glu Leu Asp Pro Gly Leu Gly Ala Gln Gly Ala Leu Asp Ala Pro Arg
            1285                1290                1295

Ser Ala Asp Val Ser Pro Asp Ala Leu Asp Pro Ala Leu Val Arg Gly
        1300                1305                1310
```

-continued

```
Cys Asp Ser Val Leu Trp Thr Val Gln Ala Leu Ala Gly Met Gly Phe
        1315                1320                1325

Arg Asp Ala Pro Arg Leu Trp Leu Leu Thr Arg Gly Ala Gln Ala Val
    1330                1335                1340

Gly Ala Gly Asp Val Ser Val Thr Gln Ala Pro Leu Leu Gly Leu Gly
1345                1350                1355                1360

Arg Val Ile Ala Met Glu His Ala Asp Leu Arg Cys Ala Arg Val Asp
            1365                1370                1375

Leu Asp Pro Ala Arg Pro Glu Gly Glu Leu Ala Ala Leu Leu Ala Glu
        1380                1385                1390

Leu Leu Ala Asp Asp Ala Glu Ala Glu Val Ala Leu Arg Gly Gly Glu
        1395                1400                1405

Arg Cys Val Ala Arg Ile Val Arg Arg Gln Pro Glu Thr Arg Pro Arg
    1410                1415                1420

Gly Arg Ile Glu Ser Cys Val Pro Thr Asp Val Thr Ile Arg Ala Asp
1425                1430                1435                1440

Ser Thr Tyr Leu Val Thr Gly Gly Leu Gly Gly Leu Gly Leu Ser Val
            1445                1450                1455

Ala Gly Trp Leu Ala Glu Arg Gly Ala Gly His Leu Val Leu Val Gly
        1460                1465                1470

Arg Ser Gly Ala Ala Ser Val Glu Gln Arg Ala Ala Val Ala Ala Leu
        1475                1480                1485

Glu Ala Arg Gly Ala Arg Val Thr Val Ala Lys Ala Asp Val Ala Asp
        1490                1495                1500

Arg Ala Gln Leu Glu Arg Ile Leu Arg Glu Val Thr Thr Ser Gly Met
1505                1510                1515                1520

Pro Leu Arg Gly Val Val His Ala Ala Gly Ile Leu Asp Asp Gly Leu
            1525                1530                1535

Leu Met Gln Gln Thr Pro Ala Arg Phe Arg Lys Val Met Ala Pro Lys
        1540                1545                1550

Val Gln Gly Ala Leu His Leu His Ala Leu Thr Arg Glu Ala Pro Leu
        1555                1560                1565

Ser Phe Phe Val Leu Tyr Ala Ser Gly Val Gly Leu Leu Gly Ser Pro
    1570                1575                1580

Gly Gln Gly Asn Tyr Ala Ala Ala Asn Thr Phe Leu Asp Ala Leu Ala
1585                1590                1595                1600

His His Arg Arg Ala Gln Gly Leu Pro Ala Leu Ser Val Asp Trp Gly
            1605                1610                1615

Leu Phe Ala Glu Val Gly Met Ala Ala Ala Gln Glu Asp Arg Gly Ala
        1620                1625                1630

Arg Leu Val Ser Arg Gly Met Arg Ser Leu Thr Pro Asp Glu Gly Leu
        1635                1640                1645

Ser Ala Leu Ala Arg Leu Leu Glu Ser Gly Arg Ala Gln Val Gly Val
    1650                1655                1660

Met Pro Val Asn Pro Arg Leu Trp Val Glu Leu Tyr Pro Ala Ala Ala
1665                1670                1675                1680

Ser Ser Arg Met Leu Ser Arg Leu Val Thr Ala His Arg Ala Ser Ala
            1685                1690                1695

Gly Gly Pro Ala Gly Asp Gly Asp Leu Leu Arg Arg Leu Ala Ala Ala
        1700                1705                1710

Glu Pro Ser Ala Arg Ser Ala Leu Leu Glu Pro Leu Leu Arg Ala Gln
        1715                1720                1725
```

-continued

```
Ile Ser Gln Val Leu Arg Leu Pro Glu Gly Lys Ile Glu Val Asp Ala
    1730                1735                1740

Pro Leu Thr Ser Leu Gly Met Asn Ser Leu Met Gly Leu Glu Leu Arg
1745                1750                1755                1760

Asn Arg Ile Glu Ala Met Leu Gly Ile Thr Val Pro Ala Thr Leu Leu
            1765                1770                1775

Trp Thr Tyr Pro Thr Val Ala Ala Leu Ser Gly His Leu Ala Arg Glu
            1780                1785                1790

Ala Cys Glu Ala Ala Pro Val Glu Ser Pro His Thr Thr Ala Asp Ser
            1795                1800                1805

Ala Val Glu Ile Glu Glu Met Ser Gln Asp Asp Leu Thr Gln Leu Ile
    1810                1815                1820

Ala Ala Lys Phe Lys Ala Leu Thr
1825                1830

<210> SEQ ID NO 5
<211> LENGTH: 7257
<212> TYPE: PRT
<213> ORGANISM: Sorangium cellulosum

<400> SEQUENCE: 5

Met Thr Thr Arg Gly Pro Thr Ala Gln Gln Asn Pro Leu Lys Gln Ala
1               5                   10                  15

Ala Ile Ile Ile Gln Arg Leu Glu Glu Arg Leu Ala Gly Leu Ala Gln
            20                  25                  30

Ala Glu Leu Glu Arg Thr Glu Pro Ile Ala Ile Val Gly Ile Gly Cys
        35                  40                  45

Arg Phe Pro Gly Gly Ala Asp Ala Pro Glu Ala Phe Trp Glu Leu Leu
    50                  55                  60

Asp Ala Glu Arg Asp Ala Val Gln Pro Leu Asp Met Arg Trp Ala Leu
65                  70                  75                  80

Val Gly Val Ala Pro Val Glu Ala Val Pro His Trp Ala Gly Leu Leu
                85                  90                  95

Thr Glu Pro Ile Asp Cys Phe Asp Ala Ala Phe Phe Gly Ile Ser Pro
            100                 105                 110

Arg Glu Ala Arg Ser Leu Asp Pro Gln His Arg Leu Leu Leu Glu Val
        115                 120                 125

Ala Trp Glu Gly Leu Glu Asp Ala Gly Ile Pro Pro Arg Ser Ile Asp
    130                 135                 140

Gly Ser Arg Thr Gly Val Phe Val Gly Ala Phe Thr Ala Asp Tyr Ala
145                 150                 155                 160

Arg Thr Val Ala Arg Leu Pro Arg Glu Glu Arg Asp Ala Tyr Ser Ala
                165                 170                 175

Thr Gly Asn Met Leu Ser Ile Ala Ala Gly Arg Leu Ser Tyr Thr Leu
            180                 185                 190

Gly Leu Gln Gly Pro Cys Leu Thr Val Asp Thr Ala Cys Ser Ser Ser
        195                 200                 205

Leu Val Ala Ile His Leu Ala Cys Arg Ser Leu Arg Ala Gly Glu Ser
    210                 215                 220

Asp Leu Ala Leu Ala Gly Gly Val Ser Ala Leu Leu Ser Pro Asp Met
225                 230                 235                 240

Met Glu Ala Ala Ala Arg Thr Gln Ala Leu Ser Pro Asp Gly Arg Cys
                245                 250                 255

Arg Thr Phe Asp Ala Ser Ala Asn Gly Phe Val Arg Gly Glu Gly Cys
            260                 265                 270
```

-continued

```
Gly Leu Val Val Leu Lys Arg Leu Ser Asp Ala Gln Arg Asp Gly Asp
            275                 280                 285
Arg Ile Trp Ala Leu Ile Arg Gly Ser Ala Ile Asn His Asp Gly Arg
290                 295                 300
Ser Thr Gly Leu Thr Ala Pro Asn Val Leu Ala Gln Glu Thr Val Leu
305                 310                 315                 320
Arg Glu Ala Leu Arg Ser Ala His Val Glu Ala Gly Ala Val Asp Tyr
                325                 330                 335
Val Glu Thr His Gly Thr Gly Thr Ser Leu Gly Asp Pro Ile Glu Val
            340                 345                 350
Glu Ala Leu Arg Ala Thr Val Gly Pro Ala Arg Ser Asp Gly Thr Arg
            355                 360                 365
Cys Val Leu Gly Ala Val Lys Thr Asn Ile Gly His Leu Glu Ala Ala
370                 375                 380
Ala Gly Val Ala Gly Leu Ile Lys Ala Ala Leu Ser Leu Thr His Glu
385                 390                 395                 400
Arg Ile Pro Arg Asn Leu Asn Phe Arg Thr Leu Asn Pro Arg Ile Arg
                405                 410                 415
Leu Glu Gly Ser Ala Leu Ala Leu Ala Thr Glu Pro Val Pro Trp Pro
            420                 425                 430
Arg Thr Asp Arg Pro Arg Phe Ala Gly Val Ser Ser Phe Gly Met Ser
            435                 440                 445
Gly Thr Asn Ala His Val Val Leu Glu Glu Ala Pro Ala Val Glu Leu
            450                 455                 460
Trp Pro Ala Ala Pro Glu Arg Ser Ala Glu Leu Leu Val Leu Ser Gly
465                 470                 475                 480
Lys Ser Glu Gly Ala Leu Asp Ala Gln Ala Ala Arg Leu Arg Glu His
                485                 490                 495
Leu Asp Met His Pro Glu Leu Gly Leu Gly Asp Val Ala Phe Ser Leu
            500                 505                 510
Ala Thr Thr Arg Ser Ala Met Ser His Arg Leu Ala Val Ala Val Thr
            515                 520                 525
Ser Arg Glu Gly Leu Leu Ala Ala Leu Ser Ala Val Ala Gln Gly Gln
            530                 535                 540
Thr Pro Ala Gly Ala Ala Arg Cys Ile Ala Ser Ser Ser Arg Gly Lys
545                 550                 555                 560
Leu Ala Phe Leu Phe Thr Gly Gln Gly Ala Gln Thr Pro Gly Met Gly
                565                 570                 575
Arg Gly Leu Cys Ala Ala Trp Pro Ala Phe Arg Glu Ala Phe Asp Arg
            580                 585                 590
Cys Val Ala Leu Phe Asp Arg Glu Leu Asp Arg Pro Leu Arg Glu Val
            595                 600                 605
Met Trp Ala Glu Ala Gly Ser Ala Glu Ser Leu Leu Leu Asp Gln Thr
            610                 615                 620
Ala Phe Thr Gln Pro Ala Leu Phe Ala Val Glu Tyr Ala Leu Thr Ala
625                 630                 635                 640
Leu Trp Arg Ser Trp Gly Val Glu Pro Glu Leu Leu Val Gly His Ser
                645                 650                 655
Ile Gly Glu Leu Val Ala Ala Cys Val Ala Gly Val Phe Ser Leu Glu
            660                 665                 670
Asp Gly Val Arg Leu Val Ala Ala Arg Gly Arg Leu Met Gln Gly Leu
            675                 680                 685
```

-continued

```
Ser Ala Gly Gly Ala Met Val Ser Leu Gly Ala Pro Glu Ala Glu Val
    690                 695                 700
Ala Ala Ala Val Ala Pro His Ala Ala Ser Val Ser Ile Ala Ala Val
705                 710                 715                 720
Asn Gly Pro Glu Gln Val Val Ile Ala Gly Val Gln Ala Val Gln
            725                 730                 735
Ala Ile Ala Ala Gly Phe Ala Ala Arg Gly Ala Arg Thr Lys Arg Leu
            740                 745                 750
His Val Ser His Ala Phe His Ser Pro Leu Met Glu Pro Met Leu Glu
            755                 760                 765
Glu Phe Gly Arg Val Ala Ala Ser Val Thr Tyr Arg Arg Pro Ser Val
    770                 775                 780
Ser Leu Val Ser Asn Leu Ser Gly Lys Val Val Thr Asp Glu Leu Ser
785                 790                 795                 800
Ala Pro Gly Tyr Trp Val Arg His Val Arg Glu Ala Val Arg Phe Ala
            805                 810                 815
Asp Gly Val Lys Ala Leu His Glu Ala Gly Ala Gly Thr Phe Val Glu
            820                 825                 830
Val Gly Pro Lys Pro Thr Leu Leu Gly Leu Leu Pro Ala Cys Leu Pro
            835                 840                 845
Glu Ala Glu Pro Thr Leu Leu Ala Ser Leu Arg Ala Gly Arg Glu Glu
    850                 855                 860
Ala Ala Gly Val Leu Glu Ala Leu Gly Arg Leu Trp Ala Ala Gly Gly
865                 870                 875                 880
Ser Val Ser Trp Pro Gly Val Phe Pro Thr Ala Gly Arg Arg Val Pro
            885                 890                 895
Leu Pro Thr Tyr Pro Trp Gln Arg Gln Arg Tyr Trp Ile Glu Ala Pro
            900                 905                 910
Ala Glu Gly Leu Gly Ala Thr Ala Ala Asp Ala Leu Ala Gln Trp Phe
            915                 920                 925
Tyr Arg Val Asp Trp Pro Glu Met Pro Arg Ser Ser Val Asp Ser Arg
    930                 935                 940
Arg Ala Arg Ser Gly Gly Trp Leu Val Leu Ala Asp Arg Gly Gly Val
945                 950                 955                 960
Gly Glu Ala Ala Ala Ala Ala Leu Ser Ser Gln Gly Cys Ser Cys Ala
            965                 970                 975
Val Leu His Ala Pro Ala Glu Ala Ser Ala Val Ala Glu Gln Val Thr
            980                 985                 990
Gln Ala Leu Gly Gly Arg Asn Asp Trp Gln Gly Val Leu Tyr Leu Trp
            995                 1000                1005
Gly Leu Asp Ala Val Val Glu Ala Gly Ala Ser Ala Glu Glu Val Ala
    1010                1015                1020
Lys Val Thr His Leu Ala Ala Pro Val Leu Ala Leu Ile Gln Ala
1025                1030                1035                1040
Leu Gly Thr Gly Pro Arg Ser Pro Arg Leu Trp Ile Val Thr Arg Gly
            1045                1050                1055
Ala Cys Thr Val Gly Gly Glu Pro Asp Ala Ala Pro Cys Gln Ala Ala
            1060                1065                1070
Leu Trp Gly Met Gly Arg Val Ala Ala Leu Glu His Pro Gly Ser Trp
            1075                1080                1085
Gly Gly Leu Val Asp Leu Asp Pro Glu Glu Ser Pro Thr Glu Val Glu
    1090                1095                1100
Ala Leu Val Ala Glu Leu Leu Ser Pro Asp Ala Glu Asp Gln Leu Ala
```

-continued

```
1105              1110              1115              1120
Phe Arg Gln Gly Arg Arg Ala Ala Arg Leu Val Ala Ala Pro Pro
            1125              1130              1135
Glu Gly Asn Ala Ala Pro Val Ser Leu Ser Ala Glu Gly Ser Tyr Leu
        1140              1145              1150
Val Thr Gly Gly Leu Gly Ala Leu Gly Leu Leu Val Ala Arg Trp Leu
    1155              1160              1165
Val Glu Arg Gly Ala Gly His Leu Val Leu Ile Ser Arg His Gly Leu
    1170              1175              1180
Pro Asp Arg Glu Glu Trp Gly Arg Asp Gln Pro Glu Val Arg Ala
1185              1190              1195              1200
Arg Ile Ala Ala Ile Glu Ala Leu Glu Ala Gln Gly Ala Arg Val Thr
            1205              1210              1215
Val Ala Ala Val Asp Val Ala Asp Ala Glu Gly Met Ala Ala Leu Leu
        1220              1225              1230
Ala Ala Val Glu Pro Pro Leu Arg Gly Val Val His Ala Ala Gly Leu
    1235              1240              1245
Leu Asp Asp Gly Leu Leu Ala His Gln Asp Ala Gly Arg Leu Ala Arg
    1250              1255              1260
Val Leu Arg Pro Lys Val Glu Gly Ala Trp Val Leu His Thr Leu Thr
1265              1270              1275              1280
Arg Glu Gln Pro Leu Asp Leu Phe Val Leu Phe Ser Ser Ala Ser Gly
            1285              1290              1295
Val Phe Gly Ser Ile Gly Gln Gly Ser Tyr Ala Ala Gly Asn Ala Phe
        1300              1305              1310
Leu Asp Ala Leu Ala Asp Leu Arg Arg Thr Gln Gly Leu Ala Ala Leu
    1315              1320              1325
Ser Ile Ala Trp Gly Leu Trp Ala Glu Gly Gly Met Gly Ser Gln Ala
    1330              1335              1340
Gln Arg Arg Glu His Glu Ala Ser Gly Ile Trp Ala Met Pro Thr Ser
1345              1350              1355              1360
Arg Ala Leu Ala Ala Met Glu Trp Leu Leu Gly Thr Arg Ala Thr Gln
            1365              1370              1375
Arg Val Val Ile Gln Met Asp Trp Ala His Ala Gly Ala Ala Pro Arg
        1380              1385              1390
Asp Ala Ser Arg Gly Arg Phe Trp Asp Arg Leu Val Thr Ala Thr Lys
    1395              1400              1405
Glu Ala Ser Ser Ser Ala Val Pro Ala Val Glu Arg Trp Arg Asn Ala
    1410              1415              1420
Ser Val Val Glu Thr Arg Ser Ala Leu Tyr Glu Leu Val Arg Gly Val
1425              1430              1435              1440
Val Ala Gly Val Met Gly Phe Thr Asp Gln Gly Thr Leu Asp Val Arg
            1445              1450              1455
Arg Gly Phe Ala Glu Gln Gly Leu Asp Ser Leu Met Ala Val Glu Ile
        1460              1465              1470
Arg Lys Arg Leu Gln Gly Glu Leu Gly Met Pro Leu Ser Ala Thr Leu
    1475              1480              1485
Ala Phe Asp His Pro Thr Val Glu Arg Leu Val Glu Tyr Leu Leu Ser
    1490              1495              1500
Gln Ala Leu Glu Leu Gln Asp Arg Thr Asp Val Arg Ser Val Arg Leu
1505              1510              1515              1520
Pro Ala Thr Glu Asp Pro Ile Ala Ile Val Gly Ala Ala Cys Arg Phe
            1525              1530              1535
```

-continued

```
Pro Gly Gly Val Glu Asp Leu Glu Ser Tyr Trp Gln Leu Leu Thr Glu
        1540                1545                1550
Gly Val Val Val Ser Thr Glu Val Pro Ala Asp Arg Trp Asn Gly Ala
        1555                1560                1565
Asp Gly Arg Val Pro Gly Ser Gly Glu Ala Gln Arg Gln Thr Tyr Val
    1570                1575                1580
Pro Arg Gly Gly Phe Leu Arg Glu Val Glu Thr Phe Asp Ala Ala Phe
1585                1590                1595                1600
Phe His Ile Ser Pro Arg Glu Ala Met Ser Leu Asp Pro Gln Gln Arg
            1605                1610                1615
Leu Leu Leu Glu Val Ser Trp Glu Ala Ile Glu Arg Ala Gly Gln Asp
        1620                1625                1630
Pro Ser Ala Leu Arg Glu Ser Pro Thr Gly Val Phe Val Gly Ala Gly
        1635                1640                1645
Pro Asn Glu Tyr Ala Glu Arg Val Gln Glu Leu Ala Asp Glu Ala Ala
    1650                1655                1660
Gly Leu Tyr Ser Gly Thr Gly Asn Met Leu Ser Val Ala Ala Gly Arg
1665                1670                1675                1680
Leu Ser Phe Phe Leu Gly Leu His Gly Pro Thr Leu Ala Val Asp Thr
            1685                1690                1695
Ala Cys Ser Ser Ser Leu Val Ala Leu His Leu Gly Cys Gln Ser Leu
        1700                1705                1710
Arg Arg Gly Glu Cys Asp Gln Ala Leu Val Gly Gly Val Asn Met Leu
    1715                1720                1725
Leu Ser Pro Lys Thr Phe Ala Leu Leu Ser Arg Met His Ala Leu Ser
    1730                1735                1740
Pro Gly Gly Arg Cys Lys Thr Phe Ser Ala Asp Ala Asp Gly Tyr Ala
1745                1750                1755                1760
Arg Ala Glu Gly Cys Ala Val Val Val Leu Lys Arg Leu Ser Asp Ala
            1765                1770                1775
Gln Arg Asp Arg Asp Pro Ile Leu Ala Val Ile Arg Gly Thr Ala Ile
            1780                1785                1790
Asn His Asp Gly Pro Ser Ser Gly Leu Thr Val Pro Ser Gly Pro Ala
    1795                1800                1805
Gln Glu Ala Leu Leu Arg Gln Ala Leu Ala His Ala Gly Val Val Pro
    1810                1815                1820
Ala Asp Val Asp Phe Val Glu Cys His Gly Thr Gly Thr Ala Leu Gly
1825                1830                1835                1840
Asp Pro Ile Glu Val Arg Ala Leu Ser Asp Val Tyr Gly Gln Ala Arg
            1845                1850                1855
Pro Ala Asp Arg Pro Leu Ile Leu Gly Ala Ala Lys Ala Asn Leu Gly
        1860                1865                1870
His Met Glu Pro Ala Ala Gly Leu Ala Gly Leu Leu Lys Ala Val Leu
    1875                1880                1885
Ala Leu Gly Gln Glu Gln Ile Pro Ala Gln Pro Glu Leu Gly Glu Leu
    1890                1895                1900
Asn Pro Leu Leu Pro Trp Glu Ala Leu Pro Val Ala Val Ala Arg Ala
1905                1910                1915                1920
Ala Val Pro Trp Pro Arg Thr Asp Arg Pro Arg Phe Ala Gly Val Ser
            1925                1930                1935
Ser Phe Gly Met Ser Gly Thr Asn Ala His Val Val Leu Glu Glu Ala
        1940                1945                1950
```

-continued

Pro Ala Val Glu Leu Trp Pro Ala Ala Pro Glu Arg Ser Ala Glu Leu
        1955                1960                1965

Leu Val Leu Ser Gly Lys Ser Glu Gly Ala Leu Asp Ala Gln Ala Ala
    1970                1975                1980

Arg Leu Arg Glu His Leu Asp Met His Pro Glu Leu Gly Leu Gly Asp
1985                1990                1995                2000

Val Ala Phe Ser Leu Ala Thr Thr Arg Ser Ala Met Asn His Arg Leu
        2005                2010                2015

Ala Val Ala Val Thr Ser Arg Glu Gly Leu Leu Ala Ala Leu Ser Ala
    2020                2025                2030

Val Ala Gln Gly Gln Thr Pro Pro Gly Ala Ala Arg Cys Ile Ala Ser
        2035                2040                2045

Ser Ser Arg Gly Lys Leu Ala Phe Leu Phe Thr Gly Gln Gly Ala Gln
    2050                2055                2060

Thr Pro Gly Met Gly Arg Gly Leu Cys Ala Ala Trp Pro Ala Phe Arg
2065                2070                2075                2080

Glu Ala Phe Asp Arg Cys Val Ala Leu Phe Asp Arg Glu Leu Asp Arg
        2085                2090                2095

Pro Leu Arg Glu Val Met Trp Ala Glu Pro Gly Ser Ala Glu Ser Leu
        2100                2105                2110

Leu Leu Asp Gln Thr Ala Phe Thr Gln Pro Ala Leu Phe Thr Val Glu
        2115                2120                2125

Tyr Ala Leu Thr Ala Leu Trp Arg Ser Trp Gly Val Glu Pro Glu Leu
        2130                2135                2140

Val Ala Gly His Ser Ala Gly Glu Leu Val Ala Ala Cys Val Ala Gly
2145                2150                2155                2160

Val Phe Ser Leu Glu Asp Gly Val Arg Leu Val Ala Ala Arg Gly Arg
        2165                2170                2175

Leu Met Gln Gly Leu Ser Ala Gly Gly Ala Met Val Ser Leu Gly Ala
            2180                2185                2190

Pro Glu Ala Glu Val Ala Ala Val Ala Pro His Ala Ala Ser Val
    2195                2200                2205

Ser Ile Ala Ala Val Asn Gly Pro Glu Gln Val Val Ile Ala Gly Val
    2210                2215                2220

Glu Gln Ala Val Gln Ala Ile Ala Ala Gly Phe Ala Ala Arg Gly Ala
2225                2230                2235                2240

Arg Thr Lys Arg Leu His Val Ser His Ala Ser His Ser Pro Leu Met
            2245                2250                2255

Glu Pro Met Leu Glu Glu Phe Gly Arg Val Ala Ala Ser Val Thr Tyr
        2260                2265                2270

Arg Arg Pro Ser Val Ser Leu Val Ser Asn Leu Ser Gly Lys Val Val
        2275                2280                2285

Ala Asp Glu Leu Ser Ala Pro Gly Tyr Trp Val Arg His Val Arg Glu
    2290                2295                2300

Ala Val Arg Phe Ala Asp Gly Val Lys Ala Leu His Glu Ala Gly Ala
2305                2310                2315                2320

Gly Thr Phe Val Glu Val Gly Pro Lys Pro Thr Leu Leu Gly Leu Leu
            2325                2330                2335

Pro Ala Cys Leu Pro Glu Ala Glu Pro Thr Leu Leu Ala Ser Leu Arg
            2340                2345                2350

Ala Gly Arg Glu Glu Ala Ala Gly Val Leu Glu Ala Leu Gly Arg Leu
        2355                2360                2365

Trp Ala Ala Gly Gly Ser Val Ser Trp Pro Gly Val Phe Pro Thr Ala

-continued

```
            2370            2375            2380
Gly Arg Arg Val Pro Leu Pro Thr Tyr Pro Trp Gln Arg Gln Arg Tyr
2385            2390            2395            2400
Trp Pro Asp Ile Glu Pro Asp Ser Arg Arg His Ala Ala Ala Asp Pro
            2405            2410            2415
Thr Gln Gly Trp Phe Tyr Arg Val Asp Trp Pro Glu Ile Pro Arg Ser
            2420            2425            2430
Leu Gln Lys Ser Glu Glu Ala Ser Arg Gly Ser Trp Leu Val Leu Ala
            2435            2440            2445
Asp Lys Gly Gly Val Gly Glu Ala Val Ala Ala Ala Leu Ser Thr Arg
2450            2455            2460
Gly Leu Pro Cys Val Val Leu His Ala Pro Ala Glu Thr Ser Ala Thr
2465            2470            2475            2480
Ala Glu Leu Val Thr Glu Ala Ala Gly Gly Arg Ser Asp Trp Gln Val
            2485            2490            2495
Val Leu Tyr Leu Trp Gly Leu Asp Ala Val Val Gly Ala Glu Ala Ser
            2500            2505            2510
Ile Asp Glu Ile Gly Asp Ala Thr Arg Arg Ala Thr Ala Pro Val Leu
            2515            2520            2525
Gly Leu Ala Arg Phe Leu Ser Thr Val Ser Cys Ser Pro Arg Leu Trp
            2530            2535            2540
Val Val Thr Arg Gly Ala Cys Ile Val Gly Asp Glu Pro Ala Ile Ala
2545            2550            2555            2560
Pro Cys Gln Ala Ala Leu Trp Gly Met Gly Arg Val Ala Ala Leu Glu
            2565            2570            2575
His Pro Gly Ala Trp Gly Gly Leu Val Asp Leu Asp Pro Arg Ala Ser
            2580            2585            2590
Pro Pro Gln Ala Ser Pro Ile Asp Gly Glu Met Leu Val Thr Glu Leu
            2595            2600            2605
Leu Ser Gln Glu Thr Glu Asp Gln Leu Ala Phe Arg His Gly Arg Arg
            2610            2615            2620
His Ala Ala Arg Leu Val Ala Ala Pro Pro Gln Gly Gln Ala Ala Pro
2625            2630            2635            2640
Val Ser Leu Ser Ala Glu Ala Ser Tyr Leu Val Thr Gly Gly Leu Gly
            2645            2650            2655
Gly Leu Gly Leu Ile Val Ala Gln Trp Leu Val Glu Leu Gly Ala Arg
            2660            2665            2670
His Leu Val Leu Thr Ser Arg Arg Gly Leu Pro Asp Arg Gln Ala Trp
            2675            2680            2685
Cys Glu Gln Gln Pro Pro Glu Ile Arg Ala Arg Ile Ala Ala Val Glu
            2690            2695            2700
Ala Leu Glu Ala Arg Gly Ala Arg Val Thr Val Ala Ala Val Asp Val
2705            2710            2715            2720
Ala Asp Val Glu Pro Met Thr Ala Leu Val Ser Ser Val Glu Pro Pro
            2725            2730            2735
Leu Arg Gly Val Val His Ala Ala Gly Val Ser Val Met Arg Pro Leu
            2740            2745            2750
Ala Glu Thr Asp Glu Thr Leu Leu Glu Ser Val Leu Arg Pro Lys Val
            2755            2760            2765
Ala Gly Ser Trp Leu Leu His Arg Leu Leu His Gly Arg Pro Leu Asp
            2770            2775            2780
Leu Phe Val Leu Phe Ser Ser Gly Ala Ala Val Trp Gly Ser His Ser
2785            2790            2795            2800
```

-continued

Gln Gly Ala Tyr Ala Ala Asn Ala Phe Leu Asp Gly Leu Ala His
            2805                2810                2815

Leu Arg Arg Ser Gln Ser Leu Pro Ala Leu Ser Val Ala Trp Gly Leu
        2820                2825                2830

Trp Ala Glu Gly Gly Met Ala Asp Ala Glu Ala His Ala Arg Leu Ser
    2835                2840                2845

Asp Ile Gly Val Leu Pro Met Ser Thr Ser Ala Ala Leu Ser Ala Leu
2850                2855                2860

Gln Arg Leu Val Glu Thr Gly Ala Ala Gln Arg Thr Val Thr Arg Met
2865                2870                2875                2880

Asp Trp Ala Arg Phe Ala Pro Val Tyr Thr Ala Arg Gly Arg Arg Asn
            2885                2890                2895

Leu Leu Ser Ala Leu Val Ala Gly Arg Asp Ile Ile Ala Pro Ser Pro
        2900                2905                2910

Pro Ala Ala Ala Thr Arg Asn Trp Arg Gly Leu Ser Val Ala Glu Ala
    2915                2920                2925

Arg Val Ala Leu His Glu Ile Val His Gly Ala Val Ala Arg Val Leu
2930                2935                2940

Gly Phe Leu Asp Pro Ser Ala Leu Asp Pro Gly Met Gly Phe Asn Glu
2945                2950                2955                2960

Gln Gly Leu Asp Ser Leu Met Ala Val Glu Ile Arg Asn Leu Leu Gln
            2965                2970                2975

Ala Glu Leu Asp Val Arg Leu Ser Thr Thr Leu Ala Phe Asp His Pro
        2980                2985                2990

Thr Val Gln Arg Leu Val Glu His Leu Leu Val Asp Val Leu Lys Leu
    2995                3000                3005

Glu Asp Arg Ser Asp Thr Gln His Val Arg Ser Leu Ala Ser Asp Glu
3010                3015                3020

Pro Ile Ala Ile Val Gly Ala Ala Cys Arg Phe Pro Gly Gly Val Glu
3025                3030                3035                3040

Asp Leu Glu Ser Tyr Trp Gln Leu Leu Ala Glu Gly Val Val Val Ser
            3045                3050                3055

Ala Glu Val Pro Ala Asp Arg Trp Asp Ala Ala Asp Trp Tyr Asp Pro
        3060                3065                3070

Asp Pro Glu Ile Pro Gly Arg Thr Tyr Val Thr Lys Gly Ala Phe Leu
    3075                3080                3085

Arg Asp Leu Gln Arg Leu Asp Ala Thr Phe Phe Arg Ile Ser Pro Arg
3090                3095                3100

Glu Ala Met Ser Leu Asp Pro Gln Gln Arg Leu Leu Leu Glu Val Ser
3105                3110                3115                3120

Trp Glu Ala Leu Glu Ser Ala Gly Ile Ala Pro Asp Thr Leu Arg Asp
            3125                3130                3135

Ser Pro Thr Gly Val Phe Val Gly Ala Gly Pro Asn Glu Tyr Tyr Thr
        3140                3145                3150

Gln Arg Leu Arg Gly Phe Thr Asp Gly Ala Ala Gly Leu Tyr Gly Gly
    3155                3160                3165

Thr Gly Asn Met Leu Ser Val Thr Ala Gly Arg Leu Ser Phe Phe Leu
3170                3175                3180

Gly Leu His Gly Pro Thr Leu Ala Met Asp Thr Ala Cys Ser Ser Ser
3185                3190                3195                3200

Leu Val Ala Leu His Leu Ala Cys Gln Ser Leu Arg Leu Gly Glu Cys
            3205                3210                3215

-continued

```
Asp Gln Ala Leu Val Gly Gly Val Asn Val Leu Ala Pro Glu Thr
        3220            3225            3230

Phe Val Leu Leu Ser Arg Met Arg Ala Leu Ser Pro Asp Gly Arg Cys
        3235            3240            3245

Lys Thr Phe Ser Ala Asp Ala Asp Gly Tyr Ala Arg Gly Glu Gly Cys
        3250            3255            3260

Ala Val Val Val Leu Lys Arg Leu Arg Asp Ala Gln Arg Ala Gly Asp
3265            3270            3275            3280

Ser Ile Leu Ala Leu Ile Arg Gly Ser Ala Val Asn His Asp Gly Pro
        3285            3290            3295

Ser Ser Gly Leu Thr Val Pro Asn Gly Pro Ala Gln Gln Ala Leu Leu
        3300            3305            3310

Arg Gln Ala Leu Ser Gln Ala Gly Val Ser Pro Val Asp Val Asp Phe
        3315            3320            3325

Val Glu Cys His Gly Thr Gly Thr Ala Leu Gly Asp Pro Ile Glu Val
        3330            3335            3340

Gln Ala Leu Ser Glu Val Tyr Gly Pro Gly Arg Ser Gly Asp Arg Pro
3345            3350            3355            3360

Leu Val Leu Gly Ala Ala Lys Ala Asn Val Ala His Leu Glu Ala Ala
        3365            3370            3375

Ser Gly Leu Ala Ser Leu Leu Lys Ala Val Leu Ala Leu Arg His Glu
        3380            3385            3390

Gln Ile Pro Ala Gln Pro Glu Leu Gly Glu Leu Asn Pro His Leu Pro
        3395            3400            3405

Trp Asn Thr Leu Pro Val Ala Val Pro Arg Lys Ala Val Pro Trp Gly
        3410            3415            3420

Arg Gly Ala Arg Pro Arg Arg Ala Gly Val Ser Ala Phe Gly Leu Ser
3425            3430            3435            3440

Gly Thr Asn Val His Val Val Leu Glu Glu Ala Pro Glu Val Glu Pro
        3445            3450            3455

Ala Pro Ala Ala Pro Ala Arg Pro Val Glu Leu Val Val Leu Ser Ala
        3460            3465            3470

Lys Ser Ala Ala Ala Leu Asp Ala Ala Ala Arg Leu Ser Ala His
        3475            3480            3485

Leu Ser Ala His Pro Glu Leu Ser Leu Gly Asp Val Ala Phe Ser Leu
        3490            3495            3500

Ala Thr Thr Arg Ser Pro Met Glu His Arg Leu Ala Ile Ala Thr Thr
3505            3510            3515            3520

Ser Arg Glu Ala Leu Arg Gly Ala Leu Asp Ala Ala Gln Gln Lys
        3525            3530            3535

Thr Pro Gln Gly Ala Val Arg Gly Lys Ala Val Ser Ser Arg Gly Lys
        3540            3545            3550

Leu Ala Phe Leu Phe Thr Gly Gln Gly Ala Gln Met Pro Gly Met Gly
        3555            3560            3565

Arg Gly Leu Tyr Glu Thr Trp Pro Ala Phe Arg Glu Ala Phe Asp Arg
        3570            3575            3580

Cys Val Ala Leu Phe Asp Arg Glu Ile Asp Gln Pro Leu Arg Glu Val
3585            3590            3595            3600

Met Trp Ala Ala Pro Gly Leu Ala Gln Ala Ala Arg Leu Asp Gln Thr
        3605            3610            3615

Ala Tyr Ala Gln Pro Ala Leu Phe Ala Leu Glu Tyr Ala Leu Ala Ala
        3620            3625            3630

Leu Trp Arg Ser Trp Gly Val Glu Pro His Val Leu Leu Gly His Ser
```

-continued

```
              3635           3640           3645
Ile Gly Glu Leu Val Ala Ala Cys Val Ala Gly Val Phe Ser Leu Glu
          3650           3655           3660
Asp Ala Val Arg Leu Val Ala Ala Arg Gly Arg Leu Met Gln Ala Leu
3665           3670           3675           3680
Pro Ala Gly Gly Ala Met Val Ala Ile Ala Ala Ser Glu Ala Glu Val
              3685           3690           3695
Ala Ala Ser Val Ala Pro His Ala Ala Thr Val Ser Ile Ala Ala Val
          3700           3705           3710
Asn Gly Pro Asp Ala Val Val Ile Ala Gly Ala Glu Val Gln Val Leu
          3715           3720           3725
Ala Leu Gly Ala Thr Phe Ala Ala Arg Gly Ile Arg Thr Lys Arg Leu
          3730           3735           3740
Ala Val Ser His Ala Phe His Ser Pro Leu Met Asp Pro Met Leu Glu
3745           3750           3755           3760
Asp Phe Gln Arg Val Ala Ala Thr Ile Ala Tyr Arg Ala Pro Asp Arg
              3765           3770           3775
Pro Val Val Ser Asn Val Thr Gly His Val Ala Gly Pro Glu Ile Ala
          3780           3785           3790
Thr Pro Glu Tyr Trp Val Arg His Val Arg Ser Ala Val Arg Phe Gly
          3795           3800           3805
Asp Gly Ala Lys Ala Leu His Ala Ala Gly Ala Ala Thr Phe Val Glu
          3810           3815           3820
Val Gly Pro Lys Pro Val Leu Leu Gly Leu Leu Pro Ala Cys Leu Gly
3825           3830           3835           3840
Glu Ala Asp Ala Val Leu Val Pro Ser Leu Arg Ala Asp Arg Ser Glu
              3845           3850           3855
Cys Glu Val Val Leu Ala Ala Leu Gly Ala Trp Tyr Ala Trp Gly Gly
              3860           3865           3870
Ala Leu Asp Trp Lys Gly Val Phe Pro Asp Gly Ala Arg Arg Val Ala
          3875           3880           3885
Leu Pro Met Tyr Pro Trp Gln Arg Glu Arg His Trp Met Asp Leu Thr
3890           3895           3900
Pro Arg Ser Ala Ala Pro Ala Gly Ile Ala Gly Arg Trp Pro Leu Ala
3905           3910           3915           3920
Gly Val Gly Leu Cys Met Pro Gly Ala Val Leu His His Val Leu Ser
              3925           3930           3935
Ile Gly Pro Arg His Gln Pro Phe Leu Gly Asp His Leu Val Phe Gly
          3940           3945           3950
Lys Val Val Pro Gly Ala Phe His Val Ala Val Ile Leu Ser Ile
          3955           3960           3965
Ala Ala Glu Arg Trp Pro Glu Arg Ala Ile Glu Leu Thr Gly Val Glu
          3970           3975           3980
Phe Leu Lys Ala Ile Ala Met Glu Pro Asp Gln Glu Val Glu Leu His
3985           3990           3995           4000
Ala Val Leu Thr Pro Glu Ala Ala Gly Asp Gly Tyr Leu Phe Glu Leu
              4005           4010           4015
Ala Thr Leu Ala Ala Pro Glu Thr Glu Arg Arg Trp Thr Thr His Ala
              4020           4025           4030
Arg Gly Arg Val Gln Pro Thr Asp Gly Ala Pro Gly Ala Leu Pro Arg
          4035           4040           4045
Leu Glu Val Leu Glu Asp Arg Ala Ile Gln Pro Leu Asp Phe Ala Gly
          4050           4055           4060
```

```
Phe Leu Asp Arg Leu Ser Ala Val Arg Ile Gly Trp Gly Pro Leu Trp
4065                4070                4075                4080

Arg Trp Leu Gln Asp Gly Arg Val Gly Asp Glu Ala Ser Leu Ala Thr
            4085                4090                4095

Leu Val Pro Thr Tyr Pro Asn Ala His Asp Val Ala Pro Leu His Pro
                4100                4105                4110

Ile Leu Leu Asp Asn Gly Phe Ala Val Ser Leu Leu Ser Thr Arg Ser
        4115                4120                4125

Glu Pro Glu Asp Asp Gly Thr Pro Pro Leu Pro Phe Ala Val Glu Arg
    4130                4135                4140

Val Arg Trp Trp Arg Ala Pro Val Gly Arg Val Arg Cys Gly Gly Val
4145                4150                4155                4160

Pro Arg Ser Gln Ala Phe Gly Val Ser Ser Phe Val Leu Val Asp Glu
            4165                4170                4175

Thr Gly Glu Val Val Ala Glu Val Glu Gly Phe Val Cys Arg Arg Ala
                4180                4185                4190

Pro Arg Glu Val Phe Leu Arg Gln Glu Ser Gly Ala Ser Thr Ala Ala
        4195                4200                4205

Leu Tyr Arg Leu Asp Trp Pro Glu Ala Pro Leu Pro Asp Ala Pro Ala
    4210                4215                4220

Glu Arg Ile Glu Glu Ser Trp Val Val Ala Ala Pro Gly Ser Glu
4225                4230                4235                4240

Met Ala Ala Ala Leu Ala Thr Arg Leu Asn Arg Cys Val Leu Ala Glu
            4245                4250                4255

Pro Lys Gly Leu Glu Ala Ala Leu Ala Gly Val Ser Pro Ala Gly Val
                4260                4265                4270

Ile Cys Leu Trp Glu Ala Gly Ala His Glu Ala Pro Ala Ala Ala
        4275                4280                4285

Gln Arg Val Ala Thr Glu Gly Leu Ser Val Val Gln Ala Leu Arg Asp
    4290                4295                4300

Arg Ala Val Arg Leu Trp Trp Val Thr Met Gly Ala Val Ala Val Glu
4305                4310                4315                4320

Ala Gly Glu Arg Val Gln Val Ala Thr Ala Pro Val Trp Gly Leu Gly
            4325                4330                4335

Arg Thr Val Met Gln Glu Arg Pro Glu Leu Ser Cys Thr Leu Val Asp
                4340                4345                4350

Leu Glu Pro Glu Ala Asp Ala Ala Arg Ser Ala Asp Val Leu Leu Arg
        4355                4360                4365

Glu Leu Gly Arg Ala Asp Asp Glu Thr Gln Val Ala Phe Arg Ser Gly
    4370                4375                4380

Lys Arg Arg Val Ala Arg Leu Val Lys Ala Thr Thr Pro Glu Gly Leu
4385                4390                4395                4400

Leu Val Pro Asp Ala Glu Ser Tyr Arg Leu Glu Ala Gly Gln Lys Gly
            4405                4410                4415

Thr Leu Asp Gln Leu Arg Leu Ala Pro Ala Gln Arg Arg Ala Pro Gly
                4420                4425                4430

Pro Gly Glu Val Glu Ile Lys Val Thr Ala Ser Gly Leu Asn Phe Arg
        4435                4440                4445

Thr Val Leu Ala Val Leu Gly Met Tyr Pro Gly Asp Ala Gly Pro Met
    4450                4455                4460

Gly Gly Asp Cys Ala Gly Val Ala Thr Ala Val Gly Gln Gly Val Arg
4465                4470                4475                4480
```

-continued

```
His Val Ala Val Gly Asp Ala Val Met Thr Leu Gly Thr Leu His Arg
            4485                4490                4495
Phe Val Thr Val Asp Ala Arg Leu Val Val Arg Gln Pro Ala Gly Leu
            4500                4505                4510
Thr Pro Ala Gln Ala Ala Thr Val Pro Val Ala Phe Leu Thr Ala Trp
            4515                4520                4525
Leu Ala Leu His Asp Leu Gly Asn Leu Arg Arg Gly Glu Arg Val Leu
            4530                4535                4540
Ile His Ala Ala Ala Gly Gly Val Gly Met Ala Ala Val Gln Ile Ala
4545                4550                4555                4560
Arg Trp Ile Gly Ala Glu Val Phe Ala Thr Ala Ser Pro Ser Lys Trp
            4565                4570                4575
Ala Ala Val Gln Ala Met Gly Val Pro Arg Thr His Ile Ala Ser Ser
            4580                4585                4590
Arg Thr Leu Glu Phe Ala Glu Thr Phe Arg Gln Val Thr Gly Gly Arg
            4595                4600                4605
Gly Val Asp Val Val Leu Asn Ala Leu Ala Gly Glu Phe Val Asp Ala
            4610                4615                4620
Ser Leu Ser Leu Leu Ser Thr Gly Gly Arg Phe Leu Glu Met Gly Lys
4625                4630                4635                4640
Thr Asp Ile Arg Asp Arg Ala Ala Val Ala Ala Ala His Pro Gly Val
            4645                4650                4655
Arg Tyr Arg Val Phe Asp Ile Leu Glu Leu Ala Pro Asp Arg Thr Arg
            4660                4665                4670
Glu Ile Leu Glu Arg Val Val Glu Gly Phe Ala Ala Gly His Leu Arg
            4675                4680                4685
Ala Leu Pro Val His Ala Phe Ala Ile Thr Lys Ala Glu Ala Ala Phe
4690                4695                4700
Arg Phe Met Ala Gln Ala Arg His Gln Gly Lys Val Val Leu Leu Pro
4705                4710                4715                4720
Ala Pro Ser Ala Ala Pro Leu Ala Pro Thr Gly Thr Val Leu Leu Thr
            4725                4730                4735
Gly Gly Leu Gly Ala Leu Gly Leu His Val Ala Arg Trp Leu Ala Gln
            4740                4745                4750
Gln Gly Val Pro His Met Val Leu Thr Gly Arg Arg Gly Leu Asp Thr
            4755                4760                4765
Pro Gly Ala Ala Lys Ala Val Ala Glu Ile Glu Ala Leu Gly Ala Arg
            4770                4775                4780
Val Thr Ile Ala Ala Ser Asp Val Ala Asp Arg Asn Ala Leu Glu Ala
4785                4790                4795                4800
Val Leu Gln Ala Ile Pro Ala Glu Trp Pro Leu Gln Gly Val Ile His
            4805                4810                4815
Ala Ala Gly Ala Leu Asp Asp Gly Val Leu Asp Glu Gln Thr Thr Asp
            4820                4825                4830
Arg Phe Ser Arg Val Leu Ala Pro Lys Val Thr Gly Ala Trp Asn Leu
            4835                4840                4845
His Glu Leu Thr Ala Gly Asn Asp Leu Ala Phe Phe Val Leu Phe Ser
4850                4855                4860
Ser Met Ser Gly Leu Leu Gly Ser Ala Gly Gln Ser Asn Tyr Ala Ala
4865                4870                4875                4880
Ala Asn Thr Phe Leu Asp Ala Leu Ala Ala His Arg Arg Ala Glu Gly
            4885                4890                4895
Leu Ala Ala Gln Ser Leu Ala Trp Gly Pro Trp Ser Asp Gly Gly Met
```

-continued

```
                4900            4905            4910
Ala Ala Gly Leu Ser Ala Ala Leu Gln Ala Arg Leu Ala Arg His Gly
            4915            4920            4925

Met Gly Ala Leu Ser Pro Ala Gln Gly Thr Ala Leu Leu Gly Gln Ala
    4930            4935            4940

Leu Ala Arg Pro Glu Thr Gln Leu Gly Ala Met Ser Leu Asp Val Arg
4945            4950            4955            4960

Ala Ala Ser Gln Ala Ser Gly Ala Ala Val Pro Pro Val Trp Arg Ala
        4965            4970            4975

Leu Val Arg Ala Glu Ala Arg His Thr Ala Ala Gly Ala Gln Gly Ala
            4980            4985            4990

Leu Ala Ala Arg Leu Gly Ala Leu Pro Glu Ala Arg Arg Ala Asp Glu
    4995            5000            5005

Val Arg Lys Val Val Gln Ala Glu Ile Ala Arg Val Leu Ser Trp Ser
    5010            5015            5020

Ala Ala Ser Ala Val Pro Val Asp Arg Pro Leu Ser Asp Leu Gly Leu
5025            5030            5035            5040

Asp Ser Leu Thr Ala Val Glu Leu Arg Asn Val Leu Gly Gln Arg Val
        5045            5050            5055

Gly Ala Thr Leu Pro Ala Thr Leu Ala Phe Asp His Pro Thr Val Asp
        5060            5065            5070

Ala Leu Thr Arg Trp Leu Leu Asp Lys Val Leu Ala Val Ala Glu Pro
    5075            5080            5085

Ser Val Ser Ser Ala Lys Ser Ser Pro Gln Val Ala Leu Asp Glu Pro
    5090            5095            5100

Ile Ala Ile Ile Gly Ile Gly Cys Arg Phe Pro Gly Gly Val Ala Asp
5105            5110            5115            5120

Pro Glu Ser Phe Trp Arg Leu Leu Glu Glu Gly Ser Asp Ala Val Val
            5125            5130            5135

Glu Val Pro His Glu Arg Trp Asp Ile Asp Ala Phe Tyr Asp Pro Asp
        5140            5145            5150

Pro Asp Val Arg Gly Lys Met Thr Thr Arg Phe Gly Gly Phe Leu Ser
    5155            5160            5165

Asp Ile Asp Arg Phe Asp Pro Ala Phe Phe Gly Ile Ser Pro Arg Glu
    5170            5175            5180

Ala Thr Thr Met Asp Pro Gln Gln Arg Leu Leu Leu Glu Thr Ser Trp
5185            5190            5195            5200

Glu Ala Phe Glu Arg Ala Gly Ile Leu Pro Glu Arg Leu Met Gly Ser
        5205            5210            5215

Asp Thr Gly Val Phe Val Gly Leu Phe Tyr Gln Glu Tyr Ala Ala Leu
        5220            5225            5230

Ala Gly Gly Ile Glu Ala Phe Asp Gly Tyr Leu Gly Thr Gly Thr Thr
    5235            5240            5245

Ala Ser Val Ala Ser Gly Arg Ile Ser Tyr Val Leu Gly Leu Lys Gly
    5250            5255            5260

Pro Ser Leu Thr Val Asp Thr Ala Cys Ser Ser Ser Leu Val Ala Val
5265            5270            5275            5280

His Leu Ala Cys Gln Ala Leu Arg Arg Gly Glu Cys Ser Val Ala Leu
            5285            5290            5295

Ala Gly Gly Val Ala Leu Met Leu Thr Pro Ala Thr Phe Val Glu Phe
        5300            5305            5310

Ser Arg Leu Arg Gly Leu Ala Pro Asp Gly Arg Cys Lys Ser Phe Ser
    5315            5320            5325
```

-continued

```
Ala Ala Ala Asp Gly Val Gly Trp Ser Glu Gly Cys Ala Met Leu Leu
    5330                5335                5340
Leu Lys Pro Leu Arg Asp Ala Gln Arg Asp Gly Asp Pro Ile Leu Ala
5345                5350                5355                5360
Val Ile Arg Gly Thr Ala Val Asn Gln Asp Gly Arg Ser Asn Gly Leu
        5365                5370                5375
Thr Ala Pro Asn Gly Ser Ser Gln Gln Glu Val Ile Arg Arg Ala Leu
    5380                5385                5390
Glu Gln Ala Gly Leu Ala Pro Ala Asp Val Ser Tyr Val Glu Cys His
        5395                5400                5405
Gly Thr Gly Thr Thr Leu Gly Asp Pro Ile Glu Val Gln Ala Leu Gly
    5410                5415                5420
Ala Val Leu Ala Gln Gly Arg Pro Ser Asp Arg Pro Leu Val Ile Gly
5425                5430                5435                5440
Ser Val Lys Ser Asn Ile Gly His Thr Gln Ala Ala Ala Gly Val Ala
        5445                5450                5455
Gly Val Ile Lys Val Ala Leu Ala Leu Glu Arg Gly Leu Ile Pro Arg
    5460                5465                5470
Ser Leu His Phe Asp Ala Pro Asn Pro His Ile Pro Trp Ser Glu Leu
    5475                5480                5485
Ala Val Gln Val Ala Ala Lys Pro Val Glu Trp Thr Arg Asn Gly Val
    5490                5495                5500
Pro Arg Arg Ala Gly Val Ser Ser Phe Gly Val Ser Gly Thr Asn Ala
5505                5510                5515                5520
His Val Val Leu Glu Glu Ala Pro Ala Ala Ala Phe Ala Pro Ala Ala
        5525                5530                5535
Ala Arg Ser Ala Glu Leu Phe Val Leu Ser Ala Lys Ser Ala Ala Ala
        5540                5545                5550
Leu Asp Ala Gln Ala Ala Arg Leu Ser Ala His Val Val Ala His Pro
    5555                5560                5565
Glu Leu Gly Leu Gly Asp Leu Ala Phe Ser Leu Ala Thr Thr Arg Ser
    5570                5575                5580
Pro Met Thr Tyr Arg Leu Ala Val Ala Ala Thr Ser Arg Glu Ala Leu
5585                5590                5595                5600
Ser Ala Ala Leu Asp Thr Ala Ala Gln Gly Gln Ala Pro Pro Ala Ala
        5605                5610                5615
Ala Arg Gly His Ala Ser Thr Gly Ser Ala Pro Lys Val Val Phe Val
        5620                5625                5630
Phe Pro Gly Gln Gly Ser Gln Trp Leu Gly Met Gly Gln Lys Leu Leu
        5635                5640                5645
Ser Glu Glu Pro Val Phe Arg Asp Ala Leu Ser Ala Cys Asp Arg Ala
    5650                5655                5660
Ile Gln Ala Glu Ala Gly Trp Ser Leu Leu Ala Glu Leu Ala Ala Asp
5665                5670                5675                5680
Glu Thr Thr Ser Gln Leu Gly Arg Ile Asp Val Val Gln Pro Ala Leu
        5685                5690                5695
Phe Ala Ile Glu Val Ala Leu Ser Ala Leu Trp Arg Ser Trp Gly Val
        5700                5705                5710
Glu Pro Asp Ala Val Val Gly His Ser Met Gly Glu Val Ala Ala Ala
    5715                5720                5725
His Val Ala Gly Ala Leu Ser Leu Glu Asp Ala Val Ala Ile Ile Cys
    5730                5735                5740
```

```
Arg Arg Ser Leu Leu Leu Arg Arg Ile Ser Gly Gln Gly Glu Met Ala
5745                5750                5755                5760

Val Val Glu Leu Ser Leu Ala Glu Ala Glu Ala Ala Leu Leu Gly Tyr
            5765                5770                5775

Glu Asp Arg Leu Ser Val Ala Val Ser Asn Ser Pro Arg Ser Thr Val
        5780                5785                5790

Leu Ala Gly Glu Pro Ala Ala Leu Ala Glu Val Leu Ala Ile Leu Ala
    5795                5800                5805

Ala Lys Gly Val Phe Cys Arg Arg Val Lys Val Asp Val Ala Ser His
5810                5815                5820

Ser Pro Gln Ile Asp Pro Leu Arg Asp Glu Leu Leu Ala Ala Leu Gly
5825                5830                5835                5840

Glu Leu Glu Pro Arg Gln Ala Thr Val Ser Met Arg Ser Thr Val Thr
            5845                5850                5855

Ser Thr Ile Met Ala Gly Pro Glu Leu Val Ala Ser Tyr Trp Ala Asp
        5860                5865                5870

Asn Val Arg Gln Pro Val Arg Phe Ala Glu Ala Val Gln Ser Leu Met
    5875                5880                5885

Glu Asp Gly His Gly Leu Phe Val Glu Met Ser Pro His Pro Ile Leu
    5890                5895                5900

Thr Thr Ser Val Glu Glu Ile Arg Arg Ala Thr Lys Arg Glu Gly Val
5905                5910                5915                5920

Ala Val Gly Ser Leu Arg Arg Gly Gln Asp Glu Arg Leu Ser Met Leu
            5925                5930                5935

Glu Ala Leu Gly Ala Leu Trp Val His Gly Gln Ala Val Gly Trp Glu
        5940                5945                5950

Arg Leu Phe Ser Ala Gly Gly Ala Gly Leu Arg Arg Val Pro Leu Pro
    5955                5960                5965

Thr Tyr Pro Trp Gln Arg Glu Arg Tyr Trp Val Asp Ala Pro Thr Gly
    5970                5975                5980

Gly Ala Ala Gly Gly Ser Arg Phe Ala His Ala Gly Ser His Pro Leu
5985                5990                5995                6000

Leu Gly Glu Met Gln Thr Leu Ser Thr Gln Arg Ser Thr Arg Val Trp
            6005                6010                6015

Glu Thr Thr Leu Asp Leu Lys Arg Leu Pro Trp Leu Gly Asp His Arg
        6020                6025                6030

Val Gln Gly Ala Val Val Phe Pro Gly Ala Ala Tyr Leu Glu Met Ala
    6035                6040                6045

Leu Ser Ser Gly Ala Glu Ala Leu Gly Asp Gly Pro Leu Gln Val Ser
    6050                6055                6060

Asp Val Val Leu Ala Glu Ala Leu Ala Phe Ala Asp Asp Thr Pro Ala
6065                6070                6075                6080

Ala Val Gln Val Met Ala Thr Glu Glu Arg Pro Gly Arg Leu Gln Phe
            6085                6090                6095

His Val Ala Ser Arg Val Pro Gly His Gly Gly Ala Ala Phe Arg Ser
        6100                6105                6110

His Ala Arg Gly Val Leu Arg Gln Ile Glu Arg Ala Glu Val Pro Ala
    6115                6120                6125

Arg Leu Asp Leu Ala Ala Leu Arg Ala Arg Leu Gln Ala Ser Ala Pro
    6130                6135                6140

Ala Ala Ala Thr Tyr Ala Ala Leu Ala Glu Met Gly Leu Glu Tyr Gly
6145                6150                6155                6160

Pro Ala Phe Gln Gly Leu Val Glu Leu Trp Arg Gly Glu Gly Glu Ala
```

```
                    6165              6170              6175
Leu Gly Arg Val Arg Leu Pro Glu Ala Ala Gly Ser Pro Ala Ala Cys
            6180              6185              6190

Arg Leu His Pro Ala Leu Leu Asp Ala Cys Phe His Val Ser Ser Ala
            6195              6200              6205

Phe Ala Asp Arg Gly Glu Ala Thr Pro Trp Val Pro Val Glu Ile Gly
            6210              6215              6220

Ser Leu Arg Trp Phe Gln Arg Pro Ser Gly Glu Leu Trp Cys His Ala
        6225              6230              6235              6240

Arg Ser Val Ser His Gly Lys Pro Thr Pro Asp Arg Arg Ser Thr Asp
            6245              6250              6255

Phe Trp Val Val Asp Ser Thr Gly Ala Ile Val Ala Glu Ile Ser Gly
            6260              6265              6270

Leu Val Ala Gln Arg Leu Ala Gly Gly Val Arg Arg Glu Glu Asp
            6275              6280              6285

Asp Trp Phe Met Glu Pro Ala Trp Glu Pro Thr Ala Val Pro Gly Ser
            6290              6295              6300

Glu Val Met Ala Gly Arg Trp Leu Leu Ile Gly Ser Gly Gly Leu
6305              6310              6315              6320

Gly Ala Ala Leu His Ser Ala Leu Thr Glu Ala Gly His Ser Val Val
            6325              6330              6335

His Ala Thr Gly Arg Gly Thr Ser Ala Ala Gly Leu Gln Ala Leu Leu
            6340              6345              6350

Thr Ala Ser Phe Asp Gly Gln Ala Pro Thr Ser Val Val His Leu Gly
            6355              6360              6365

Ser Leu Asp Glu Arg Gly Val Leu Asp Ala Asp Ala Pro Phe Asp Ala
            6370              6375              6380

Asp Ala Leu Glu Glu Ser Leu Val Arg Gly Cys Asp Ser Val Leu Trp
6385              6390              6395              6400

Thr Val Gln Ala Val Ala Gly Ala Gly Phe Arg Asp Pro Pro Arg Leu
            6405              6410              6415

Trp Leu Val Thr Arg Gly Ala Gln Ala Ile Gly Ala Gly Asp Val Ser
            6420              6425              6430

Val Ala Gln Ala Pro Leu Leu Gly Leu Gly Arg Val Ile Ala Leu Glu
            6435              6440              6445

His Ala Glu Leu Arg Cys Ala Arg Ile Asp Leu Asp Pro Ala Arg Arg
            6450              6455              6460

Asp Gly Glu Val Asp Glu Leu Leu Ala Glu Leu Leu Ala Asp Ala
6465              6470              6475              6480

Glu Glu Glu Val Ala Phe Arg Gly Gly Glu Arg Arg Val Ala Arg Leu
            6485              6490              6495

Val Arg Arg Leu Pro Glu Thr Asp Cys Arg Glu Lys Ile Glu Pro Ala
            6500              6505              6510

Glu Gly Arg Pro Phe Arg Leu Glu Ile Asp Gly Ser Gly Val Leu Asp
            6515              6520              6525

Asp Leu Val Leu Arg Ala Thr Glu Arg Arg Pro Gly Pro Gly Glu
            6530              6535              6540

Val Glu Ile Ala Val Glu Ala Ala Gly Leu Asn Phe Leu Asp Val Met
6545              6550              6555              6560

Arg Ala Met Gly Ile Tyr Pro Gly Pro Gly Asp Gly Pro Val Ala Leu
            6565              6570              6575

Gly Ala Glu Cys Ser Gly Arg Ile Val Ala Met Gly Glu Gly Val Glu
            6580              6585              6590
```

-continued

```
Ser Leu Arg Ile Gly Gln Asp Val Val Ala Val Ala Pro Phe Ser Phe
    6595                6600                6605

Gly Thr His Val Thr Ile Asp Ala Arg Met Leu Ala Pro Arg Pro Ala
    6610                6615                6620

Ala Leu Thr Ala Ala Gln Ala Ala Ala Leu Pro Val Ala Phe Met Thr
6625                6630                6635                6640

Ala Trp Tyr Gly Leu Val His Leu Gly Arg Leu Arg Ala Gly Glu Arg
    6645                6650                6655

Val Leu Ile His Ser Ala Thr Gly Gly Thr Gly Leu Ala Ala Val Gln
    6660                6665                6670

Ile Ala Arg His Leu Gly Ala Glu Ile Phe Ala Thr Ala Gly Thr Pro
    6675                6680                6685

Glu Lys Arg Ala Trp Leu Arg Glu Gln Gly Ile Ala His Val Met Asp
    6690                6695                6700

Ser Arg Ser Leu Asp Phe Ala Glu Gln Val Leu Ala Ala Thr Lys Gly
6705                6710                6715                6720

Glu Gly Val Asp Val Val Leu Asn Ser Leu Ser Gly Ala Ala Ile Asp
                6725                6730                6735

Ala Ser Leu Ser Thr Leu Val Pro Asp Gly Arg Phe Ile Glu Leu Gly
    6740                6745                6750

Lys Thr Asp Ile Tyr Ala Asp Arg Ser Leu Gly Leu Ala His Phe Arg
    6755                6760                6765

Lys Ser Leu Ser Tyr Ser Ala Val Asp Leu Ala Gly Leu Ala Val Arg
    6770                6775                6780

Arg Pro Glu Arg Val Ala Ala Leu Leu Ala Glu Val Val Asp Leu Leu
6785                6790                6795                6800

Ala Arg Gly Ala Leu Gln Pro Leu Pro Val Glu Ile Phe Pro Leu Ser
    6805                6810                6815

Arg Ala Ala Asp Ala Phe Arg Lys Met Ala Gln Ala Gln His Leu Gly
    6820                6825                6830

Lys Leu Val Leu Ala Leu Glu Asp Pro Asp Val Arg Ile Arg Val Pro
    6835                6840                6845

Gly Glu Ser Gly Val Ala Ile Arg Ala Asp Gly Ala Tyr Leu Val Thr
    6850                6855                6860

Gly Gly Leu Gly Gly Leu Gly Leu Ser Val Ala Gly Trp Leu Ala Glu
6865                6870                6875                6880

Gln Gly Ala Gly His Leu Val Leu Val Gly Arg Ser Gly Ala Val Ser
    6885                6890                6895

Ala Glu Gln Gln Thr Ala Val Ala Ala Leu Glu Ala His Gly Ala Arg
    6900                6905                6910

Val Thr Val Ala Arg Ala Asp Val Ala Asp Arg Ala Gln Met Glu Arg
    6915                6920                6925

Ile Leu Arg Glu Val Thr Ala Ser Gly Met Pro Leu Arg Gly Val Val
    6930                6935                6940

His Ala Ala Gly Ile Leu Asp Asp Gly Leu Leu Met Gln Gln Thr Pro
6945                6950                6955                6960

Ala Arg Phe Arg Ala Val Met Ala Pro Lys Val Arg Gly Ala Leu His
    6965                6970                6975

Leu His Ala Leu Thr Arg Glu Ala Pro Leu Ser Phe Phe Val Leu Tyr
    6980                6985                6990

Ala Ser Gly Ala Gly Leu Leu Gly Ser Pro Gly Gln Gly Asn Tyr Ala
    6995                7000                7005
```

-continued

Ala Ala Asn Thr Phe Leu Asp Ala Leu Ala His His Arg Arg Ala Gln
     7010                7015                7020

Gly Leu Pro Ala Leu Ser Ile Asp Trp Gly Leu Phe Ala Asp Val Gly
7025                7030                7035                7040

Leu Ala Ala Gly Gln Gln Asn Arg Gly Ala Arg Leu Val Thr Arg Gly
             7045                7050                7055

Thr Arg Ser Leu Thr Pro Asp Glu Gly Leu Trp Ala Leu Glu Arg Leu
        7060                7065                7070

Leu Asp Gly Asp Arg Thr Gln Ala Gly Val Met Pro Phe Asp Val Arg
    7075                7080                7085

Gln Trp Val Glu Phe Tyr Pro Ala Ala Ser Ser Arg Arg Leu Ser
    7090                7095                7100

Arg Leu Met Thr Ala Arg Arg Val Ala Ser Gly Arg Leu Ala Gly Asp
7105                7110                7115                7120

Arg Asp Leu Leu Glu Arg Leu Ala Thr Ala Glu Ala Gly Ala Arg Ala
            7125                7130                7135

Gly Met Leu Gln Glu Val Val Arg Ala Gln Val Ser Gln Val Leu Arg
        7140                7145                7150

Leu Ser Glu Gly Lys Leu Asp Val Asp Ala Pro Leu Thr Ser Leu Gly
    7155                7160                7165

Met Asp Ser Leu Met Gly Leu Glu Leu Arg Asn Arg Ile Glu Ala Val
7170                7175                7180

Leu Gly Ile Thr Met Pro Ala Thr Leu Leu Trp Thr Tyr Pro Thr Val
7185                7190                7195                7200

Ala Ala Leu Ser Ala His Leu Ala Ser His Val Val Ser Thr Gly Asp
            7205                7210                7215

Gly Glu Ser Ala Arg Pro Pro Asp Thr Gly Ser Val Ala Pro Thr Thr
        7220                7225                7230

His Glu Val Ala Ser Leu Asp Glu Asp Gly Leu Phe Ala Leu Ile Asp
    7235                7240                7245

Glu Ser Leu Ala Arg Ala Gly Lys Arg
    7250                7255

<210> SEQ ID NO 6
<211> LENGTH: 3798
<212> TYPE: PRT
<213> ORGANISM: Sorangium cellulosum

<400> SEQUENCE: 6

Val Thr Asp Arg Glu Gly Gln Leu Leu Glu Arg Leu Arg Glu Val Thr
 1               5                  10                  15

Leu Ala Leu Arg Lys Thr Leu Asn Glu Arg Asp Thr Leu Glu Leu Glu
            20                  25                  30

Lys Thr Glu Pro Ile Ala Ile Val Gly Ile Gly Cys Arg Phe Pro Gly
        35                  40                  45

Gly Ala Gly Thr Pro Glu Ala Phe Trp Glu Leu Leu Asp Asp Gly Arg
    50                  55                  60

Asp Ala Ile Arg Pro Leu Glu Glu Arg Trp Ala Leu Val Gly Val Asp
65                  70                  75                  80

Pro Gly Asp Asp Val Pro Arg Trp Ala Gly Leu Leu Thr Glu Ala Ile
                85                  90                  95

Asp Gly Phe Asp Ala Ala Phe Phe Gly Ile Ala Pro Arg Glu Ala Arg
            100                 105                 110

Ser Leu Asp Pro Gln His Arg Leu Leu Leu Glu Val Ala Trp Glu Gly
        115                 120                 125

-continued

```
Phe Glu Asp Ala Gly Ile Pro Pro Arg Ser Leu Val Gly Ser Arg Thr
    130                 135                 140

Gly Val Phe Val Gly Val Cys Ala Thr Glu Tyr Leu His Ala Ala Val
145                 150                 155                 160

Ala His Gln Pro Arg Glu Arg Asp Ala Tyr Ser Thr Thr Gly Asn
                165                 170                 175

Met Leu Ser Ile Ala Ala Gly Arg Leu Ser Tyr Thr Leu Gly Leu Gln
            180                 185                 190

Gly Pro Cys Leu Thr Val Asp Thr Ala Cys Ser Ser Ser Leu Val Ala
        195                 200                 205

Ile His Leu Ala Cys Arg Ser Leu Arg Ala Arg Glu Ser Asp Leu Ala
    210                 215                 220

Leu Ala Gly Gly Val Asn Met Leu Leu Ser Pro Asp Thr Met Arg Ala
225                 230                 235                 240

Leu Ala Arg Thr Gln Ala Leu Ser Pro Asn Gly Arg Cys Gln Thr Phe
                245                 250                 255

Asp Ala Ser Ala Asn Gly Phe Val Arg Gly Glu Gly Cys Gly Leu Ile
            260                 265                 270

Val Leu Lys Arg Leu Ser Asp Ala Arg Arg Asp Gly Asp Arg Ile Trp
        275                 280                 285

Ala Leu Ile Arg Gly Ser Ala Ile Asn Gln Asp Gly Arg Ser Thr Gly
    290                 295                 300

Leu Thr Ala Pro Asn Val Leu Ala Gln Gly Ala Leu Leu Arg Glu Ala
305                 310                 315                 320

Leu Arg Asn Ala Gly Val Glu Ala Glu Ala Ile Gly Tyr Ile Glu Thr
                325                 330                 335

His Gly Ala Ala Thr Ser Leu Gly Asp Pro Ile Glu Ile Glu Ala Leu
            340                 345                 350

Arg Ala Val Val Gly Pro Ala Arg Ala Asp Gly Ala Arg Cys Val Leu
        355                 360                 365

Gly Ala Val Lys Thr Asn Leu Gly His Leu Glu Gly Ala Ala Gly Val
    370                 375                 380

Ala Gly Leu Ile Lys Ala Thr Leu Ser Leu His His Glu Arg Ile Pro
385                 390                 395                 400

Arg Asn Leu Asn Phe Arg Thr Leu Asn Pro Arg Ile Arg Ile Glu Gly
                405                 410                 415

Thr Ala Leu Ala Leu Ala Thr Glu Pro Val Pro Trp Pro Arg Thr Gly
            420                 425                 430

Arg Thr Arg Phe Ala Gly Val Ser Ser Phe Gly Met Ser Gly Thr Asn
        435                 440                 445

Ala His Val Val Leu Glu Glu Ala Pro Ala Val Glu Pro Glu Ala Ala
    450                 455                 460

Ala Pro Glu Arg Ala Ala Glu Leu Phe Val Leu Ser Ala Lys Ser Ala
465                 470                 475                 480

Ala Ala Leu Asp Ala Gln Ala Ala Arg Leu Arg Asp His Leu Glu Lys
                485                 490                 495

His Val Glu Leu Gly Leu Gly Asp Val Ala Phe Ser Leu Ala Thr Thr
            500                 505                 510

Arg Ser Ala Met Glu His Arg Leu Ala Val Ala Ala Ser Ser Arg Glu
        515                 520                 525

Ala Leu Arg Gly Ala Leu Ser Ala Ala Gln Gly His Thr Pro Pro
    530                 535                 540
```

```
-continued

Gly Ala Val Arg Gly Arg Ala Ser Gly Ser Ala Pro Lys Val Val
545                 550                 555                 560

Phe Val Phe Pro Gly Gln Gly Ser Gln Trp Val Gly Met Gly Arg Lys
                565                 570                 575

Leu Met Ala Glu Glu Pro Val Phe Arg Ala Ala Leu Glu Gly Cys Asp
            580                 585                 590

Arg Ala Ile Glu Ala Glu Ala Gly Trp Ser Leu Leu Gly Glu Leu Ser
        595                 600                 605

Ala Asp Glu Ala Ala Ser Gln Leu Gly Arg Ile Asp Val Val Gln Pro
    610                 615                 620

Val Leu Phe Ala Met Glu Val Ala Leu Ser Ala Leu Trp Arg Ser Trp
625                 630                 635                 640

Gly Val Glu Pro Glu Ala Val Val Gly His Ser Met Gly Glu Val Ala
                645                 650                 655

Ala Ala His Val Ala Gly Ala Leu Ser Leu Glu Asp Ala Val Ala Ile
            660                 665                 670

Ile Cys Arg Arg Ser Arg Leu Leu Arg Arg Ile Ser Gly Gln Gly Glu
        675                 680                 685

Met Ala Leu Val Glu Leu Ser Leu Glu Glu Ala Glu Ala Ala Leu Arg
690                 695                 700

Gly His Glu Gly Arg Leu Ser Val Ala Val Ser Asn Ser Pro Arg Ser
705                 710                 715                 720

Thr Val Leu Ala Gly Glu Pro Ala Ala Leu Ser Glu Val Leu Ala Ala
                725                 730                 735

Leu Thr Ala Lys Gly Val Phe Trp Arg Gln Val Lys Val Asp Val Ala
            740                 745                 750

Ser His Ser Pro Gln Val Asp Pro Leu Arg Glu Leu Ile Ala Ala
        755                 760                 765

Leu Gly Ala Ile Arg Pro Arg Ala Ala Val Pro Met Arg Ser Thr
    770                 775                 780

Val Thr Gly Gly Val Ile Ala Gly Pro Glu Leu Gly Ala Ser Tyr Trp
785                 790                 795                 800

Ala Asp Asn Leu Arg Gln Pro Val Arg Phe Ala Ala Ala Gln Ala
                805                 810                 815

Leu Leu Glu Gly Gly Pro Ala Leu Phe Ile Glu Met Ser Pro His Pro
            820                 825                 830

Ile Leu Val Pro Pro Leu Asp Glu Ile Gln Thr Ala Ala Glu Gln Gly
        835                 840                 845

Gly Ala Ala Val Gly Ser Leu Arg Arg Gly Gln Asp Glu Arg Ala Thr
    850                 855                 860

Leu Leu Glu Ala Leu Gly Thr Leu Trp Ala Ser Gly Tyr Pro Val Ser
865                 870                 875                 880

Trp Ala Arg Leu Phe Pro Ala Gly Gly Arg Arg Val Pro Leu Pro Thr
                885                 890                 895

Tyr Pro Trp Gln His Glu Arg Cys Trp Ile Glu Val Glu Pro Asp Ala
            900                 905                 910

Arg Arg Leu Ala Ala Ala Asp Pro Thr Lys Asp Trp Phe Tyr Arg Thr
        915                 920                 925

Asp Trp Pro Glu Val Pro Arg Ala Ala Pro Lys Ser Glu Thr Ala His
    930                 935                 940

Gly Ser Trp Leu Leu Leu Ala Asp Arg Gly Gly Val Gly Glu Ala Val
945                 950                 955                 960

Ala Ala Ala Leu Ser Thr Arg Gly Leu Ser Cys Thr Val Leu His Ala
```

```
                965                 970                 975
Ser Ala Asp Ala Ser Thr Val Ala Glu Gln Val Ser Glu Ala Ala Ser
                980                 985                 990

Arg Arg Asn Asp Trp Gln Gly Val Leu Tyr Leu Trp Gly Leu Asp Ala
            995                1000                1005

Val Val Asp Ala Gly Ala Ser Ala Asp Glu Val Ser Glu Ala Thr Arg
   1010                1015                1020

Arg Ala Thr Ala Pro Val Leu Gly Leu Val Arg Phe Leu Ser Ala Ala
1025                1030                1035                1040

Pro His Pro Pro Arg Phe Trp Val Val Thr Arg Gly Ala Cys Thr Val
                1045                1050                1055

Gly Gly Glu Pro Glu Ala Ser Leu Cys Gln Ala Ala Leu Trp Gly Leu
            1060                1065                1070

Ala Arg Val Ala Ala Leu Glu His Pro Ala Ala Trp Gly Gly Leu Val
        1075                1080                1085

Asp Leu Asp Pro Gln Lys Ser Pro Thr Glu Ile Glu Pro Leu Val Ala
        1090                1095                1100

Glu Leu Leu Ser Pro Asp Ala Glu Asp Gln Leu Ala Phe Arg Ser Gly
1105                1110                1115                1120

Arg Arg His Ala Ala Arg Leu Val Ala Ala Pro Pro Glu Gly Asp Val
            1125                1130                1135

Ala Pro Ile Ser Leu Ser Ala Glu Gly Ser Tyr Leu Val Thr Gly Gly
        1140                1145                1150

Leu Gly Gly Leu Gly Leu Leu Val Ala Arg Trp Leu Val Glu Arg Gly
        1155                1160                1165

Ala Arg His Leu Val Leu Thr Ser Arg His Gly Leu Pro Glu Arg Gln
    1170                1175                1180

Ala Ser Gly Gly Glu Gln Pro Pro Glu Ala Arg Ala Arg Ile Ala Ala
1185                1190                1195                1200

Val Glu Gly Leu Glu Ala Gln Gly Ala Arg Val Thr Val Ala Ala Val
            1205                1210                1215

Asp Val Ala Glu Ala Asp Pro Met Thr Ala Leu Leu Ala Ala Ile Glu
        1220                1225                1230

Pro Pro Leu Arg Gly Val Val His Ala Ala Gly Val Phe Pro Val Arg
        1235                1240                1245

His Leu Ala Glu Thr Asp Glu Ala Leu Leu Glu Ser Val Leu Arg Pro
    1250                1255                1260

Lys Val Ala Gly Ser Trp Leu Leu His Arg Leu Leu Arg Asp Arg Pro
1265                1270                1275                1280

Leu Asp Leu Phe Val Leu Phe Ser Ser Gly Ala Ala Val Trp Gly Gly
            1285                1290                1295

Lys Gly Gln Gly Ala Tyr Ala Ala Ala Asn Ala Phe Leu Asp Gly Leu
        1300                1305                1310

Ala His His Arg Arg Ala His Ser Leu Pro Ala Leu Ser Leu Ala Trp
        1315                1320                1325

Gly Leu Trp Ala Glu Gly Gly Met Val Asp Ala Lys Ala His Ala Arg
    1330                1335                1340

Leu Ser Asp Ile Gly Val Leu Pro Met Ala Thr Gly Pro Ala Leu Ser
1345                1350                1355                1360

Ala Leu Glu Arg Leu Val Asn Thr Ser Ala Val Gln Arg Ser Val Thr
            1365                1370                1375

Arg Met Asp Trp Ala Arg Phe Ala Pro Val Tyr Ala Ala Arg Gly Arg
        1380                1385                1390
```

-continued

```
Arg Asn Leu Leu Ser Ala Leu Val Ala Glu Asp Glu Arg Ala Ala Ser
    1395                1400                1405

Pro Pro Val Pro Thr Ala Asn Arg Ile Trp Arg Gly Leu Ser Val Ala
    1410                1415                1420

Glu Ser Arg Ser Ala Leu Tyr Glu Leu Val Arg Gly Ile Val Ala Arg
1425                1430                1435                1440

Val Leu Gly Phe Ser Asp Pro Gly Ala Leu Asp Val Gly Arg Gly Phe
                1445                1450                1455

Ala Glu Gln Gly Leu Asp Ser Leu Met Ala Leu Glu Ile Arg Asn Arg
            1460                1465                1470

Leu Gln Arg Glu Leu Gly Glu Arg Leu Ser Ala Thr Leu Ala Phe Asp
    1475                1480                1485

His Pro Thr Val Glu Arg Leu Val Ala His Leu Leu Thr Asp Val Leu
    1490                1495                1500

Lys Leu Glu Asp Arg Ser Asp Thr Arg His Ile Arg Ser Val Ala Ala
1505                1510                1515                1520

Asp Asp Asp Ile Ala Ile Val Gly Ala Ala Cys Arg Phe Pro Gly Gly
                1525                1530                1535

Asp Glu Gly Leu Glu Thr Tyr Trp Arg His Leu Ala Glu Gly Met Val
            1540                1545                1550

Val Ser Thr Glu Val Pro Ala Asp Arg Trp Arg Ala Ala Asp Trp Tyr
    1555                1560                1565

Asp Pro Asp Pro Glu Val Pro Gly Arg Thr Tyr Val Ala Lys Gly Ala
    1570                1575                1580

Phe Leu Arg Asp Val Arg Ser Leu Asp Ala Ala Phe Phe Ala Ile Ser
1585                1590                1595                1600

Pro Arg Glu Ala Met Ser Leu Asp Pro Gln Gln Arg Leu Leu Leu Glu
                1605                1610                1615

Val Ser Trp Glu Ala Ile Glu Arg Ala Gly Gln Asp Pro Met Ala Leu
            1620                1625                1630

Arg Glu Ser Ala Thr Gly Val Phe Val Gly Met Ile Gly Ser Glu His
    1635                1640                1645

Ala Glu Arg Val Gln Gly Leu Asp Asp Asp Ala Ala Leu Leu Tyr Gly
    1650                1655                1660

Thr Thr Gly Asn Leu Leu Ser Val Ala Ala Gly Arg Leu Ser Phe Phe
1665                1670                1675                1680

Leu Gly Leu His Gly Pro Thr Met Thr Val Asp Thr Ala Cys Ser Ser
                1685                1690                1695

Ser Leu Val Ala Leu His Leu Ala Cys Gln Ser Leu Arg Leu Gly Glu
            1700                1705                1710

Cys Asp Gln Ala Leu Ala Gly Gly Ser Ser Val Leu Leu Ser Pro Arg
    1715                1720                1725

Ser Phe Val Ala Ala Ser Arg Met Arg Leu Leu Ser Pro Asp Gly Arg
    1730                1735                1740

Cys Lys Thr Phe Ser Ala Ala Asp Gly Phe Ala Arg Ala Glu Gly
1745                1750                1755                1760

Cys Ala Val Val Val Leu Lys Arg Leu Arg Asp Ala Gln Arg Asp Arg
                1765                1770                1775

Asp Pro Ile Leu Ala Val Val Arg Ser Thr Ala Ile Asn His Asp Gly
            1780                1785                1790

Pro Ser Ser Gly Leu Thr Val Pro Ser Gly Pro Ala Gln Gln Ala Leu
    1795                1800                1805
```

-continued

Leu Arg Gln Ala Leu Ala Gln Ala Gly Val Ala Pro Ala Glu Val Asp
    1810                1815                1820

Phe Val Glu Cys His Gly Thr Gly Thr Ala Leu Gly Asp Pro Ile Glu
1825                1830                1835                1840

Val Gln Ala Leu Gly Ala Val Tyr Gly Arg Gly Arg Pro Ala Glu Arg
                1845                1850                1855

Pro Leu Trp Leu Gly Ala Val Lys Ala Asn Leu Gly His Leu Glu Ala
        1860                1865                1870

Ala Ala Gly Leu Ala Gly Val Leu Lys Val Leu Ala Leu Glu His
    1875                1880                1885

Glu Gln Ile Pro Ala Gln Pro Glu Leu Asp Glu Leu Asn Pro His Ile
    1890                1895                1900

Pro Trp Ala Glu Leu Pro Val Ala Val Arg Arg Ala Val Pro Trp
1905                1910                1915                1920

Pro Arg Gly Ala Arg Pro Arg Arg Ala Gly Val Ser Ala Phe Gly Leu
            1925                1930                1935

Ser Gly Thr Asn Ala His Val Val Leu Glu Glu Ala Pro Ala Val Glu
            1940                1945                1950

Pro Val Ala Ala Ala Pro Glu Arg Ala Ala Glu Leu Phe Val Leu Ser
        1955                1960                1965

Ala Lys Ser Ala Ala Ala Leu Asp Ala Gln Ala Ala Arg Leu Arg Asp
    1970                1975                1980

His Leu Glu Lys His Val Glu Leu Gly Leu Gly Asp Val Ala Phe Ser
1985                1990                1995                2000

Leu Ala Thr Thr Arg Ser Ala Met Glu His Arg Leu Ala Val Ala Ala
                2005                2010                2015

Ser Ser Arg Glu Ala Leu Arg Gly Ala Leu Ser Ala Ala Ala Gln Gly
        2020                2025                2030

His Thr Pro Pro Gly Ala Val Arg Gly Arg Ala Ser Gly Gly Ser Ala
    2035                2040                2045

Pro Lys Val Val Phe Val Phe Pro Gly Gln Gly Ser Gln Trp Val Gly
    2050                2055                2060

Met Gly Arg Lys Leu Met Ala Glu Glu Pro Val Phe Arg Ala Ala Leu
2065                2070                2075                2080

Glu Gly Cys Asp Arg Ala Ile Glu Ala Glu Ala Gly Trp Ser Leu Leu
            2085                2090                2095

Gly Glu Leu Ser Ala Asp Glu Ala Ala Ser Gln Leu Gly Arg Ile Asp
        2100                2105                2110

Val Val Gln Pro Val Leu Phe Ala Met Glu Val Ala Leu Ser Ala Leu
        2115                2120                2125

Trp Arg Ser Trp Gly Val Glu Pro Glu Ala Val Val Gly His Ser Met
    2130                2135                2140

Gly Glu Val Ala Ala Ala His Val Ala Gly Ala Leu Ser Leu Glu Asp
2145                2150                2155                2160

Ala Val Ala Ile Ile Cys Arg Arg Ser Arg Leu Leu Arg Arg Ile Ser
            2165                2170                2175

Gly Gln Gly Glu Met Ala Leu Val Glu Leu Ser Leu Glu Glu Ala Glu
        2180                2185                2190

Ala Ala Leu Arg Gly His Glu Gly Arg Leu Ser Val Ala Val Ser Asn
    2195                2200                2205

Ser Pro Arg Ser Thr Val Leu Ala Gly Glu Pro Ala Ala Leu Ser Glu
    2210                2215                2220

Val Leu Ala Ala Leu Thr Ala Lys Gly Val Phe Trp Arg Gln Val Lys

-continued

```
     2225                2230                2235                2240

Val Asp Val Ala Ser His Ser Pro Gln Val Asp Pro Leu Arg Glu Glu
            2245                2250                2255

Leu Ile Ala Ala Leu Gly Ala Ile Arg Pro Arg Ala Ala Ala Val Pro
            2260                2265                2270

Met Arg Ser Thr Val Thr Gly Gly Val Ile Ala Gly Pro Glu Leu Gly
            2275                2280                2285

Ala Ser Tyr Trp Ala Asp Asn Leu Arg Gln Pro Val Arg Phe Ala Ala
            2290                2295                2300

Ala Ala Gln Ala Leu Leu Glu Gly Gly Pro Ala Leu Phe Ile Glu Met
2305                2310                2315                2320

Ser Pro His Pro Ile Leu Val Pro Pro Leu Asp Glu Ile Gln Thr Ala
            2325                2330                2335

Ala Glu Gln Gly Gly Ala Ala Val Gly Ser Leu Arg Arg Gly Gln Asp
            2340                2345                2350

Glu Arg Ala Thr Leu Leu Glu Ala Leu Gly Thr Leu Trp Ala Ser Gly
            2355                2360                2365

Tyr Pro Val Ser Trp Ala Arg Leu Phe Pro Ala Gly Gly Arg Arg Val
            2370                2375                2380

Pro Leu Pro Thr Tyr Pro Trp Gln His Glu Arg Tyr Trp Ile Glu Asp
2385                2390                2395                2400

Ser Val His Gly Ser Lys Pro Ser Leu Arg Leu Arg Gln Leu Arg Asn
            2405                2410                2415

Gly Ala Thr Asp His Pro Leu Leu Gly Ala Pro Leu Leu Val Ser Ala
            2420                2425                2430

Arg Pro Gly Ala His Leu Trp Glu Gln Ala Leu Ser Asp Glu Arg Leu
            2435                2440                2445

Ser Tyr Leu Ser Glu His Arg Val His Gly Glu Ala Val Leu Pro Ser
            2450                2455                2460

Ala Ala Tyr Val Glu Met Ala Leu Ala Ala Gly Val Asp Leu Tyr Gly
2465                2470                2475                2480

Thr Ala Thr Leu Val Leu Glu Gln Leu Ala Leu Glu Arg Ala Leu Ala
            2485                2490                2495

Val Pro Ser Glu Gly Gly Arg Ile Val Gln Val Ala Leu Ser Glu Glu
            2500                2505                2510

Gly Pro Gly Arg Ala Ser Phe Gln Val Ser Ser Arg Glu Glu Ala Gly
            2515                2520                2525

Arg Ser Trp Val Arg His Ala Thr Gly His Val Cys Ser Gly Gln Ser
2530                2535                2540

Ser Ala Val Gly Ala Leu Lys Glu Ala Pro Trp Glu Ile Gln Arg Arg
2545                2550                2555                2560

Cys Pro Ser Val Leu Ser Ser Glu Ala Leu Tyr Pro Leu Leu Asn Glu
            2565                2570                2575

His Ala Leu Asp Tyr Gly Pro Cys Phe Gln Gly Val Glu Gln Val Trp
            2580                2585                2590

Leu Gly Thr Gly Glu Val Leu Gly Arg Val Arg Leu Pro Gly Asp Met
            2595                2600                2605

Ala Ser Ser Ser Gly Ala Tyr Arg Ile His Pro Ala Leu Leu Asp Ala
            2610                2615                2620

Cys Phe Gln Val Leu Thr Ala Leu Leu Thr Thr Pro Glu Ser Ile Glu
2625                2630                2635                2640

Ile Arg Arg Arg Leu Thr Asp Leu His Glu Pro Asp Leu Pro Arg Ser
            2645                2650                2655
```

-continued

```
Arg Ala Pro Val Asn Gln Ala Val Ser Asp Thr Trp Leu Trp Asp Ala
        2660            2665            2670

Ala Leu Asp Gly Gly Arg Arg Gln Ser Ala Ser Val Pro Val Asp Leu
        2675            2680            2685

Val Leu Gly Ser Phe His Ala Lys Trp Glu Val Met Glu Arg Leu Ala
        2690            2695            2700

Gln Ala Tyr Ile Ile Gly Thr Leu Arg Ile Trp Asn Val Phe Cys Ala
2705            2710            2715            2720

Ala Gly Glu Arg His Thr Ile Asp Glu Leu Leu Val Arg Leu Gln Ile
        2725            2730            2735

Ser Val Val Tyr Arg Lys Val Ile Lys Arg Trp Met Glu His Leu Val
        2740            2745            2750

Ala Ile Gly Ile Leu Val Gly Asp Gly Glu His Phe Val Ser Ser Gln
        2755            2760            2765

Pro Leu Pro Glu Pro Asp Leu Ala Ala Val Leu Glu Glu Ala Gly Arg
        2770            2775            2780

Val Phe Ala Asp Leu Pro Val Leu Phe Glu Trp Cys Lys Phe Ala Gly
2785            2790            2795            2800

Glu Arg Leu Ala Asp Val Leu Thr Gly Lys Thr Leu Ala Leu Glu Ile
        2805            2810            2815

Leu Phe Pro Gly Gly Ser Phe Asp Met Ala Glu Arg Ile Tyr Arg Asp
        2820            2825            2830

Ser Pro Ile Ala Arg Tyr Ser Asn Gly Ile Val Arg Gly Val Val Glu
        2835            2840            2845

Ser Ala Ala Arg Val Val Ala Pro Ser Gly Met Phe Ser Ile Leu Glu
        2850            2855            2860

Ile Gly Ala Gly Thr Gly Ala Thr Thr Ala Ala Val Leu Pro Val Leu
2865            2870            2875            2880

Leu Pro Asp Arg Thr Glu Tyr His Phe Thr Asp Val Ser Pro Leu Phe
        2885            2890            2895

Leu Ala Arg Ala Glu Gln Arg Phe Arg Asp Tyr Pro Phe Leu Lys Tyr
        2900            2905            2910

Gly Ile Leu Asp Val Asp Gln Glu Pro Ala Gly Gln Gly Tyr Ala His
        2915            2920            2925

Gln Arg Phe Asp Val Ile Val Ala Ala Asn Val Ile His Ala Thr Arg
        2930            2935            2940

Asp Ile Arg Ala Thr Ala Lys Arg Leu Leu Ser Leu Leu Ala Pro Gly
2945            2950            2955            2960

Gly Leu Leu Val Leu Val Glu Gly Thr Gly His Pro Ile Trp Phe Asp
        2965            2970            2975

Ile Thr Thr Gly Leu Ile Glu Gly Trp Gln Lys Tyr Glu Asp Asp Leu
        2980            2985            2990

Arg Ile Asp His Pro Leu Leu Pro Ala Arg Thr Trp Cys Asp Val Leu
        2995            3000            3005

Arg Arg Val Gly Phe Ala Asp Ala Val Ser Leu Pro Gly Asp Gly Ser
        3010            3015            3020

Pro Ala Gly Ile Leu Gly Gln His Val Ile Leu Ser Arg Ala Pro Gly
3025            3030            3035            3040

Ile Ala Gly Ala Ala Cys Asp Ser Ser Gly Glu Ser Ala Thr Glu Ser
                3045            3050            3055

Pro Ala Ala Arg Ala Val Arg Gln Glu Trp Ala Asp Gly Ser Ala Asp
        3060            3065            3070
```

-continued

```
Val Val His Arg Met Ala Leu Glu Arg Met Tyr Phe His Arg Arg Pro
    3075                3080                3085
Gly Arg Gln Val Trp Val His Gly Arg Leu Arg Thr Gly Gly Gly Ala
    3090                3095                3100
Phe Thr Lys Ala Leu Ala Gly Asp Leu Leu Leu Phe Glu Asp Thr Gly
3105                3110                3115                3120
Gln Val Val Ala Glu Val Gln Gly Leu Arg Leu Pro Gln Leu Glu Ala
            3125                3130                3135
Ser Ala Phe Ala Pro Arg Asp Pro Arg Glu Glu Trp Leu Tyr Ala Leu
            3140                3145                3150
Glu Trp Gln Arg Lys Asp Pro Ile Pro Glu Ala Pro Ala Ala Ser
        3155                3160                3165
Ser Ser Ser Ala Gly Ala Trp Leu Val Leu Met Asp Gln Gly Gly Thr
    3170                3175                3180
Gly Ala Ala Leu Val Ser Leu Leu Glu Gly Arg Gly Glu Ala Cys Val
3185                3190                3195                3200
Arg Val Ile Ala Gly Thr Ala Tyr Ala Cys Leu Ala Pro Gly Leu Tyr
            3205                3210                3215
Gln Val Asp Pro Ala Gln Pro Asp Gly Phe His Thr Leu Leu Arg Asp
            3220                3225                3230
Ala Phe Gly Glu Asp Arg Ile Cys Arg Ala Val Val His Met Trp Ser
        3235                3240                3245
Leu Asp Ala Thr Ala Ala Gly Glu Arg Ala Thr Ala Glu Ser Leu Gln
    3250                3255                3260
Ala Asp Gln Leu Leu Gly Ser Leu Ser Ala Leu Ser Leu Val Gln Ala
3265                3270                3275                3280
Leu Val Arg Arg Arg Trp Arg Asn Met Pro Arg Leu Trp Leu Leu Thr
            3285                3290                3295
Arg Ala Val His Ala Val Gly Ala Glu Asp Ala Ala Ala Ser Val Ala
            3300                3305                3310
Gln Ala Pro Val Trp Gly Leu Gly Arg Thr Leu Ala Leu Glu His Pro
        3315                3320                3325
Glu Leu Arg Cys Thr Leu Val Asp Val Asn Pro Ala Pro Ser Pro Glu
    3330                3335                3340
Asp Ala Ala Ala Leu Ala Val Glu Leu Gly Ala Ser Asp Arg Glu Asp
3345                3350                3355                3360
Gln Val Ala Leu Arg Ser Asp Gly Arg Tyr Val Ala Arg Leu Val Arg
            3365                3370                3375
Ser Ser Phe Ser Gly Lys Pro Ala Thr Asp Cys Gly Ile Arg Ala Asp
            3380                3385                3390
Gly Ser Tyr Val Ile Thr Asp Gly Met Gly Arg Val Gly Leu Ser Val
        3395                3400                3405
Ala Gln Trp Met Val Met Gln Gly Ala Arg His Val Val Leu Val Asp
    3410                3415                3420
Arg Gly Gly Ala Ser Glu Ala Ser Arg Asp Ala Leu Arg Ser Met Ala
3425                3430                3435                3440
Glu Ala Gly Ala Glu Val Gln Ile Val Glu Ala Asp Val Ala Arg Arg
            3445                3450                3455
Asp Asp Val Ala Arg Leu Leu Ser Lys Ile Glu Pro Ser Met Pro Pro
            3460                3465                3470
Leu Arg Gly Ile Val Tyr Val Asp Gly Thr Phe Gln Gly Asp Ser Ser
        3475                3480                3485
Met Leu Glu Leu Asp Ala Arg Arg Phe Lys Glu Trp Met Tyr Pro Lys
```

-continued

```
                   3490              3495                 3500

Val Leu Gly Ala Trp Asn Leu His Ala Leu Thr Arg Asp Arg Ser Leu
          3505                3510                3515                3520

Asp Phe Val Leu Tyr Ser Ser Gly Thr Ser Leu Leu Gly Leu Pro
                      3525                3530                3535

Gly Gln Gly Ser Arg Ala Ala Gly Asp Ala Phe Leu Asp Ala Ile Ala
                  3540                3545                3550

His His Arg Cys Lys Val Gly Leu Thr Ala Met Ser Ile Asn Trp Gly
                  3555                3560                3565

Leu Leu Ser Glu Ala Ser Ser Pro Ala Thr Pro Asn Asp Gly Gly Ala
          3570                3575                3580

Arg Leu Glu Tyr Arg Gly Met Glu Gly Leu Thr Leu Glu Gln Gly Ala
          3585                3590                3595                3600

Ala Ala Leu Gly Arg Leu Leu Ala Arg Pro Arg Ala Gln Val Gly Val
                          3605                3610                3615

Met Arg Leu Asn Leu Arg Gln Trp Leu Glu Phe Tyr Pro Asn Ala Ala
                      3620                3625                3630

Arg Leu Ala Leu Trp Ala Glu Leu Leu Lys Glu Arg Asp Arg Ala Asp
                  3635                3640                3645

Arg Gly Ala Ser Asn Ala Ser Asn Leu Arg Glu Ala Leu Gln Ser Ala
                  3650                3655                3660

Arg Pro Glu Asp Arg Gln Leu Ile Leu Glu Lys His Leu Ser Glu Leu
          3665                3670                3675                3680

Leu Gly Arg Gly Leu Arg Leu Pro Pro Glu Arg Ile Glu Arg His Val
                          3685                3690                3695

Pro Phe Ser Asn Leu Gly Met Asp Ser Leu Ile Gly Leu Glu Leu Arg
                      3700                3705                3710

Asn Arg Ile Glu Ala Ala Leu Gly Ile Thr Val Pro Ala Thr Leu Leu
                  3715                3720                3725

Trp Thr Tyr Pro Asn Val Ala Ala Leu Ser Gly Ser Leu Leu Asp Ile
                  3730                3735                3740

Leu Phe Pro Asn Ala Gly Ala Thr His Ala Pro Ala Thr Glu Arg Glu
          3745                3750                3755                3760

Lys Ser Phe Glu Asn Asp Ala Ala Asp Leu Glu Ala Leu Arg Gly Met
                      3765                3770                3775

Thr Asp Glu Gln Lys Asp Ala Leu Leu Ala Glu Lys Leu Ala Gln Leu
                          3780                3785                3790

Ala Gln Ile Val Gly Glu
                  3795

<210> SEQ ID NO 7
<211> LENGTH: 2439
<212> TYPE: PRT
<213> ORGANISM: Sorangium cellulosum

<400> SEQUENCE: 7

Met Ala Thr Thr Asn Ala Gly Lys Leu Glu His Ala Leu Leu Leu Met
  1               5                  10                  15

Asp Lys Leu Ala Lys Lys Asn Ala Ser Leu Glu Gln Glu Arg Thr Glu
              20                  25                  30

Pro Ile Ala Ile Val Gly Ile Gly Cys Arg Phe Pro Gly Gly Ala Asp
          35                  40                  45

Thr Pro Glu Ala Phe Trp Glu Leu Leu Asp Ser Gly Arg Asp Ala Val
      50                  55                  60
```

```
Gln Pro Leu Asp Arg Arg Trp Ala Leu Val Gly Val His Pro Ser Glu
 65                  70                  75                  80

Glu Val Pro Arg Trp Ala Gly Leu Leu Thr Glu Ala Val Asp Gly Phe
                 85                  90                  95

Asp Ala Ala Phe Phe Gly Thr Ser Pro Arg Glu Ala Arg Ser Leu Asp
            100                 105                 110

Pro Gln Gln Arg Leu Leu Leu Glu Val Thr Trp Glu Gly Leu Glu Asp
        115                 120                 125

Ala Gly Ile Ala Pro Gln Ser Leu Asp Gly Ser Arg Thr Gly Val Phe
    130                 135                 140

Leu Gly Ala Cys Ser Ser Asp Tyr Ser His Thr Val Ala Gln Gln Arg
145                 150                 155                 160

Arg Glu Glu Gln Asp Ala Tyr Asp Ile Thr Gly Asn Thr Leu Ser Val
                165                 170                 175

Ala Ala Gly Arg Leu Ser Tyr Thr Leu Gly Leu Gln Gly Pro Cys Leu
            180                 185                 190

Thr Val Asp Thr Ala Cys Ser Ser Leu Val Ala Ile His Leu Ala
        195                 200                 205

Cys Arg Ser Leu Arg Ala Arg Glu Ser Asp Leu Ala Leu Ala Gly Gly
    210                 215                 220

Val Asn Met Leu Leu Ser Ser Lys Thr Met Ile Met Leu Gly Arg Ile
225                 230                 235                 240

Gln Ala Leu Ser Pro Asp Gly His Cys Arg Thr Phe Asp Ala Ser Ala
                245                 250                 255

Asn Gly Phe Val Arg Gly Glu Gly Cys Gly Met Val Val Leu Lys Arg
            260                 265                 270

Leu Ser Asp Ala Gln Arg His Gly Asp Arg Ile Trp Ala Leu Ile Arg
        275                 280                 285

Gly Ser Ala Met Asn Gln Asp Gly Arg Ser Thr Gly Leu Met Ala Pro
    290                 295                 300

Asn Val Leu Ala Gln Glu Ala Leu Leu Arg Glu Ala Leu Gln Ser Ala
305                 310                 315                 320

Arg Val Asp Ala Gly Ala Ile Gly Tyr Val Glu Thr His Gly Thr Gly
                325                 330                 335

Thr Ser Leu Gly Asp Pro Ile Glu Val Glu Ala Leu Arg Ala Val Leu
            340                 345                 350

Gly Pro Ala Arg Ala Asp Gly Ser Arg Cys Val Leu Gly Ala Val Lys
        355                 360                 365

Thr Asn Leu Gly His Leu Glu Gly Ala Ala Gly Val Ala Gly Leu Ile
    370                 375                 380

Lys Ala Ala Leu Ala Leu His His Glu Leu Ile Pro Arg Asn Leu His
385                 390                 395                 400

Phe His Thr Leu Asn Pro Arg Ile Arg Ile Glu Gly Thr Ala Leu Ala
                405                 410                 415

Leu Ala Thr Glu Pro Val Pro Trp Pro Arg Ala Gly Arg Pro Arg Phe
            420                 425                 430

Ala Gly Val Ser Ala Phe Gly Leu Ser Gly Thr Asn Val His Val Val
        435                 440                 445

Leu Glu Glu Ala Pro Ala Thr Val Leu Ala Pro Thr Pro Gly Arg
    450                 455                 460

Ser Ala Glu Leu Leu Val Leu Ser Ala Lys Ser Ala Ala Leu Asp
465                 470                 475                 480

Ala Gln Ala Ala Arg Leu Ser Ala His Ile Ala Ala Tyr Pro Glu Gln
```

-continued

```
                485                 490                 495
Gly Leu Gly Asp Val Ala Phe Ser Leu Val Ser Thr Arg Ser Pro Met
                500                 505                 510
Glu His Arg Leu Ala Val Ala Ala Thr Ser Arg Glu Ala Leu Arg Ser
                515                 520                 525
Ala Leu Glu Val Ala Ala Gln Gly Gln Thr Pro Ala Gly Ala Ala Arg
                530                 535                 540
Gly Arg Ala Ala Ser Ser Pro Gly Lys Leu Ala Phe Leu Phe Ala Gly
545                 550                 555                 560
Gln Gly Ala Gln Val Pro Gly Met Gly Arg Gly Leu Trp Glu Ala Trp
                    565                 570                 575
Pro Ala Phe Arg Glu Thr Phe Asp Arg Cys Val Thr Leu Phe Asp Arg
                580                 585                 590
Glu Leu His Gln Pro Leu Cys Glu Val Met Trp Ala Glu Pro Gly Ser
                595                 600                 605
Ser Arg Ser Ser Leu Leu Asp Gln Thr Ala Phe Thr Gln Pro Ala Leu
610                 615                 620
Phe Ala Leu Glu Tyr Ala Leu Ala Ala Leu Phe Arg Ser Trp Gly Val
625                 630                 635                 640
Glu Pro Glu Leu Val Ala Gly His Ser Leu Gly Glu Leu Val Ala Ala
                    645                 650                 655
Cys Val Ala Gly Val Phe Ser Leu Glu Asp Ala Val Arg Leu Val Val
                    660                 665                 670
Ala Arg Gly Arg Leu Met Gln Ala Leu Pro Ala Gly Gly Ala Met Val
                675                 680                 685
Ser Ile Ala Ala Pro Glu Ala Asp Val Ala Ala Val Ala Pro His
                690                 695                 700
Ala Ala Leu Val Ser Ile Ala Ala Val Asn Gly Pro Glu Gln Val Val
705                 710                 715                 720
Ile Ala Gly Ala Glu Lys Phe Val Gln Gln Ile Ala Ala Ala Phe Ala
                    725                 730                 735
Ala Arg Gly Ala Arg Thr Lys Pro Leu His Val Ser His Ala Phe His
                740                 745                 750
Ser Pro Leu Met Asp Pro Met Leu Glu Ala Phe Arg Arg Val Thr Glu
                755                 760                 765
Ser Val Thr Tyr Arg Arg Pro Ser Ile Ala Leu Val Ser Asn Leu Ser
770                 775                 780
Gly Lys Pro Cys Thr Asp Glu Val Ser Ala Pro Gly Tyr Trp Val Arg
785                 790                 795                 800
His Ala Arg Glu Ala Val Arg Phe Ala Asp Gly Val Lys Ala Leu His
                805                 810                 815
Ala Ala Gly Ala Gly Leu Phe Val Glu Val Gly Pro Lys Pro Thr Leu
                820                 825                 830
Leu Gly Leu Val Pro Ala Cys Leu Pro Asp Ala Arg Pro Val Leu Leu
                835                 840                 845
Pro Ala Ser Arg Ala Gly Arg Asp Glu Ala Ala Ser Ala Leu Glu Ala
                850                 855                 860
Leu Gly Gly Phe Trp Val Val Gly Gly Ser Val Thr Trp Ser Gly Val
865                 870                 875                 880
Phe Pro Ser Gly Gly Arg Arg Val Pro Leu Pro Thr Tyr Pro Trp Gln
                    885                 890                 895
Arg Glu Arg Tyr Trp Ile Glu Ala Pro Val Asp Arg Glu Ala Asp Gly
                    900                 905                 910
```

```
Thr Gly Arg Ala Arg Ala Gly Gly His Pro Leu Leu Gly Glu Val Phe
    915                 920                 925

Ser Val Ser Thr His Ala Gly Leu Arg Leu Trp Glu Thr Thr Leu Asp
    930                 935                 940

Arg Lys Arg Leu Pro Trp Leu Gly Glu His Arg Ala Gln Gly Glu Val
945                 950                 955                 960

Val Phe Pro Gly Ala Gly Tyr Leu Glu Met Ala Leu Ser Ser Gly Ala
                965                 970                 975

Glu Ile Leu Gly Asp Gly Pro Ile Gln Val Thr Asp Val Val Leu Ile
                980                 985                 990

Glu Thr Leu Thr Phe Ala Gly Asp Thr Ala Val Pro Val Gln Val Val
        995                 1000                1005

Thr Thr Glu Glu Arg Pro Gly Arg Leu Arg Phe Gln Val Ala Ser Arg
    1010                1015                1020

Glu Pro Gly Glu Arg Arg Ala Pro Phe Arg Ile His Ala Arg Gly Val
1025                1030                1035                1040

Leu Arg Arg Ile Gly Arg Val Glu Thr Pro Ala Arg Ser Asn Leu Ala
                1045                1050                1055

Ala Leu Arg Ala Arg Leu His Ala Ala Val Pro Ala Ala Ala Ile Tyr
                1060                1065                1070

Gly Ala Leu Ala Glu Met Gly Leu Gln Tyr Gly Pro Ala Leu Arg Gly
                1075                1080                1085

Leu Ala Glu Leu Trp Arg Gly Gly Glu Ala Leu Gly Arg Val Arg
    1090                1095                1100

Leu Pro Glu Ala Ala Gly Ser Ala Thr Ala Tyr Gln Leu His Pro Val
1105                1110                1115                1120

Leu Leu Asp Ala Cys Val Gln Met Ile Val Gly Ala Phe Ala Asp Arg
                1125                1130                1135

Asp Glu Ala Thr Pro Trp Ala Pro Val Glu Val Gly Ser Val Arg Leu
            1140                1145                1150

Phe Gln Arg Ser Pro Gly Glu Leu Trp Cys His Ala Arg Val Val Ser
    1155                1160                1165

Asp Gly Gln Gln Ala Ser Ser Arg Trp Ser Ala Asp Phe Glu Leu Met
    1170                1175                1180

Asp Gly Thr Gly Ala Val Val Ala Glu Ile Ser Arg Leu Val Val Glu
1185                1190                1195                1200

Arg Leu Ala Ser Gly Val Arg Arg Asp Ala Asp Asp Trp Phe Leu
                1205                1210                1215

Glu Leu Asp Trp Glu Pro Ala Ala Leu Gly Gly Pro Lys Ile Thr Ala
            1220                1225                1230

Gly Arg Trp Leu Leu Leu Gly Glu Gly Gly Leu Gly Arg Ser Leu
            1235                1240                1245

Cys Ser Ala Leu Lys Ala Ala Gly His Val Val Val His Ala Ala Gly
    1250                1255                1260

Asp Asp Thr Ser Thr Ala Gly Met Arg Ala Leu Leu Ala Asn Ala Phe
1265                1270                1275                1280

Asp Gly Gln Ala Pro Thr Ala Val Val His Leu Ser Ser Leu Asp Gly
            1285                1290                1295

Gly Gly Gln Leu Gly Pro Gly Leu Gly Ala Gln Gly Ala Leu Asp Ala
            1300                1305                1310

Pro Arg Ser Pro Asp Val Asp Ala Asp Ala Leu Glu Ser Ala Leu Met
    1315                1320                1325
```

-continued

```
Arg Gly Cys Asp Ser Val Leu Ser Leu Val Gln Ala Leu Val Gly Met
    1330                1335                1340

Asp Leu Arg Asn Ala Pro Arg Leu Trp Leu Leu Thr Arg Gly Ala Gln
1345                1350                1355                1360

Ala Ala Ala Ala Gly Asp Val Ser Val Val Gln Ala Pro Leu Leu Gly
                1365                1370                1375

Leu Gly Arg Thr Ile Ala Leu Glu His Ala Glu Leu Arg Cys Ile Ser
            1380                1385                1390

Val Asp Leu Asp Pro Ala Glu Pro Glu Gly Glu Ala Asp Ala Leu Leu
        1395                1400                1405

Ala Glu Leu Leu Ala Asp Asp Ala Glu Glu Val Ala Leu Arg Gly
    1410                1415                1420

Gly Asp Arg Leu Val Ala Arg Leu Val His Arg Leu Pro Asp Ala Gln
1425                1430                1435                1440

Arg Arg Glu Lys Val Glu Pro Ala Gly Asp Arg Pro Phe Arg Leu Glu
                1445                1450                1455

Ile Asp Glu Pro Gly Ala Leu Asp Gln Leu Val Leu Arg Ala Thr Gly
            1460                1465                1470

Arg Arg Ala Pro Gly Pro Gly Glu Val Glu Ile Ser Val Glu Ala Ala
        1475                1480                1485

Gly Leu Asp Ser Ile Asp Ile Gln Leu Ala Leu Gly Val Ala Pro Asn
    1490                1495                1500

Asp Leu Pro Gly Glu Glu Ile Glu Pro Leu Val Leu Gly Ser Glu Cys
1505                1510                1515                1520

Ala Gly Arg Ile Val Ala Val Gly Glu Gly Val Asn Gly Leu Val Val
                1525                1530                1535

Gly Gln Pro Val Ile Ala Leu Ala Ala Gly Val Phe Ala Thr His Val
            1540                1545                1550

Thr Thr Ser Ala Thr Leu Val Leu Pro Arg Pro Leu Gly Leu Ser Ala
            1555                1560                1565

Thr Glu Ala Ala Ala Met Pro Leu Ala Tyr Leu Thr Ala Trp Tyr Ala
    1570                1575                1580

Leu Asp Lys Val Ala His Leu Gln Ala Gly Glu Arg Val Leu Ile His
1585                1590                1595                1600

Ala Glu Ala Gly Gly Val Gly Leu Cys Ala Val Arg Trp Ala Gln Arg
                1605                1610                1615

Val Gly Ala Glu Val Tyr Ala Thr Ala Asp Thr Pro Glu Asn Arg Ala
            1620                1625                1630

Tyr Leu Glu Ser Leu Gly Val Arg Tyr Val Ser Asp Ser Arg Ser Gly
        1635                1640                1645

Arg Phe Val Thr Asp Val His Ala Trp Thr Asp Gly Glu Gly Val Asp
    1650                1655                1660

Val Val Leu Asp Ser Leu Ser Gly Glu Arg Ile Asp Lys Ser Leu Met
1665                1670                1675                1680

Val Leu Arg Ala Cys Gly Arg Leu Val Lys Leu Gly Arg Arg Asp Asp
                1685                1690                1695

Cys Ala Asp Thr Gln Pro Gly Leu Pro Pro Leu Leu Arg Asn Phe Ser
            1700                1705                1710

Phe Ser Gln Val Asp Leu Arg Gly Met Met Leu Asp Gln Pro Ala Arg
        1715                1720                1725

Ile Arg Ala Leu Leu Asp Glu Leu Phe Gly Leu Val Ala Ala Gly Ala
    1730                1735                1740

Ile Ser Pro Leu Gly Ser Gly Leu Arg Val Gly Gly Ser Leu Thr Pro
```

```
                    1745              1750              1755              1760
Pro Pro Val Glu Thr Phe Pro Ile Ser Arg Ala Ala Glu Ala Phe Arg
                1765              1770              1775
Arg Met Ala Gln Gly Gln His Leu Gly Lys Leu Val Leu Thr Leu Asp
            1780              1785              1790
Asp Pro Glu Val Arg Ile Arg Ala Pro Ala Glu Ser Ser Val Ala Val
        1795              1800              1805
Arg Ala Asp Gly Thr Tyr Leu Val Thr Gly Gly Leu Gly Gly Leu Gly
    1810              1815              1820
Leu Arg Val Ala Gly Trp Leu Ala Glu Arg Gly Ala Gly Gln Leu Val
1825              1830              1835              1840
Leu Val Gly Arg Ser Gly Ala Ala Ser Ala Glu Gln Arg Ala Ala Val
            1845              1850              1855
Ala Ala Leu Glu Ala His Gly Ala Arg Val Thr Val Ala Lys Ala Asp
            1860              1865              1870
Val Ala Asp Arg Ser Gln Ile Glu Arg Val Leu Arg Glu Val Thr Ala
            1875              1880              1885
Ser Gly Met Pro Leu Arg Gly Val Val His Ala Ala Gly Leu Val Asp
    1890              1895              1900
Asp Gly Leu Leu Met Gln Gln Thr Pro Ala Arg Phe Arg Thr Val Met
1905              1910              1915              1920
Gly Pro Lys Val Gln Gly Ala Leu His Leu His Thr Leu Thr Arg Glu
                1925              1930              1935
Ala Pro Leu Ser Phe Phe Val Leu Tyr Ala Ser Ala Ala Gly Leu Phe
            1940              1945              1950
Gly Ser Pro Gly Gln Gly Asn Tyr Ala Ala Ala Asn Ala Phe Leu Asp
        1955              1960              1965
Ala Leu Ser His His Arg Arg Ala Gln Gly Leu Pro Ala Leu Ser Ile
    1970              1975              1980
Asp Trp Gly Met Phe Thr Glu Val Gly Met Ala Val Ala Gln Glu Asn
1985              1990              1995              2000
Arg Gly Ala Arg Gln Ile Ser Arg Gly Met Arg Gly Ile Thr Pro Asp
            2005              2010              2015
Glu Gly Leu Ser Ala Leu Ala Arg Leu Leu Glu Gly Asp Arg Val Gln
            2020              2025              2030
Thr Gly Val Ile Pro Ile Thr Pro Arg Gln Trp Val Glu Phe Tyr Pro
        2035              2040              2045
Ala Thr Ala Ala Ser Arg Arg Leu Ser Arg Leu Val Thr Thr Gln Arg
2050              2055              2060
Ala Val Ala Asp Arg Thr Ala Gly Asp Arg Asp Leu Leu Glu Gln Leu
2065              2070              2075              2080
Ala Ser Ala Glu Pro Ser Ala Arg Ala Gly Leu Leu Gln Asp Val Val
            2085              2090              2095
Arg Val Gln Val Ser His Val Leu Arg Leu Pro Glu Asp Lys Ile Glu
        2100              2105              2110
Val Asp Ala Pro Leu Ser Ser Met Gly Met Asp Ser Leu Met Ser Leu
    2115              2120              2125
Glu Leu Arg Asn Arg Ile Glu Ala Ala Leu Gly Val Ala Ala Pro Ala
    2130              2135              2140
Ala Leu Gly Trp Thr Tyr Pro Thr Val Ala Ala Ile Thr Arg Trp Leu
2145              2150              2155              2160
Leu Asp Asp Ala Leu Val Val Arg Leu Gly Gly Gly Ser Asp Thr Asp
            2165              2170              2175
```

-continued

Glu Ser Thr Ala Ser Ala Gly Ser Phe Val His Val Leu Arg Phe Arg
              2180                2185                2190

Pro Val Val Lys Pro Arg Ala Arg Leu Phe Cys Phe His Gly Ser Gly
            2195                2200                2205

Gly Ser Pro Glu Gly Phe Arg Ser Trp Ser Glu Lys Ser Glu Trp Ser
        2210                2215                2220

Asp Leu Glu Ile Val Ala Met Trp His Asp Arg Ser Leu Ala Ser Glu
2225                2230                2235                2240

Asp Ala Pro Gly Lys Lys Tyr Val Gln Glu Ala Ala Ser Leu Ile Gln
            2245                2250                2255

His Tyr Ala Asp Ala Pro Phe Ala Leu Val Gly Phe Ser Leu Gly Val
              2260                2265                2270

Arg Phe Val Met Gly Thr Ala Val Glu Leu Ala Ser Arg Ser Gly Ala
        2275                2280                2285

Pro Ala Pro Leu Ala Val Phe Thr Leu Gly Gly Ser Leu Ile Ser Ser
        2290                2295                2300

Ser Glu Ile Thr Pro Glu Met Glu Thr Asp Ile Ile Ala Lys Leu Phe
2305                2310                2315                2320

Phe Arg Asn Ala Ala Gly Phe Val Arg Ser Thr Gln Gln Val Gln Ala
            2325                2330                2335

Asp Ala Arg Ala Asp Lys Val Ile Thr Asp Thr Met Val Ala Pro Ala
            2340                2345                2350

Pro Gly Asp Ser Lys Glu Pro Pro Val Lys Ile Ala Val Pro Ile Val
            2355                2360                2365

Ala Ile Ala Gly Ser Asp Asp Val Ile Val Pro Pro Ser Asp Val Gln
        2370                2375                2380

Asp Leu Gln Ser Arg Thr Thr Glu Arg Phe Tyr Met His Leu Leu Pro
2385                2390                2395                2400

Gly Asp His Glu Phe Leu Val Asp Arg Gly Arg Glu Ile Met His Ile
              2405                2410                2415

Val Asp Ser His Leu Asn Pro Leu Leu Ala Ala Arg Thr Thr Ser Ser
            2420                2425                2430

Gly Pro Ala Phe Glu Ala Lys
        2435

<210> SEQ ID NO 8
<211> LENGTH: 419
<212> TYPE: PRT
<213> ORGANISM: Sorangium cellulosum

<400> SEQUENCE: 8

Met Thr Gln Glu Gln Ala Asn Gln Ser Glu Thr Lys Pro Ala Phe Asp
  1               5                  10                  15

Phe Lys Pro Phe Ala Pro Gly Tyr Ala Glu Asp Pro Phe Pro Ala Ile
             20                  25                  30

Glu Arg Leu Arg Glu Ala Thr Pro Ile Phe Tyr Trp Asp Glu Gly Arg
         35                  40                  45

Ser Trp Val Leu Thr Arg Tyr His Asp Val Ser Ala Val Phe Arg Asp
     50                  55                  60

Glu Arg Phe Ala Val Ser Arg Glu Glu Trp Ser Ser Ala Glu Tyr
 65                  70                  75                  80

Ser Ser Ala Ile Pro Glu Leu Ser Asp Met Lys Lys Tyr Gly Leu Phe
                 85                  90                  95

Gly Leu Pro Pro Glu Asp His Ala Arg Val Arg Lys Leu Val Asn Pro

-continued

```
                        100                 105                 110
        Ser Phe Thr Ser Arg Ala Ile Asp Leu Leu Arg Ala Glu Ile Gln Arg
                        115                 120                 125

Thr Val Asp Gln Leu Leu Asp Ala Arg Ser Gly Gln Glu Glu Phe Asp
                        130                 135                 140

Val Val Arg Asp Tyr Ala Glu Gly Ile Pro Met Arg Ala Ile Ser Ala
        145                 150                 155                 160

Leu Leu Lys Val Pro Ala Glu Cys Asp Glu Lys Phe Arg Arg Phe Gly
                        165                 170                 175

Ser Ala Thr Ala Arg Ala Leu Gly Val Gly Leu Val Pro Gln Val Asp
                        180                 185                 190

Glu Glu Thr Lys Thr Leu Val Ala Ser Val Thr Glu Gly Leu Ala Leu
                        195                 200                 205

Leu His Asp Val Leu Asp Glu Arg Arg Asn Pro Leu Glu Asn Asp
                        210                 215                 220

Val Leu Thr Met Leu Leu Gln Ala Glu Ala Asp Gly Ser Arg Leu Ser
        225                 230                 235                 240

Thr Lys Glu Leu Val Ala Leu Val Gly Ala Ile Ile Ala Ala Gly Thr
                        245                 250                 255

Asp Thr Thr Ile Tyr Leu Ile Ala Phe Ala Val Leu Asn Leu Leu Arg
                        260                 265                 270

Ser Pro Glu Ala Leu Glu Leu Val Lys Ala Glu Pro Gly Leu Met Arg
                        275                 280                 285

Asn Ala Leu Asp Glu Val Leu Arg Phe Asp Asn Ile Leu Arg Ile Gly
                        290                 295                 300

Thr Val Arg Phe Ala Arg Gln Asp Leu Glu Tyr Cys Gly Ala Ser Ile
        305                 310                 315                 320

Lys Lys Gly Glu Met Val Phe Leu Leu Ile Pro Ser Ala Leu Arg Asp
                        325                 330                 335

Gly Thr Val Phe Ser Arg Pro Asp Val Phe Asp Val Arg Arg Asp Thr
                        340                 345                 350

Gly Ala Ser Leu Ala Tyr Gly Arg Gly Pro His Val Cys Pro Gly Val
                        355                 360                 365

Ser Leu Ala Arg Leu Glu Ala Glu Ile Ala Val Gly Thr Ile Phe Arg
                        370                 375                 380

Arg Phe Pro Glu Met Lys Leu Lys Glu Thr Pro Val Phe Gly Tyr His
        385                 390                 395                 400

Pro Ala Phe Arg Asn Ile Glu Ser Leu Asn Val Ile Leu Lys Pro Ser
                        405                 410                 415

Lys Ala Gly

<210> SEQ ID NO 9
<211> LENGTH: 607
<212> TYPE: PRT
<213> ORGANISM: Sorangium cellulosum

<400> SEQUENCE: 9

Ala Ser Leu Asp Ala Leu Phe Ala Arg Ala Thr Ser Ala Arg Val Leu
        1               5                   10                  15

Asp Asp Gly His Gly Arg Ala Thr Glu Arg His Val Leu Ala Glu Ala
                        20                  25                  30

Arg Gly Ile Glu Asp Leu Arg Ala Leu Arg Glu His Leu Arg Ile Gln
                        35                  40                  45

Glu Gly Gly Pro Ser Phe His Cys Met Cys Leu Gly Asp Leu Thr Val
```

```
              50                      55                      60
Glu Leu Leu Ala His Asp Gln Pro Leu Ala Ser Ile Ser Phe His His
 65                      70                      75                      80

Ala Arg Ser Leu Arg His Pro Asp Trp Thr Ser Asp Ala Met Leu Val
                         85                      90                      95

Asp Gly Pro Ala Leu Val Arg Trp Leu Ala Ala Arg Gly Ala Pro Gly
                        100                     105                     110

Pro Leu Arg Glu Tyr Glu Glu Arg Glu Arg Ala Arg Thr Ala Gln
                        115                     120                     125

Glu Ala Arg Arg Leu Trp Leu Ala Ala Pro Pro Cys Phe Ala Pro
                130                     135                     140

Asp Leu Pro Arg Phe Glu Asp Ala Asn Gly Leu Pro Leu Gly Pro
145                     150                     155                     160

Met Ser Pro Glu Val Ala Glu Ala Glu Arg Arg Leu Arg Ala Ser Tyr
                        165                     170                     175

Ala Thr Pro Glu Leu Ala Cys Ala Ala Leu Leu Ala Trp Leu Gly Thr
                        180                     185                     190

Gly Ala Gly Pro Trp Ser Gly Tyr Pro Ala Tyr Glu Met Leu Pro Glu
                195                     200                     205

Asn Leu Leu Gly Phe Gly Leu Pro Thr Ala Ile Ala Ala Ala Ser
210                     215                     220

Ala Pro Gly Thr Ser Glu Ala Ala Leu Arg Gly Ala Ala Arg Leu Phe
225                     230                     235                     240

Ala Ser Trp Glu Val Val Ser Ser Lys Lys Ser Gln Leu Gly Asn Ile
                        245                     250                     255

Pro Glu Ala Leu Trp Glu Arg Leu Arg Thr Ile Val Arg Ala Met Gly
                260                     265                     270

Asn Ala Asp Asn Leu Ser Arg Phe Glu Arg Ala Glu Ala Ile Ala Ala
                275                     280                     285

Glu Val Arg Arg Leu Arg Ala Gln Pro Ala Pro Phe Ala Ala Gly Ala
                290                     295                     300

Gly Leu Ala Val Ala Gly Val Ser Ser Ser Gly Arg Leu Ser Gly Leu
305                     310                     315                     320

Val Thr Asp Gly Asp Ala Leu Tyr Ser Gly Asp Gly Asn Asp Ile Val
                        325                     330                     335

Met Phe Gln Pro Gly Arg Ile Ser Pro Val Val Leu Leu Ala Gly Thr
                        340                     345                     350

Asp Pro Phe Phe Glu Leu Ala Pro Pro Leu Ser Gln Met Leu Phe Val
                        355                     360                     365

Ala His Ala Asn Ala Gly Thr Ile Ser Lys Val Leu Thr Glu Gly Ser
                        370                     375                     380

Pro Leu Ile Val Met Ala Arg Asn Gln Ala Arg Pro Met Ser Leu Val
385                     390                     395                     400

His Ala Arg Gly Phe Met Ala Trp Val Asn Gln Ala Met Val Pro Asp
                        405                     410                     415

Pro Glu Arg Gly Ala Pro Phe Val Gln Arg Ser Thr Ile Met Glu
                        420                     425                     430

Phe Glu His Pro Thr Pro Arg Cys Leu His Glu Pro Ala Gly Ser Ala
                        435                     440                     445

Phe Ser Leu Ala Cys Asp Glu Glu His Leu Tyr Trp Cys Glu Leu Ser
                        450                     455                     460

Ala Gly Arg Leu Glu Leu Trp Arg His Pro His His Arg Pro Gly Ala
465                     470                     475                     480
```

-continued

```
Pro Ser Arg Phe Ala Tyr Leu Gly Glu His Pro Ile Ala Ala Thr Trp
            485                 490                 495

Tyr Pro Ser Leu Thr Leu Asn Ala Thr His Val Leu Trp Ala Asp Pro
        500                 505                 510

Asp Arg Arg Ala Ile Leu Gly Val Asp Lys Arg Thr Gly Val Glu Pro
        515                 520                 525

Ile Val Leu Ala Glu Thr Arg His Pro Ala His Val Val Ser Glu
    530                 535                 540

Asp Arg Asp Ile Phe Ala Leu Thr Gly Gln Pro Asp Ser Arg Asp Trp
545                 550                 555                 560

His Val Glu His Ile Arg Ser Gly Ala Ser Thr Val Val Ala Asp Tyr
            565                 570                 575

Gln Arg Gln Leu Trp Asp Arg Pro Asp Met Val Leu Asn Arg Arg Gly
        580                 585                 590

Leu Phe Phe Thr Thr Asn Asp Arg Ile Leu Thr Leu Ala Arg Ser
        595                 600                 605

<210> SEQ ID NO 10
<211> LENGTH: 423
<212> TYPE: PRT
<213> ORGANISM: Sorangium cellulosum

<400> SEQUENCE: 10

Met Gly Ala Leu Ile Ser Val Ala Ala Pro Gly Cys Ala Leu Gly Gly
  1               5                  10                  15

Ala Glu Glu Glu Gly Gln Pro Gly Gln Asp Ala Gly Ala Gly Ala Leu
                20                  25                  30

Ala Pro Ala Arg Glu Val Met Ala Ala Glu Val Ala Ala Gly Gln Met
            35                  40                  45

Pro Gly Ala Val Trp Leu Val Ala Arg Gly Asp Asp Val His Val Asp
        50                  55                  60

Ala Val Gly Val Thr Glu Leu Gly Gly Ser Ala Pro Met Arg Arg Asp
 65                  70                  75                  80

Thr Ile Phe Arg Ile Ala Ser Met Thr Lys Ala Val Thr Ala Thr Ala
                85                  90                  95

Val Met Met Leu Val Glu Glu Gly Lys Leu Asp Leu Asp Ser Pro Val
                100                 105                 110

Asp Arg Trp Leu Pro Glu Leu Ala Asn Arg Lys Val Leu Ala Arg Ile
            115                 120                 125

Asp Gly Pro Ile Asp Glu Thr Val Pro Ala Glu Arg Pro Ile Thr Val
        130                 135                 140

Arg Asp Leu Met Thr Phe Thr Met Gly Phe Gly Ile Ser Phe Asp Ala
145                 150                 155                 160

Ser Ser Pro Ile Gln Arg Ala Ile Asp Glu Leu Gly Leu Val Asn Ala
                165                 170                 175

Gln Pro Val Pro Met Thr Pro His Gly Pro Asp Glu Trp Ile Arg Arg
            180                 185                 190

Leu Gly Thr Leu Pro Leu Met His Gln Pro Gly Ala Gln Trp Met Tyr
        195                 200                 205

Asn Thr Gly Ser Leu Val Gln Gly Val Leu Val Gly Arg Ala Ala Asp
    210                 215                 220

Gln Gly Phe Asp Ala Phe Val Arg Glu Arg Ile Leu Ala Pro Leu Gly
225                 230                 235                 240

Met Arg Asp Thr Asp Phe His Val Pro Ala Asp Lys Leu Ala Arg Phe
```

-continued

```
            245                 250                 255
Ala Gly Cys Gly Tyr Phe Thr Asp Glu Gln Thr Gly Glu Lys Thr Arg
            260                 265                 270

Met Asp Arg Asp Gly Ala Glu Ser Ala Tyr Ala Ser Pro Pro Ala Phe
            275                 280                 285

Pro Ser Gly Ala Ala Gly Leu Val Ser Thr Val Asp Asp Tyr Leu Leu
            290                 295                 300

Phe Ala Arg Met Leu Met Asn Gly Gly Val His Glu Gly Arg Arg Leu
305                 310                 315                 320

Leu Ser Ala Ala Ser Val Arg Glu Met Thr Ala Asp His Leu Thr Pro
                    325                 330                 335

Ala Gln Lys Ala Ala Ser Ser Phe Phe Pro Gly Phe Phe Glu Thr His
            340                 345                 350

Gly Trp Gly Tyr Gly Met Ala Val Val Thr Ala Pro Asp Ala Val Ser
            355                 360                 365

Glu Val Pro Gly Arg Tyr Gly Trp Asp Gly Gly Phe Gly Thr Ser Trp
            370                 375                 380

Ile Asn Asp Pro Gly Arg Glu Leu Ile Gly Ile Val Met Thr Gln Ser
385                 390                 395                 400

Ala Gly Phe Leu Phe Ser Gly Ala Leu Glu Arg Phe Trp Arg Ser Val
                    405                 410                 415

Tyr Val Ala Thr Glu Ser Ala
            420

<210> SEQ ID NO 11
<211> LENGTH: 713
<212> TYPE: PRT
<213> ORGANISM: Sorangium cellulosum

<400> SEQUENCE: 11

Met His Gly Leu Thr Glu Arg Gln Val Leu Leu Ser Leu Val Thr Leu
  1               5                  10                  15

Ala Leu Ile Leu Val Thr Ala Arg Ala Ser Gly Glu Leu Ala Arg Arg
            20                  25                  30

Leu Arg Gln Pro Glu Val Leu Gly Glu Leu Phe Gly Gly Val Val Leu
        35                  40                  45

Gly Pro Ser Val Val Gly Ala Leu Ala Pro Gly Phe His Arg Ala Leu
    50                  55                  60

Phe Gln Glu Pro Ala Val Gly Val Val Leu Ser Gly Ile Ser Trp Ile
65                  70                  75                  80

Gly Ala Leu Leu Leu Leu Leu Met Ala Gly Ile Glu Val Asp Val Gly
                85                  90                  95

Ile Leu Arg Lys Glu Ala Arg Pro Gly Ala Leu Ser Ala Leu Gly Ala
            100                 105                 110

Ile Ala Pro Pro Leu Ala Ala Gly Ala Ala Phe Ser Ala Leu Val Leu
        115                 120                 125

Asp Arg Pro Leu Pro Ser Gly Leu Phe Leu Gly Ile Val Leu Ser Val
    130                 135                 140

Thr Ala Val Ser Val Ile Ala Lys Val Leu Ile Glu Arg Glu Ser Met
145                 150                 155                 160

Arg Arg Ser Tyr Ala Gln Val Thr Leu Ala Ala Gly Val Val Ser Glu
                165                 170                 175

Val Ala Ala Trp Val Leu Val Ala Met Thr Ser Ser Ser Tyr Gly Ala
            180                 185                 190
```

-continued

```
Ser Pro Ala Leu Ala Val Ala Arg Ser Ala Leu Leu Ala Ser Gly Phe
        195                 200                 205

Leu Leu Phe Met Val Leu Val Gly Arg Arg Leu Thr His Leu Ala Met
        210                 215                 220

Arg Trp Val Ala Asp Ala Thr Arg Val Ser Lys Gly Gln Val Ser Leu
225                 230                 235                 240

Val Leu Val Leu Thr Phe Leu Ala Ala Leu Thr Gln Arg Leu Gly
                245                 250                 255

Leu His Pro Leu Leu Gly Ala Phe Ala Leu Gly Val Leu Leu Asn Ser
                260                 265                 270

Ala Pro Arg Thr Asn Arg Pro Leu Leu Asp Gly Val Gln Thr Leu Val
                275                 280                 285

Ala Gly Leu Phe Ala Pro Val Phe Phe Val Leu Ala Gly Met Arg Val
        290                 295                 300

Asp Val Ser Gln Leu Arg Thr Pro Ala Ala Trp Gly Thr Val Ala Leu
305                 310                 315                 320

Leu Leu Ala Thr Ala Thr Ala Ala Lys Val Val Pro Ala Ala Leu Gly
                325                 330                 335

Ala Arg Leu Gly Gly Leu Arg Gly Ser Glu Ala Ala Leu Val Ala Val
                340                 345                 350

Gly Leu Asn Met Lys Gly Gly Thr Asp Leu Ile Val Ala Ile Val Gly
                355                 360                 365

Val Glu Leu Gly Leu Leu Ser Asn Glu Ala Tyr Thr Met Tyr Ala Val
        370                 375                 380

Val Ala Leu Val Thr Val Thr Ala Ser Pro Ala Leu Leu Ile Trp Leu
385                 390                 395                 400

Glu Lys Arg Ala Pro Pro Thr Gln Glu Glu Ser Ala Arg Leu Glu Arg
                405                 410                 415

Glu Glu Ala Ala Arg Arg Ala Tyr Ile Pro Gly Val Glu Arg Ile Leu
                420                 425                 430

Val Pro Ile Val Ala His Ala Leu Pro Gly Phe Ala Thr Asp Ile Val
        435                 440                 445

Glu Ser Ile Val Ala Ser Lys Arg Lys Leu Gly Glu Thr Val Asp Ile
        450                 455                 460

Thr Glu Leu Ser Val Glu Gln Gln Ala Pro Gly Pro Ser Arg Ala Ala
465                 470                 475                 480

Gly Glu Ala Ser Arg Gly Leu Ala Arg Leu Gly Ala Arg Leu Arg Val
                485                 490                 495

Gly Ile Trp Arg Gln Arg Arg Glu Leu Arg Gly Ser Ile Gln Ala Ile
                500                 505                 510

Leu Arg Ala Ser Arg Asp His Asp Leu Leu Val Ile Gly Ala Arg Ser
        515                 520                 525

Pro Ala Arg Ala Arg Gly Met Ser Phe Gly Arg Leu Gln Asp Ala Ile
        530                 535                 540

Val Gln Arg Ala Glu Ser Asn Val Leu Val Val Gly Asp Pro Pro
545                 550                 555                 560

Ala Ala Glu Arg Ala Ser Ala Arg Arg Ile Leu Val Pro Ile Ile Gly
                565                 570                 575

Leu Glu Tyr Ser Phe Ala Ala Ala Asp Leu Ala Ala His Val Ala Leu
                580                 585                 590

Ala Trp Asp Ala Glu Leu Val Leu Leu Ser Ser Ala Gln Thr Asp Pro
        595                 600                 605

Gly Ala Val Val Trp Arg Asp Arg Glu Pro Ser Arg Val Arg Ala Val
```

```
            610                 615                 620
Ala Arg Ser Val Val Asp Glu Ala Val Phe Arg Gly Arg Leu Gly
625                 630                 635                 640

Val Arg Val Ser Ser Arg Val His Val Gly Ala His Pro Ser Asp Glu
                645                 650                 655

Ile Thr Arg Glu Leu Ala Arg Ala Pro Tyr Asp Leu Val Leu Gly
            660                 665                 670

Cys Tyr Asp His Gly Pro Leu Gly Arg Leu Tyr Leu Gly Ser Thr Val
                675                 680                 685

Glu Ser Val Val Arg Ser Arg Val Pro Val Ala Leu Leu Val Ala
    690                 695                 700

His Gly Gly Thr Arg Glu Gln Val Arg
705                 710

<210> SEQ ID NO 12
<211> LENGTH: 126
<212> TYPE: PRT
<213> ORGANISM: Sorangium cellulosum

<400> SEQUENCE: 12

Met Asp Lys Pro Ile Gly Arg Thr Arg Cys Ala Ile Ala Glu Gly Tyr
1               5                   10                  15

Ile Pro Gly Gly Ser Asn Gly Pro Glu Pro Gln Met Thr Ser His Glu
            20                  25                  30

Thr Ala Cys Leu Leu Asn Ala Ser Asp Arg Asp Ala Gln Val Ala Ile
        35                  40                  45

Thr Val Tyr Phe Ser Asp Arg Asp Pro Ala Gly Pro Tyr Arg Val Thr
    50                  55                  60

Val Pro Ala Arg Arg Thr Arg His Val Arg Phe Asn Asp Leu Thr Glu
65                  70                  75                  80

Pro Glu Pro Ile Pro Arg Asp Thr Asp Tyr Ala Ser Val Ile Glu Ser
                85                  90                  95

Asp Ala Pro Ile Val Val Gln His Thr Arg Leu Asp Ser Arg Gln Ala
            100                 105                 110

Glu Asn Ala Leu Leu Ser Thr Ile Ala Tyr Thr Asp Arg Glu
        115                 120                 125

<210> SEQ ID NO 13
<211> LENGTH: 149
<212> TYPE: PRT
<213> ORGANISM: Sorangium cellulosum

<400> SEQUENCE: 13

Met Lys His Val Asp Thr Gly Arg Arg Phe Gly Arg Arg Ile Gly His
1               5                   10                  15

Thr Leu Gly Leu Leu Ala Ser Met Ala Leu Ala Gly Cys Gly Gly Pro
            20                  25                  30

Ser Glu Lys Thr Val Gln Gly Thr Arg Leu Ala Pro Gly Ala Asp Ala
        35                  40                  45

Arg Val Thr Ala Asp Val Asp Pro Asp Ala Ala Thr Thr Arg Leu Ala
    50                  55                  60

Val Asp Val Val His Leu Ser Pro Pro Glu Arg Leu Glu Ala Gly Ser
65                  70                  75                  80

Glu Arg Phe Val Val Trp Gln Arg Pro Ser Pro Glu Ser Pro Trp Arg
                85                  90                  95

Arg Val Gly Val Leu Asp Tyr Asn Ala Asp Ser Arg Arg Gly Lys Leu
```

-continued

```
                    100                 105                 110
Ala Glu Thr Thr Val Pro Tyr Ala Asn Phe Glu Leu Leu Ile Thr Ala
            115                 120                 125
Glu Lys Gln Ser Ser Pro Gln Ser Pro Ser Ser Ala Ala Val Ile Gly
    130                 135                 140
Pro Thr Ser Val Gly
145

<210> SEQ ID NO 14
<211> LENGTH: 184
<212> TYPE: PRT
<213> ORGANISM: Sorangium cellulosum

<400> SEQUENCE: 14

Val Thr Ser Glu Glu Val Pro Gly Ala Ala Leu Gly Ala Gln Ser Ser
  1               5                  10                  15
Leu Val Arg Ala Gln His Ala Ala Arg His Val Arg Pro Cys Thr Arg
             20                  25                  30
Ala Glu Glu Pro Pro Ala Leu Met His Gly Leu Thr Glu Arg Gln Val
         35                  40                  45
Leu Leu Ser Leu Val Ala Leu Ala Leu Val Leu Thr Ala Arg Ala
     50                  55                  60
Phe Gly Glu Leu Ala Arg Arg Leu Arg Gln Pro Glu Val Leu Gly Glu
 65                  70                  75                  80
Leu Phe Gly Gly Val Leu Gly Pro Ser Val Gly Ala Leu Ala
                 85                  90                  95
Pro Gly Phe His Arg Val Leu Phe Gln Asp Pro Ala Val Gly Val Val
                100                 105                 110
Leu Ser Gly Ile Ser Trp Ile Gly Ala Leu Val Leu Leu Met Ala
            115                 120                 125
Gly Ile Glu Val Asp Val Ser Ile Leu Arg Lys Glu Ala Arg Pro Gly
    130                 135                 140
Ala Leu Ser Ala Leu Gly Ala Ile Ala Pro Leu Arg Thr Pro Gly
145                 150                 155                 160
Pro Leu Val Gln Arg Met Gln Gly Ala Phe Thr Trp Asp Leu Asp Val
                165                 170                 175
Ser Pro Arg Arg Ser Ala Gln Ala
            180

<210> SEQ ID NO 15
<211> LENGTH: 145
<212> TYPE: PRT
<213> ORGANISM: Sorangium cellulosum

<400> SEQUENCE: 15

Val Asn Ala Pro Cys Met Arg Cys Thr Ser Gly Pro Gly Val Arg Ser
  1               5                  10                  15
Gly Gly Ala Ile Ala Pro Ser Ala Glu Ser Ala Pro Gly Arg Ala Ser
             20                  25                  30
Leu Arg Arg Met Leu Thr Ser Thr Ile Pro Ala Met Ser Ser Arg
         35                  40                  45
Thr Ser Ala Pro Ile Gln Glu Met Pro Glu Ser Thr Thr Pro Thr Ala
     50                  55                  60
Gly Ser Trp Lys Arg Thr Arg Trp Asn Pro Gly Ala Ser Ala Pro Thr
 65                  70                  75                  80
Thr Asp Gly Pro Ser Thr Thr Pro Pro Lys Ser Ser Pro Ser Thr Ser
```

```
                    85                  90                  95
Gly Trp Arg Ser Arg Arg Ala Ser Ser Pro Lys Ala Arg Ala Val Arg
                100                 105                 110

Arg Thr Ser Ala Arg Ala Thr Ser Glu Ser Arg Thr Cys Arg Ser Val
            115                 120                 125

Arg Pro Cys Ile Arg Ala Gly Gly Ser Ser Ala Arg Val Gln Gly Arg
        130                 135                 140

Thr
145

<210> SEQ ID NO 16
<211> LENGTH: 185
<212> TYPE: PRT
<213> ORGANISM: Sorangium cellulosum

<400> SEQUENCE: 16

Val Leu Ala Pro Pro Ala Asp Ile Arg Pro Pro Ala Ala Ala Gln Leu
  1               5                  10                  15

Glu Pro Asp Ser Pro Asp Asp Glu Ala Asp Glu Ala Asp Glu Ala Leu
                 20                  25                  30

Arg Pro Phe Arg Asp Ala Ile Ala Ala Tyr Ser Glu Ala Val Arg Trp
             35                  40                  45

Ala Glu Ala Ala Gln Arg Pro Arg Leu Glu Ser Leu Val Arg Leu Ala
         50                  55                  60

Ile Val Arg Leu Gly Lys Ala Leu Asp Lys Val Pro Phe Ala His Thr
 65                  70                  75                  80

Thr Ala Gly Val Ser Gln Ile Ala Gly Arg Leu Gln Asn Asp Ala Val
                 85                  90                  95

Trp Phe Asp Val Ala Ala Arg Tyr Ala Ser Phe Arg Ala Ala Thr Glu
                100                 105                 110

His Ala Leu Arg Asp Ala Ala Ser Ala Met Glu Ala Leu Ala Ala Gly
            115                 120                 125

Pro Tyr Arg Gly Ser Ser Arg Val Ser Ala Ala Val Gly Glu Phe Arg
        130                 135                 140

Gly Glu Ala Ala Arg Leu His Pro Ala Asp Arg Val Pro Ala Ser Asp
145                 150                 155                 160

Gln Gln Ile Leu Thr Ala Leu Arg Ala Ala Glu Arg Ala Leu Ile Ala
                165                 170                 175

Leu Tyr Thr Ala Phe Ala Arg Glu Glu
            180                 185

<210> SEQ ID NO 17
<211> LENGTH: 146
<212> TYPE: PRT
<213> ORGANISM: Sorangium cellulosum

<400> SEQUENCE: 17

Met Ala Asp Ala Ala Ser Arg Ser Ala Cys Ser Val Ala Ala Arg Lys
  1               5                  10                  15

Leu Ala Tyr Arg Ala Ala Thr Ser Asn Gln Thr Ala Ser Phe Trp Ser
                 20                  25                  30

Leu Pro Ala Ile Trp Glu Thr Pro Ala Val Val Cys Ala Lys Gly Thr
             35                  40                  45

Leu Ser Ser Ala Leu Pro Ser Arg Thr Ile Ala Ser Arg Thr Arg Leu
         50                  55                  60

Ser Ser Arg Gly Arg Cys Ala Ala Ser Ala His Arg Thr Ala Ser Glu
```

-continued

```
                65                  70                  75                  80
Tyr Ala Ile Ala Ser Arg Asn Gly Arg Ser Ala Ser Ala Ser
                    85                  90                  95

Ser Ala Ser Ser Ser Gly Glu Ser Gly Ser Ser Trp Ala Ala Gly
                100                 105                 110

Gly Arg Met Ser Ala Gly Ala Ser Thr Gly Glu Val Tyr Glu Gln
            115                 120                 125

Ala Pro Arg Leu Arg Leu Ala Gln Ser Val Ala Arg Arg Arg Asp
    130                 135                 140

Pro Thr
145

<210> SEQ ID NO 18
<211> LENGTH: 288
<212> TYPE: PRT
<213> ORGANISM: Sorangium cellulosum

<400> SEQUENCE: 18

Val Thr Val Ser Ser Met Pro Arg Ser Trp Ser Ser Arg Val Arg Thr
  1               5                  10                  15

Val Val Thr Ala Leu Gly Cys Ala Arg Arg Leu Ser Gly Ser Ile Ser
                 20                  25                  30

Arg Leu Arg Arg His Pro Glu Ala Gly Arg Ala Pro Arg Ser Arg Leu
             35                  40                  45

Arg Ala Trp Arg Arg Leu Pro Gln His Ile Ser Ser Pro Trp Arg His
     50                  55                  60

Leu Pro Pro Gly Ala Arg Val Gly Thr Ser Cys Pro Ala Asp Arg Arg
 65                  70                  75                  80

Ile Leu Pro Ser His Arg Thr Ala Asp Leu Gly Thr Ser Gly Gly Thr
                 85                  90                  95

Leu Val Ala Arg Met Ser Gly His Val Ala Arg Asn Pro His Ala Ala
                100                 105                 110

Val Leu Val Gly Asp Gly Ser Ala Arg Gly Arg Arg Leu Ser Asn
            115                 120                 125

Arg Arg Ala Glu Arg Arg Val Ser Asp Val Thr Cys Arg Glu Gly Gly
    130                 135                 140

Glu Ala Met Gln Lys Ile Ala Gly Lys Leu Val Val Gly Leu Ile Ser
145                 150                 155                 160

Val Ser Gly Met Ser Leu Leu Ala Cys Gly Gly Glu Lys Arg Ser
                165                 170                 175

Gly Gly Glu Ala Gln Thr Pro Gly Gly Ala Gln Gly Glu Ala Pro Val
            180                 185                 190

Pro Val Gly Ser Ala Val Asp Ser Ile Val Ala Ala Arg Cys Asp Arg
        195                 200                 205

Glu Ala Arg Cys Asn Asn Ile Gly Gln Asp Arg Glu Tyr Ser Ser Lys
    210                 215                 220

Asp Ala Cys Ser Asn Lys Ile Arg Ser Glu Trp Arg Asp Glu Leu Thr
225                 230                 235                 240

Phe Gly Glu Cys Pro Gly Gly Ile Asp Ala Lys Gln Leu Asn Glu Cys
                245                 250                 255

Leu Glu Gly Ile Arg Asn Glu Gly Cys Gly Asn Pro Phe Asp Thr Leu
            260                 265                 270

Gly Arg Val Val Ala Cys Arg Ser Ser Asp Leu Cys Arg Asp Ala Arg
        275                 280                 285
```

```
<210> SEQ ID NO 19
<211> LENGTH: 288
<212> TYPE: PRT
<213> ORGANISM: Sorangium cellulosum

<400> SEQUENCE: 19

Val Thr Val Ser Ser Met Pro Arg Ser Trp Ser Arg Val Arg Thr
 1               5                  10                  15

Val Val Thr Ala Leu Gly Cys Ala Arg Arg Leu Ser Gly Ser Ile Ser
            20                  25                  30

Arg Leu Arg Arg His Pro Glu Ala Gly Arg Ala Pro Arg Ser Arg Leu
        35                  40                  45

Arg Ala Trp Arg Arg Leu Pro Gln His Ile Ser Ser Pro Trp Arg His
    50                  55                  60

Leu Pro Pro Gly Ala Arg Val Gly Thr Ser Cys Pro Ala Asp Arg Arg
65                  70                  75                  80

Ile Leu Pro Ser His Arg Thr Ala Asp Leu Gly Thr Ser Gly Gly Thr
                85                  90                  95

Leu Val Ala Arg Met Ser Gly His Val Ala Arg Asn Pro His Ala Ala
            100                 105                 110

Val Leu Val Gly Asp Gly Ser Ala Arg Gly Arg Arg Leu Ser Asn
            115                 120                 125

Arg Arg Ala Glu Arg Arg Val Ser Asp Val Thr Cys Arg Glu Gly Gly
    130                 135                 140

Glu Ala Met Gln Lys Ile Ala Gly Lys Leu Val Val Gly Leu Ile Ser
145                 150                 155                 160

Val Ser Gly Met Ser Leu Leu Ala Cys Gly Gly Glu Lys Arg Ser
                165                 170                 175

Gly Gly Glu Ala Gln Thr Pro Gly Gly Ala Gln Gly Glu Ala Pro Val
            180                 185                 190

Pro Val Gly Ser Ala Val Asp Ser Ile Val Ala Ala Arg Cys Asp Arg
            195                 200                 205

Glu Ala Arg Cys Asn Asn Ile Gly Gln Asp Arg Glu Tyr Ser Ser Lys
    210                 215                 220

Asp Ala Cys Ser Asn Lys Ile Arg Ser Glu Trp Arg Asp Glu Leu Thr
225                 230                 235                 240

Phe Gly Glu Cys Pro Gly Gly Ile Asp Ala Lys Gln Leu Asn Glu Cys
                245                 250                 255

Leu Glu Gly Ile Arg Asn Glu Gly Cys Gly Asn Pro Phe Asp Thr Leu
            260                 265                 270

Gly Arg Val Val Ala Cys Arg Ser Ser Asp Leu Cys Arg Asp Ala Arg
            275                 280                 285

<210> SEQ ID NO 20
<211> LENGTH: 155
<212> TYPE: PRT
<213> ORGANISM: Sorangium cellulosum

<400> SEQUENCE: 20

Met Asp Pro Arg Ala Arg Arg Glu Lys Arg Pro Ser Leu Leu Asp Ser
 1               5                  10                  15

Arg Gly Arg Gln Pro Lys Arg Ser Gln Gln Gly Gly His Met Glu Lys
            20                  25                  30

Pro Ile Gly Arg Thr Arg Trp Ala Ile Ala Glu Gly Tyr Ile Pro Gly
        35                  40                  45
```

```
Arg Ser Asn Gly Pro Glu Pro Gln Met Thr Ser His Glu Thr Ala Cys
     50                  55                  60

Leu Leu Asn Ala Ser Asp Arg Asp Ala Gln Val Ala Ile Thr Val Tyr
 65                  70                  75                  80

Phe Ser Asp Arg Asp Pro Ala Gly Pro Tyr Arg Val Thr Val Pro Ala
                 85                  90                  95

Arg Arg Thr Arg His Val Arg Phe Asn Asp Leu Thr Glu Pro Glu Pro
                100                 105                 110

Ile Pro Arg Asp Thr Asp Tyr Ala Ser Val Ile Glu Ser Asp Val Pro
            115                 120                 125

Ile Val Val Gln His Thr Arg Leu Asp Ser Arg Gln Ala Glu Asn Ala
        130                 135                 140

Leu Ile Ser Thr Ile Ala Tyr Thr Asp Arg Glu
145                 150                 155

<210> SEQ ID NO 21
<211> LENGTH: 156
<212> TYPE: PRT
<213> ORGANISM: Sorangium cellulosum

<400> SEQUENCE: 21

Val Arg Arg Ser Arg Trp Gln Met Lys His Val Asp Thr Gly Arg Arg
 1               5                  10                  15

Val Gly Arg Arg Ile Gly Leu Thr Leu Gly Leu Leu Ala Ser Met Ala
                20                  25                  30

Leu Ala Gly Cys Gly Gly Pro Ser Glu Lys Ile Val Gln Gly Thr Arg
             35                  40                  45

Leu Ala Pro Gly Ala Asp Ala His Val Ala Ala Asp Val Asp Pro Asp
 50                  55                  60

Ala Ala Thr Thr Arg Leu Ala Val Asp Val Val His Leu Ser Pro Pro
 65                  70                  75                  80

Glu Arg Ile Glu Ala Gly Ser Glu Arg Phe Val Val Trp Gln Arg Pro
                 85                  90                  95

Ser Ser Glu Ser Pro Trp Gln Arg Val Gly Val Leu Asp Tyr Asn Ala
                100                 105                 110

Ala Ser Arg Arg Gly Lys Leu Ala Glu Thr Thr Val Pro His Ala Asn
            115                 120                 125

Phe Glu Leu Leu Ile Thr Val Glu Lys Gln Ser Ser Pro Gln Ser Pro
130                 135                 140

Ser Ser Ala Ala Val Ile Gly Pro Thr Ser Val Gly
145                 150                 155

<210> SEQ ID NO 22
<211> LENGTH: 305
<212> TYPE: PRT
<213> ORGANISM: Sorangium cellulosum

<400> SEQUENCE: 22

Met Glu Lys Glu Ser Arg Ile Ala Ile Tyr Gly Ala Ile Ala Ala Asn
 1               5                  10                  15

Val Ala Ile Ala Ala Val Lys Phe Ile Ala Ala Val Thr Gly Ser
                20                  25                  30

Ser Ala Met Leu Ser Glu Gly Val His Ser Leu Val Asp Thr Ala Asp
             35                  40                  45

Gly Leu Leu Leu Leu Leu Gly Lys His Arg Ser Ala Arg Pro Pro Asp
 50                  55                  60
```

-continued

Ala Glu His Pro Phe Gly His Gly Lys Glu Leu Tyr Phe Trp Thr Leu
 65                  70                  75                  80

Ile Val Ala Ile Met Ile Phe Ala Ala Gly Gly Val Ser Ile Tyr
                 85                  90                  95

Glu Gly Ile Leu His Leu Leu His Pro Arg Gln Ile Glu Asp Pro Thr
            100                 105                 110

Trp Asn Tyr Val Val Leu Gly Ala Ala Val Phe Glu Gly Thr Ser
        115                 120                 125

Leu Ile Ile Ser Ile His Glu Phe Lys Lys Asp Gly Gln Gly Tyr
    130                 135                 140

Leu Ala Ala Met Arg Ser Ser Lys Asp Pro Thr Thr Phe Thr Ile Val
145                 150                 155                 160

Leu Glu Asp Ser Ala Ala Leu Ala Gly Leu Thr Ile Ala Phe Leu Gly
                165                 170                 175

Val Trp Leu Gly His Arg Leu Gly Asn Pro Tyr Leu Asp Gly Ala Ala
            180                 185                 190

Ser Ile Gly Ile Gly Leu Val Leu Ala Val Ala Val Phe Leu Ala
        195                 200                 205

Ser Gln Ser Arg Gly Leu Leu Val Gly Glu Ser Ala Asp Arg Glu Leu
    210                 215                 220

Leu Ala Ala Ile Arg Ala Leu Ala Ser Ala Asp Pro Gly Val Ser Ala
225                 230                 235                 240

Val Gly Arg Pro Leu Thr Met His Phe Gly Pro His Glu Val Leu Val
                245                 250                 255

Val Leu Arg Ile Glu Phe Asp Ala Ala Leu Thr Ala Ser Gly Val Ala
            260                 265                 270

Glu Ala Ile Glu Arg Ile Glu Thr Arg Ile Arg Ser Glu Arg Pro Asp
        275                 280                 285

Val Lys His Ile Tyr Val Glu Ala Arg Ser Leu His Gln Arg Ala Arg
    290                 295                 300

Ala
305

<210> SEQ ID NO 23
<211> LENGTH: 135
<212> TYPE: PRT
<213> ORGANISM: Sorangium cellulosum

<400> SEQUENCE: 23

Val Gln Thr Ser Ser Phe Asp Ala Arg Tyr Ala Gly Cys Lys Ser Ser
 1               5                  10                  15

Arg Arg Ile Ala Arg Ser Gly Ser Ala Gly Ala Arg Ala Gly Arg Ala
                20                  25                  30

His Glu Gly Ala Ala Ser Ala Gly Phe Glu Gly Gly Asp Val Met Arg
            35                  40                  45

Lys Ala Arg Ala His Gly Ala Met Leu Gly Gly Arg Asp Asp Gly Trp
        50                  55                  60

Arg Arg Gly Leu Pro Gly Ala Gly Ala Leu Arg Ala Ala Leu Gln Arg
 65                  70                  75                  80

Gly Arg Ser Arg Asp Leu Ala Arg Arg Leu Ile Ala Ser Val Ser
                 85                  90                  95

Leu Ala Gly Gly Ala Ser Met Ala Val Val Ser Leu Phe Gln Leu Gly
            100                 105                 110

Ile Ile Glu Arg Leu Pro Asp Pro Pro Leu Pro Gly Phe Asp Ser Ala
        115                 120                 125

Lys Val Thr Ser Ser Asp Ile
    130             135

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: universal
      reverse primer

<400> SEQUENCE: 24
ggaaacagct atgaccatg                                                    19

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: universal
      forward primer

<400> SEQUENCE: 25
gtaaaacgac ggccagt                                                      17

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: PCR primer
      NH24 end "B"

<400> SEQUENCE: 26
gtgactggcg cctggaatct gcatgagc                                          28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: PCR primer
      NH2 end "A"

<400> SEQUENCE: 27
agcgggagct tgctagacat tctgtttc                                          28

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: PCR primer
      NH2 end "B"

<400> SEQUENCE: 28
gacgcgcctc gggcagcgcc ccaa                                              24

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: PCR primer
      pEPO15-NH6 end "B"

<400> SEQUENCE: 29

```
caccgaagcg tcgatctggt ccatc                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: PCR primer
      pEPO15H2.7 end "A"

<400> SEQUENCE: 30
cggtcagatc gacgacgggc tttcc                                          25
```